United States Patent
Fleetham et al.

(10) Patent No.: US 12,245,504 B2
(45) Date of Patent: Mar. 4, 2025

(54) ORGANIC ELECTROLUMINESCENT MATERIALS AND DEVICES

(71) Applicant: UNIVERSAL DISPLAY CORPORATION, Ewing, NJ (US)

(72) Inventors: Tyler Fleetham, Yardley, PA (US); Morgan C. MacInnis, Yardley, PA (US); Noah Horwitz, Ewing, NJ (US); Jerald Feldman, Cherry Hill, NJ (US); Hsiao-Fan Chen, Lawrence Township, NJ (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 723 days.

(21) Appl. No.: 17/501,114

(22) Filed: Oct. 14, 2021

(65) Prior Publication Data
US 2022/0131088 A1   Apr. 28, 2022

Related U.S. Application Data

(60) Provisional application No. 63/107,244, filed on Oct. 29, 2020, provisional application No. 63/105,845, filed on Oct. 26, 2020.

(51) Int. Cl.
| | |
|---|---|
| C07D 403/04 | (2006.01) |
| C07F 5/02 | (2006.01) |
| C07F 7/08 | (2006.01) |
| C09K 11/02 | (2006.01) |
| C09K 11/06 | (2006.01) |
| H10K 85/30 | (2023.01) |
| H10K 85/40 | (2023.01) |
| H10K 85/60 | (2023.01) |
| H10K 50/11 | (2023.01) |
| H10K 101/10 | (2023.01) |
| H10K 101/30 | (2023.01) |
| H10K 101/40 | (2023.01) |

(52) U.S. Cl.
CPC ....... *H10K 85/6572* (2023.02); *C07D 403/04* (2013.01); *C07F 5/02* (2013.01); *C07F 5/027* (2013.01); *C07F 7/0816* (2013.01); *C09K 11/02* (2013.01); *C09K 11/06* (2013.01); *H10K 85/322* (2023.02); *H10K 85/40* (2023.02); *H10K 85/623* (2023.02); *H10K 85/654* (2023.02); *H10K 85/6574* (2023.02); *C09K 2211/1007* (2013.01); *C09K 2211/1014* (2013.01); *C09K 2211/1022* (2013.01); *C09K 2211/1029* (2013.01); *C09K 2211/1044* (2013.01); *C09K 2211/185* (2013.01); *H10K 50/11* (2023.02); *H10K 2101/10* (2023.02); *H10K 2101/30* (2023.02); *H10K 2101/40* (2023.02)

(58) Field of Classification Search
None
See application file for complete search history.

(56) References Cited

U.S. PATENT DOCUMENTS

| | | | |
|---|---|---|---|
| 4,769,292 | A | 9/1988 | Tang et al. |
| 5,061,569 | A | 10/1991 | VanSlyke et al. |
| 5,247,190 | A | 9/1993 | Friend et al. |
| 5,703,436 | A | 12/1997 | Forrest et al. |
| 5,707,745 | A | 1/1998 | Forrest et al. |
| 5,834,893 | A | 11/1998 | Bulovic et al. |
| 5,844,363 | A | 12/1998 | Gu et al. |
| 6,013,982 | A | 1/2000 | Thompson et al. |
| 6,087,196 | A | 7/2000 | Sturm et al. |
| 6,091,195 | A | 7/2000 | Forrest et al. |
| 6,097,147 | A | 8/2000 | Baldo et al. |
| 6,294,398 | B1 | 9/2001 | Kim et al. |
| 6,303,238 | B1 | 10/2001 | Thompson et al. |
| 6,337,102 | B1 | 1/2002 | Forrest et al. |
| 6,468,819 | B1 | 10/2002 | Kim et al. |

(Continued)

FOREIGN PATENT DOCUMENTS

| | | |
|---|---|---|
| DE | 102021108423 | 10/2021 |
| EP | 0650955 | 5/1995 |

(Continued)

OTHER PUBLICATIONS

Adachi, Chihaya et al., "Organic Electroluminescent Device Having a Hole Conductor as an Emitting Layer," Appl. Phys. Lett., 55(15): 1489-1491 (1989).

(Continued)

*Primary Examiner* — Robert S Loewe
(74) *Attorney, Agent, or Firm* — DUANE MORRIS LLP

(57) ABSTRACT

Provided are novel organic compounds having a structure of Formula I:

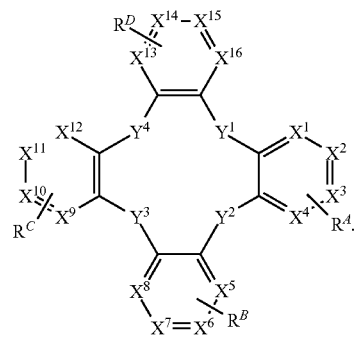

Also provided are formulations having these organic compounds. Further provided are OLEDs and related consumer products that utilize these organic compounds.

20 Claims, 2 Drawing Sheets

(56) References Cited

U.S. PATENT DOCUMENTS

| | | |
|---|---|---|
| 6,528,187 B1 | 3/2003 | Okada |
| 6,687,266 B1 | 2/2004 | Ma et al. |
| 6,835,469 B2 | 12/2004 | Kwong et al. |
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 9,978,956 B2 | 5/2018 | Tsang et al. |
| 10,566,546 B2 | 2/2020 | Kwong et al. |
| 11,038,121 B2 | 6/2021 | Xia |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0152802 A1 | 8/2003 | Tsuboyama et al. |
| 2003/0162053 A1 | 8/2003 | Marks et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Garashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0240285 A1* | 10/2006 | Uchida ............... H10K 85/656 428/917 |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Wakuma et al. |
| 2009/0030202 A1 | 1/2009 | Wakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2016/0013422 A1 | 1/2016 | Kwong |
| 2017/0018721 A1* | 1/2017 | Tsang ............... C07D 225/04 |
| 2018/0108844 A1* | 4/2018 | Lee ............... C07D 497/04 |
| 2019/0252623 A1* | 8/2019 | Layek ............... C07D 487/16 |
| 2020/0017508 A1 | 1/2020 | Chen |

FOREIGN PATENT DOCUMENTS

| | | |
|---|---|---|
| EP | 1725079 | 11/2006 |
| EP | 2034538 | 3/2009 |
| JP | 200511610 | 1/2005 |
| JP | 2007123392 | 5/2007 |
| JP | 2007254297 | 10/2007 |
| JP | 2008074939 | 4/2008 |
| WO | 01/39234 | 5/2001 |
| WO | 02/02714 | 1/2002 |
| WO | 02015654 | 2/2002 |
| WO | 03040257 | 5/2003 |
| WO | 03060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009021126 | 2/2009 |
| WO | 2009050290 | 4/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |

OTHER PUBLICATIONS

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90, Apr. 30, 2007, 183503-1-183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 1, 4-6 (1999).

Gao, Zhiqiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 1: 15-20 (2000).

Hamada, Yuji et al., "High Luminance in Organic Electroluminescent Devices with Bis(10-hydroxybenzo[h]quinolinato) beryllium as an Emitter, " Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

(56) References Cited

OTHER PUBLICATIONS

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2, N)iridium(III) Derivatives," Adv. Mater., 19:739-743 (2007).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Hung, L.S. et al., "Anode Modification in Organic Light-Emitting Diodes by Low-Frequency Plasma Polymerization of CHF3," Appl. Phys. Lett., 78(5):673-675 (2001).

Ikai, Masamichi et al., "Highly Efficient Phosphorescence From Organic Light-Emitting Devices with an Exciton-Block Layer," Appl. Phys. Lett., 79(2):156-158 (2001).

Ikeda, Hisao et al., "P-185 Low-Drive-Voltage OLEDs with a Buffer Layer Having Molybdenum Oxide," SID Symposium Digest, 37:923-926 (2006).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

Kido, Junji et al., 1,2,4-Triazole Derivative as an Electron Transport Layer in Organic Electroluminescent Devices, Jpn. J. Appl. Phys., 32:L917-L920 (1993).

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).

Kwong, Raymond C. et al., "High Operational Stability of Electrophosphorescent Devices," Appl. Phys. Lett., 81(1) 162-164 (2002).

Lamansky, Sergey et al., "Synthesis and Characterization of Phosphorescent Cyclometalated Iridium Complexes," Inorg. Chem., 40(7):1704-1711 (2001).

Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).

Lo, Shih-Chun et al., "Blue Phosphorescence from Iridium(III) Complexes at Room Temperature," Chem. Mater., 18(21)5119-5129 (2006).

Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).

Mi, Bao-Xiu et al., "Thermally Stable Hole-Transporting Material for Organic Light-Emitting Diode an Isoindole Derivative," Chem. Mater., 15(16):3148-3151 (2003).

Nishida, Jun-ichi et al., "Preparation, Characterization, and Electroluminescence Characteristics of a-Diimine-type Platinum(II) Complexes with Perfluorinated Phenyl Groups as Ligands," Chem. Lett., 34(4): 592-593 (2005).

Niu, Yu-Hua et al., "Highly Efficient Electrophosphorescent Devices with Saturated Red Emission from a Neutral Osmium Complex," Chem. Mater., 17(13):3532-3536 (2005).

Noda, Tetsuya and Shirota, Yasuhiko, "5,5'-Bis(dimesitylboryl)-2,2'-bithiophene and 5,5"-Bis (dimesitylboryl)-2,2'5',2"-terthiophene as a Novel Family of Electron-Transporting Amorphous Molecular Materials," J. Am. Chem. Soc., 120 (37):9714-9715 (1998).

Okumoto, Kenji et al., "Green Fluorescent Organic Light-Emitting Device with External Quantum Efficiency of Nearly 10%," Appl. Phys. Lett., 89:063504-1-063504-3 (2006).

Palilis, Leonidas C., "High Efficiency Molecular Organic Light-Emitting Diodes Based on Silole Derivatives and Their Exciplexes," Organic Electronics, 4:113-121 (2003).

Paulose, Betty Marie Jennifer S. et al., "First Examples of Alkenyl Pyridines as Organic Ligands for Phosphorescent ridium Complexes," Adv. Mater., 16(22):2003-2007 (2004).

Ranjan, Sudhir et al., "Realizing Green Phosphorescent Light-Emitting Materials from Rhenium(I) Pyrazolato Diimine Complexes," Inorg. Chem., 42(4):1248-1255 (2003).

Sakamoto, Youichi et al., "Synthesis, Characterization, and Electron-Transport Property of Perfluorinated Phenylene Dendrimers," J. Am. Chem. Soc., 122(8):1832-1833 (2000).

Salbeck, J. et al., "Low Molecular Organic Glasses for Blue Electroluminescence," Synthetic Metals, 91: 209-215 (1997).

Shirota, Yasuhiko et al., "Starburst Molecules Based on pi-Electron Systems as Materials for Organic Electroluminescent Devices," Journal of Luminescence, 72-74:985-991 (1997).

Sotoyama, Wataru et al., "Efficient Organic Light-Emitting Diodes with Phosphorescent Platinum Complexes Containing N^C^N-Co-ordinating Tridentate Ligand," Appl. Phys. Lett., 86:153505-1-153505-3 (2005).

Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).

T. Östergard et al., "Langmuir-Blodgett Light-Emitting Diodes of Poly(3-Hexylthiophene) Electro-Optical Characteristics Related to Structure," Synthetic Metals, 88:171-177 (1997).

Takizawa, Shin-ya et al., "Phosphorescent Iridium Complexes Based on 2-Phenylimidazo[1,2- α]pyridine Ligands Tuning of Emission Color toward the Blue Region and Application to Polymer Light-Emitting Devices," Inorg. Chem., 46(10):4308-4319 (2007).

Tang, C.W. and VanSlyke, S.A., "Organic Electroluminescent Diodes," Appl. Phys. Lett., 51(12):913-915 (1987).

Tung, Yung-Liang et al., "Organic Light-Emitting Diodes Based on Charge-Neutral Ru II PHosphorescent Emitters," Adv. Mater., 17(8)1059-1064 (2005).

Van Slyke, S. A. et al., "Organic Electroluminescent Devices with Improved Stability," Appl. Phys. Lett., 69 (15):2160-2162 (1996).

Wang, Y. et al., "Highly Efficient Electroluminescent Materials Based on Fluorinated Organometallic Iridium Compounds," Appl. Phys. Lett., 79(4):449-451 (2001).

Wong, Keith Man-Chung et al., A Novel Class of Phosphorescent Gold(III) Alkynyl-Based Organic Light-Emitting Devices with Tunable Colour, Chem. Commun., 2906-2908 (2005).

Wong, Wai-Yeung, "Multifunctional Iridium Complexes Based on Carbazole Modules as Highly Efficient Electrophosphors," Angew. Chem. Int. Ed., 45:7800-7803 (2006).

\* cited by examiner

ORGANIC ELECTROLUMINESCENT MATERIALS AND DEVICES

This application claims priority under 35 U.S.C. § 119(e) to U.S. Provisional Application No. 63/105,845, filed on Oct. 26, 2020, and to U.S. Provisional Application No. 63/107,244, filed on Oct. 29, 2020, the entire contents of both applications are incorporated herein by reference.

FIELD

The present disclosure generally relates to organometallic compounds and formulations and their various uses including as emitters/hosts in devices such as organic light emitting diodes and related electronic devices.

BACKGROUND

Opto-electronic devices that make use of organic materials are becoming increasingly desirable for various reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting diodes/devices (OLEDs), organic phototransistors, organic photovoltaic cells, and organic photodetectors. For OLEDs, the organic materials may have performance advantages over conventional materials.

OLEDs make use of thin organic films that emit light when voltage is applied across the device. OLEDs are becoming an increasingly interesting technology for use in applications such as flat panel displays, illumination, and backlighting.

One application for phosphorescent emissive molecules is a full color display. Industry standards for such a display call for pixels adapted to emit particular colors, referred to as "saturated" colors. In particular, these standards call for saturated red, green, and blue pixels. Alternatively, the OLED can be designed to emit white light. In conventional liquid crystal displays emission from a white backlight is filtered using absorption filters to produce red, green and blue emission. The same technique can also be used with OLEDs. The white OLED can be either a single emissive layer (EML) device or a stack structure. Color may be measured using CIE coordinates, which are well known to the art.

SUMMARY

In one aspect, the present disclosure provides a compound comprising a structure of Formula I:

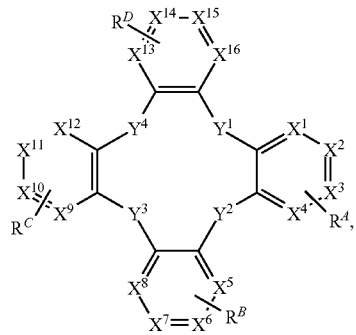

wherein $X^1$ to $X^{16}$ are each independently C or N; $Y^1$ to $Y^4$ are each independently selected from the group consisting of direct bond, NR, PR, O, S, Se, CRR', SiRR', GeRR', BR, and BRR'; at least two adjacent sites from $X^1$ to $X^{16}$ are both carbon and are fused to one of Formula II, Formula III or Formula IV as described herein; $R^A$, $R^B$, $R^C$, and $R^D$ each independently represent mono to the maximum allowable substitution, or no substitution; each R, R', $R^A$, $R^B$, $R^C$, $R^D$, and $R^E$ is independently a hydrogen or a substituent selected from the group consisting of the general substituents as described herein; and any two adjacent R, R', $R^A$, $R^B$, $R^C$, and $R^D$ may be joined or fused to form a ring.

In another aspect, the present disclosure provides a formulation of a compound comprising a structure of Formula I as described herein.

In yet another aspect, the present disclosure provides an OLED having an organic layer comprising a compound comprising a structure of Formula I as described herein.

In yet another aspect, the present disclosure provides a consumer product comprising an OLED with an organic layer comprising a compound comprising a structure of Formula I as described herein.

DETAILED DESCRIPTION

A. Terminology

Figure 1:
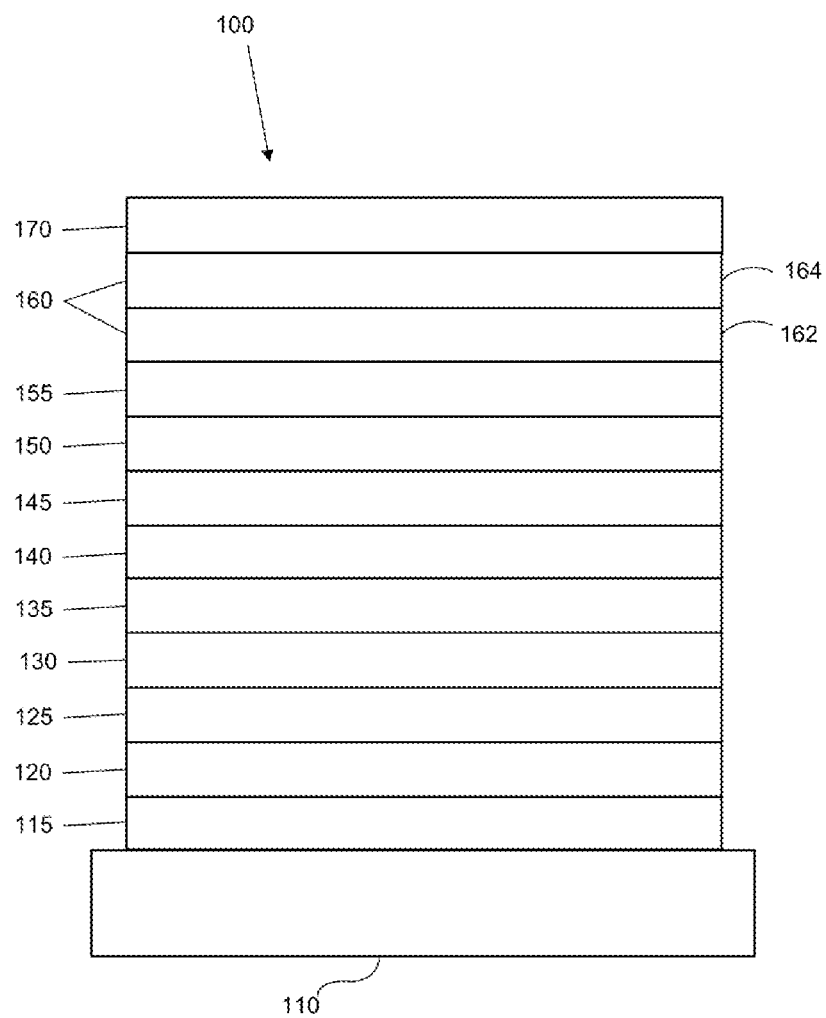
FIG. 1 shows an organic light emitting device.

Unless otherwise specified, the below terms used herein are defined as follows:

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processable" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

The terms "halo," "halogen," and "halide" are used interchangeably and refer to fluorine, chlorine, bromine, and iodine.

The term "acyl" refers to a substituted carbonyl radical (C(O)—$R_s$).

The term "ester" refers to a substituted oxycarbonyl (—O—C(O)—$R_s$ or —C(O)—O—$R_s$) radical.

The term "ether" refers to an —O$R_s$ radical.

The terms "sulfanyl" or "thio-ether" are used interchangeably and refer to a —S$R_s$ radical.

The term "selenyl" refers to a —Se$R_s$ radical.

The term "sulfinyl" refers to a —S(O)—$R_s$ radical.

The term "sulfonyl" refers to a —SO$_2$—$R_s$ radical.

The term "phosphino" refers to a —P($R_s$)$_3$ radical, wherein each $R_s$ can be same or different.

The term "silyl" refers to a —Si($R_s$)$_3$ radical, wherein each $R_s$ can be same or different.

The term "germyl" refers to a —Ge($R_s$)$_3$ radical, wherein each $R_s$ can be same or different.

The term "boryl" refers to a —B($R_s$)$_2$ radical or its Lewis adduct —B($R_s$)$_3$ radical, wherein $R_s$ can be same or different.

In each of the above, $R_s$ can be hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, and combination thereof. Preferred $R_s$ is selected from the group consisting of alkyl, cycloalkyl, aryl, heteroaryl, and combination thereof.

The term "alkyl" refers to and includes both straight and branched chain alkyl radicals. Preferred alkyl groups are those containing from one to fifteen carbon atoms and includes methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, and the like. Additionally, the alkyl group may be optionally substituted.

The term "cycloalkyl" refers to and includes monocyclic, polycyclic, and spiro alkyl radicals. Preferred cycloalkyl groups are those containing 3 to 12 ring carbon atoms and includes cyclopropyl, cyclopentyl, cyclohexyl, bicyclo[3.1.1]heptyl, spiro[4.5]decyl, spiro[5.5]undecyl, adamantyl, and the like. Additionally, the cycloalkyl group may be optionally substituted.

The terms "heteroalkyl" or "heterocycloalkyl" refer to an alkyl or a cycloalkyl radical, respectively, having at least one carbon atom replaced by a heteroatom. Optionally the at least one heteroatom is selected from O, S, N, P, B, Si and Se, preferably, O, S or N. Additionally, the heteroalkyl or heterocycloalkyl group may be optionally substituted.

The term "alkenyl" refers to and includes both straight and branched chain alkene radicals. Alkenyl groups are essentially alkyl groups that include at least one carbon-carbon double bond in the alkyl chain. Cycloalkenyl groups are essentially cycloalkyl groups that include at least one carbon-carbon double bond in the cycloalkyl ring. The term "heteroalkenyl" as used herein refers to an alkenyl radical having at least one carbon atom replaced by a heteroatom. Optionally the at least one heteroatom is selected from O, S, N, P, B, Si, and Se, preferably, O, S, or N. Preferred alkenyl, cycloalkenyl, or heteroalkenyl groups are those containing two to fifteen carbon atoms. Additionally, the alkenyl, cycloalkenyl, or heteroalkenyl group may be optionally substituted.

The term "alkynyl" refers to and includes both straight and branched chain alkyne radicals. Alkynyl groups are essentially alkyl groups that include at least one carbon-carbon triple bond in the alkyl chain. Preferred alkynyl groups are those containing two to fifteen carbon atoms. Additionally, the alkynyl group may be optionally substituted.

The terms "aralkyl" or "arylalkyl" are used interchangeably and refer to an alkyl group that is substituted with an aryl group. Additionally, the aralkyl group may be optionally substituted.

The term "heterocyclic group" refers to and includes aromatic and non-aromatic cyclic radicals containing at least one heteroatom. Optionally the at least one heteroatom is selected from O, S, N, P, B, Si, and Se, preferably, O, S, or N. Hetero-aromatic cyclic radicals may be used interchangeably with heteroaryl. Preferred hetero-non-aromatic cyclic groups are those containing 3 to 7 ring atoms which includes at least one hetero atom, and includes cyclic amines such as morpholino, piperidino, pyrrolidino, and the like, and cyclic ethers/thio-ethers, such as tetrahydrofuran, tetrahydropyran, tetrahydrothiophene, and the like. Additionally, the heterocyclic group may be optionally substituted.

The term "aryl" refers to and includes both single-ring aromatic hydrocarbyl groups and polycyclic aromatic ring systems. The polycyclic rings may have two or more rings in which two carbons are common to two adjoining rings (the rings are "fused") wherein at least one of the rings is an aromatic hydrocarbyl group, e.g., the other rings can be cycloalkyls, cycloalkenyls, aryl, heterocycles, and/or heteroaryls. Preferred aryl groups are those containing six to thirty carbon atoms, preferably six to twenty carbon atoms, more preferably six to twelve carbon atoms. Especially preferred is an aryl group having six carbons, ten carbons or twelve carbons. Suitable aryl groups include phenyl, biphenyl, triphenyl, triphenylene, tetraphenylene, naphthalene, anthracene, phenalene, phenanthrene, fluorene, pyrene, chrysene, perylene, and azulene, preferably phenyl, biphenyl, triphenyl, triphenylene, fluorene, and naphthalene. Additionally, the aryl group may be optionally substituted.

The term "heteroaryl" refers to and includes both single-ring aromatic groups and polycyclic aromatic ring systems that include at least one heteroatom. The heteroatoms include, but are not limited to O, S, N, P, B, Si, and Se. In many instances, O, S, or N are the preferred heteroatoms. Hetero-single ring aromatic systems are preferably single rings with 5 or 6 ring atoms, and the ring can have from one to six heteroatoms. The hetero-polycyclic ring systems can have two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. The hetero-polycyclic aromatic ring systems can have from one to six heteroatoms per ring of the polycyclic aromatic ring system. Preferred heteroaryl groups are those containing three to thirty carbon atoms, preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group may be optionally substituted.

Of the aryl and heteroaryl groups listed above, the groups of triphenylene, naphthalene, anthracene, dibenzothiophene, dibenzofuran, dibenzoselenophene, carbazole, indolocarbazole, imidazole, pyridine, pyrazine, pyrimidine, triazine, and benzimidazole, and the respective aza-analogs of each thereof are of particular interest.

The terms alkyl, cycloalkyl, heteroalkyl, heterocycloalkyl, alkenyl, cycloalkenyl, heteroalkenyl, alkynyl, aralkyl, heterocyclic group, aryl, and heteroaryl, as used herein, are independently unsubstituted, or independently substituted, with one or more general substituents.

In many instances, the general substituents are selected from the group consisting of deuterium, halogen, alkyl, cycloalkyl, heteroalkyl, heterocycloalkyl, arylalkyl, alkoxy, aryloxy, amino, silyl, germyl, boryl, selenyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof.

In some instances, the preferred general substituents are selected from the group consisting of deuterium, fluorine, alkyl, cycloalkyl, heteroalkyl, alkoxy, aryloxy, amino, silyl, boryl, alkenyl, cycloalkenyl, heteroalkenyl, aryl, heteroaryl, nitrile, isonitrile, sulfanyl, and combinations thereof.

In some instances, the preferred general substituents are selected from the group consisting of deuterium, fluorine, alkyl, cycloalkyl, alkoxy, aryloxy, amino, silyl, boryl, aryl, heteroaryl, sulfanyl, and combinations thereof.

In yet other instances, the more preferred general substituents are selected from the group consisting of deuterium, fluorine, alkyl, cycloalkyl, aryl, heteroaryl, and combinations thereof.

The terms "substituted" and "substitution" refer to a substituent other than H that is bonded to the relevant position, e.g., a carbon or nitrogen. For example, when $R^1$ represents mono-substitution, then one $R^1$ must be other than H (i.e., a substitution). Similarly, when $R^1$ represents di-substitution, then two of $R^1$ must be other than H. Similarly, when $R^1$ represents zero or no substitution, $R^1$, for example, can be a hydrogen for available valencies of ring atoms, as in carbon atoms for benzene and the nitrogen atom in pyrrole, or simply represents nothing for ring atoms with fully filled valencies, e.g., the nitrogen atom in pyridine. The maximum number of substitutions possible in a ring structure will depend on the total number of available valencies in the ring atoms.

As used herein, "combinations thereof" indicates that one or more members of the applicable list are combined to form a known or chemically stable arrangement that one of ordinary skill in the art can envision from the applicable list. For example, an alkyl and deuterium can be combined to form a partial or fully deuterated alkyl group; a halogen and alkyl can be combined to form a halogenated alkyl substituent; and a halogen, alkyl, and aryl can be combined to form a halogenated arylalkyl. In one instance, the term substitution includes a combination of two to four of the listed groups. In another instance, the term substitution includes a combination of two to three groups. In yet another instance, the term substitution includes a combination of two groups. Preferred combinations of substituent groups are those that contain up to fifty atoms that are not hydrogen or deuterium, or those which include up to forty atoms that are not hydrogen or deuterium, or those that include up to thirty atoms that are not hydrogen or deuterium. In many instances, a preferred combination of substituent groups will include up to twenty atoms that are not hydrogen or deuterium.

The "aza" designation in the fragments described herein, i.e. aza-dibenzofuran, aza-dibenzothiophene, etc. means that one or more of the C—H groups in the respective aromatic ring can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

As used herein, "deuterium" refers to an isotope of hydrogen. Deuterated compounds can be readily prepared using methods known in the art. For example, U.S. Pat. No. 8,557,400, Patent Pub. No. WO 2006/095951, and U.S. Pat. Application Pub. No. US 2011/0037057, which are hereby incorporated by reference in their entireties, describe the making of deuterium-substituted organometallic complexes. Further reference is made to Ming Yan, et al., *Tetrahedron* 2015, 71, 1425-30 and Atzrodt et al., *Angew. Chem. Int. Ed. (Reviews)* 2007, 46, 7744-65, which are incorporated by reference in their entireties, describe the deuteration of the methylene hydrogens in benzyl amines and efficient pathways to replace aromatic ring hydrogens with deuterium, respectively.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

In some instance, a pair of adjacent substituents can be optionally joined or fused into a ring. The preferred ring is a five, six, or seven-membered carbocyclic or heterocyclic ring, includes both instances where the portion of the ring formed by the pair of substituents is saturated and where the portion of the ring formed by the pair of substituents is unsaturated. As used herein, "adjacent" means that the two substituents involved can be on the same ring next to each other, or on two neighboring rings having the two closest available substitutable positions, such as 2, 2' positions in a biphenyl, or 1, 8 position in a naphthalene, as long as they can form a stable fused ring system.

B. The Compounds of the Present Disclosure

In one aspect, the present disclosure provides a compound comprising a structure of Formula I:

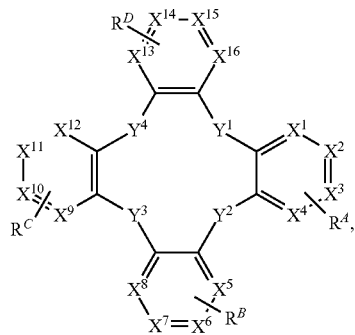

wherein:
$X^1$ to $X^{16}$ are each independently C or N;
$Y^1$ to $Y^4$ are each independently selected from the group consisting of direct bond, NR, PR, O, S, Se, CRR', SiRR', GeRR', BR, and BRR';
at least two adjacent sites from $X^1$ to $X^{16}$ are both carbon and are fused to one of Formula II, Formula III or Formula IV:

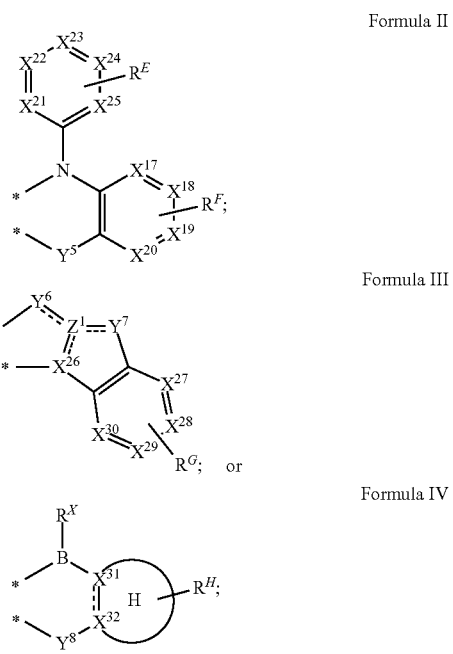

wherein:
indicates the attachment point for each structure;
$Y^5$ and $Y^8$ are each independently selected from the group consisting of direct bond, NR, PR, O, S, Se, CRR', SiRR', GeRR', BR, and BRR';
$Y^6$ and $Y^7$ are each independently selected from the group consisting of N, NR, PR, O, S, Se, CR, CRR', SiRR', GeRR', BR, and BRR';
$Z^1$ is C;
===== is a single or double bond;
$X^{17}$ to $X^{32}$ are each independently C or N;
if $X^{21}$ to $X^{25}$ are all C, then at least one of $R^E$ is comprises a boron atom;
Ring H is a 5 membered or 6 membered carbocyclic or heterocyclic ring;
$R^A$, $R^B$, $R^C$, $R^D$, $R^E$, $R^F$, $R^G$, and $R^H$ each independently represent mono to the maximum allowable substitution, or no substitution;
each R, R', $R^A$, $R^B$, $R^C$, $R^D$, $R^E$, $R^F$, $R^G$, $R^H$, and $R^X$ is independently a hydrogen or a substituent selected from the group consisting of deuterium, halogen, alkyl, cycloalkyl, heteroalkyl, heterocycloalkyl, arylalkyl, alkoxy, aryloxy, amino, silyl, germyl, boryl, selenyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof; and
any two adjacent R, R', $R^A$, $R^B$, $R^C$, $R^D$, $R^E$, $R^F$, $R^G$, $R^H$, and $R^X$ may be joined or fused to form a ring.

In some embodiments, each R, R', $R^A$, $R^B$, $R^C$, $R^D$, $R^E$, $R^F$, $R^G$, $R^H$, and $R^X$ can be independently a hydrogen or a substituent selected from the group consisting of deuterium, fluorine, alkyl, cycloalkyl, heteroalkyl, alkoxy, aryloxy, amino, silyl, boryl, alkenyl, cycloalkenyl, heteroalkenyl, aryl, heteroaryl, nitrile, isonitrile, sulfanyl, and combinations thereof.

In some embodiments, at least two adjacent sites from $X^1$ to $X^{16}$ can be both carbon and are fused to Formula II. In some embodiments, $X^1$ and $X^2$ are both C, and are fused to Formula II. In some embodiments, $X^2$ and $X^3$ are both C, and are fused to Formula II. In some embodiments, a second Formula II can also be fused to the compound. In some embodiments, the second Formula II can be fused to Formula I through $X^5$ and $X^6$ when both are C. In some embodiments, the second Formula II can be fused to Formula I through $X^6$ and $X^7$ when both are C. In some embodiments, the second Formula II can be fused to Formula I through $X^9$ and $X^{10}$ when both are C. In some embodiments, the second Formula II can be fused to Formula I through $X^{10}$ and $X^{11}$ when both are C. In some embodiments, Formula III can also be fused to the compound in addition to Formula II. In some embodiments, Formula IV can also be fused to the compound in addition to Formula II.

In some embodiments, at least two adjacent sites from $X^1$ to $X^{16}$ can be both carbon and are fused to Formula III. In some embodiments, $X^1$ and $X^2$ are both C, and are fused to Formula III. In some embodiments, $X^2$ and $X^3$ are both C, and are fused to Formula III. In some embodiments, a second Formula III can also be fused to the compound. In some embodiments, Formula II can also be fused to the compound in addition to Formula III. In some embodiments, Formula IV can also be fused to the compound in addition to Formula III.

In some embodiments, at least two adjacent sites from $X^1$ to $X^{16}$ can be both carbon and are fused to Formula IV. In some embodiments, $X^1$ and $X^2$ are both C, and are fused to Formula IV. In some embodiments, $X^2$ and $X^3$ are both C, and are fused to Formula IV. In some embodiments, a second Formula IV can also be fused to the compound. In some embodiments, the second Formula IV can be fused to Formula I through $X^5$ and $X^6$ when both are C. In some embodiments, the second Formula IV can be fused to Formula I through $X^6$ and $X^7$ when both are C. In some embodiments, the second Formula IV can be fused to Formula I through $X^9$ and $X^{10}$ when both are C. In some embodiments, the second Formula IV can be fused to Formula I through $X^{10}$ and $X^{11}$ when both are C. In some embodiments, Formula II can also be fused to the compound in addition to Formula IV. In some embodiments, Formula III can also be fused to the compound in addition to Formula IV.

It should be understood that $X^1$ and $X^{16}$ are also considered to be adjacent for Formula I. Likewise, $X^4$ and $X^5$, $X^8$ and $X^9$, and $X^{12}$ and $X^{13}$ are also considered to be adjacent. Consequently, each of these pairs can be independently fused to Formula II, Formula III, and/or Formula IV.

In some embodiments when Formula II are attached to Formula I, at least one of $X^{21}$ to $X^{25}$ can be N. In some embodiments, at least one of $X^{21}$, $X^{23}$, and $X^{25}$ can be N. In some embodiments, at least two of $X^{21}$ to $X^{25}$ can be N. In some embodiments, at least two of $X^{21}$, $X^{23}$, and $X^{25}$ can be N. In some embodiments, $X^{21}$, $X^{23}$, and $X^{25}$ can be each independently N. In some embodiments, at least one of $R^E$ can comprise a carbazole. In some embodiments, at least one of $R^E$ can comprise a silane. In some embodiments, $X^{17}$-$X^{20}$ can be each independently C. In some embodiments, one of $X^{17}$-$X^{20}$ can be N.

In some embodiments when Formula II are attached to Formula I, $X^{21}$ to $X^{25}$ are each independently C, at least one of $R^E$ can comprise a boron atom. In some embodiments, $X^{21}$ to $X^{25}$ are each independently C, at least one of $R^E$ can comprise a BRR'. In some embodiments, $X^{21}$ to $X^{25}$ are each independently C, exactly one of $R^E$ can comprise a boron atom. In some embodiments, $X^{21}$ to $X^{25}$ are each independently C, exactly one of $R^E$ can comprise a BRR'.

In some embodiments when Formula III are attached to Formula I, $X^{26}$ and $Y^7$ can be both N, the bond from $Z^1$ to $Y^7$ is a double bond, and the bond from $Z^1$ to $Y^6$ is a single bond. In some embodiments, $X^{26}$ and $Y^6$ can be both N and the bond from $Z^1$ to $Y^6$ is a double bond, and the bond from $Z^1$ to $Y^7$ is a single bond. In some embodiments, $X^{27}$-$X^{30}$ can be each independently C. In some embodiments, one of $X^{27}$-$X^{30}$ can be N. In some embodiments, exactly one of $X^{27}$-$X^{30}$ can be N.

In some embodiments when Formula IV are attached to Formula I, ring H can comprise a 5-membered ring. In some embodiments, ring H can comprise a 6-membered ring. In some embodiments, ring H can comprise an aromatic ring. In some embodiments, ring H can be selected from the group consisting of benzene, pyridine, pyrimidine, pyridazine, pyrazine, triazine, imidazole, pyrazole, pyrrole, oxazole, furan, thiophene, and thiazole. In some embodiments, two $R^H$ can be joined to form a ring fused to ring H. In some embodiments, two $R^H$ can be joined to form a 5-membered or 6-membered aromatic ring fused to ring H. In some embodiments, $R^X$ and $R^H$ can be joined to form a ring. In some embodiments, $R^X$ can be joined with one of $R^A$, $R^B$, $R^C$, or $R^D$ to form a ring.

In some embodiments, $Y^1$ to $Y^4$ can be each independently a direct bond. In some embodiments, at least one of $Y^1$ to $Y^4$ can be selected from the group consisting of NR, O, S, SiRR, and BR. In some embodiments, exactly one of $Y^1$ to $Y^4$ can be selected from the group consisting of NR, O, S, SiRR, and BR, and the remaining ones are each direct bonds. In some embodiments, two of $Y^1$ to $Y^4$ can be selected from the group consisting of NR, O, S, SiRR, and BR. In some embodiments, exactly two of $Y^1$ to $Y^4$ can be selected from the group consisting of NR, O, S, SiRR, and BR, and the remaining ones are each direct bonds. In some embodiments, at least one of $Y^1$ to $Y^4$ can be NR. In some embodiments, exactly one of $Y^1$ to $Y^4$ can be NR, and the remaining ones are each direct bonds. In some embodiments, two of $Y^1$ to $Y^4$ can be NR. In some embodiments, exactly two of $Y^1$ to $Y^4$ can be NR, and the remaining ones are each direct bonds. In some embodiments, at least one of $Y^1$ to $Y^4$ can be O. In some embodiments, exactly one of $Y^1$ to $Y^4$ can be O, and the remaining ones are each direct bonds. In some embodiments, two of $Y^1$ to $Y^4$ can be O. In some embodiments, exactly two of $Y^1$ to $Y^4$ can be O, and the remaining ones are each direct bonds.

In some embodiments, $X^1$-$X^{16}$ can be each independently C. In some embodiments, exactly one of $X^1$-$X^{16}$ can be N. In some embodiments, at least one of $X^1$-$X^{16}$ can be N. In some embodiments, two of $X^1$-$X^{16}$ can be N. In some embodiments, one of $X^1$-$X^4$ can be N, and one of $X^5$-$X^8$ can be N. In some embodiments, one of $X^1$-$X^4$ can be N, and one of $X^9$-$X^1$ can be N. In some embodiments, two of $X^1$-$X^4$ can be N.

In some embodiments, the compound may comprise only one structure of Formula I, meaning the compound having just one core structure of Formula I. In these embodiments, one or more of Formula II may be fused to Formula I. In these embodiments, one or more of Formula III may be fused to Formula I. In these embodiments, one or more of Formula IV may be fused to Formula I. It should also be understood that additional Formula II, Formula III or Formula IV can be further fused to a structure of Formula I already fused with Formula II, Formula III, or Formula IV.

In some embodiments, the compound may comprise two structures of Formula I, meaning the compound having two core structures of Formula I. In these embodiments, one or more of Formula II may be fused to the same core structure or to the different core structures. In these embodiments, one or more of Formula III may be fused to the same core structure or to the different core structures. In these embodiments, one or more of Formula IV may be fused to the same core structure or to the different core structures. It should also be understood that additional Formula II, Formula III or Formula IV can be further fused to the two core structures of Formula I already fused with Formula II, Formula III, or Formula IV.

In some embodiments, the compound can be selected from the group consisting of:

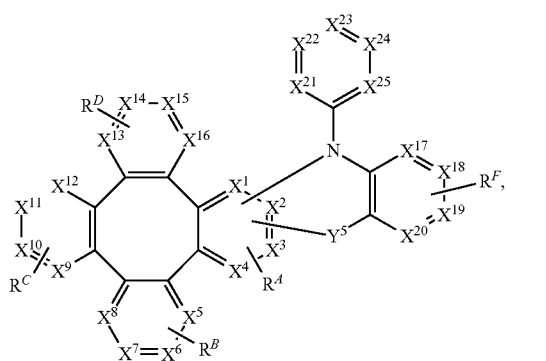

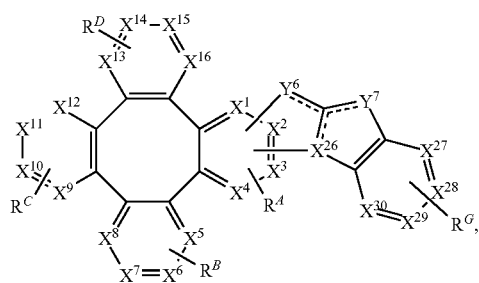

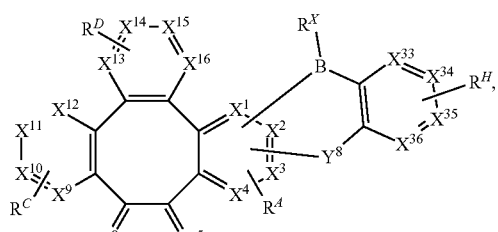

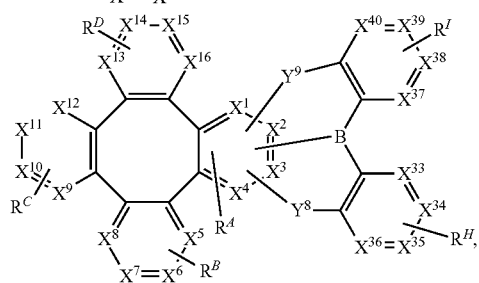

-continued

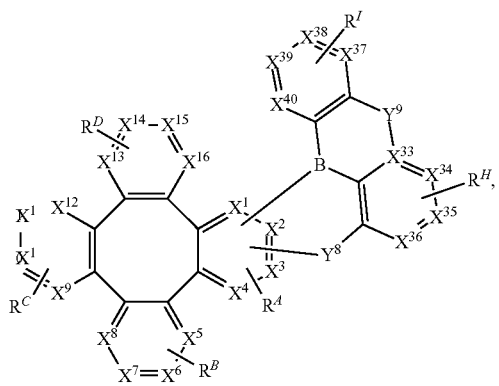

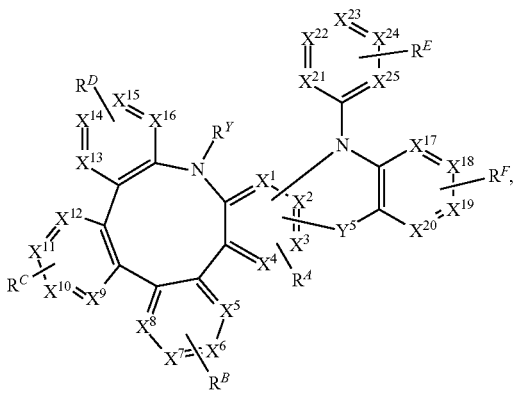

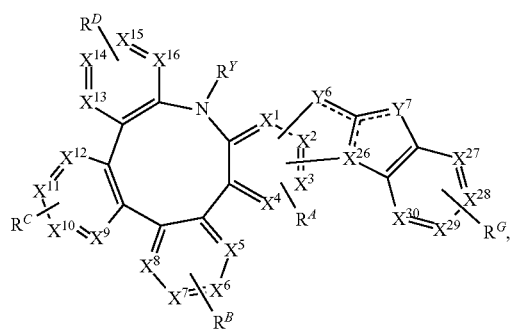

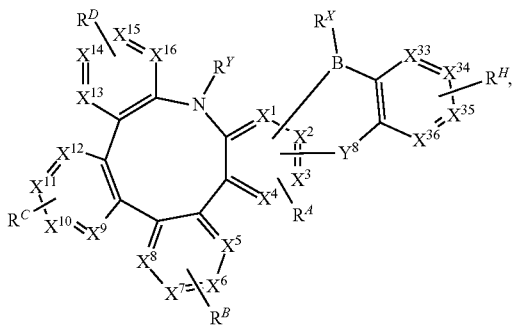

-continued
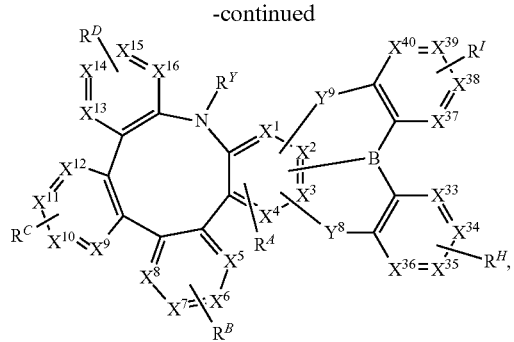
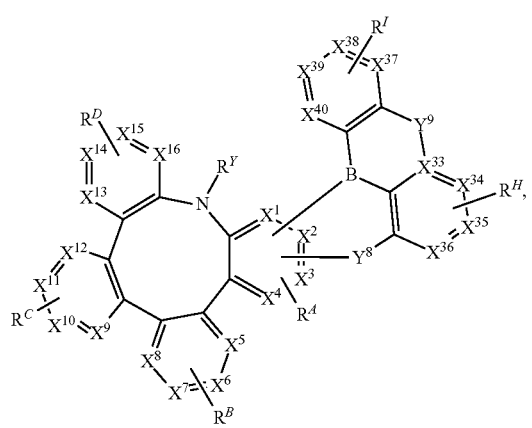
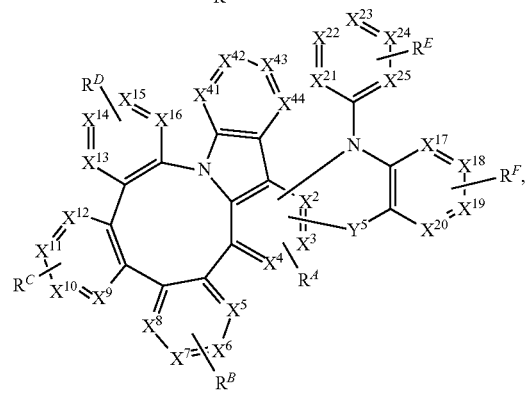
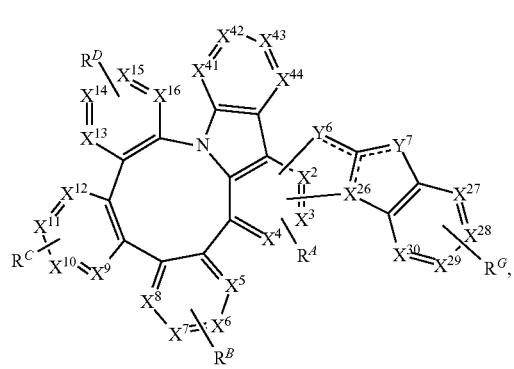
-continued
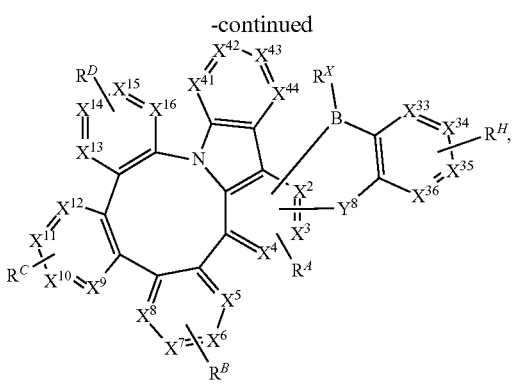
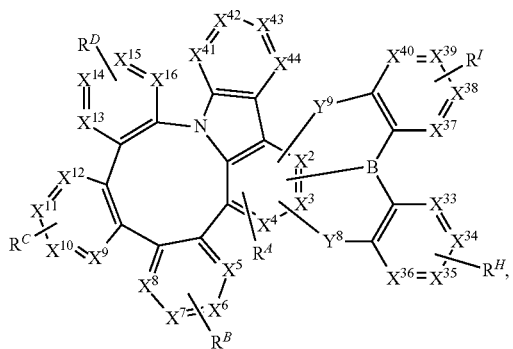
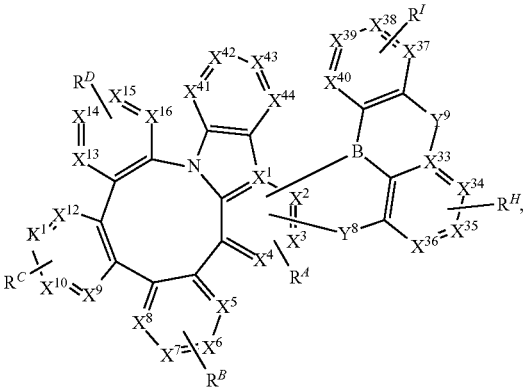
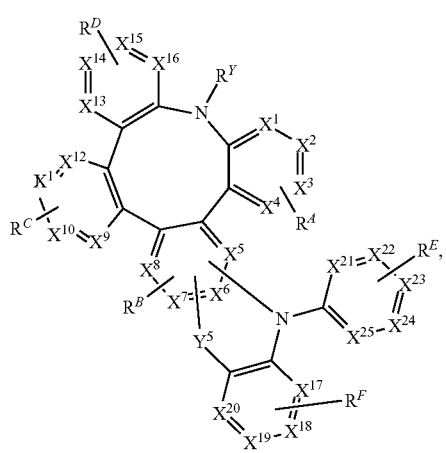

-continued

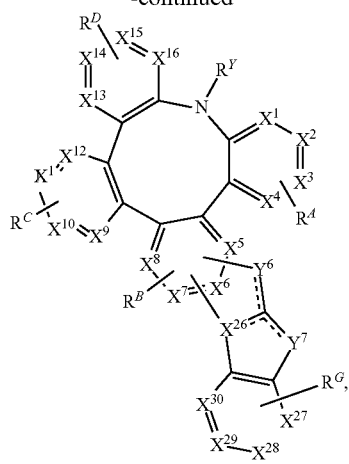

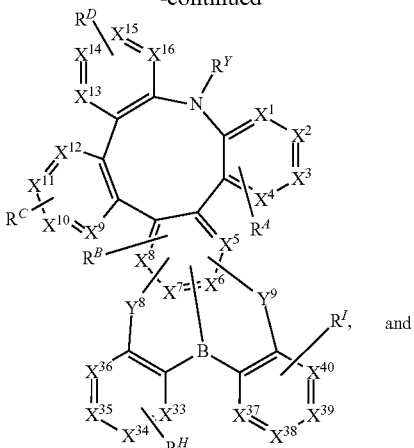

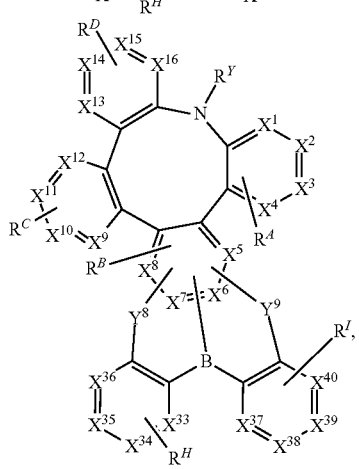

wherein $X^3$ to $X^{43}$ are each independently C or N;
$Y^9$ is selected from the group consisting of direct bond, NR, PR, O, S, Se, CRR', SiRR', GeRR', BR, BRR':
$R^I$ has the same definition as $R^A$ to $R^H$; and
$R^Y$ has the same definition as $R^X$.

In some embodiments, the compound can be selected from the group consisting of

| Compound | Structure of compound |
| --- | --- |
| Compound-1-(Rm)(Rn)(Ro), wherein Compound-1-(R1)(R1)(R1) to Compound-1-(R23)(R84)(R84) having the structure |  |

| Compound | Structure of compound |
|---|---|
| Compound-2-(Rm)(Rn)(Ro), wherein Compound-2-(R1)(R1)(R1) to Compound-2-(R23)(R84)(R84) having the structure | |
| Compound-3-(Rm)(Rn)(Ro), wherein Compound-3-(R1)(R1)(R1) to Compound-3-(R23)(R84)(R84) having the structure | |
| Compound-4-(Rn)(Ro)(Rp), wherein Compound-4-(R1)(R1)(R1) to Compound-4-(R84)(R84)(R71) having the structure | |
| Compound-5-(Rn)(Ro)(Rp), wherein Compound-5-(R1)(R1)(R1) to Compound-5-(R84)(R84)(R71) having the structure | |

| Compound | Structure of compound |
|---|---|
| Compound-6-(Rn)(Ro)(Rp), wherein Compound-6-(R1)(R1)(R1) to Compound-6-(R84)(R84)(R71) having the structure | |
| Compound-7-(Rn)(Ro)(Rp), wherein Compound-7-(R1)(R1)(R1) to Compound-7-(R84)(R84)(R71) having the structure | |
| Compound-8-(Rn)(Ro)(Rp), wherein Compound-8-(R1)(R1)(R1) to Compound-8-(R84)(R84)(R71) having the structure | |
| Compound-9-(Rn)(Ro)(Rp), wherein Compound-9-(R1)(R1)(R1) to Compound-9-(R84)(R84)(R71) having the structure | |

| Compound | Structure of compound |
|---|---|
| Compound-10-(Rn)(Ro)(Rp)(Yq), wherein Compound-10-(R1)(R1)(R1)(Y1) to Compound-10-(R84)(R84)(R71)(Y76) having the structure | 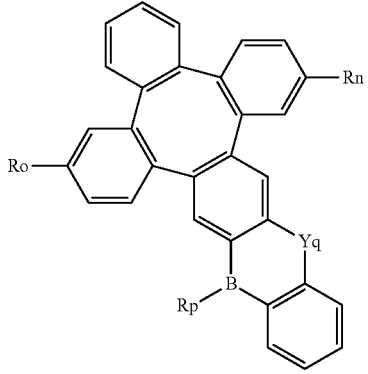 |
| Compound-11-(Rn)(Ro)(Rp)(Yq), wherein Compound-11-(R1)(R1)(R1)(Y1) to Compound-11-(R84)(R84)(R71)(Y76) having the structure | 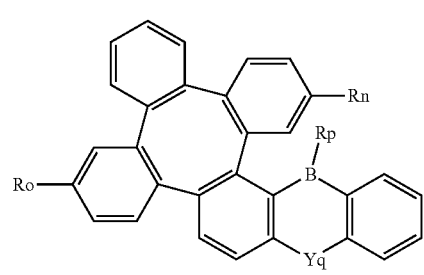 |
| Compound-12-(Rn)(Rp)(Yq), wherein Compound-12-(R1)(R1)(Y1) to Compound-12-(R84)(R71)(Y76) having the structure | 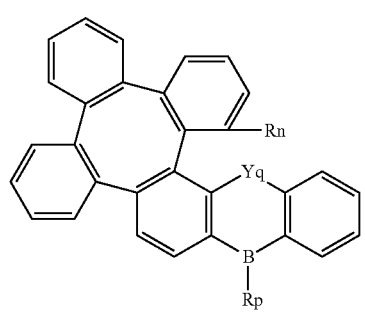 |
| Compound-13-(Rn)(Yq)(Yr), wherein Compound-13-(R1)(Y1)(Y1) to Compound-13-(R84)(Y76)(Y76) having the structure | 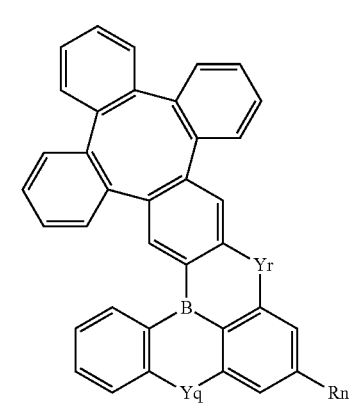 |

-continued

| Compound | Structure of compound |
|---|---|
| Compound-14-(Rn)(Yq)(Yr), wherein Compound-14-(R1)(Y1)(Y1) to Compound-14-(R84)(Y76)(Y76) having the structure | |
| Compound-15-(Rn)(Ro)(Yq)(Yr), wherein Compound-15-(R1)(R1)(Y1)(Y1) to Compound-15-(R84)(R84)(Y76)(Y76) having the structure | |
| Compound-16-(Yq)(Yr)(Ys)(Yt), wherein Compound-16-(Y1)(Y1)(Y1)(Y1) to Compound-16-(Y76)(Y76)(Y76)(Y76) having the structure | |
| Compound-17-(Yq)(Yr)(Ys)(Yt), wherein Compound-17-(Y1)(Y1)(Y1)(Y1) to Compound-17-(Y76)(Y76)(Y76)(Y76) having the structure | |

| Compound | Structure of compound |
|---|---|
| Compound-18-(Rn)(Ro)(Yq)(Yr), wherein Compound-18-(R1)(R1)(Y1)(Y1) to Compound-18-(R84)(R84)(Y76)(Y76) having the structure | 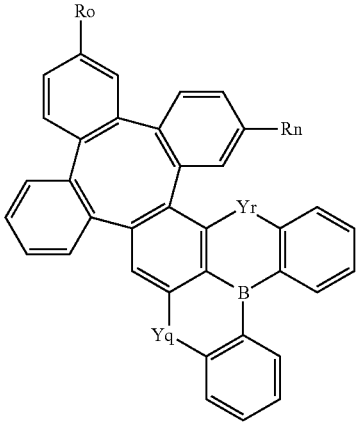 |
| Compound-19-(Rn)(Ro), wherein Compound-19-(R1)(R1) to Compound-19-(R84)(R84) having the structure | 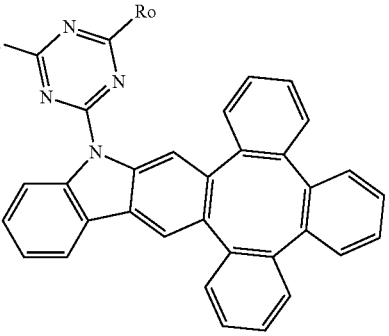 |
| Compound-20-(Rn)(Ro), wherein Compound-20-(R1)(R1) to Compound-20-(R84)(R84) having the structure | 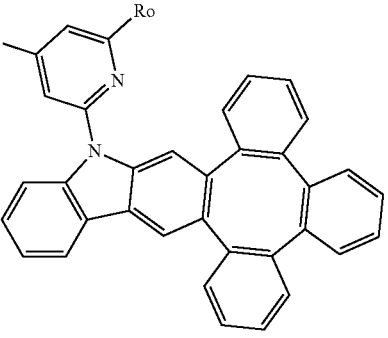 |
| Compound-21-(Rn)(Ro), wherein Compound-21-(R1)(R1) to Compound-21-(R84)(R84) having the structure | 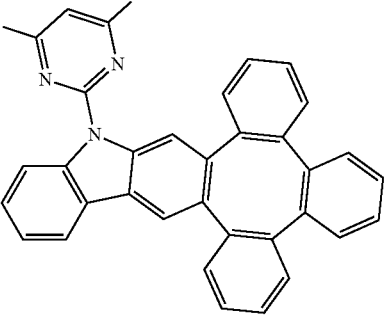 |

| Compound | Structure of compound |
|---|---|
| Compound-22-(Rn)(Ro), wherein Compound-22-(R1)(R1) to Compound-22-(R84)(R84) having the structure | 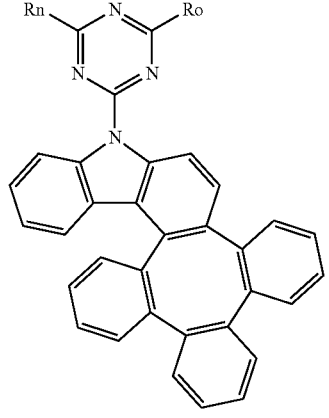 |
| Compound-23-(Rn)(Ro), wherein Compound-23-(R1)(R1) to Compound-23-(R84)(R84) having the structure | 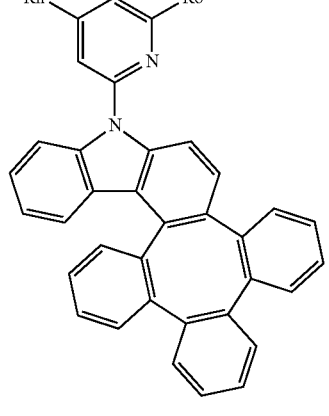 |
| Compound-24-(Rn)(Ro), wherein Compound-24-(R1)(R1) to Compound-24-(R84)(R84) having the structure | 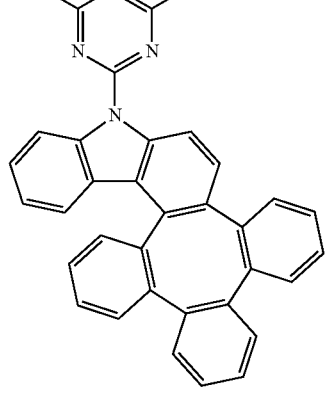 |
| Compound-25-(Rn), wherein Compound-25-(R1) to Compound-25-(R84) having the structure | 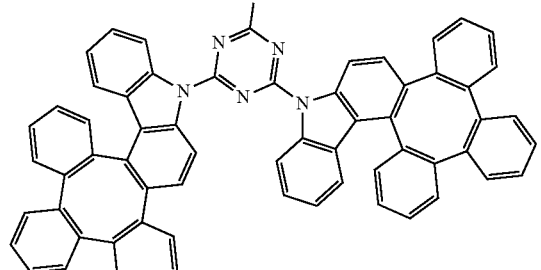 |

-continued

| Compound | Structure of compound |
|---|---|
| Compound-26-(Rn), wherein Compound-26-(R1) to Compound-26-(R84) having the structure | |
| Compound-27-(Rm)(Rn)(Ro), wherein Compound-27-(R1)(R1)(R1) to Compound-27-(R23)(R84)(R84) having the structure | |
| Compound-28-(Rm)(Rn)(Ro), wherein Compound-28-(R1)(R1)(R1) to Compound-28-(R23)(R84)(R84) having the structure | |
| Compound-29-(Rm)(Rn)(Ro), wherein Compound-29-(R1)(R1)(R1) to Compound-29-(R23)(R84)(R84) having the structure | |

-continued

| Compound | Structure of compound |
|---|---|
| Compound-30-(Rm)(Rn)(Ro), wherein Compound-30-(R1)(R1)(R1) to Compound-30-(R23)(R84)(R84) having the structure | |
| Compound-31-(Rn)(Ro)(Rp), wherein Compound-31-(R1)(R1)(R1) to Compound-31-(R84)(R84)(R71) having the structure | |
| Compound-32-(Rn)(Ro)(Rp), wherein Compound-32-(R1)(R1)(R1) to Compound-32-(R84)(R84)(R71) having the structure | |

| Compound | Structure of compound |
|---|---|
| Compound-33-(Rn)(Ro)(Rp), wherein Compound-33-(R1)(R1)(R1) to Compound-33-(R84)(R84)(R71) having the structure | |
| Compound-34-(Rn)(Ro)(Rp), wherein Compound-34-(R1)(R1)(R1) to Compound-34-(R84)(R84)(R71) having the structure | |
| Compound-35-(Rn)(Rp)(Yq), wherein Compound-35-(R1)(R1)(Y1) to Compound-35-(R84)(R71)(Y76) having the structure | |

| Compound | Structure of compound |
|---|---|
| Compound-36-(Rn)(Rp)(Yq), wherein Compound-36-(R1)(R1)(Y1) to Compound-36-(R84)(R71)(Y76) having the structure | 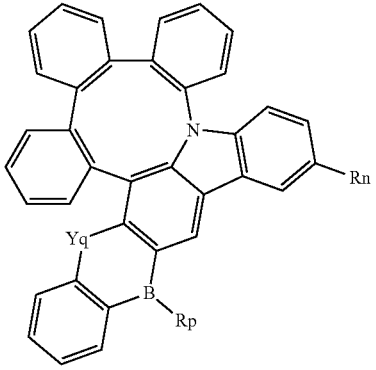 |
| Compound-37-(Rp)(Rp)(Yq), wherein Compound-37-(R1)(R1)(Y1) to Compound-37-(R84)(R71)(Y76) having the structure | 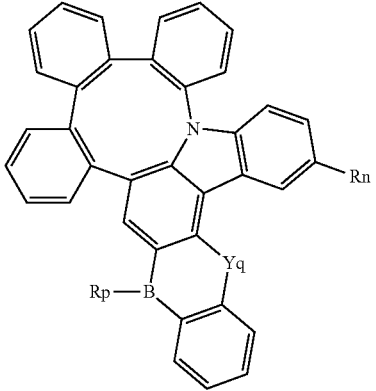 |
| Compound-38-(Rn)(Rp)(Yq), wherein Compound-38-(R1)(R1)(Y1) to Compound-38-(R84)(R71)(Y76) having the structure | 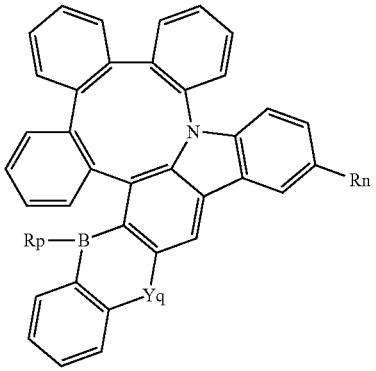 |
| Compound-39-(Rn)(Yq)(Yr), wherein Compound-39-(R1)(Y1)(Y1) to Compound-39-(R84)(Y76)(Y76) having the structure | 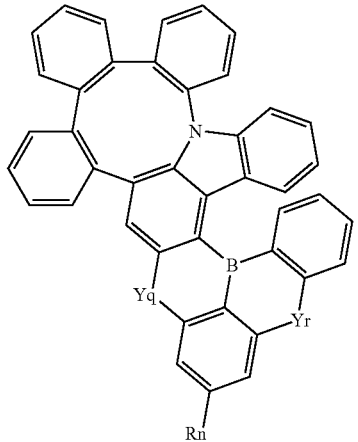 |

| Compound | Structure of compound |
|---|---|
| Compound-40-(Rn)(Yq)(Yr), wherein Compound-40-(R1)(Y1)(Y1) to Compound-40-(R84)(Y76)(Y76) having the structure | |
| Compound-41-(Rn)(Yq)(Yr), wherein Compound-41-(R1)(Y1)(Y1) to Compound-41-(R84)(Y76)(Y76) having the structure | |
| Compound-42-(Rn)(Yq)(Yr), wherein Compound-42-(R1)(Y1)(Y1) to Compound-42-(R84)(Y76)(Y76) having the structure | |

-continued

| Compound | Structure of compound |
|---|---|
| Compound-43-(Rn)(Yq)(Yr), wherein Compound-43-(R1)(Y1)(Y1) to Compound-43-(R84)(Y76)(Y76) having the structure | (structure shown) | wherein m is an integer from 1 to 15, n and o are each independently an integer from 1 to 84, p is an integer from 1 to 71, and q, r, s, and t are each independently an integer from 1 to 76;

wherein Y1 to Y71 are NR1 to NR71, respectively, Y72 is O, Y73 is S, Y74 is Se, Y75 is $CMe_2$, and Y76 is $SiPh_2$; and wherein R1 to R84 are defined as

| | Structure |
|---|---|
| R1 | 4,6-diphenylpyridin-2-yl |
| R2 | 2,6-diphenylpyridin-4-yl |
| R3 | 4,6-diphenylpyrimidin-2-yl |
| R4 | 2,6-diphenylpyrimidin-4-yl |

-continued

| | Structure |
|---|---|
| R5 | 4,6-diphenyl-1,3,5-triazin-2-yl |
| R6 | 9-(4-phenylpyridin-2-yl)-9H-carbazole |
| R7 | 9-(6-phenylpyridin-2-yl)-9H-carbazole |
| R8 | 9-(6-phenylpyrimidin-4-yl)-9H-carbazole |

| | Structure |
|---|---|
| R9 | 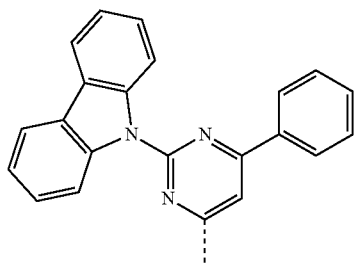 |
| R10 | 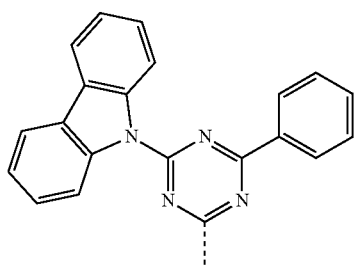 |
| R11 | 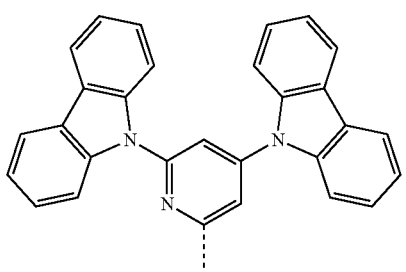 |
| R12 | 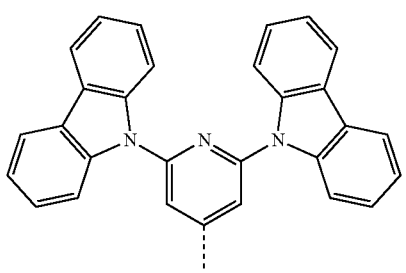 |
| R13 | 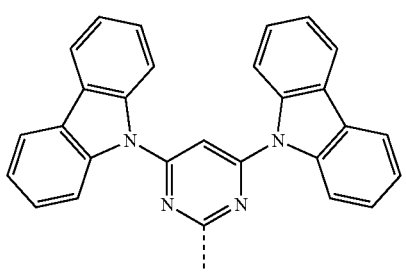 |
| R14 | 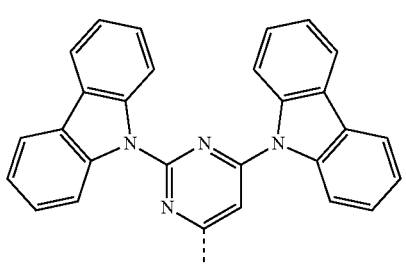 |
| R15 | 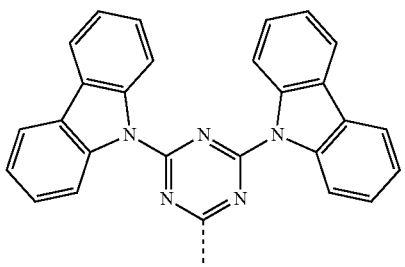 |
| R16 | 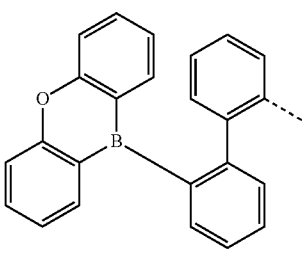 |
| R17 | 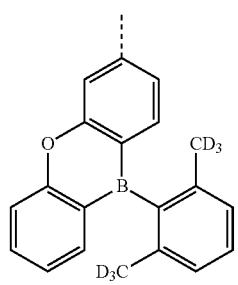 |
| R18 | 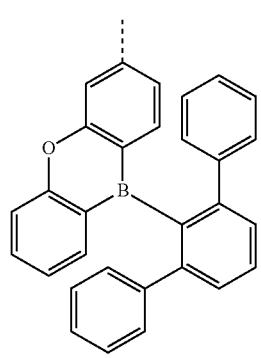 |
| R19 | 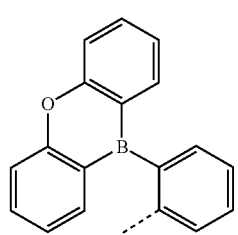 |

| Structure | |
|---|---|
| R20 | 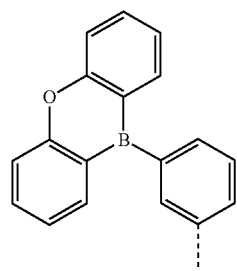 |
| R21 | 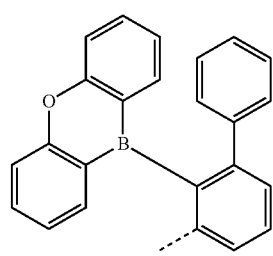 |
| R22 | 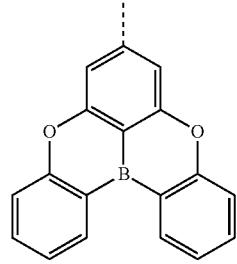 |
| R23 | 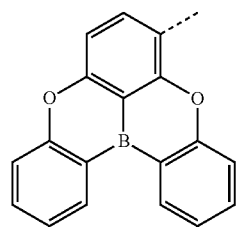 |
| R24 | 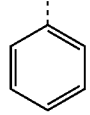 |
| R25 | 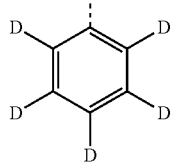 |
| R26 | 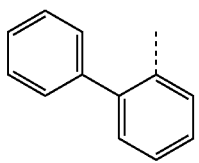 |
| Structure | |
|---|---|
| R27 | 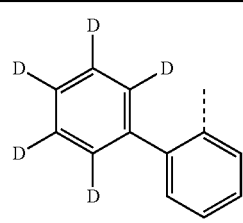 |
| R28 | 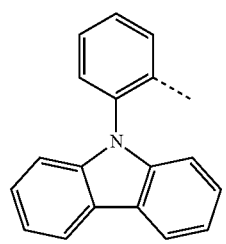 |
| R29 | 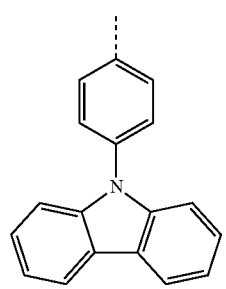 |
| R30 | 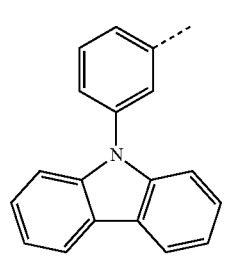 |
| R31 | 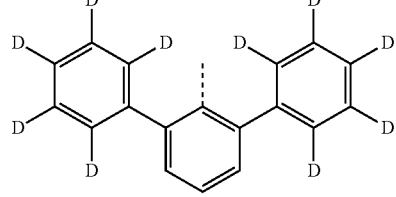 |
| R32 | 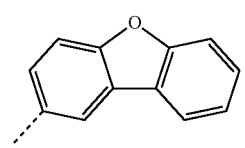 |
| R33 | 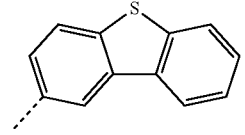 |

-continued
| | Structure |
|---|---|
| R34 | 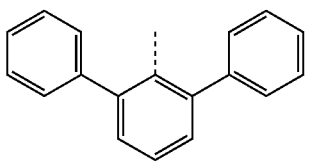 |
| R35 | 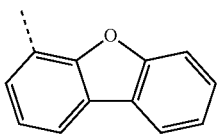 |
| R36 | 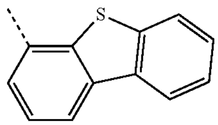 |
| R37 | 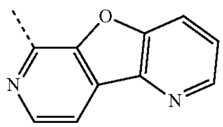 |
| R38 | 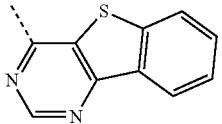 |
| R39 | 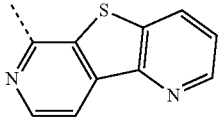 |
| R40 | 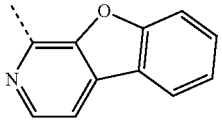 |
| R41 | 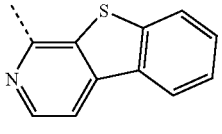 |
| R42 | 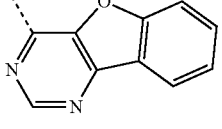 |
| R43 | 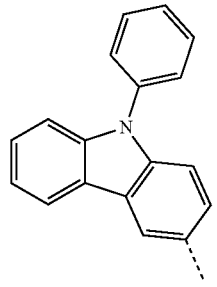 |
-continued
| | Structure |
|---|---|
| R44 | 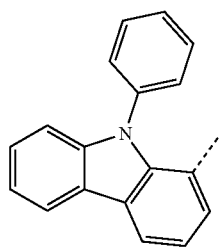 |
| R45 | 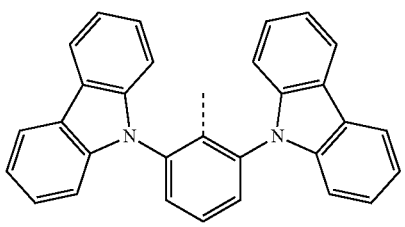 |
| R46 | 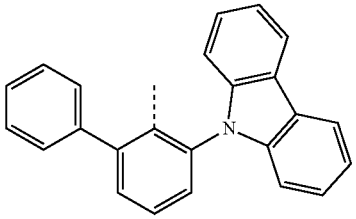 |
| R47 | 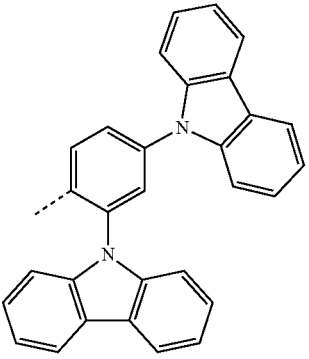 |
| R48 | 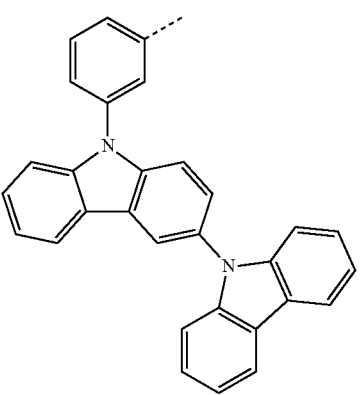 |

-continued
| Structure |
|---|
| R49 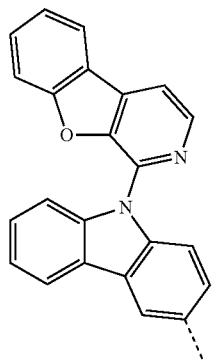 |
| R50 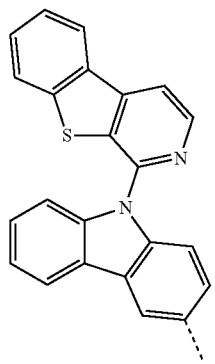 |
| R51 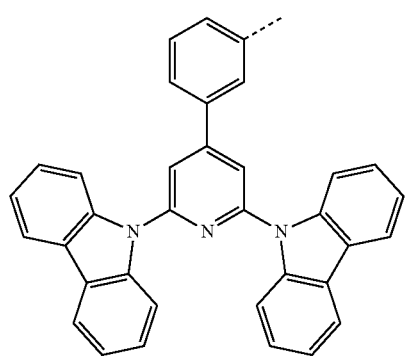 |
| R52 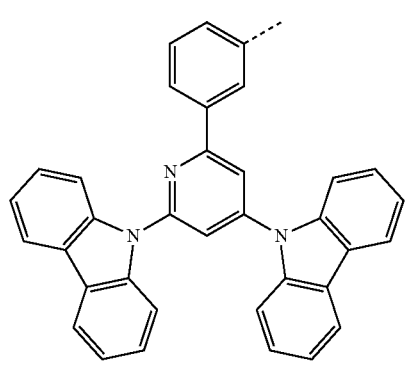 |
-continued
| Structure |
|---|
| R53 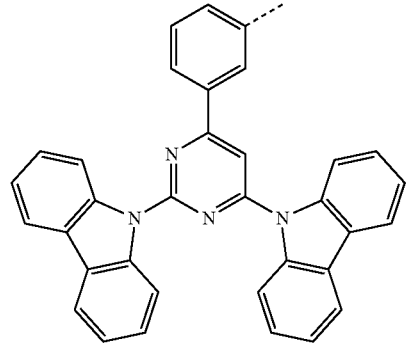 |
| R54 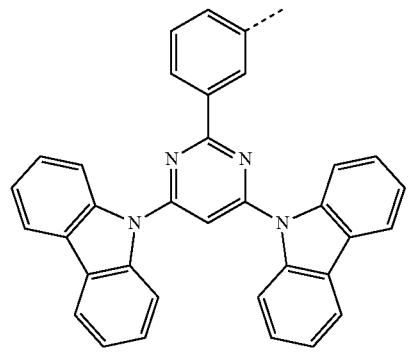 |
| R55 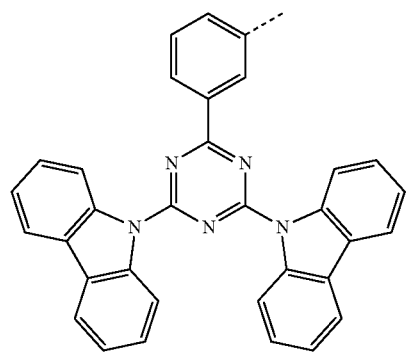 |
| R56 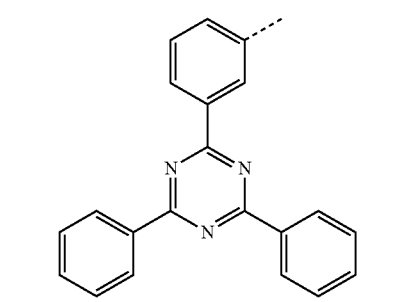 |

| | |
|---|---|
| R57 | 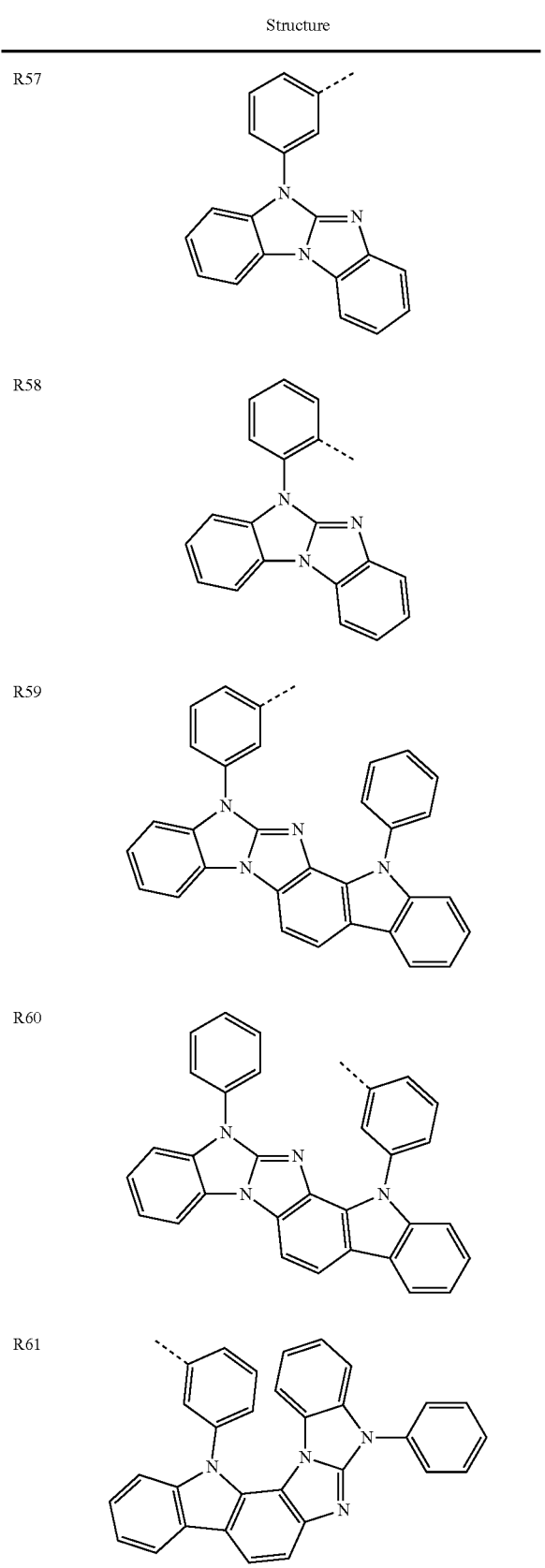 |
| R58 | |
| R59 | |
| R60 | |
| R61 | |
| | |
|---|---|
| R62 | 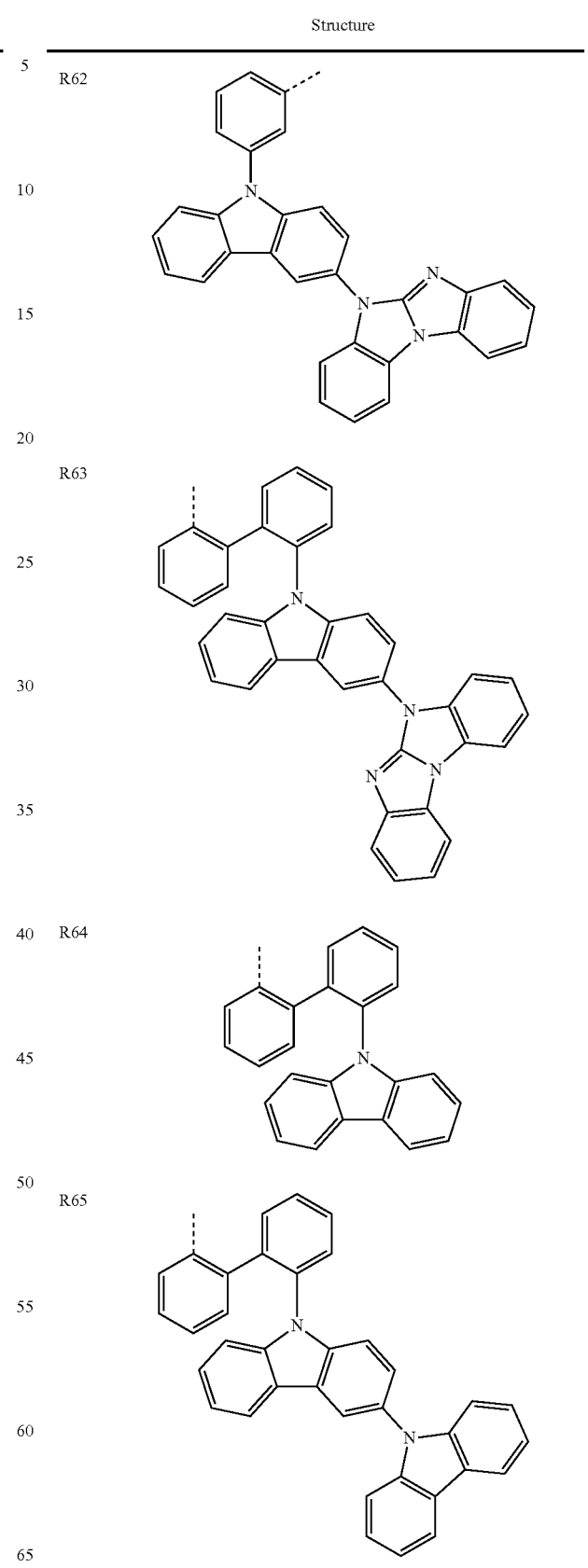 |
| R63 | |
| R64 | |
| R65 | |

| | |
|---|---|
| 51 -continued | 52 -continued |
| Structure | Structure |
| R66 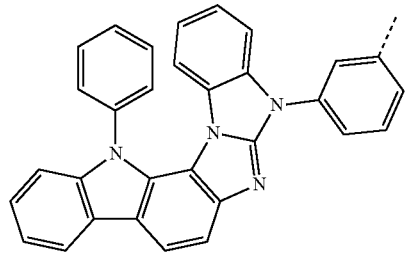 | R72 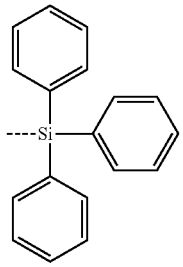 |
| R67 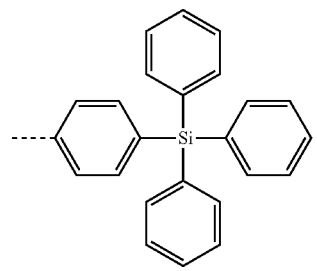 | R73 ----H |
| | R74 ----D |
| | R75 ----C≡N |
| R68 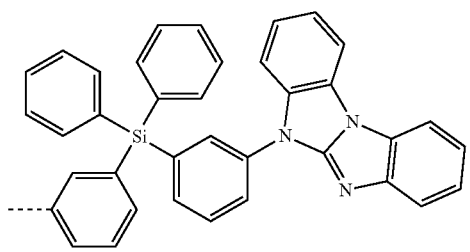 | R76 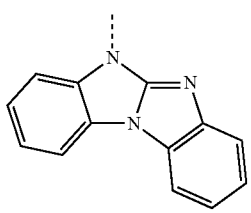 |
| R69 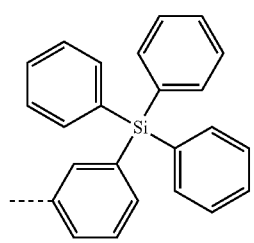 | R77 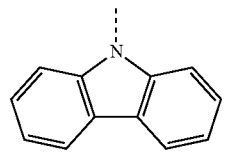 |
| R70 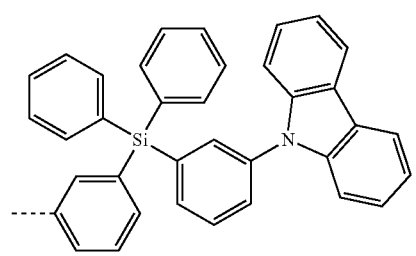 | R78 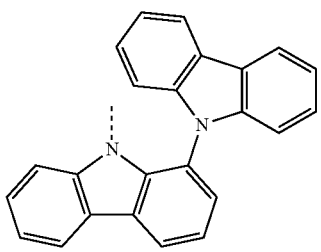 |
| R71 | R79 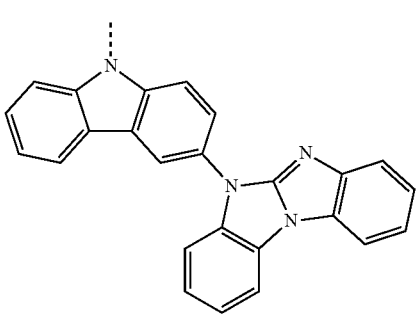 |

-continued
| | Structure |
|---|---|
| R80 | 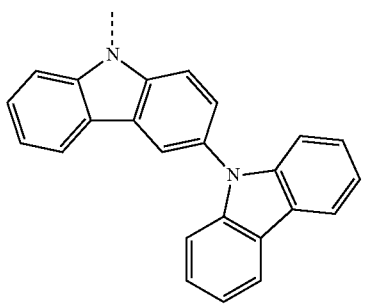 |
| R81 | 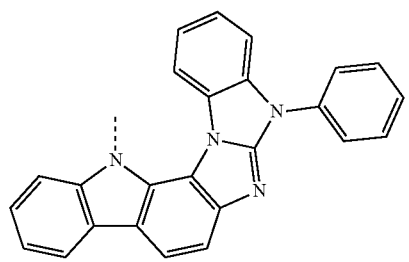 |
-continued
| | Structure |
|---|---|
| R82 | 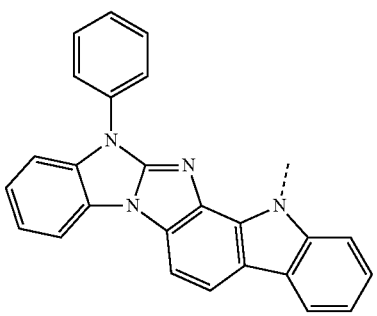 |
| R83 | 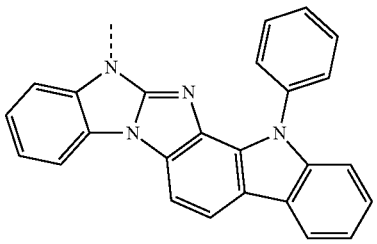 |
| R84 | 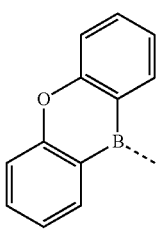 |
In some embodiments, the compound can be selected from the group consisting of:
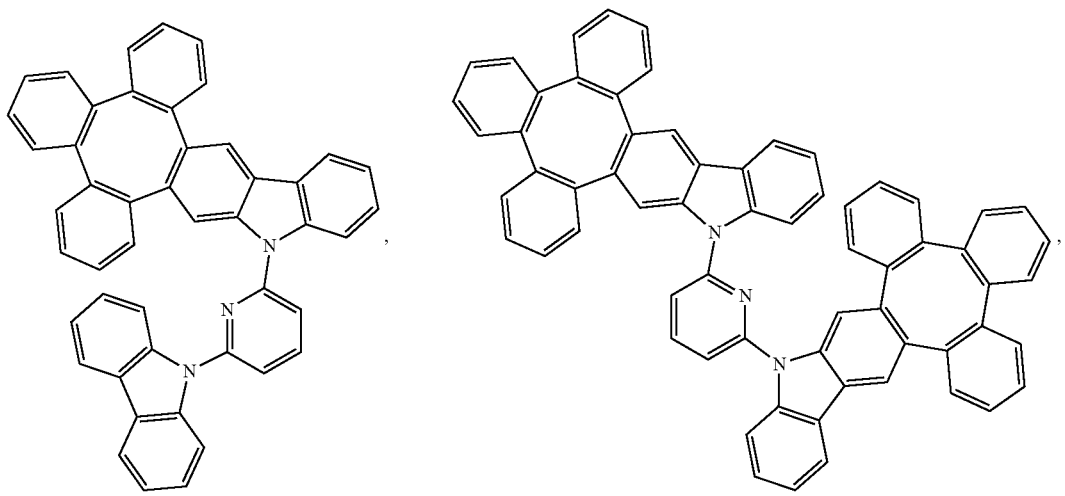

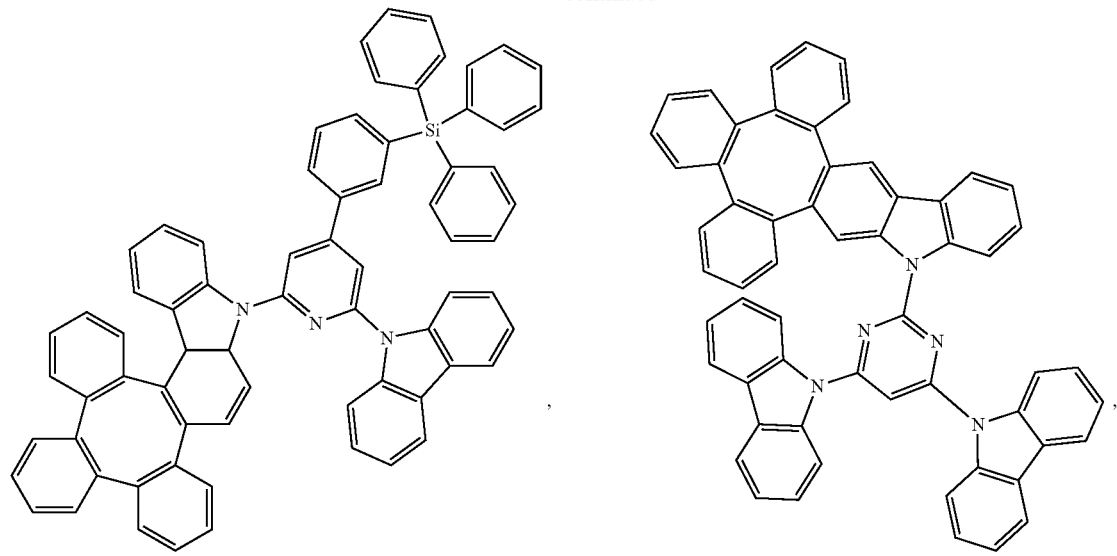
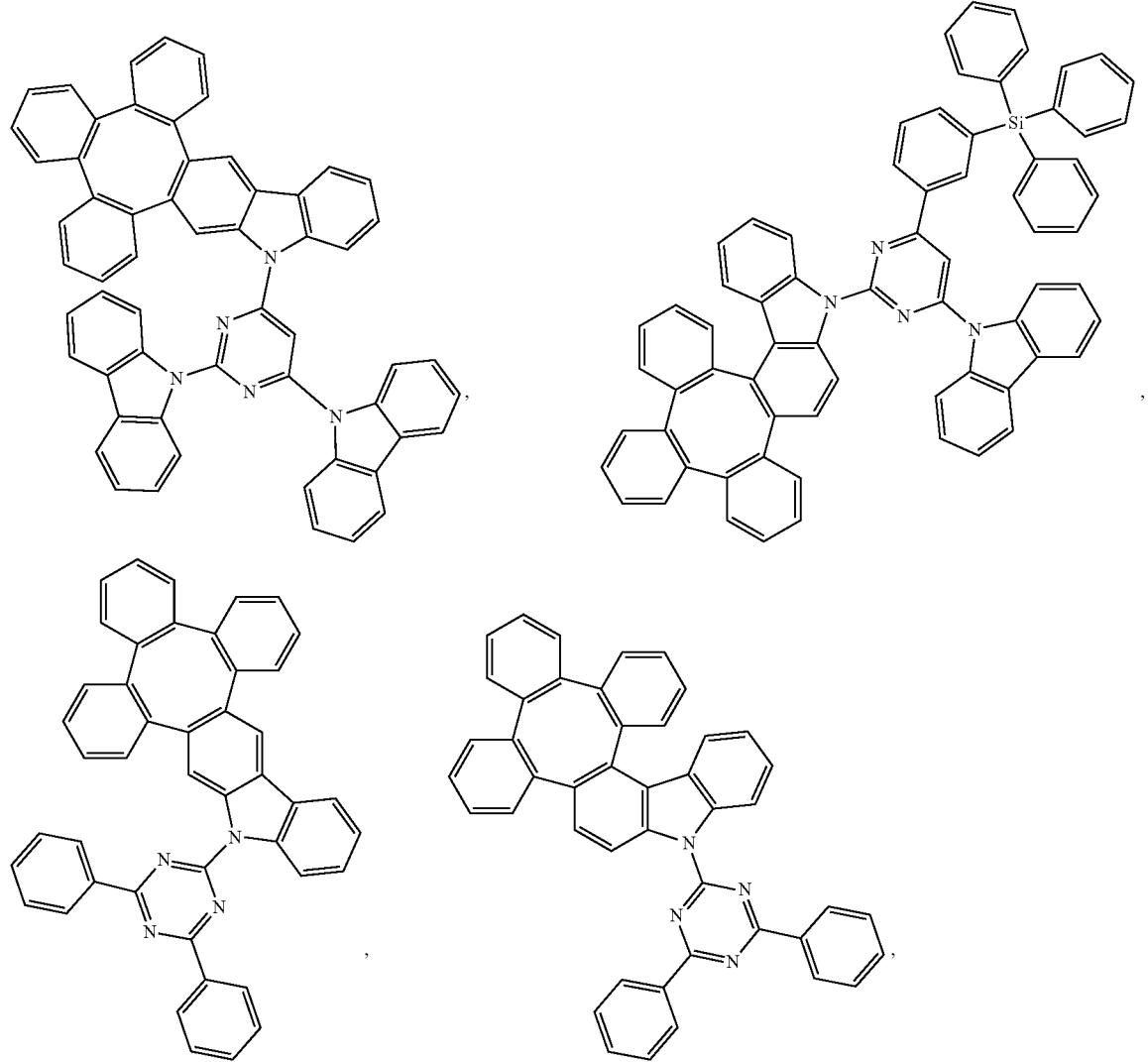

-continued
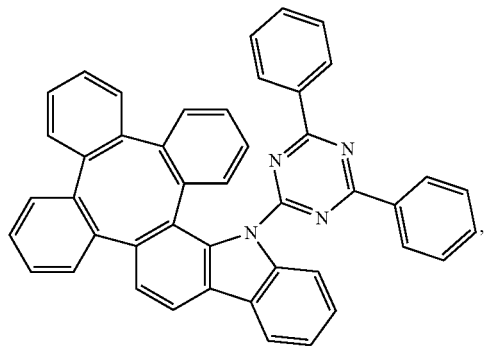
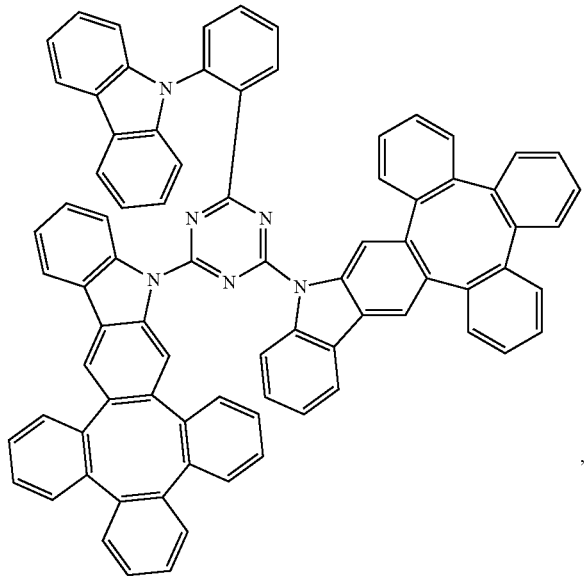
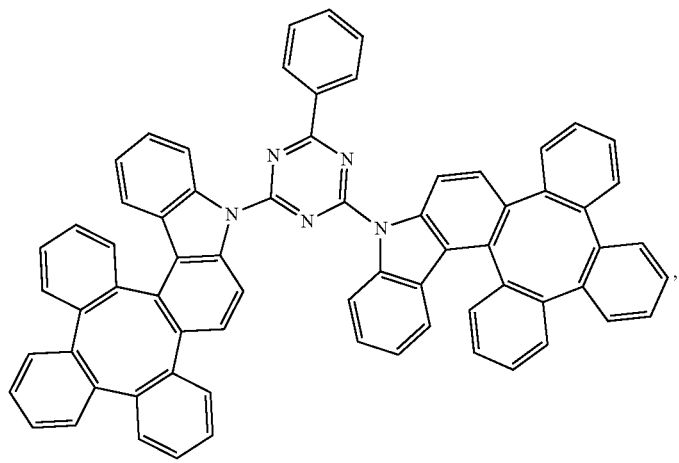
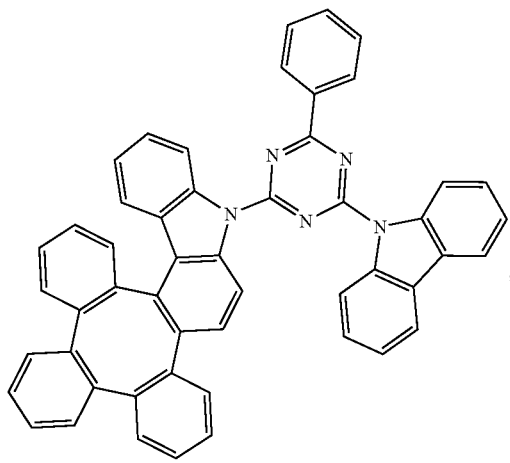
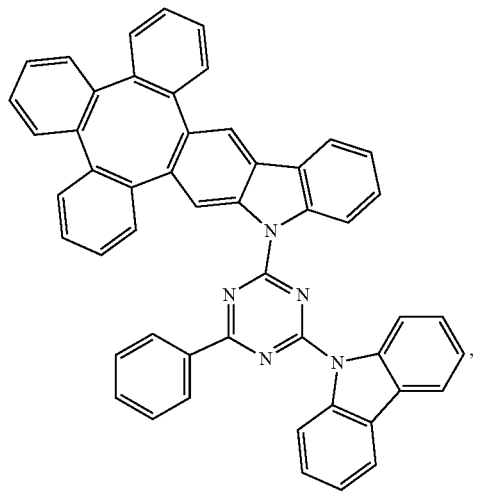
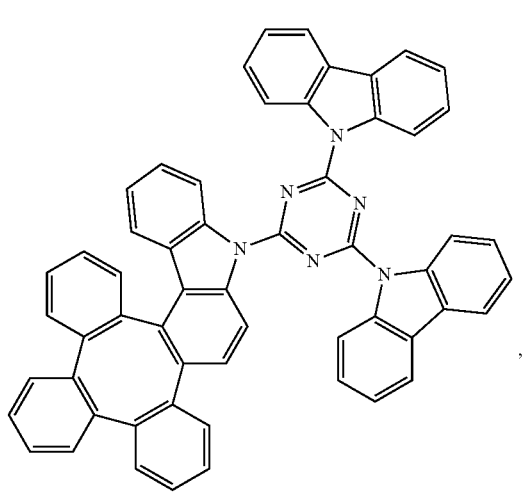

-continued
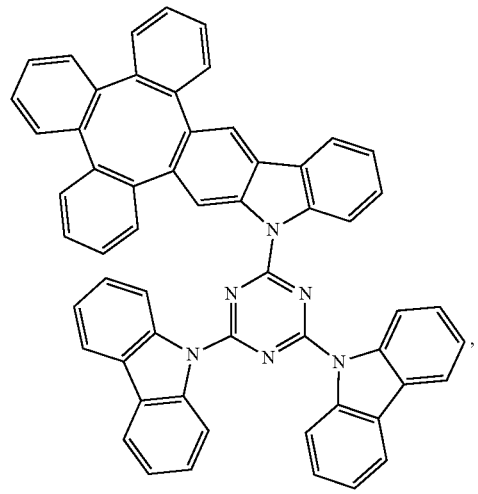
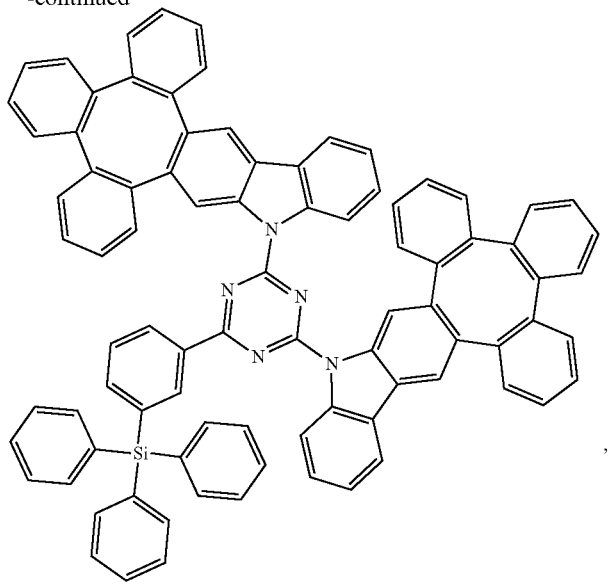
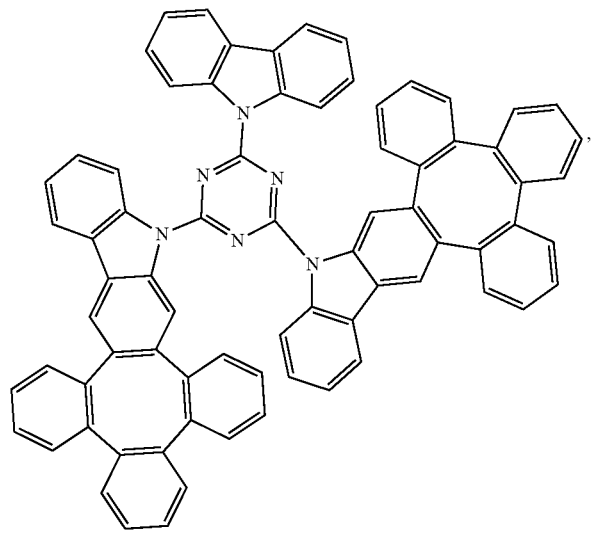
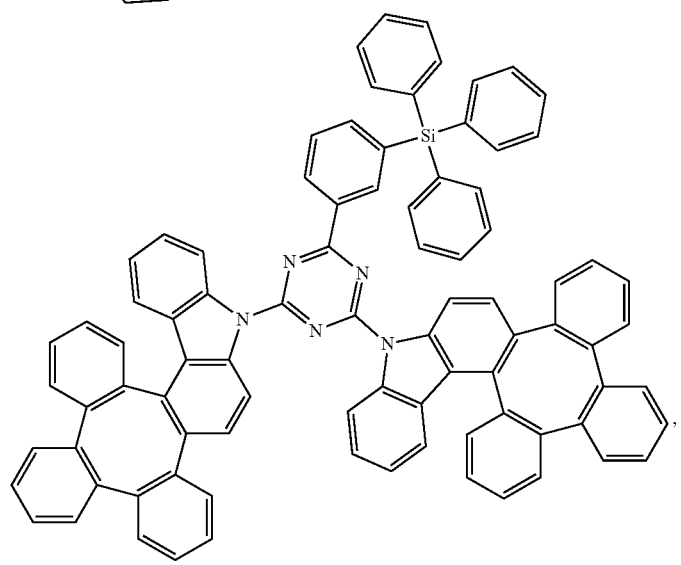

-continued
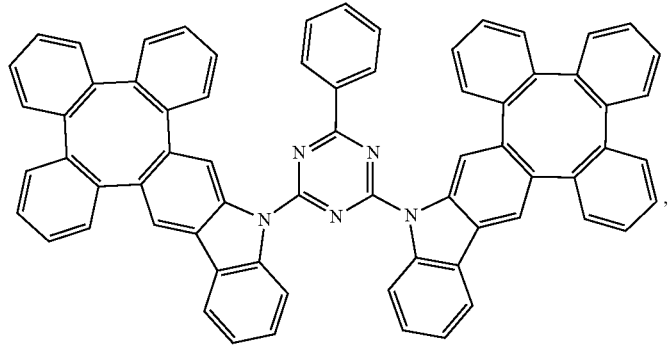
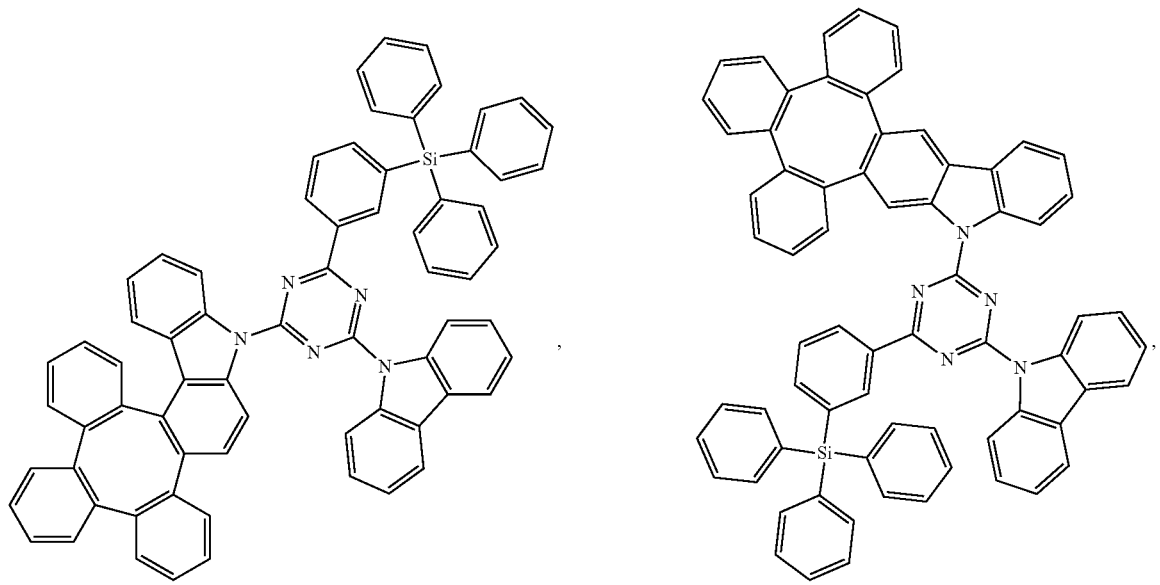
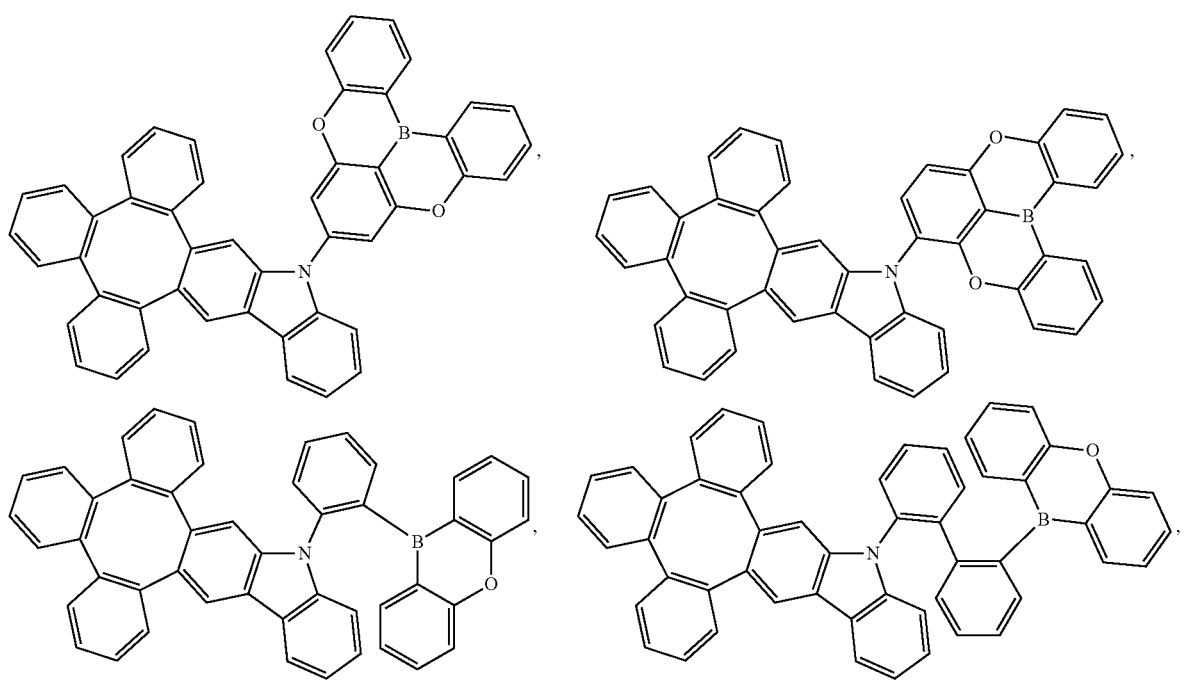

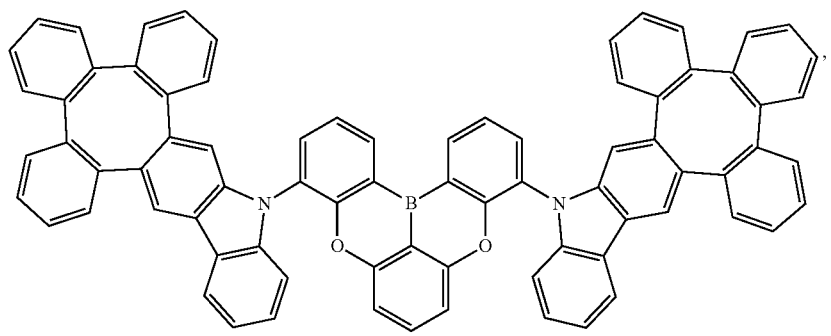
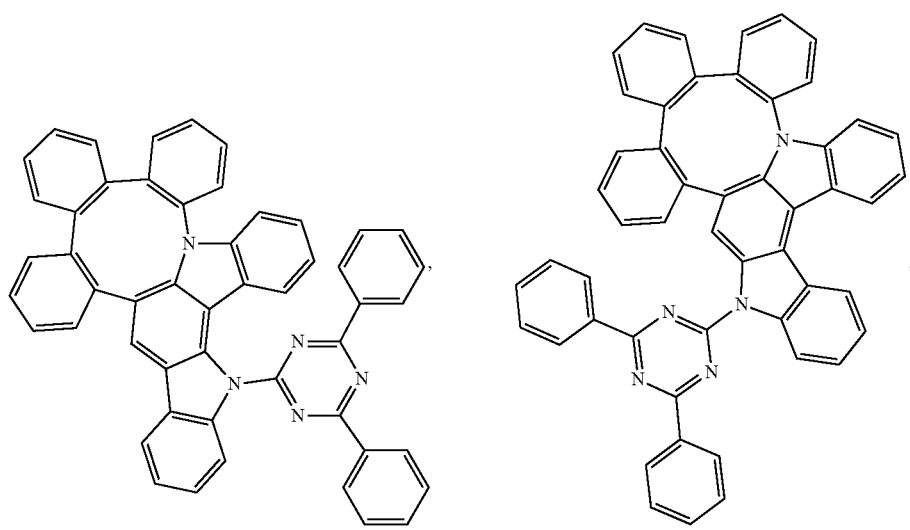
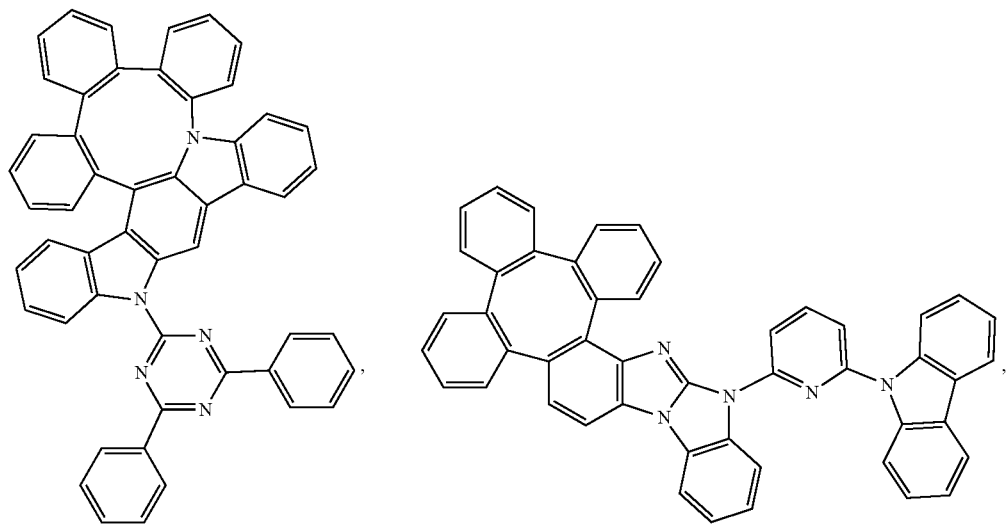

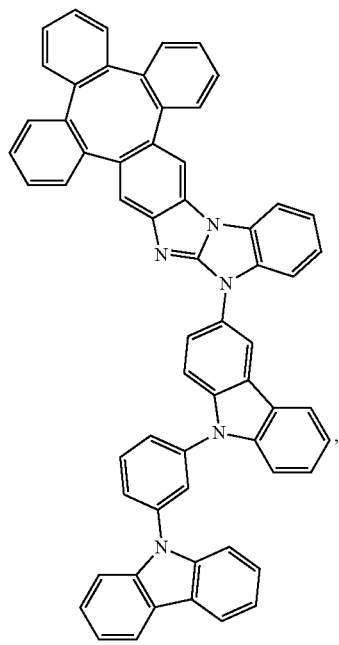
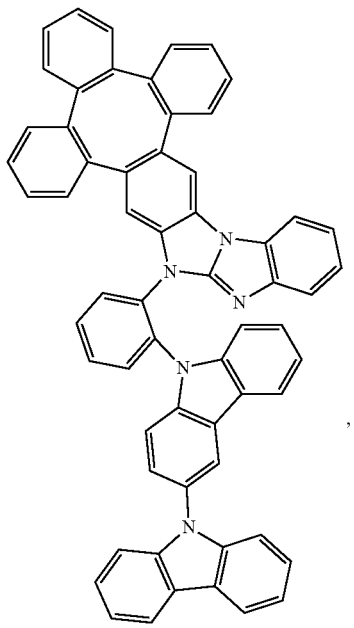
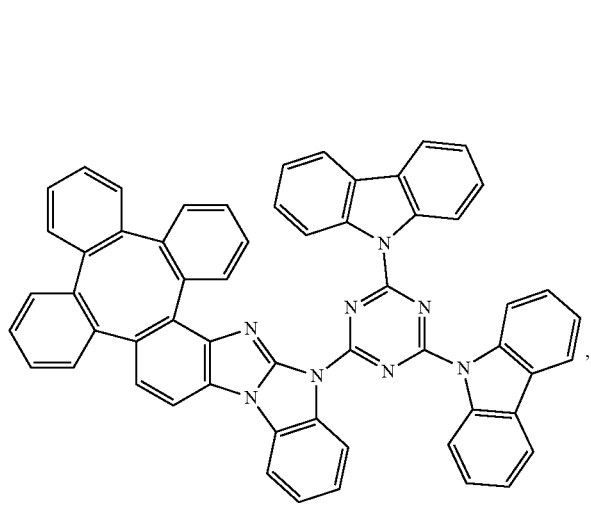
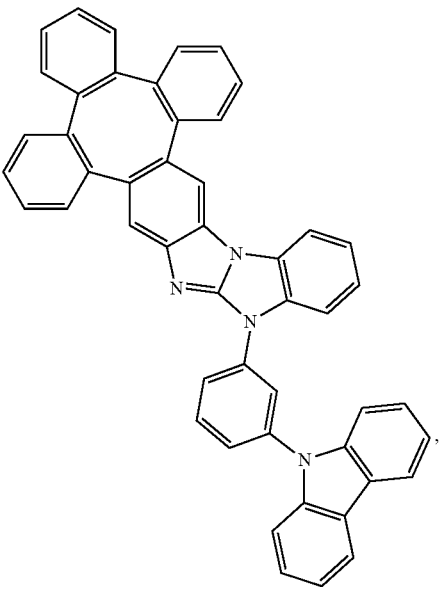

-continued
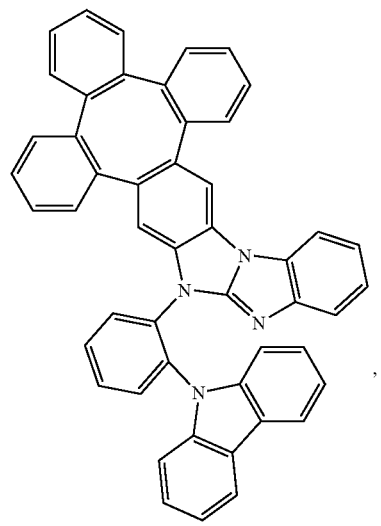 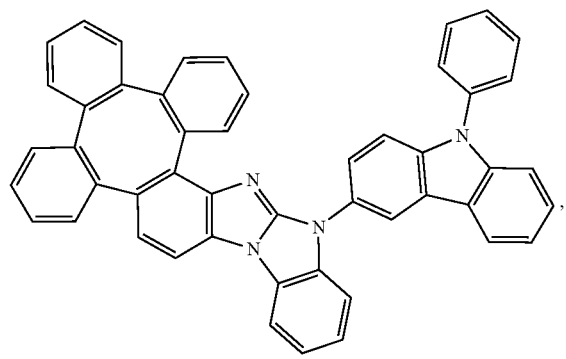
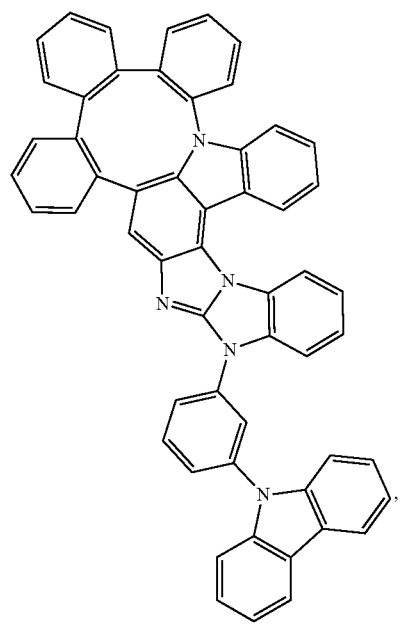 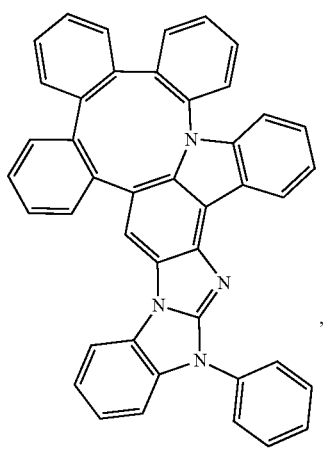 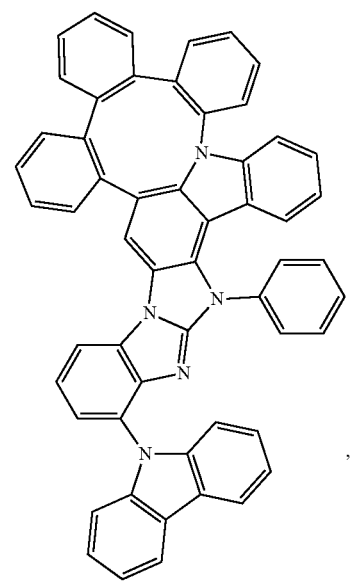
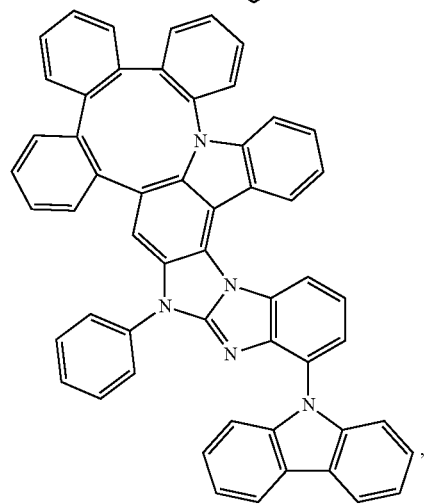 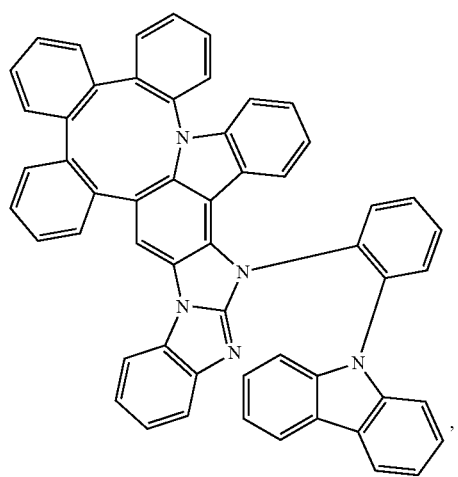

-continued
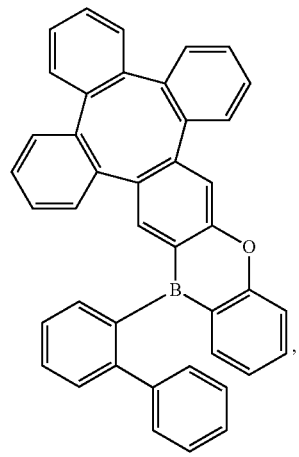 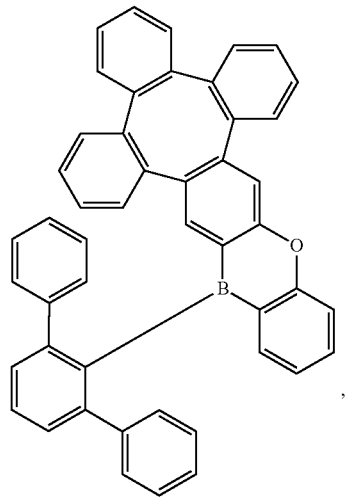 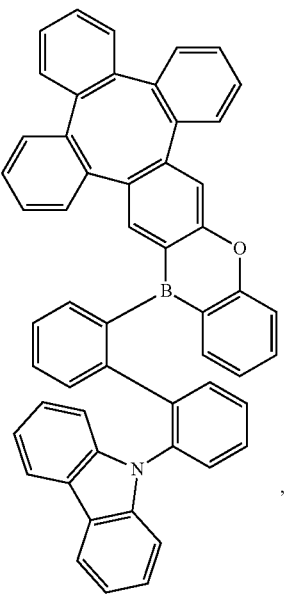
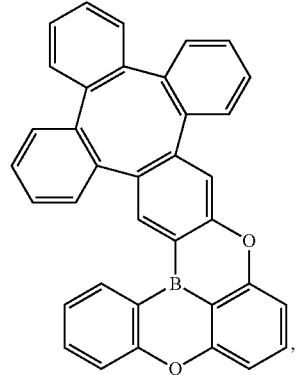 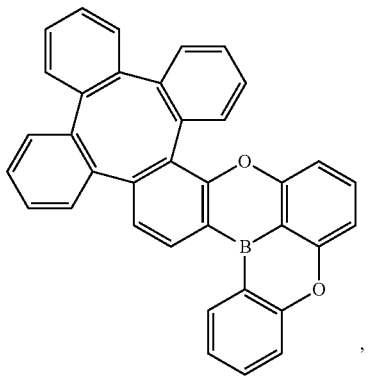 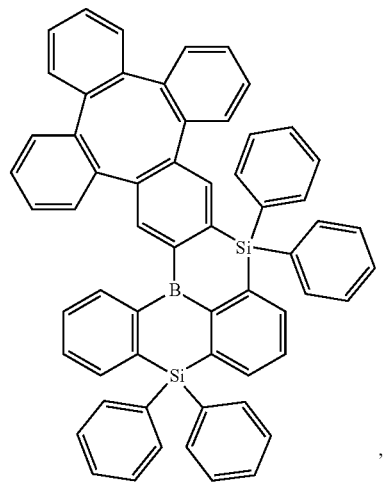
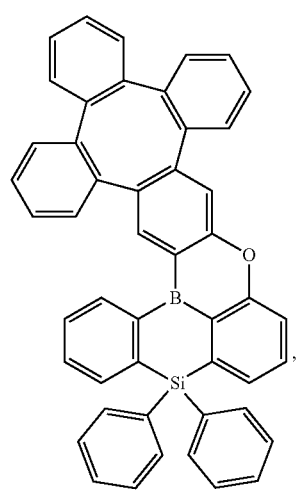 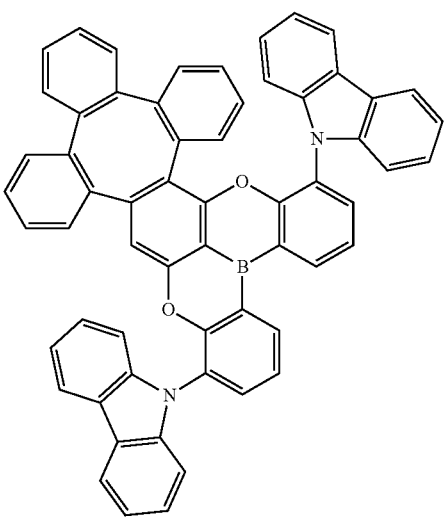 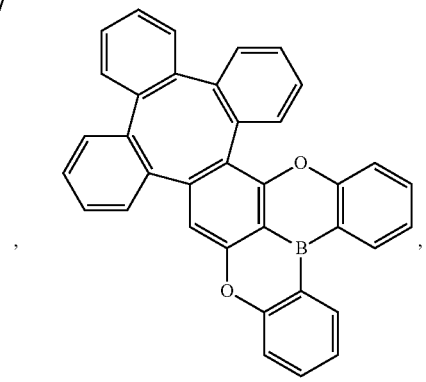

-continued
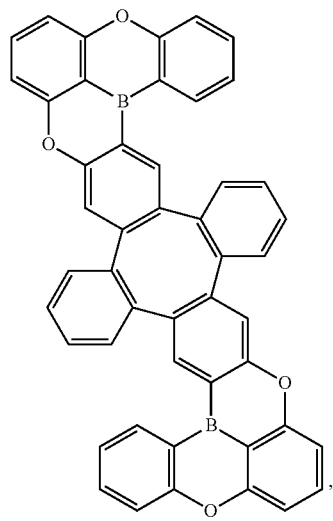
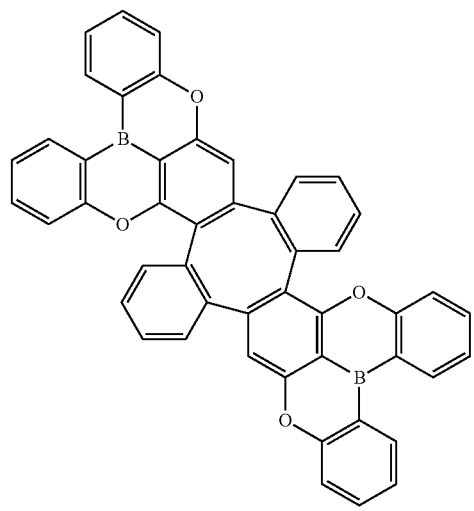
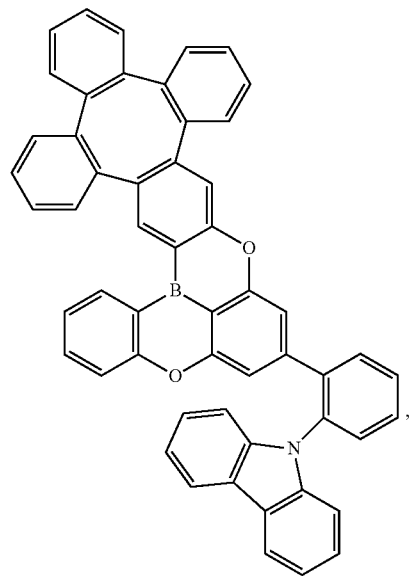
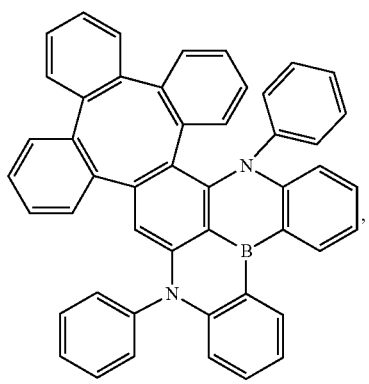
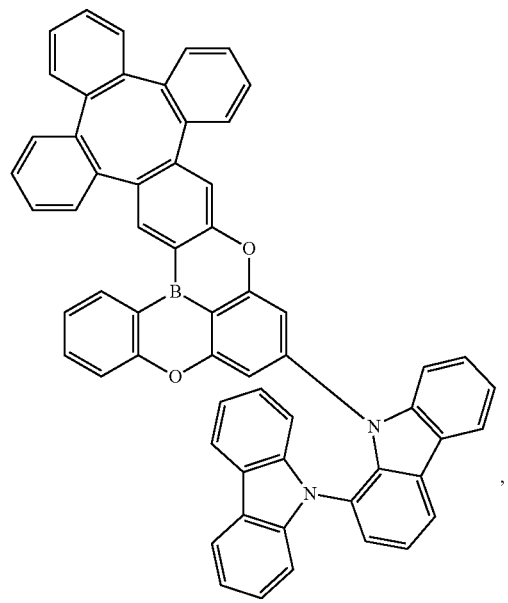
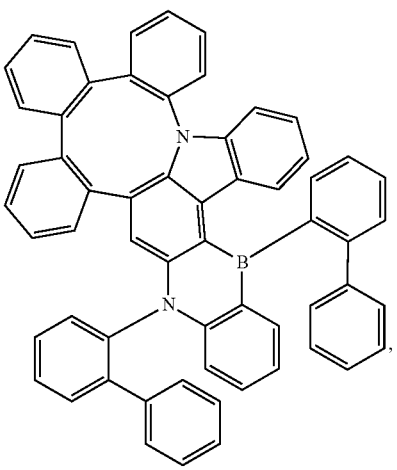

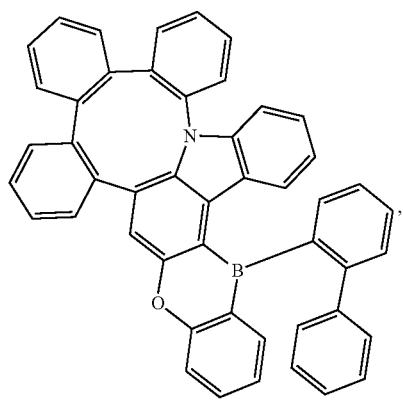 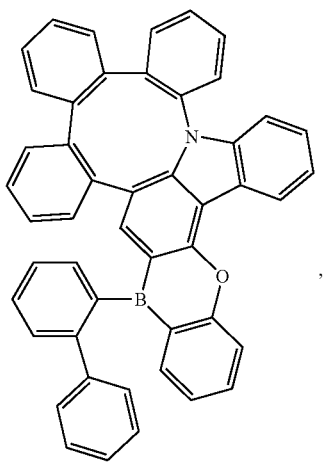 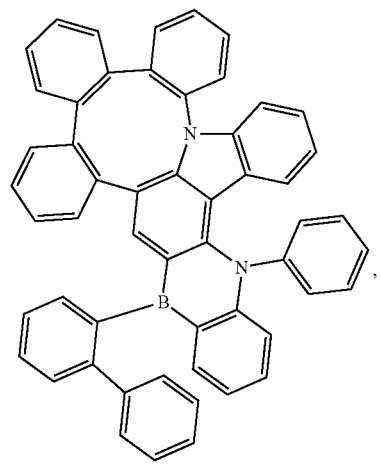
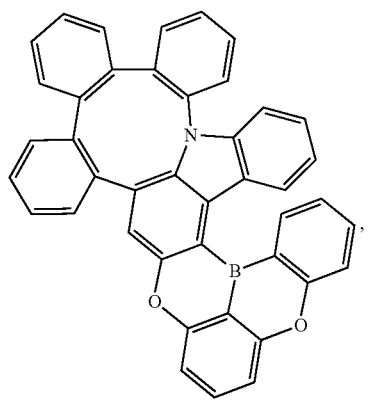 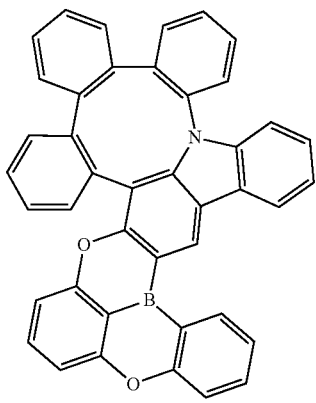 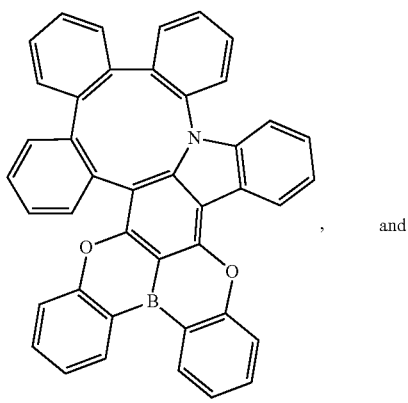, and
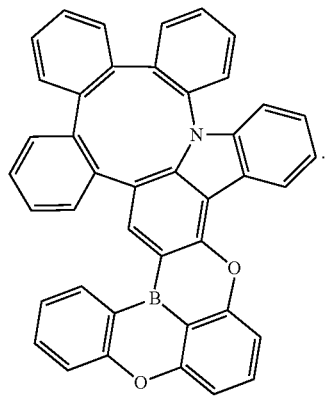.

In some embodiments, the compound having Formula I described herein can be at least 30% deuterated, at least 40% deuterated, at least 50% deuterated, at least 60% deuterated, at least 70% deuterated, at least 80% deuterated, at least 90% deuterated, at least 95% deuterated, at least 99% deuterated, or 100% deuterated. As used herein, percent deuteration has its ordinary meaning and includes the percent of possible hydrogen atoms (e.g., positions that are hydrogen, deuterium, or halogen) that are replaced by deuterium atoms.

C. The OLEDs and the Devices of the Present Disclosure

In another aspect, the present disclosure also provides an OLED device comprising an organic layer that contains a compound as disclosed in the above compounds section of the present disclosure.

In some embodiments, the organic layer can comprise a compound comprising a structure of Formula I:

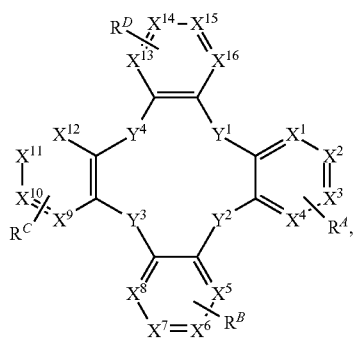

wherein $X^1$ to $X^{16}$ are each independently C or N; $Y^1$ to $Y^4$ are each independently selected from the group consisting of direct bond, NR, PR, O, S, Se, CRR', SiRR', GeRR', BR, and BRR'; at least two adjacent sites from $X^1$ to $X^{16}$ are both carbon and are fused to one of Formula II, Formula III or Formula IV as described herein; $R^A$, $R^B$, $R^C$, and $R^D$ each independently represent mono to the maximum allowable substitution, or no substitution; each R, R', $R^A$, $R^B$, $R^C$, $R^D$, and $R^E$ is independently a hydrogen or a substituent selected from the group consisting of the general substituents as described herein; and any two adjacent R, R', $R^A$, $R^B$, $R^C$, and $R^D$ may be joined or fused to form a ring.

In some embodiments, the compound may be a host, and the organic layer may be an emissive layer that comprises a phosphorescent emitter.

In some embodiments, the phosphorescent emitter may be a transition metal complex having at least one ligand or part of the ligand if the ligand is more than bidentate selected from the group consisting of:

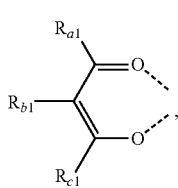

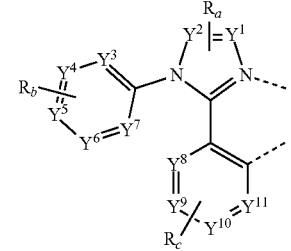

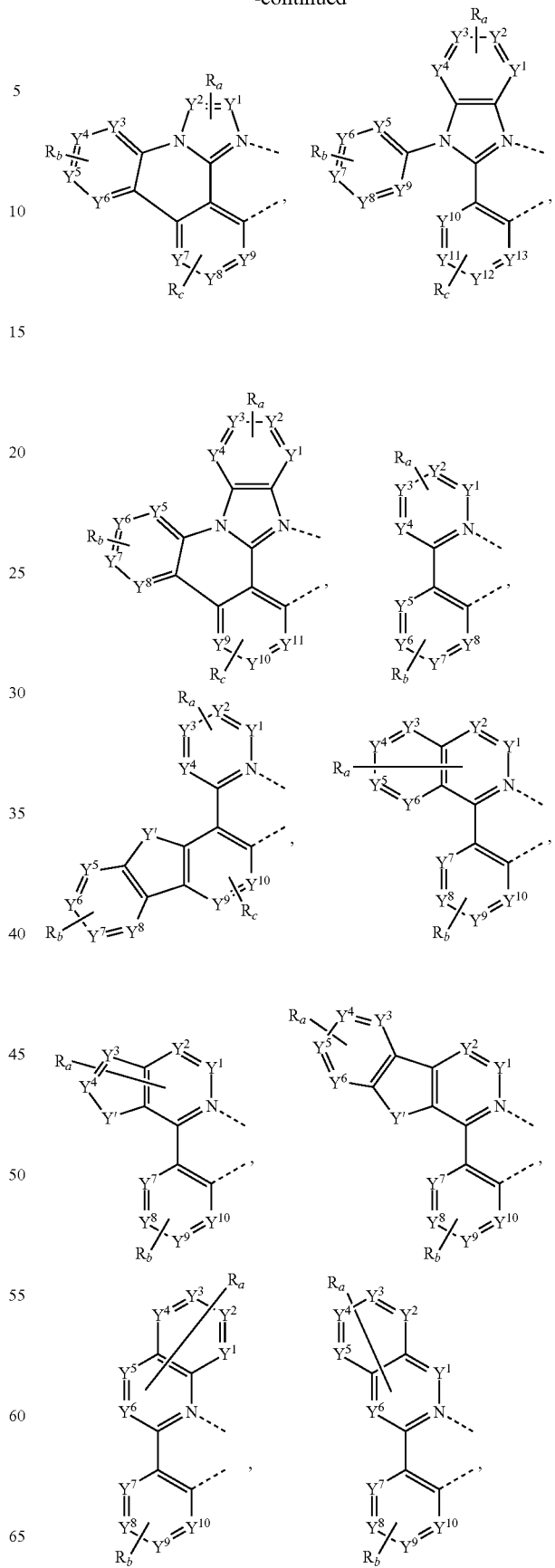

wherein:

T is selected from the group consisting of B, Al, Ga, and In;

each of $Y^1$ to $Y^{13}$ is independently selected from the group consisting of carbon and nitrogen;

Y' is selected from the group consisting of $BR_e$, $NR_e$, $PR_e$, O, S, Se, C=O, S=O, $SO_2$, $CR_eR_f$, $SiR_eR_f$, and $GeR_eR_f$;

$R_e$ and $R_f$ can be fused or joined to form a ring;

each $R_a$, $R_b$, $R_c$, and $R_d$ independently represent zero, mono, or up to a maximum allowed number of substitutions to its associated ring;

each of $R_{a1}$, $R_{b1}$, $R_{c1}$, $R_{d1}$, $R_a$, $R_b$, $R_c$, $R_d$, $R_e$ and $R_f$ is independently a hydrogen or a substituent selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; the general substituents defined herein; and any two adjacent $R_a$, $R_b$, $R_c$, $R_d$, $R_e$ and $R_f$ can be fused or joined to form a ring or form a multidentate ligand.

In some embodiments, the compound may be an acceptor, and the OLED may further comprise a sensitizer selected from the group consisting of a delayed fluorescence emitter, a phosphorescent emitter, and combination thereof.

In some embodiments, the compound may be a fluorescent emitter, a delayed fluorescence emitter, or a component of an exciplex that is a fluorescent emitter or a delayed fluorescence emitter.

In yet another aspect, the OLED of the present disclosure may also comprise an emissive region containing a compound as disclosed in the above compounds section of the present disclosure.

In some embodiments, the emissive region may a compound comprising a structure of Formula I:

wherein $X^1$ to $X^{16}$ are each independently C or N; $Y^1$ to $Y^4$ are each independently selected from the group consisting of direct bond, NR, PR, O, S, Se, CRR', SiRR', GeRR', BR, and BRR'; at least two adjacent sites from $X^1$ to $X^{16}$ are both carbon and are fused to one of Formula II, Formula III or Formula IV as described herein; $R^A$, $R^B$, $R^C$, and $R^D$ each independently represent mono to the maximum allowable substitution, or no substitution; each R, R', $R^A$, $R^B$, $R^C$, $R^D$, and $R^E$ is independently a hydrogen or a substituent selected from the group consisting of the general substituents as described herein; and any two adjacent R, R', $R^A$, $R^B$, $R^C$, and $R^D$ may be joined or fused to form a ring.

In some embodiments, at least one of the anode, the cathode, or a new layer disposed over the organic emissive layer functions as an enhancement layer. The enhancement layer comprises a plasmonic material exhibiting surface plasmon resonance that non-radiatively couples to the emitter material and transfers excited state energy from the emitter material to non-radiative mode of surface plasmon polariton. The enhancement layer is provided no more than a threshold distance away from the organic emissive layer, wherein the emitter material has a total non-radiative decay rate constant and a total radiative decay rate constant due to the presence of the enhancement layer and the threshold distance is where the total non-radiative decay rate constant is equal to the total radiative decay rate constant. In some embodiments, the OLED further comprises an outcoupling layer. In some embodiments, the outcoupling layer is disposed over the enhancement layer on the opposite side of the organic emissive layer. In some embodiments, the outcoupling layer is disposed on opposite side of the emissive layer from the enhancement layer but still outcouples energy from the surface plasmon mode of the enhancement layer. The outcoupling layer scatters the energy from the surface plasmon polaritons. In some embodiments this energy is scattered as photons to free space. In other embodiments, the energy is scattered from the surface plasmon mode into other modes of the device such as but not limited to the organic waveguide mode, the substrate mode, or another waveguiding mode. If energy is scattered to the non-free space mode of the OLED other outcoupling schemes could be incorporated to extract that energy to free space. In some embodiments, one or more intervening layer can be disposed between the enhancement layer and the outcoupling layer. The examples for interventing layer(s) can be dielectric materials, including organic, inorganic, perovskites, oxides, and may include stacks and/or mixtures of these materials.

The enhancement layer modifies the effective properties of the medium in which the emitter material resides resulting in any or all of the following: a decreased rate of emission, a modification of emission line-shape, a change in emission intensity with angle, a change in the stability of the emitter material, a change in the efficiency of the OLED, and reduced efficiency roll-off of the OLED device. Placement of the enhancement layer on the cathode side, anode side, or on both sides results in OLED devices which take advantage of any of the above-mentioned effects. In addition to the specific functional layers mentioned herein and illustrated in the various OLED examples shown in the figures, the OLEDs according to the present disclosure may include any of the other functional layers often found in OLEDs.

The enhancement layer can be comprised of plasmonic materials, optically active metamaterials, or hyperbolic metamaterials. As used herein, a plasmonic material is a material in which the real part of the dielectric constant crosses zero in the visible or ultraviolet region of the electromagnetic spectrum. In some embodiments, the plasmonic material includes at least one metal. In such embodiments the metal may include at least one of Ag, Al, Au, Ir, Pt, Ni, Cu, W, Ta, Fe, Cr, Mg, Ga, Rh, Ti, Ru, Pd, In, Bi, Ca alloys or mixtures of these materials, and stacks of these materials. In general, a metamaterial is a medium composed of different materials where the medium as a whole acts differently than the sum of its material parts. In particular, we define optically active metamaterials as materials which have both negative permittivity and negative permeability. Hyperbolic metamaterials, on the other hand, are anisotropic media in which the permittivity or permeability are of different sign for different spatial directions. Optically active metamaterials and hyperbolic metamaterials are strictly distinguished from many other photonic structures such as Distributed Bragg Reflectors ("DBRs") in that the medium should appear uniform in the direction of propagation on the length scale of the wavelength of light. Using terminology that one skilled in the art can understand: the dielectric constant of the metamaterials in the direction of propagation can be described with the effective medium approximation. Plasmonic materials and metamaterials provide methods for controlling the propagation of light that can enhance OLED performance in a number of ways.

In some embodiments, the enhancement layer is provided as a planar layer. In other embodiments, the enhancement layer has wavelength-sized features that are arranged periodically, quasi-periodically, or randomly, or sub-wavelength-sized features that are arranged periodically, quasi-periodically, or randomly. In some embodiments, the wavelength-sized features and the sub-wavelength-sized features have sharp edges.

In some embodiments, the outcoupling layer has wavelength-sized features that are arranged periodically, quasi-periodically, or randomly, or sub-wavelength-sized features that are arranged periodically, quasi-periodically, or randomly. In some embodiments, the outcoupling layer may be composed of a plurality of nanoparticles and in other embodiments the outcoupling layer is composed of a plurality of nanoparticles disposed over a material. In these embodiments the outcoupling may be tunable by at least one of varying a size of the plurality of nanoparticles, varying a shape of the plurality of nanoparticles, changing a material of the plurality of nanoparticles, adjusting a thickness of the material, changing the refractive index of the material or an additional layer disposed on the plurality of nanoparticles, varying a thickness of the enhancement layer, and/or varying the material of the enhancement layer. The plurality of nanoparticles of the device may be formed from at least one of metal, dielectric material, semiconductor materials, an alloy of metal, a mixture of dielectric materials, a stack or layering of one or more materials, and/or a core of one type of material and that is coated with a shell of a different type of material. In some embodiments, the outcoupling layer is composed of at least metal nanoparticles wherein the metal is selected from the group consisting of Ag, Al, Au, Ir, Pt, Ni, Cu, W, Ta, Fe, Cr, Mg, Ga, Rh, Ti, Ru, Pd, In, Bi, Ca, alloys or mixtures of these materials, and stacks of these materials. The plurality of nanoparticles may have additional layer disposed over them. In some embodiments, the polarization of the emission can be tuned using the outcoupling layer. Varying the dimensionality and periodicity of the outcoupling layer can select a type of polarization that is preferentially outcoupled to air. In some embodiments the outcoupling layer also acts as an electrode of the device.

In yet another aspect, the present disclosure also provides a consumer product comprising an organic light-emitting device (OLED) having an anode; a cathode; and an organic layer disposed between the anode and the cathode, wherein the organic layer may comprise a compound as disclosed in the above compounds section of the present disclosure.

In some embodiments, the consumer product comprises an organic light-emitting device (OLED) having an anode; a cathode; and an organic layer disposed between the anode and the cathode, wherein the organic layer may comprise a compound comprising a structure of Formula I:

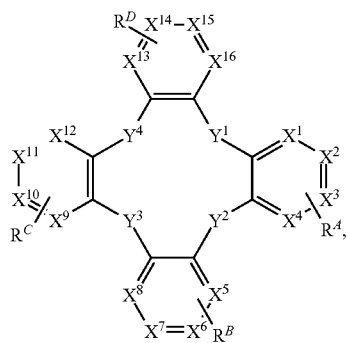

wherein $X^1$ to $X^{16}$ are each independently C or N; $Y^1$ to $Y^4$ are each independently selected from the group consisting of direct bond, NR, PR, O, S, Se, CRR', SiRR', GeRR', BR, and BRR'; at least two adjacent sites from $X^1$ to $X^{16}$ are both carbon and are fused to one of Formula II, Formula III or Formula IV as described herein; $R^A$, $R^B$, $R^C$, and $R^D$ each independently represent mono to the maximum allowable substitution, or no substitution; each R, R', $R^A$, $R^B$, $R^C$, $R^D$, and $R^E$ is independently a hydrogen or a substituent selected from the group consisting of the general substituents as described herein; and any two adjacent R, R', $R^A$, $R^B$, $R^C$, and $R^D$ may be joined or fused to form a ring.

In some embodiments, the consumer product can be one of a flat panel display, a computer monitor, a medical monitor, a television, a billboard, a light for interior or exterior illumination and/or signaling, a heads-up display, a fully or partially transparent display, a flexible display, a laser printer, a telephone, a cell phone, tablet, a phablet, a personal digital assistant (PDA), a wearable device, a laptop computer, a digital camera, a camcorder, a viewfinder, a micro-display that is less than 2 inches diagonal, a 3-D display, a virtual reality or augmented reality display, a vehicle, a video wall comprising multiple displays tiled together, a theater or stadium screen, a light therapy device, and a sign.

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

Several OLED materials and configurations are described in U.S. Pat. Nos. 5,844,363, 6,303,238, and 5,707,745, which are incorporated herein by reference in their entirety.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), are incorporated by reference in their entireties. Phosphorescence is described in more detail in U.S. Pat. No. 7,279,704 at cols. 5-6, which are incorporated by reference.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
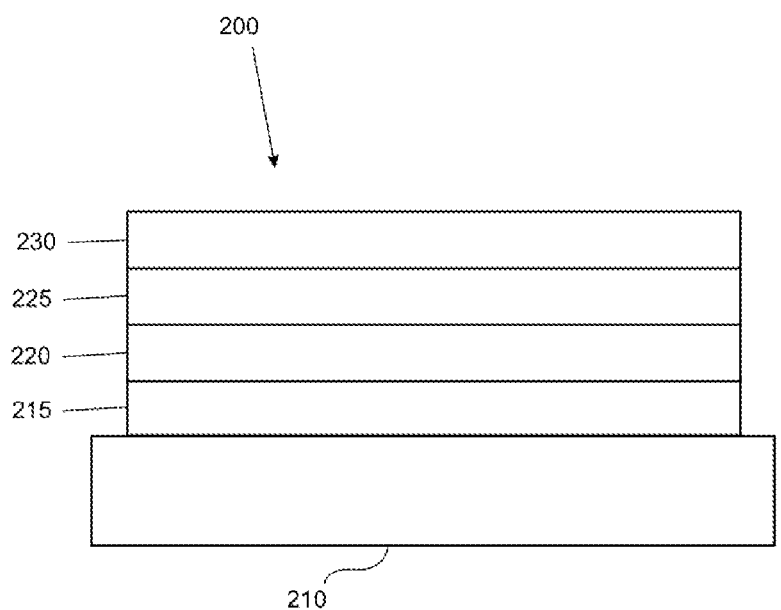
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the present disclosure may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and organic vapor jet printing (OVJP). Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons are a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the present disclosure may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the present disclosure can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the present disclosure can be incorporated into a wide variety of consumer products that have one or more of the electronic component modules (or units) incorporated therein. A consumer product comprising an OLED that includes the compound of the present disclosure in the organic layer in the OLED is disclosed. Such consumer products would include any kind of products that include one or more light source(s) and/or one or more of some type of visual displays. Some examples of such consumer products include flat panel displays, curved displays, computer monitors, medical monitors, televisions, billboards, lights for interior or exterior illumination and/or signaling, heads-up displays, fully or partially transparent displays, flexible displays, rollable displays, foldable displays, stretchable displays, laser printers, telephones, mobile phones, tablets, phablets, personal digital assistants (PDAs), wearable devices, laptop computers, digital cameras, camcorders, viewfinders, micro-displays (displays that are less than 2 inches diagonal), 3-D displays, virtual reality or augmented reality displays, vehicles, video walls comprising multiple displays tiled together, theater or stadium screen, a light therapy device, and a sign. Various control mechanisms may be used to control devices fabricated in accordance with the present disclosure, including passive matrix and active matrix. Many of the devices are intended for use in a temperature range comfortable to humans, such as 18 degrees C. to 30 degrees C., and more preferably at room temperature (20-25° C.), but could be used outside this temperature range, for example, from −40 degree C. to +80° C.

More details on OLEDs, and the definitions described above, can be found in U.S. Pat. No. 7,279,704, which is incorporated herein by reference in its entirety.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

In some embodiments, the OLED has one or more characteristics selected from the group consisting of being flexible, being rollable, being foldable, being stretchable, and being curved. In some embodiments, the OLED is transparent or semi-transparent. In some embodiments, the OLED further comprises a layer comprising carbon nanotubes.

In some embodiments, the OLED further comprises a layer comprising a delayed fluorescent emitter. In some embodiments, the OLED comprises a RGB pixel arrangement or white plus color filter pixel arrangement. In some embodiments, the OLED is a mobile device, a hand held device, or a wearable device. In some embodiments, the OLED is a display panel having less than 10 inch diagonal or 50 square inch area. In some embodiments, the OLED is a display panel having at least 10 inch diagonal or 50 square inch area. In some embodiments, the OLED is a lighting panel.

In some embodiments, the compound can be an emissive dopant. In some embodiments, the compound can produce emissions via phosphorescence, fluorescence, thermally activated delayed fluorescence, i.e., TADF (also referred to as E-type delayed fluorescence; see, e.g., U.S. application Ser. No. 15/700,352, which is hereby incorporated by reference in its entirety), triplet-triplet annihilation, or combinations of these processes. In some embodiments, the emissive dopant can be a racemic mixture, or can be enriched in one enantiomer. In some embodiments, the compound can be homoleptic (each ligand is the same). In some embodiments, the compound can be heteroleptic (at least one ligand is different from others). When there are more than one ligand coordinated to a metal, the ligands can all be the same in some embodiments. In some other embodiments, at least one ligand is different from the other ligands. In some embodiments, every ligand can be different from each other. This is also true in embodiments where a ligand being coordinated to a metal can be linked with other ligands being coordinated to that metal to form a tridentate, tetradentate, pentadentate, or hexadentate ligands. Thus, where the coordinating ligands are being linked together, all of the ligands can be the same in some embodiments, and at least one of the ligands being linked can be different from the other ligand(s) in some other embodiments.

In some embodiments, the compound can be used as a phosphorescent sensitizer in an OLED where one or multiple layers in the OLED contains an acceptor in the form of one or more fluorescent and/or delayed fluorescence emitters. In some embodiments, the compound can be used as one component of an exciplex to be used as a sensitizer. As a phosphorescent sensitizer, the compound must be capable of energy transfer to the acceptor and the acceptor will emit the energy or further transfer energy to a final emitter. The acceptor concentrations can range from 0.001% to 100%. The acceptor could be in either the same layer as the phosphorescent sensitizer or in one or more different layers. In some embodiments, the acceptor is a TADF emitter. In some embodiments, the acceptor is a fluorescent emitter. In some embodiments, the emission can arise from any or all of the sensitizer, acceptor, and final emitter.

According to another aspect, a formulation comprising the compound described herein is also disclosed.

The OLED disclosed herein can be incorporated into one or more of a consumer product, an electronic component module, and a lighting panel. The organic layer can be an emissive layer and the compound can be an emissive dopant in some embodiments, while the compound can be a non-emissive dopant in other embodiments.

In yet another aspect of the present disclosure, a formulation that comprises the novel compound disclosed herein is described. The formulation can include one or more components selected from the group consisting of a solvent, a host, a hole injection material, hole transport material, electron blocking material, hole blocking material, and an electron transport material, disclosed herein.

The present disclosure encompasses any chemical structure comprising the novel compound of the present disclosure, or a monovalent or polyvalent variant thereof. In other words, the inventive compound, or a monovalent or polyvalent variant thereof, can be a part of a larger chemical structure. Such chemical structure can be selected from the group consisting of a monomer, a polymer, a macromolecule, and a supramolecule (also known as supermolecule). As used herein, a "monovalent variant of a compound" refers to a moiety that is identical to the compound except that one hydrogen has been removed and replaced with a bond to the rest of the chemical structure. As used herein, a "polyvalent variant of a compound" refers to a moiety that is identical to the compound except that more than one hydrogen has been removed and replaced with a bond or bonds to the rest of the chemical structure. In the instance of a supramolecule, the inventive compound can also be incorporated into the supramolecule complex without covalent bonds.

D. Combination of the Compounds of the Present Disclosure with Other Materials The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

a) Conductivity Dopants:

A charge transport layer can be doped with conductivity dopants to substantially alter its density of charge carriers, which will in turn alter its conductivity. The conductivity is increased by generating charge carriers in the matrix material, and depending on the type of dopant, a change in the Fermi level of the semiconductor may also be achieved. Hole-transporting layer can be doped by p-type conductivity dopants and n-type conductivity dopants are used in the electron-transporting layer.

Non-limiting examples of the conductivity dopants that may be used in an OLED in combination with materials disclosed herein are exemplified below together with references that disclose those materials: EP01617493, EP01968131, EP2020694, EP2684932, US20050139810, US20070160905, US20090167167, US2010288362, WO06081780, WO2009003455, WO2009008277, WO2009011327, WO2014009310, US2007252140, US2015060804, US20150123047, and US2012146012.

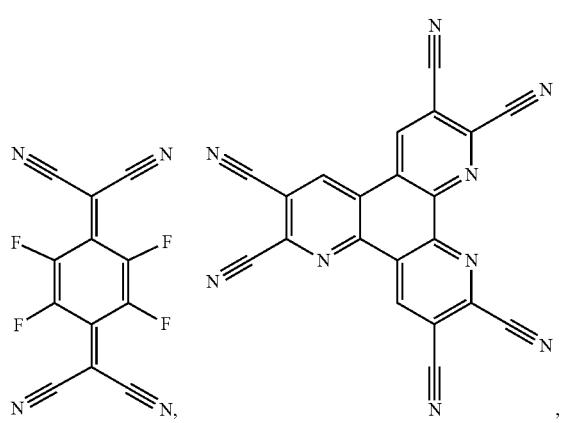

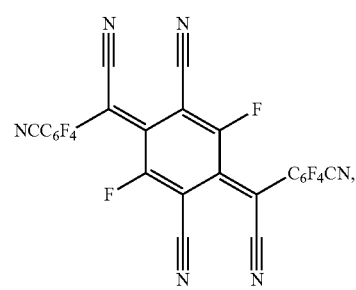

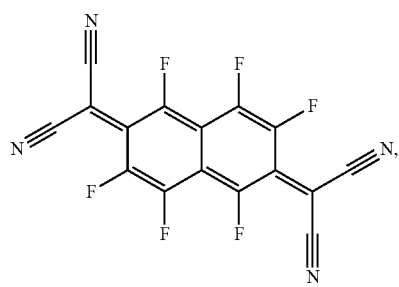

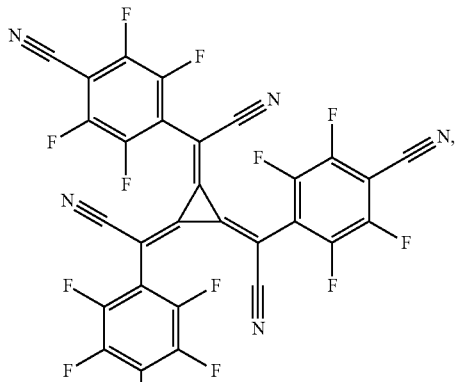

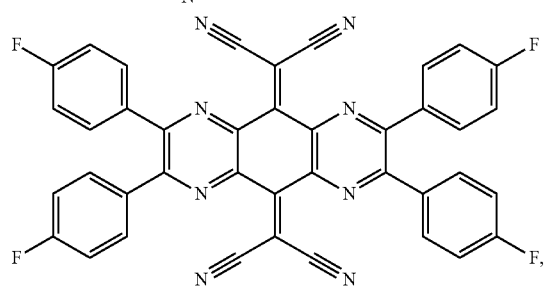

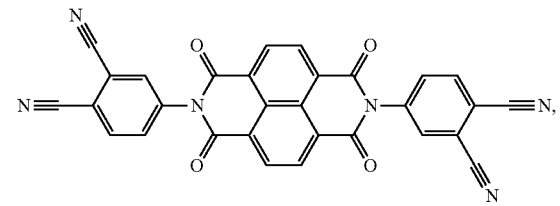

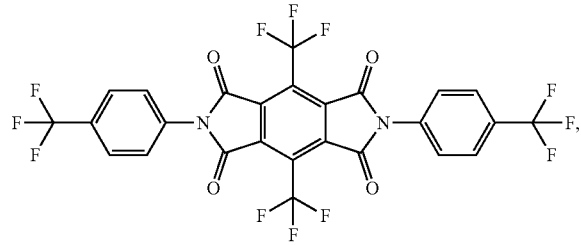

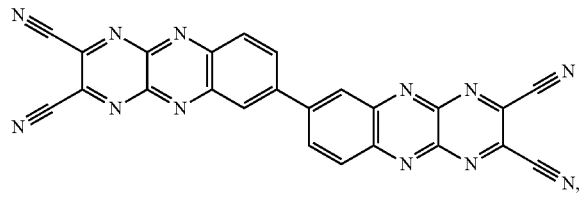

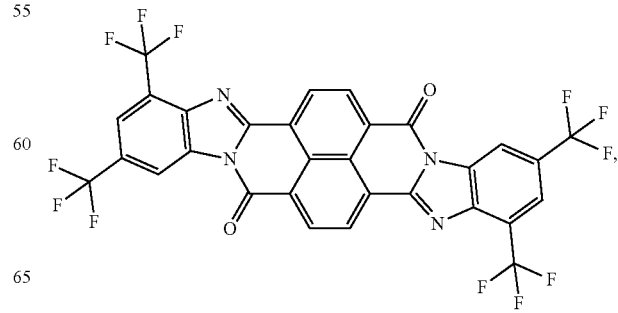

-continued

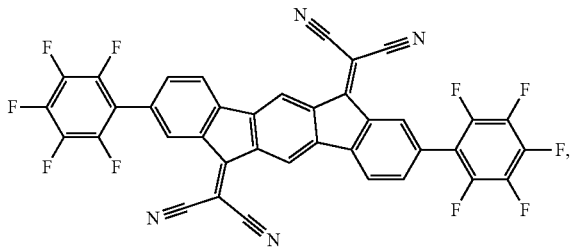

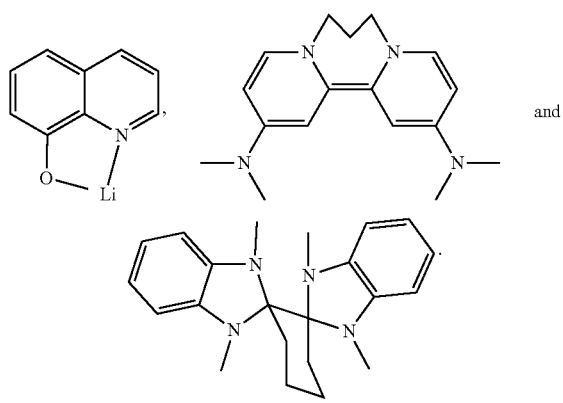

b) HIL/HTL:

A hole injecting/transporting material to be used in the present disclosure is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

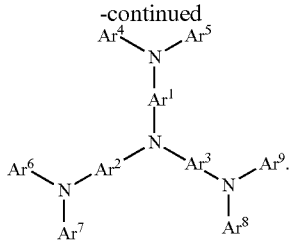

Each of $Ar^1$ to $Ar^9$ is selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each Ar may be unsubstituted or may be substituted by a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof.

In one aspect, $Ar^1$ to $Ar^9$ is independently selected from the group consisting of:

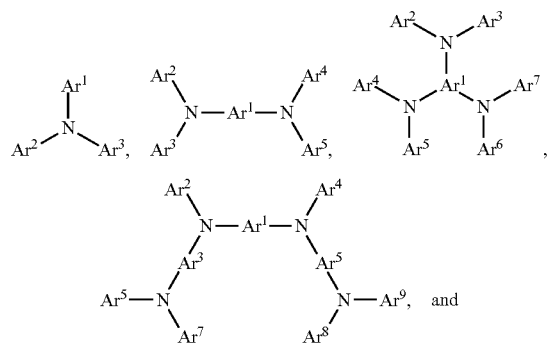

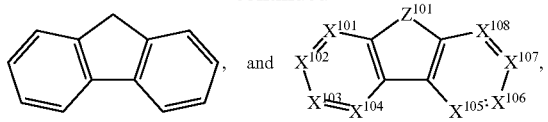

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but are not limited to the following general formula:

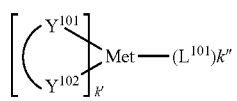

wherein Met is a metal, which can have an atomic weight greater than 40; ($Y^{101}$-$Y^{102}$) is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, ($Y^{101}$-$Y^{102}$) is a 2-phenylpyridine derivative. In another aspect, ($Y^{101}$-$Y^{102}$) is a carbene ligand. In another aspect, Met is selected from Ir, Pt, Os, and Zn. In a further aspect, the metal complex has a smallest oxidation potential in solution vs. $Fc^+/Fc$ couple less than about 0.6 V.

Non-limiting examples of the HIL and HTL materials that may be used in an OLED in combination with materials disclosed herein are exemplified below together with references that disclose those materials: CN102702075, DE102012005215, EP01624500, EP01698613, EP01806334, EP01930964, EP01972613, EP01997799, EP02011790, EP02055700, EP02055701, EP1725079, EP2085382, EP2660300, EP650955, JP07-073529, JP2005112765, JP2007091719, JP2008021687, JP2014-009196, KR20110088898, KR20130077473, TW201139402, U.S. Ser. No. 06/517,957, US20020158242, US20030162053, US20050123751, US20060182993, US20060240279, US20070145888, US20070181874, US20070278938, US20080014464, US20080091025, US20080106190, US20080124572, US20080145707, US20080220265, US20080233434, US20080303417, US2008107919, US20090115320, US20090167161, US2009066235, US2011007385, US20110163302, US2011240968, US2011278551, US2012205642, US2013241401, US20140117329, US2014183517, U.S. Pat. Nos. 5,061,569, 5,639,914, WO05075451, WO07125714, WO08023550, WO08023759, WO2009145016, WO2010061824, WO2011075644, WO2012177006, WO2013018530, WO2013039073, WO2013087142, WO2013118812, WO2013120577, WO2013157367, WO2013175747, WO2014002873, WO2014015935, WO2014015937, WO2014030872, WO2014030921, WO2014034791, WO2014104514, WO2014157018.

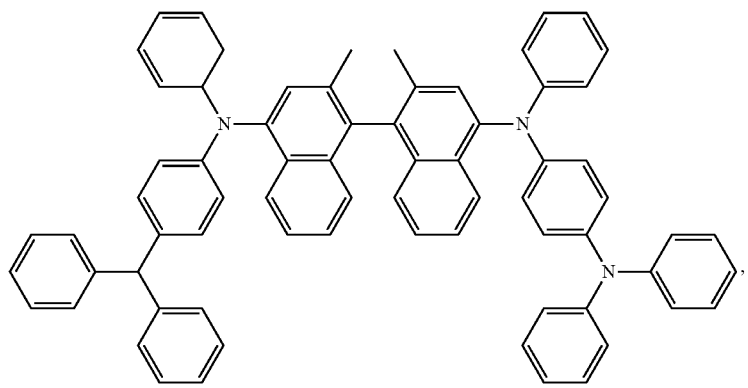

-continued
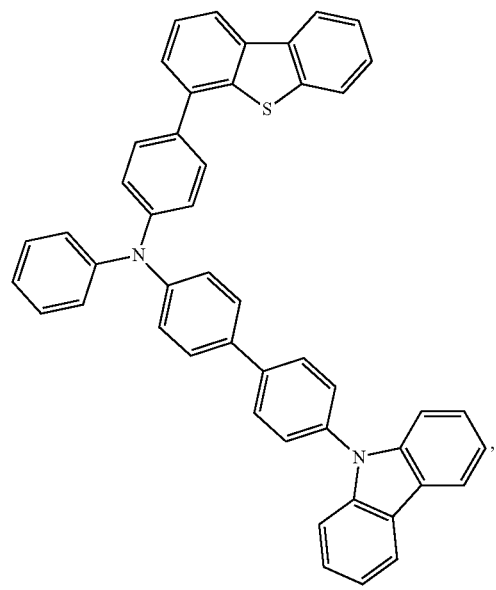
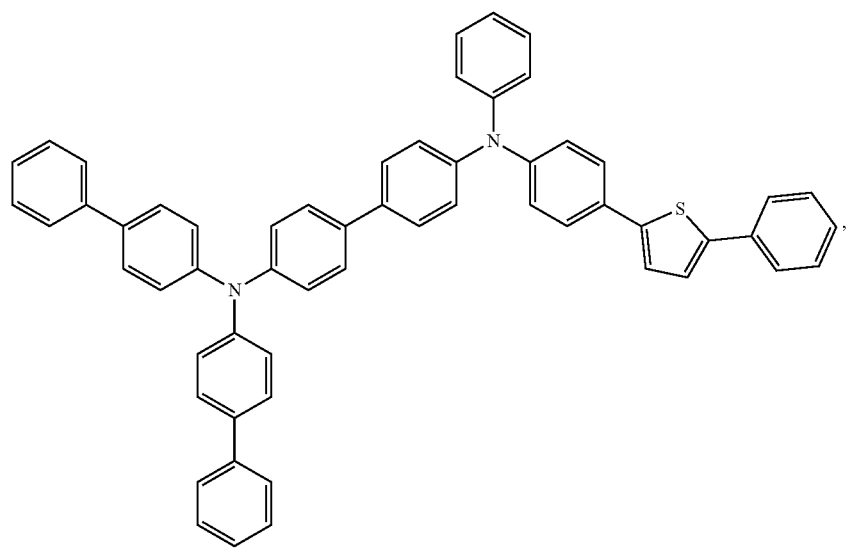
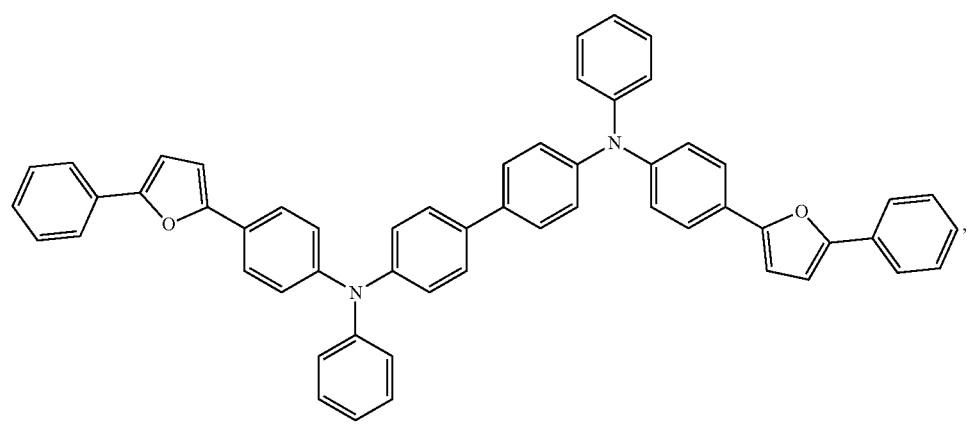

-continued
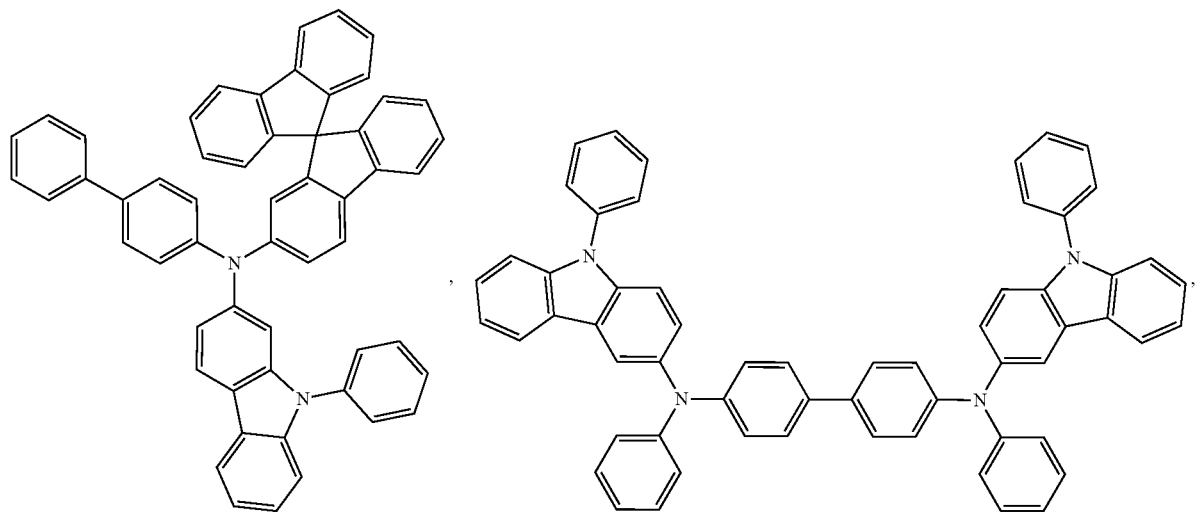
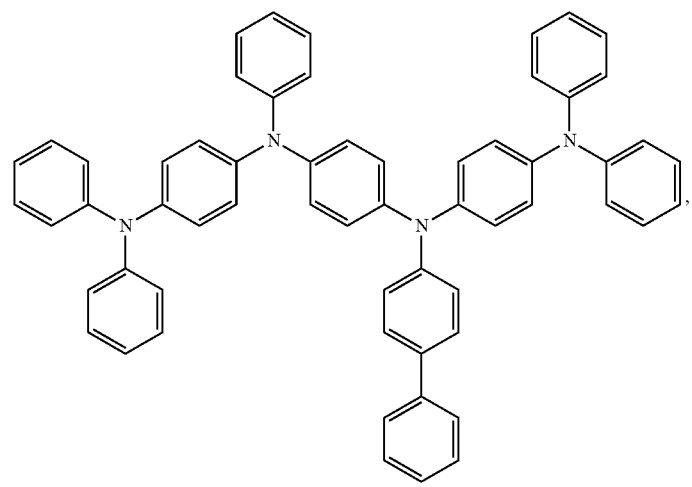
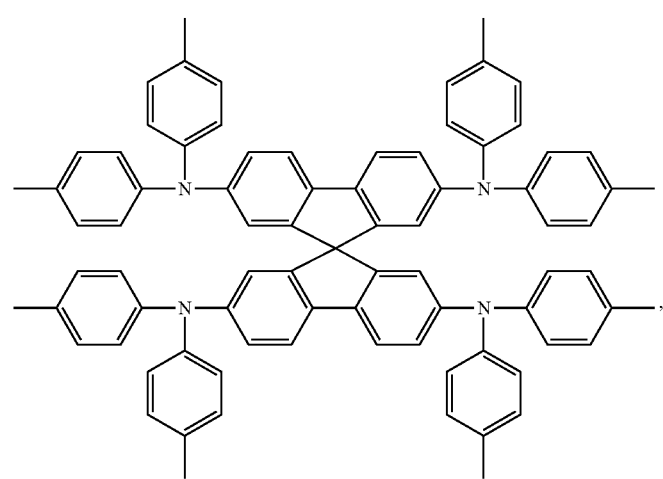

-continued
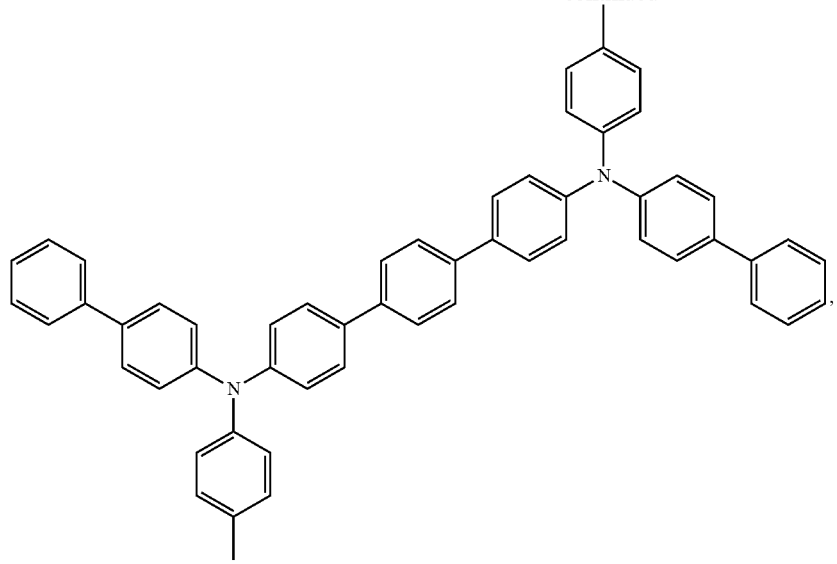
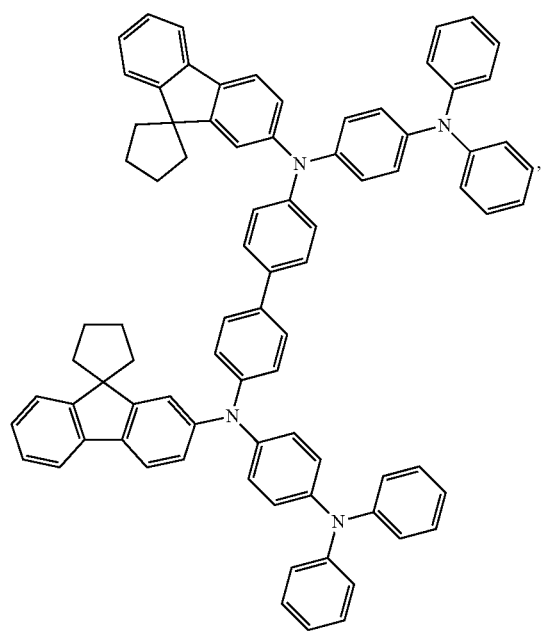
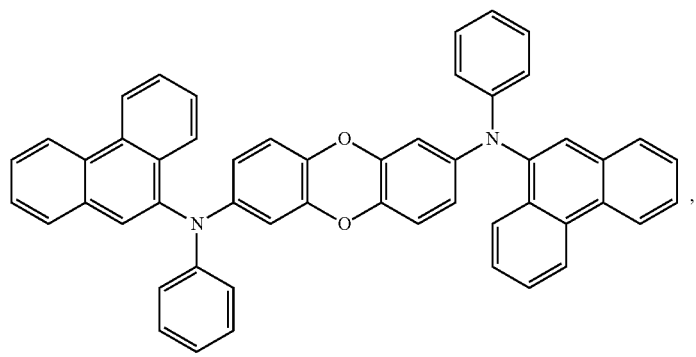

-continued
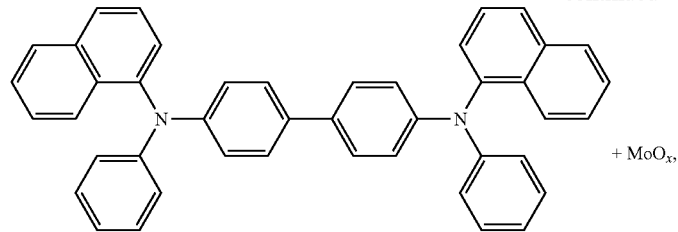
+ MoOx,
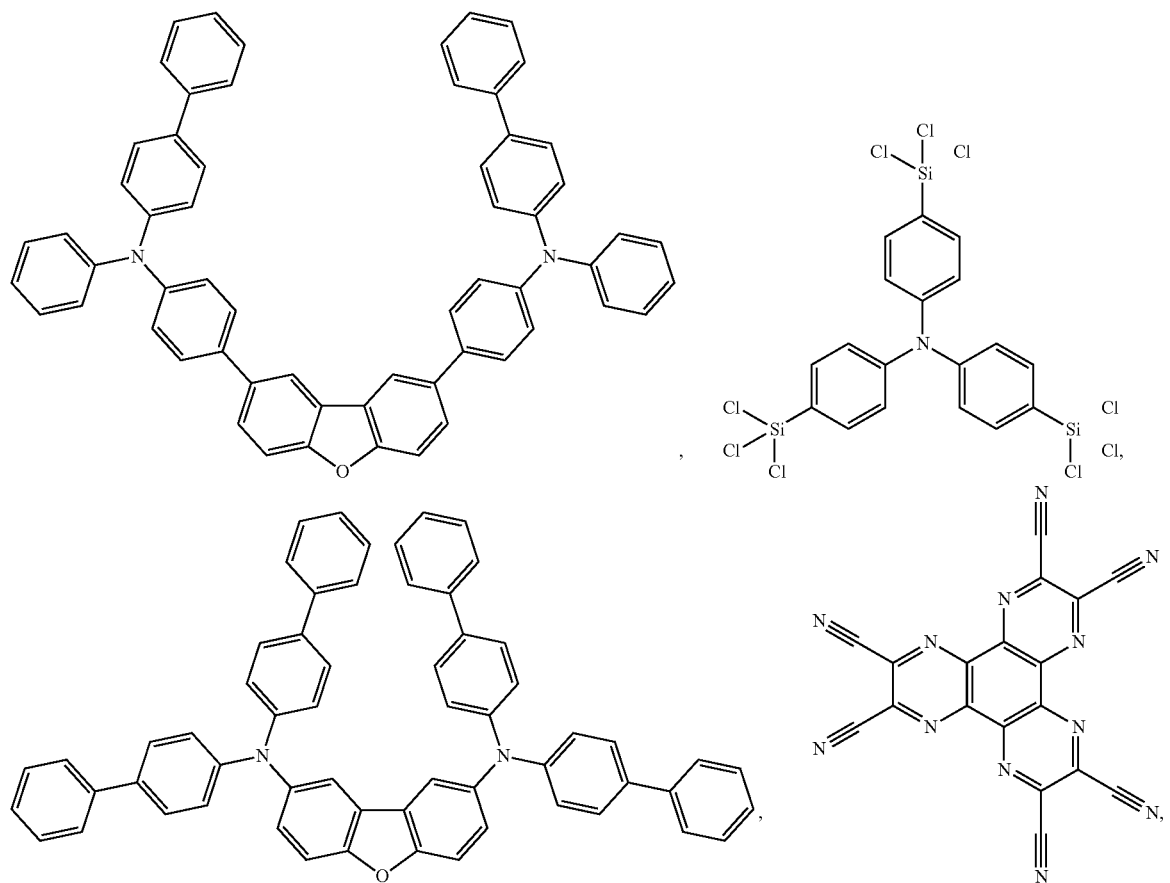
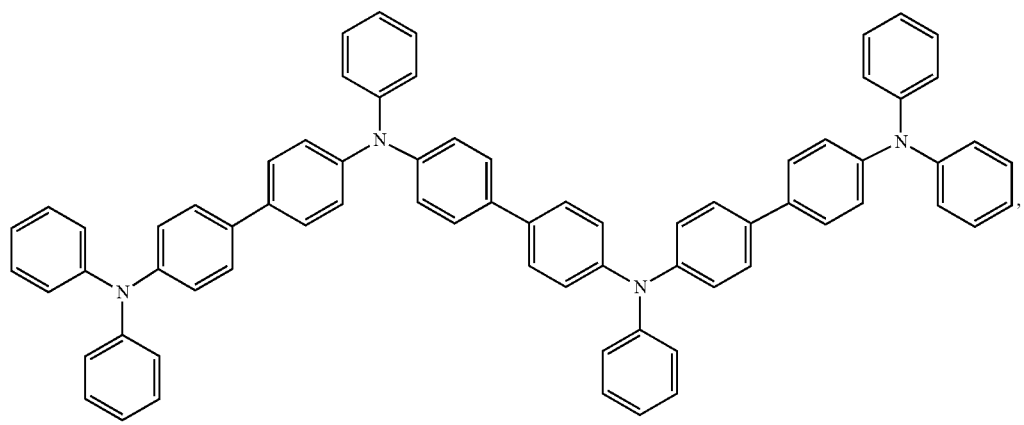

-continued
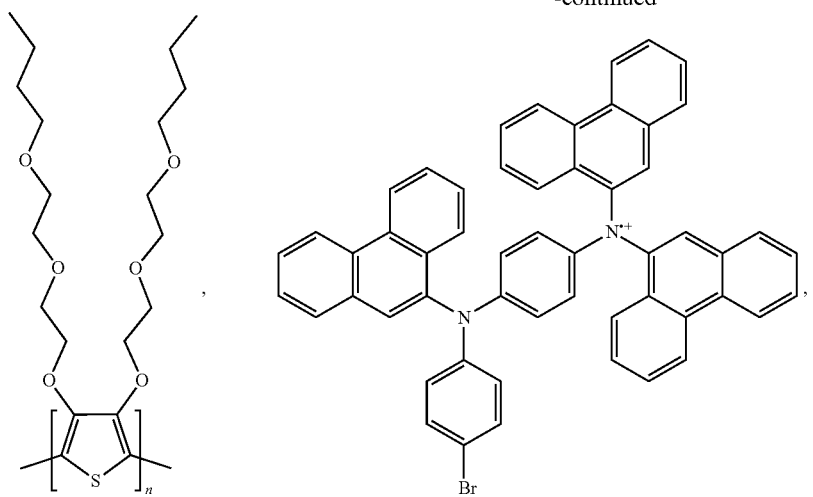
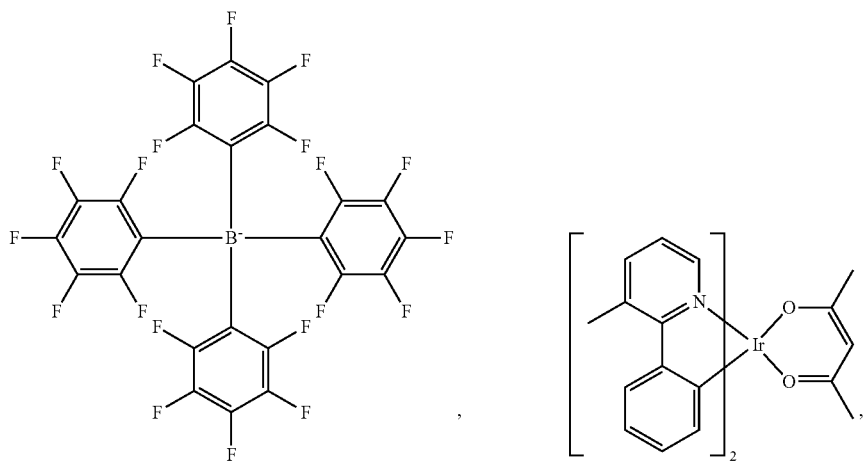
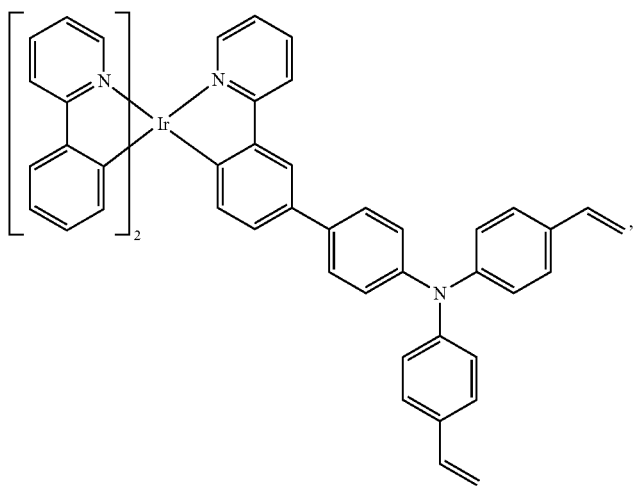

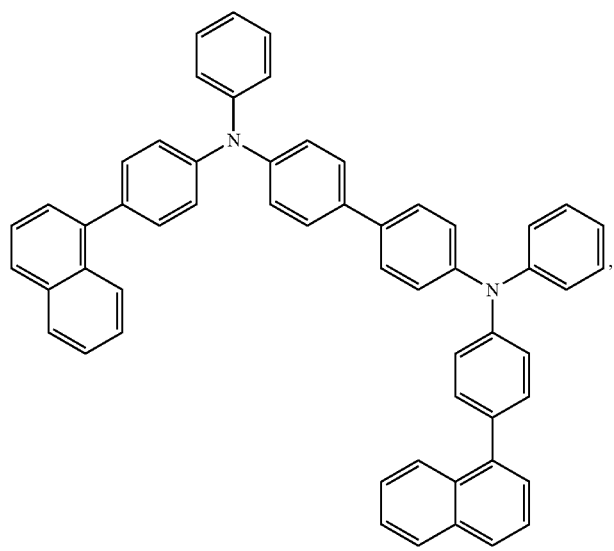
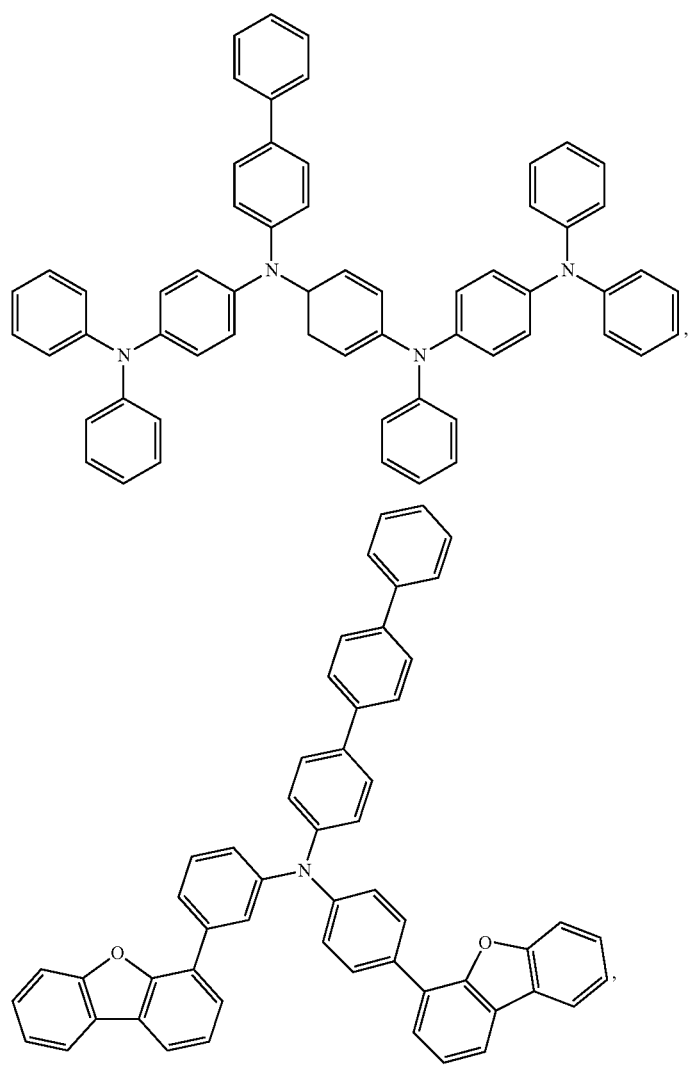

-continued
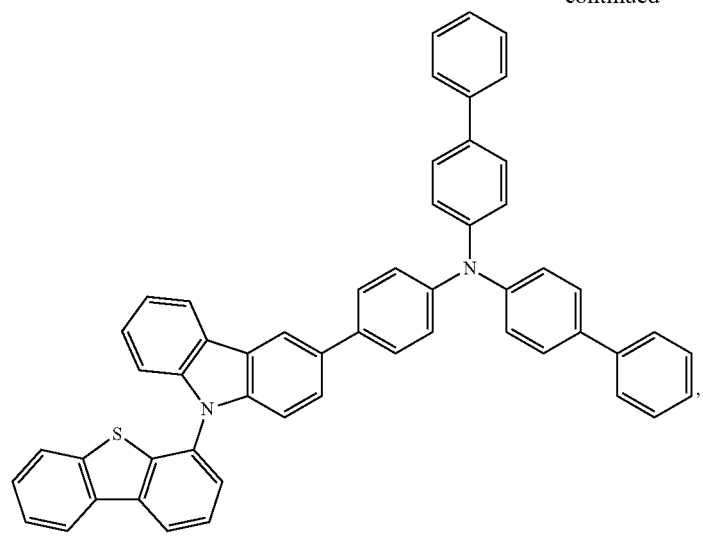
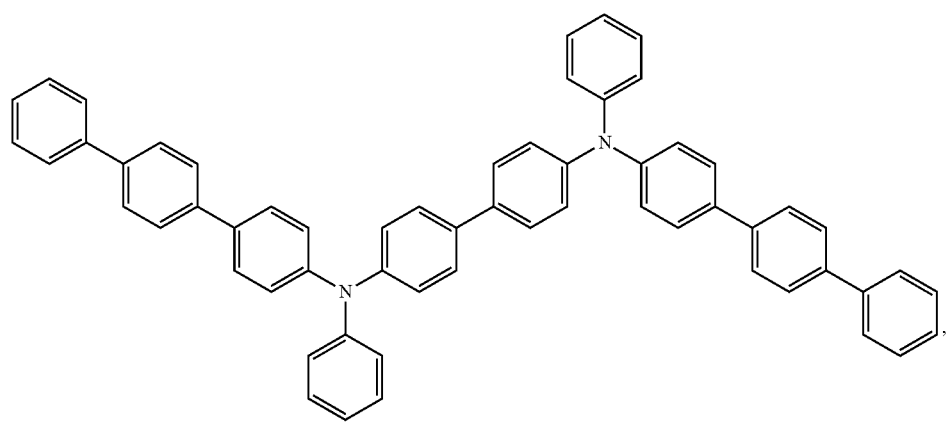
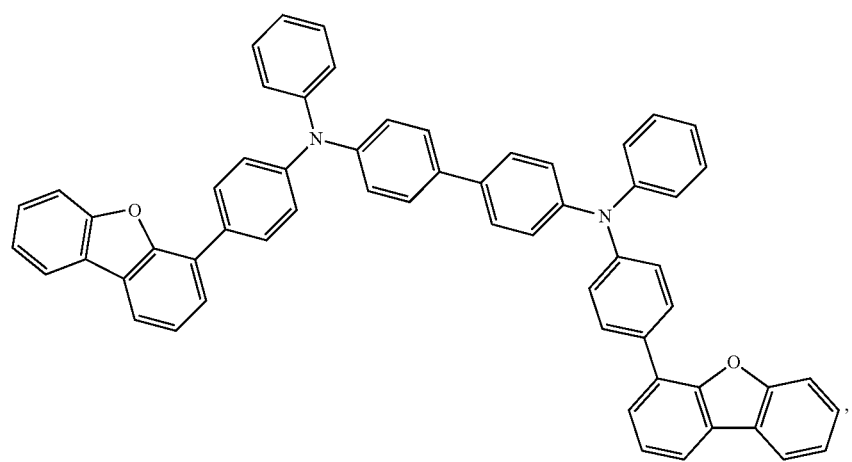

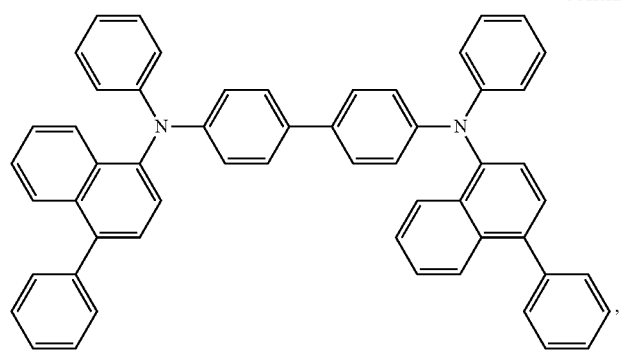
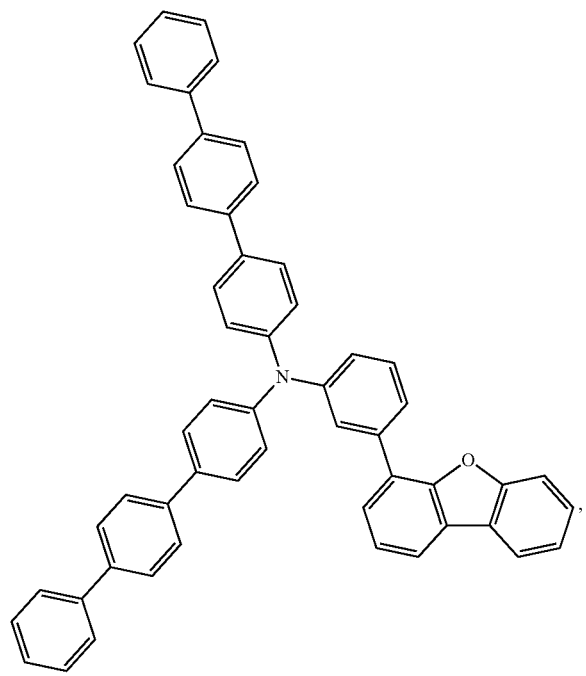
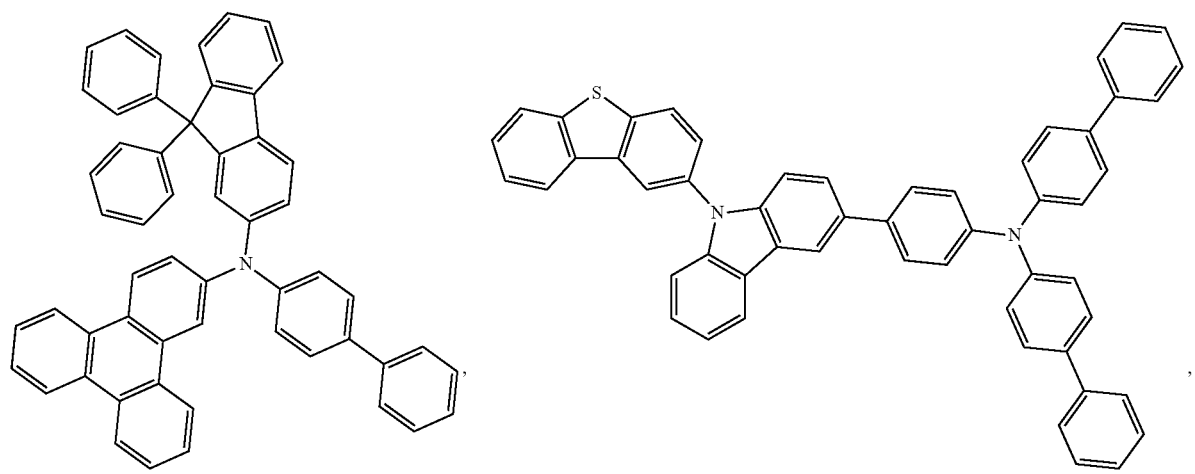

109
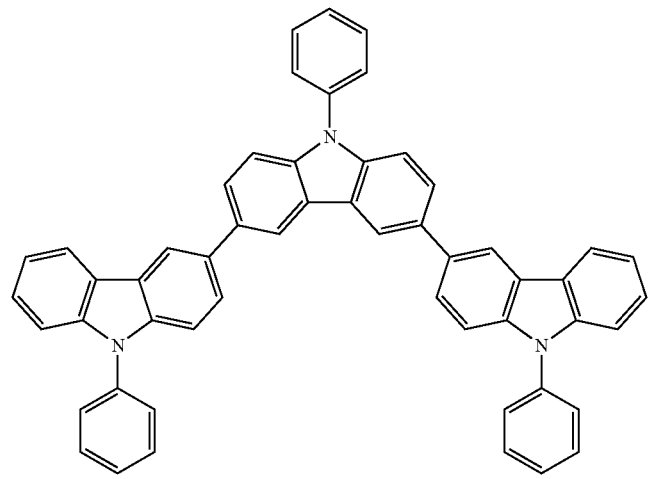
110
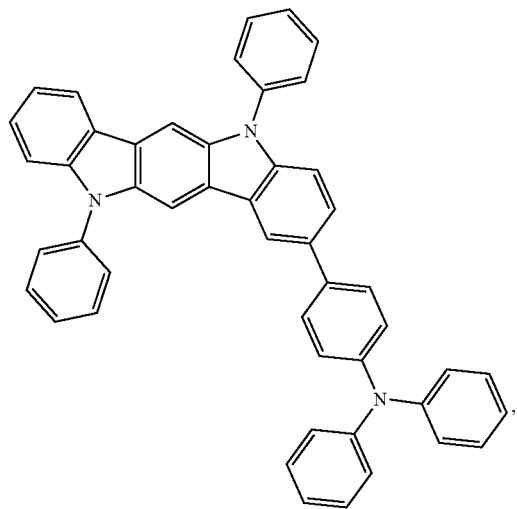
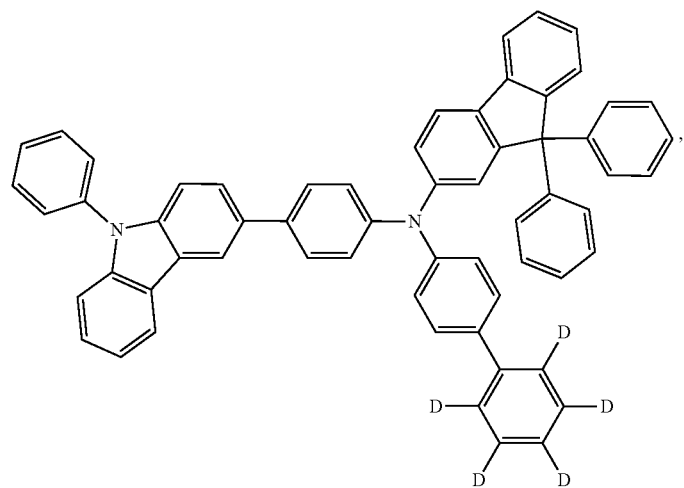
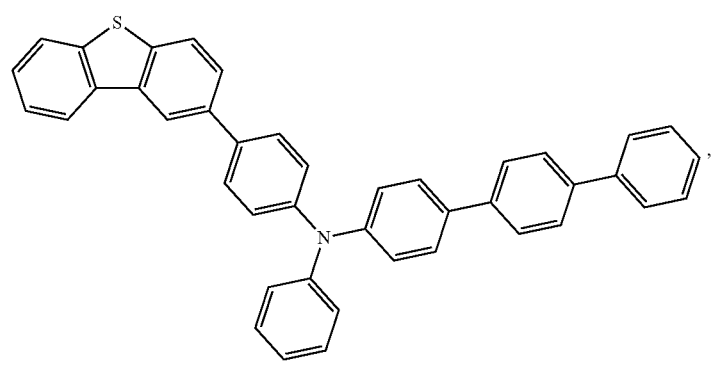

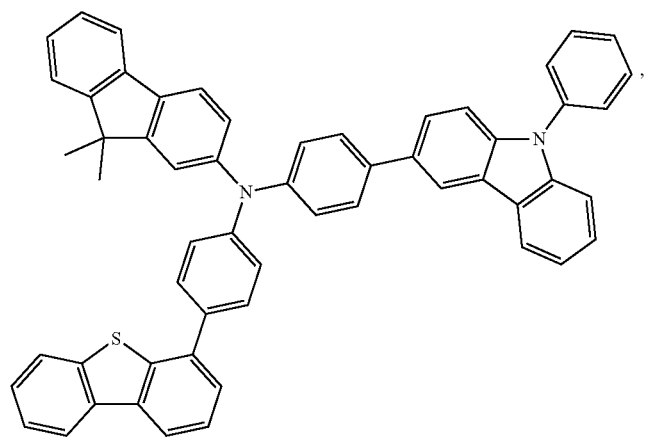
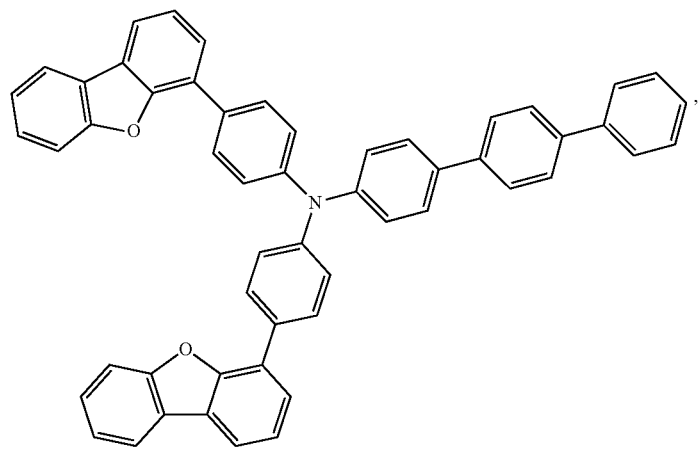
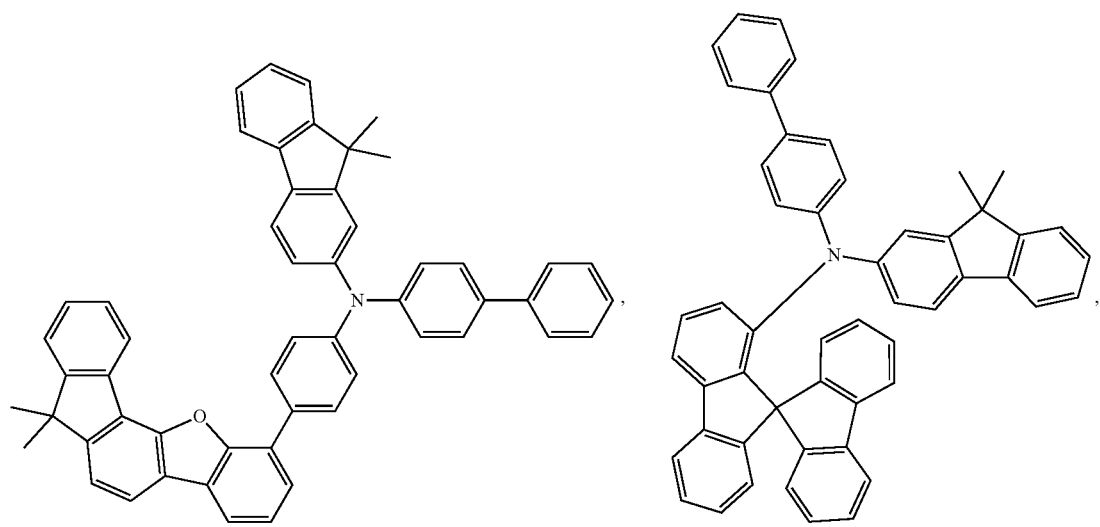

-continued
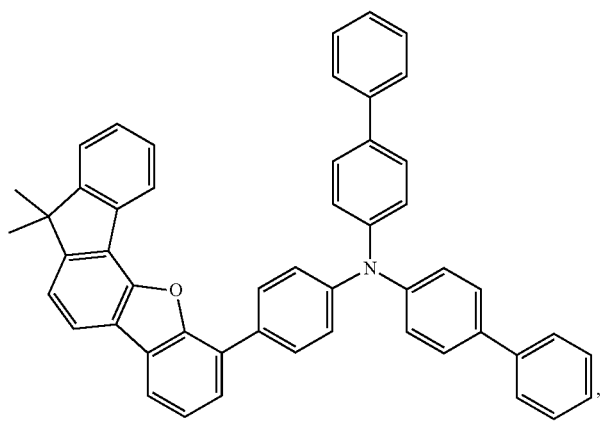
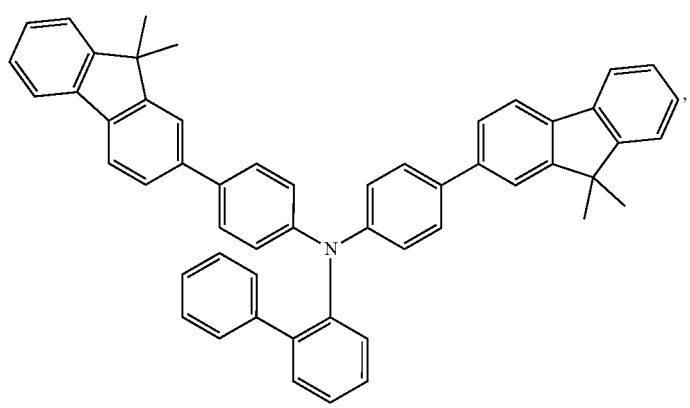
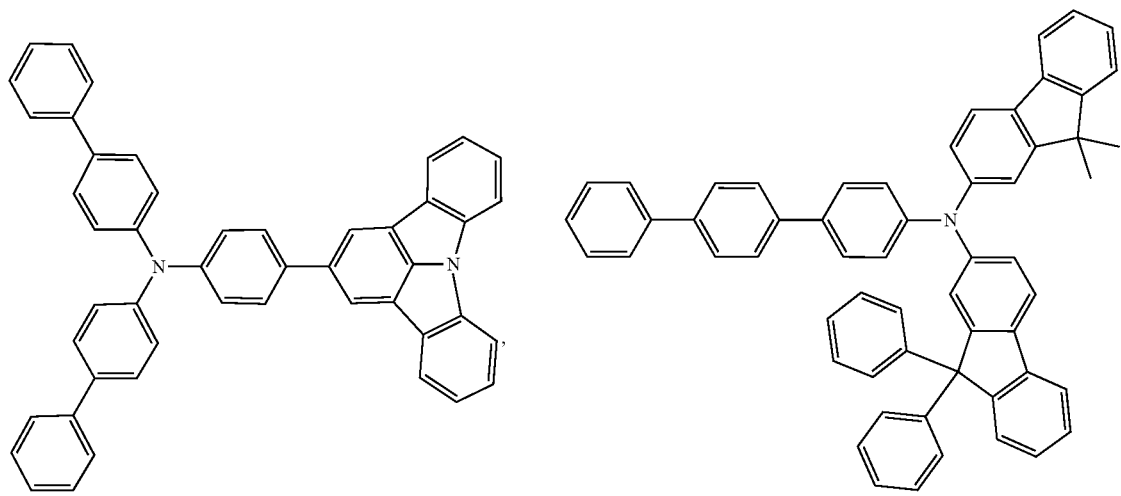

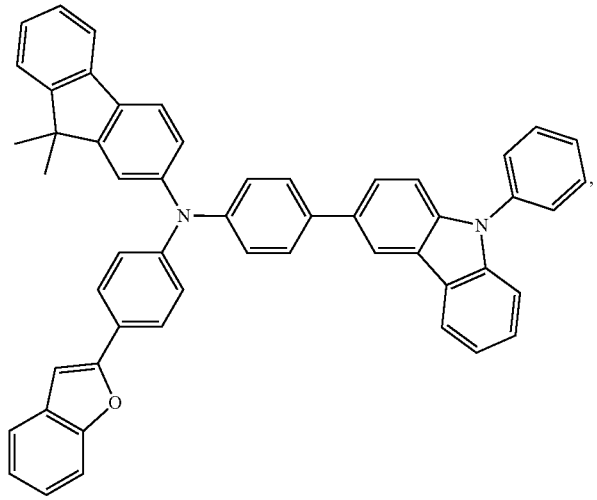
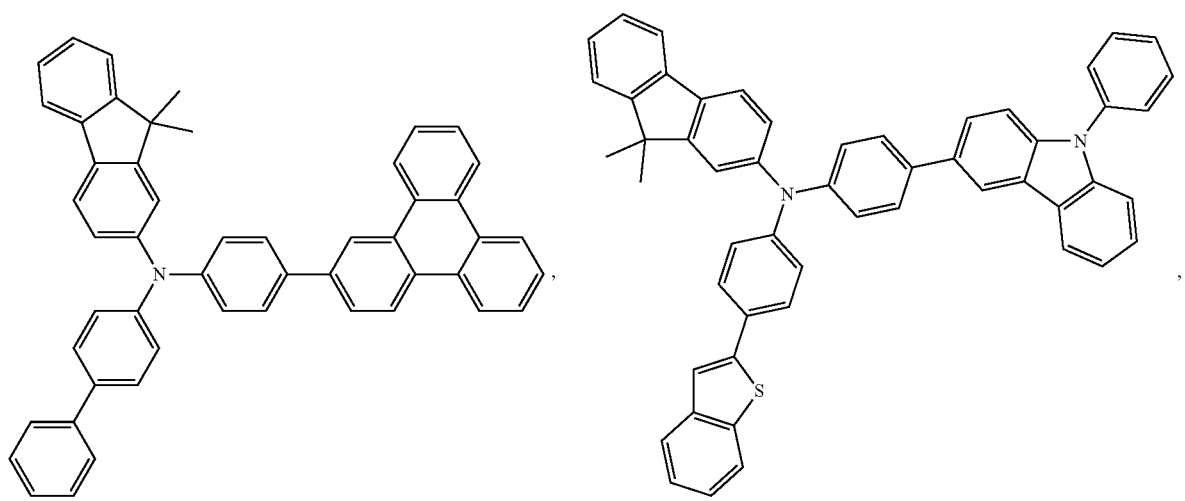
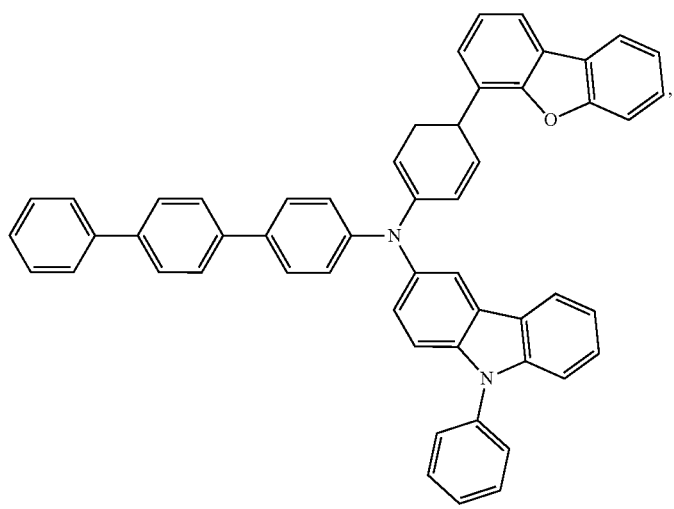

117 118
-continued
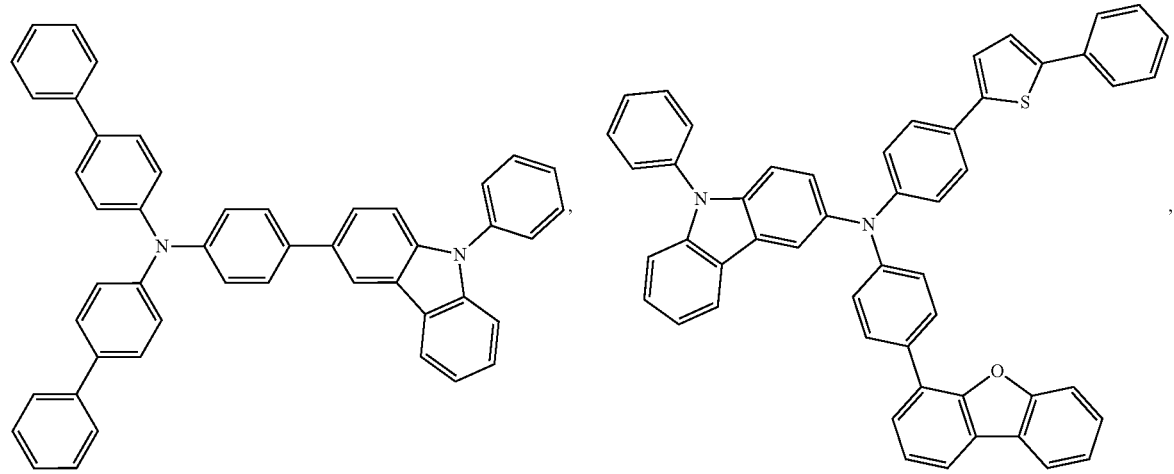
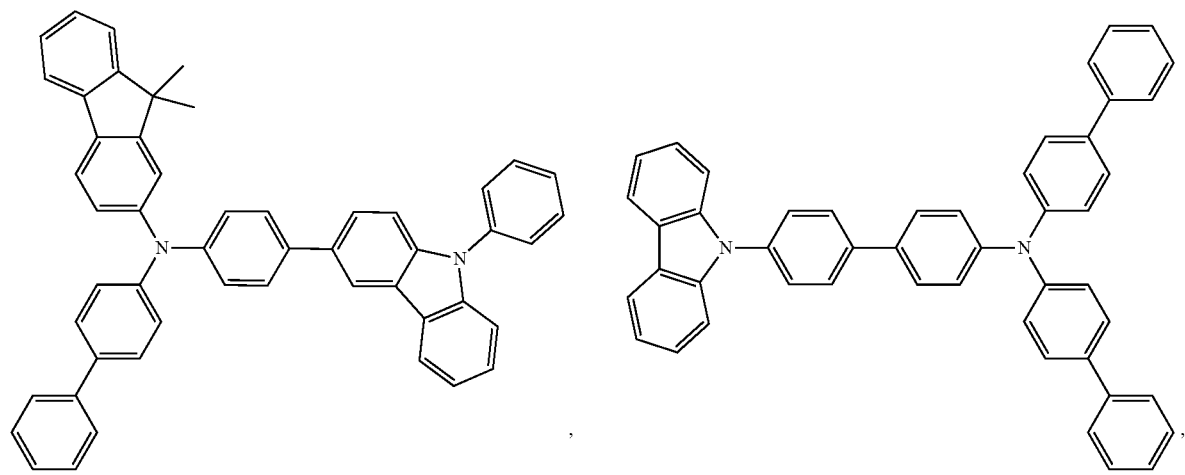
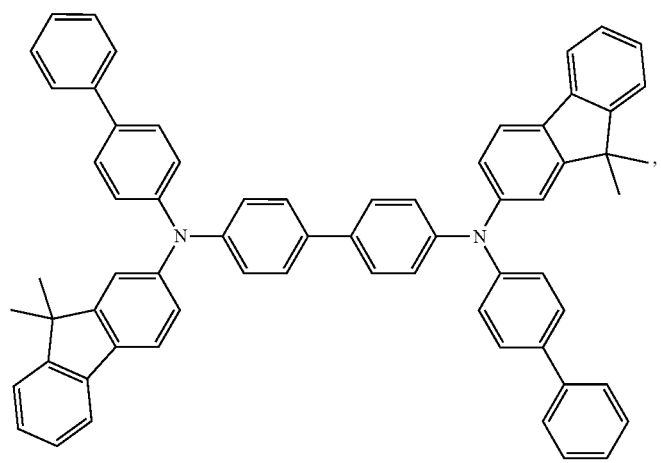

-continued
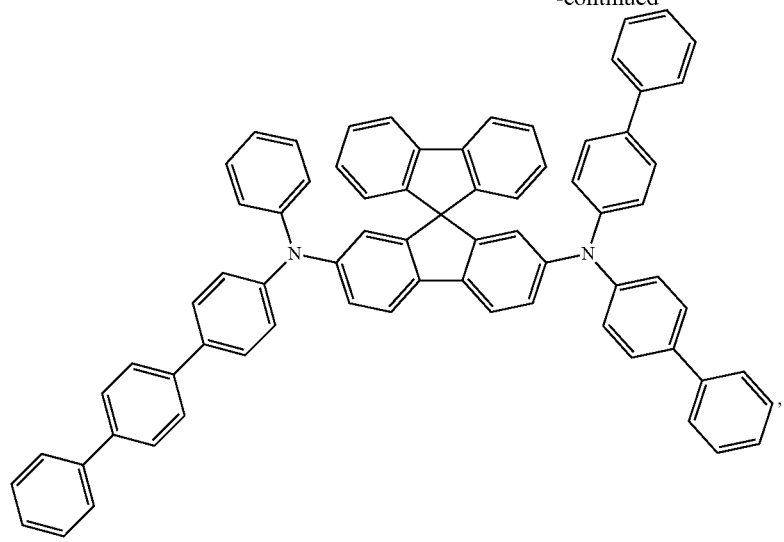
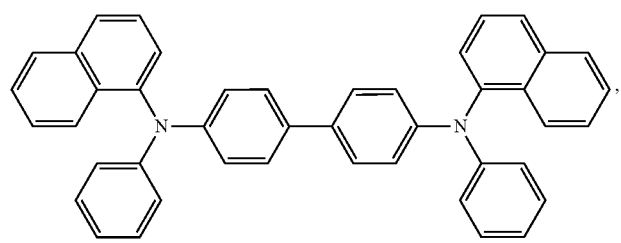
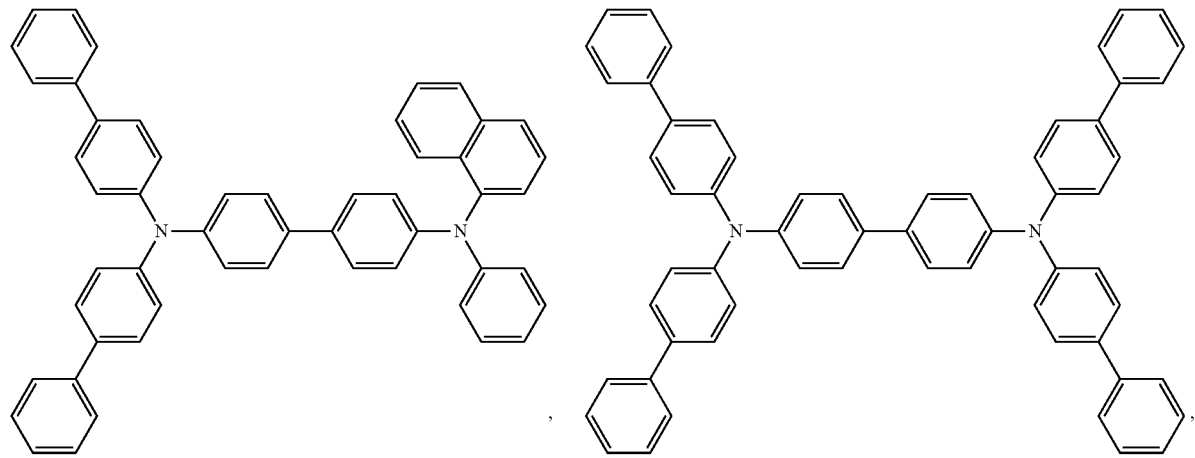
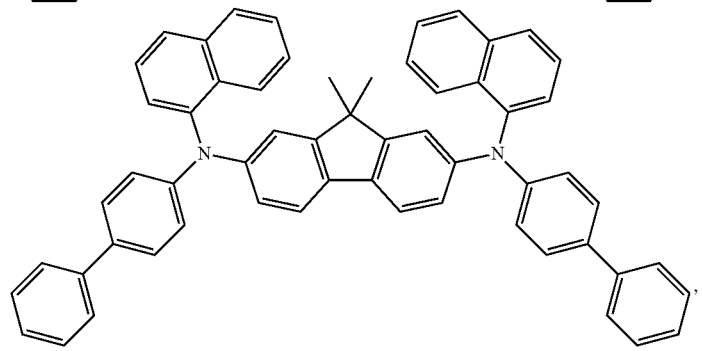

-continued
121
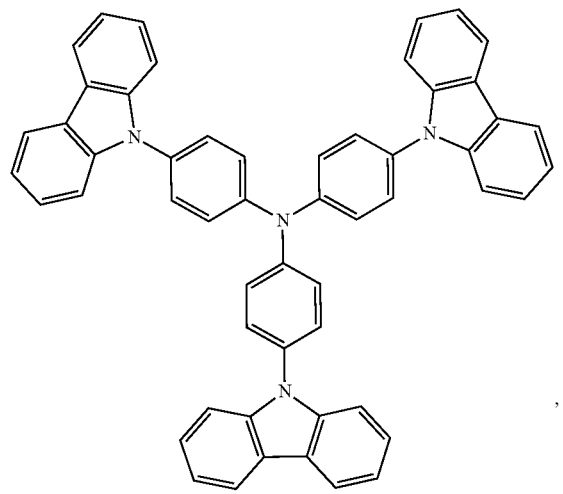
122
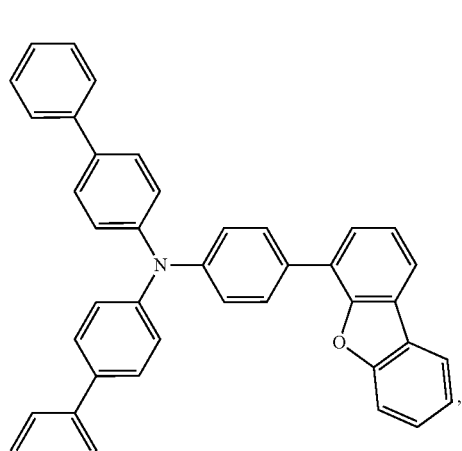
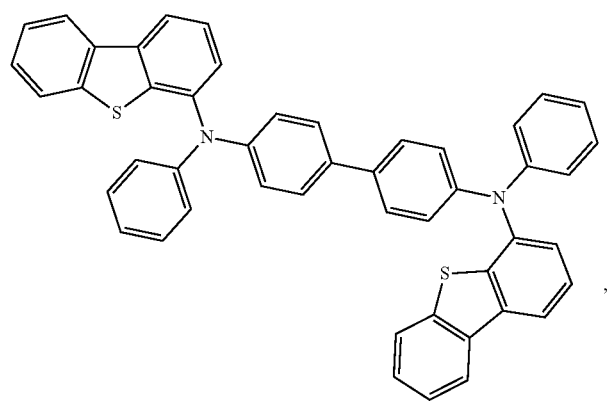
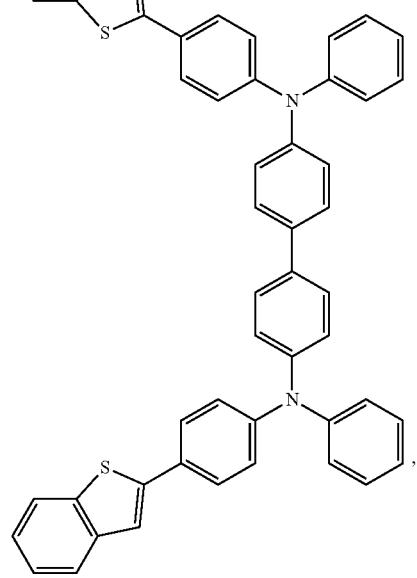
and
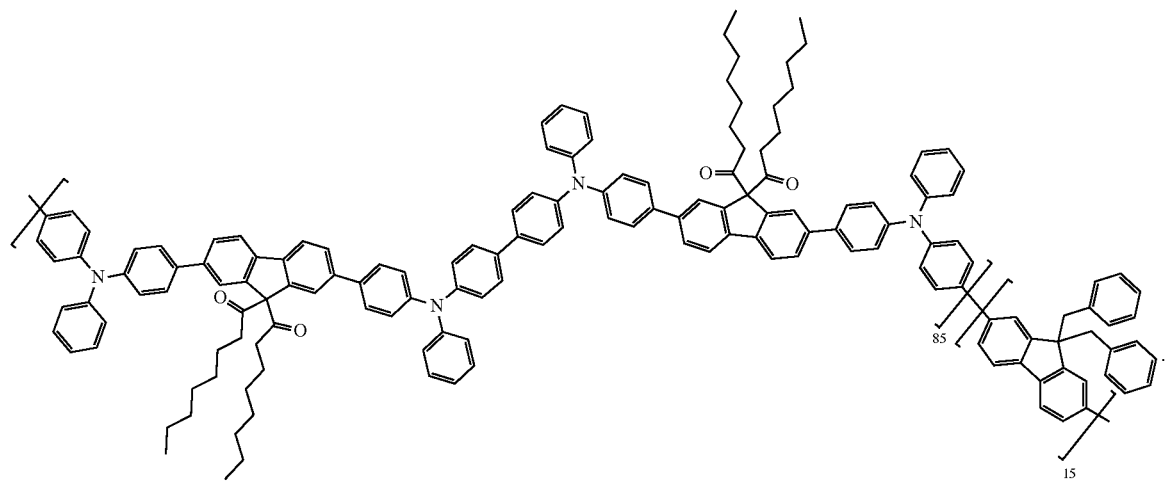

c) EBL:

An electron blocking layer (EBL) may be used to reduce the number of electrons and/or excitons that leave the emissive layer. The presence of such a blocking layer in a device may result in substantially higher efficiencies, and/or longer lifetime, as compared to a similar device lacking a blocking layer. Also, a blocking layer may be used to confine emission to a desired region of an OLED. In some embodiments, the EBL material has a higher LUMO (closer to the vacuum level) and/or higher triplet energy than the emitter closest to the EBL interface. In some embodiments, the EBL material has a higher LUMO (closer to the vacuum level) and/or higher triplet energy than one or more of the hosts closest to the EBL interface. In one aspect, the compound used in EBL contains the same molecule or the same functional groups used as one of the hosts described below.

d) Hosts:

The light emitting layer of the organic EL device of the present disclosure preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. Any host material may be used with any dopant so long as the triplet criteria is satisfied.

Examples of metal complexes used as host are preferred to have the following general formula:

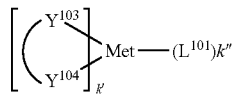

wherein Met is a metal; ($Y^{103}$-$Y^{104}$) is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

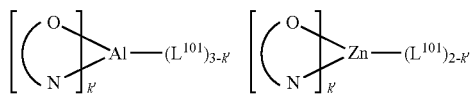

wherein (O—N) is a bidentate ligand, having metal coordinated to atoms O and N.

In another aspect, Met is selected from Ir and Pt. In a further aspect, ($Y^{103}$-$Y^{104}$) is a carbene ligand.

In one aspect, the host compound contains at least one of the following groups selected from the group consisting of aromatic hydrocarbon cyclic compounds such as benzene, biphenyl, triphenyl, triphenylene, tetraphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each option within each group may be unsubstituted or may be substituted by a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof.

In one aspect, the host compound contains at least one of the following groups in the molecule:

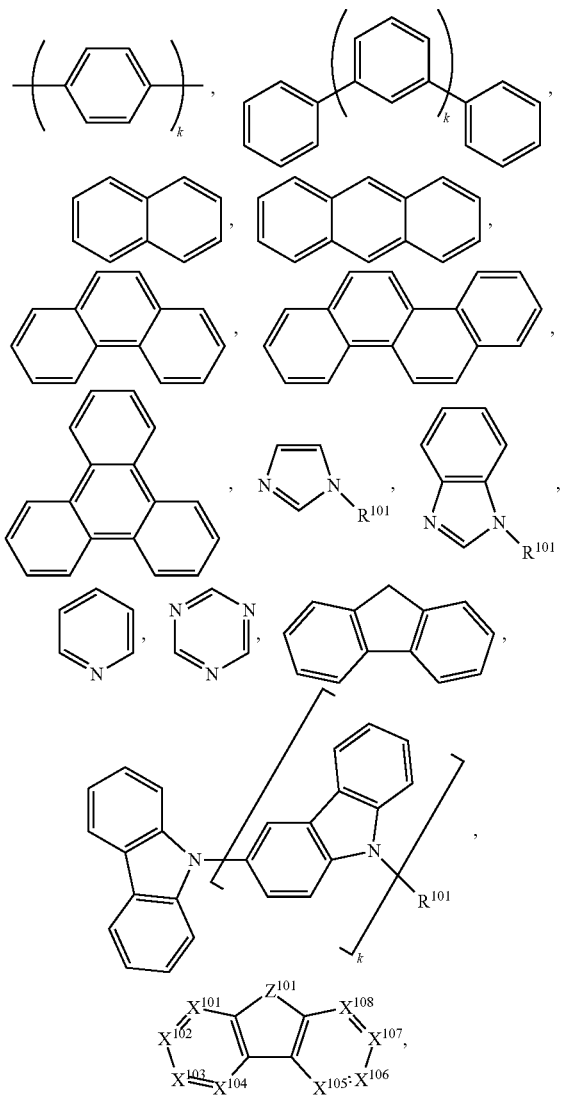

-continued

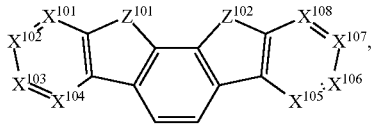

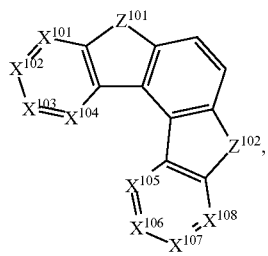

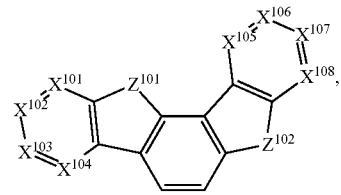

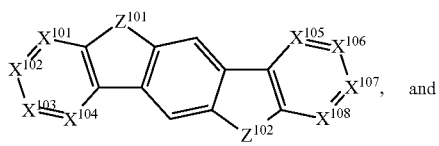

-continued

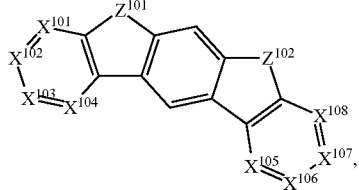

wherein $R^{101}$ is selected from the group consisting of hydrogen, deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof, and when it is aryl or heteroaryl, it has the similar definition as Ar's mentioned above. k is an integer from 0 to 20 or 1 to 20. $X^{101}$ to $X^{108}$ are independently selected from C (including CH) or N. $Z^{101}$ and $Z^{102}$ are independently selected from $NR^{101}$, O, or S.

Non-limiting examples of the host materials that may be used in an OLED in combination with materials disclosed herein are exemplified below together with references that disclose those materials: EP2034538, EP2034538A, EP2757608, JP2007254297, KR20100079458, KR20120088644, KR20120129733, KR20130115564, TW201329200, US20030175553, US20050238919, US20060280965, US20090017330, US20090030202, US20090167162, US20090302743, US20090309488, US20100012931, US20100084966, US20100187984, US2010187984, US2012075273, US2012126221, US2013009543, US2013105787, US2013175519, US2014001446, US20140183503, US20140225088, US2014034914, U.S. Pat. No. 7,154,114, WO2001039234, WO2004093207, WO2005014551, WO2005089025, WO2006072002, WO2006114966, WO2007063754, WO2008056746, WO2009003898, WO2009021126, WO2009063833, WO2009066778, WO2009066779, WO2009086028, WO2010056066, WO2010107244, WO2011081423, WO2011081431, WO2011086863, WO2012128298, WO2012133644, WO2012133649, WO2013024872, WO2013035275, WO2013081315, WO2013191404, WO2014142472, US20170263869, US20160163995, U.S. Pat. No. 9,466,803,

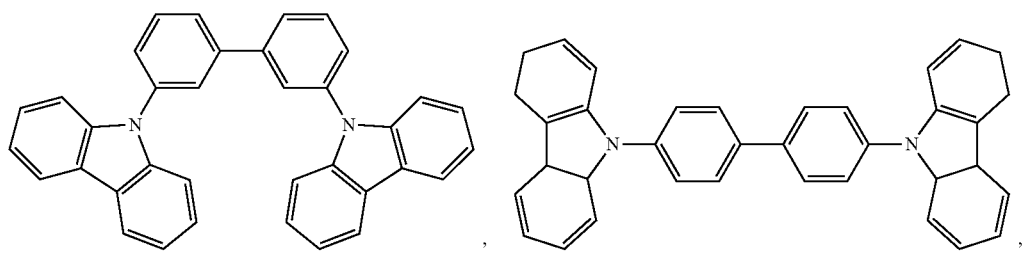

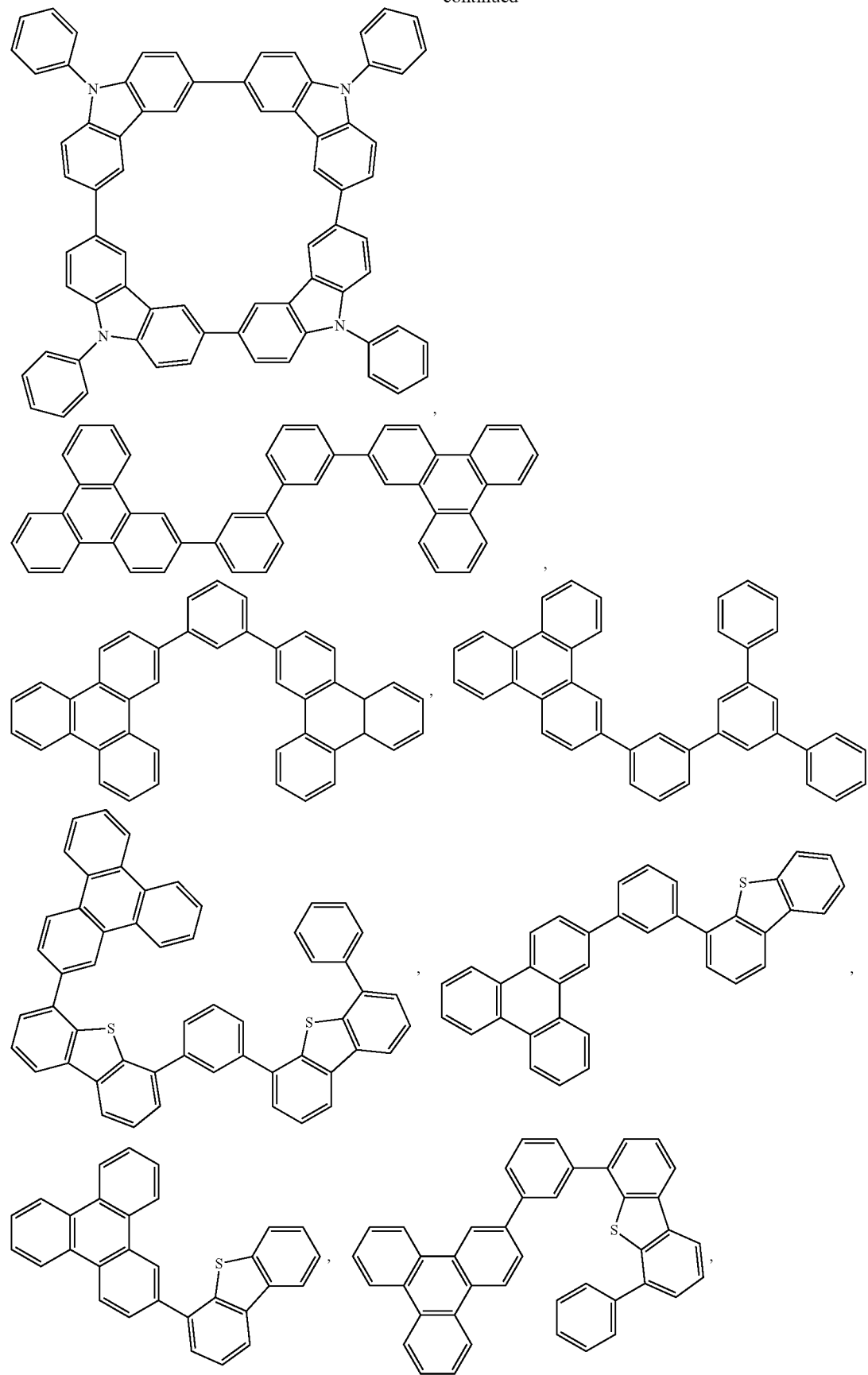

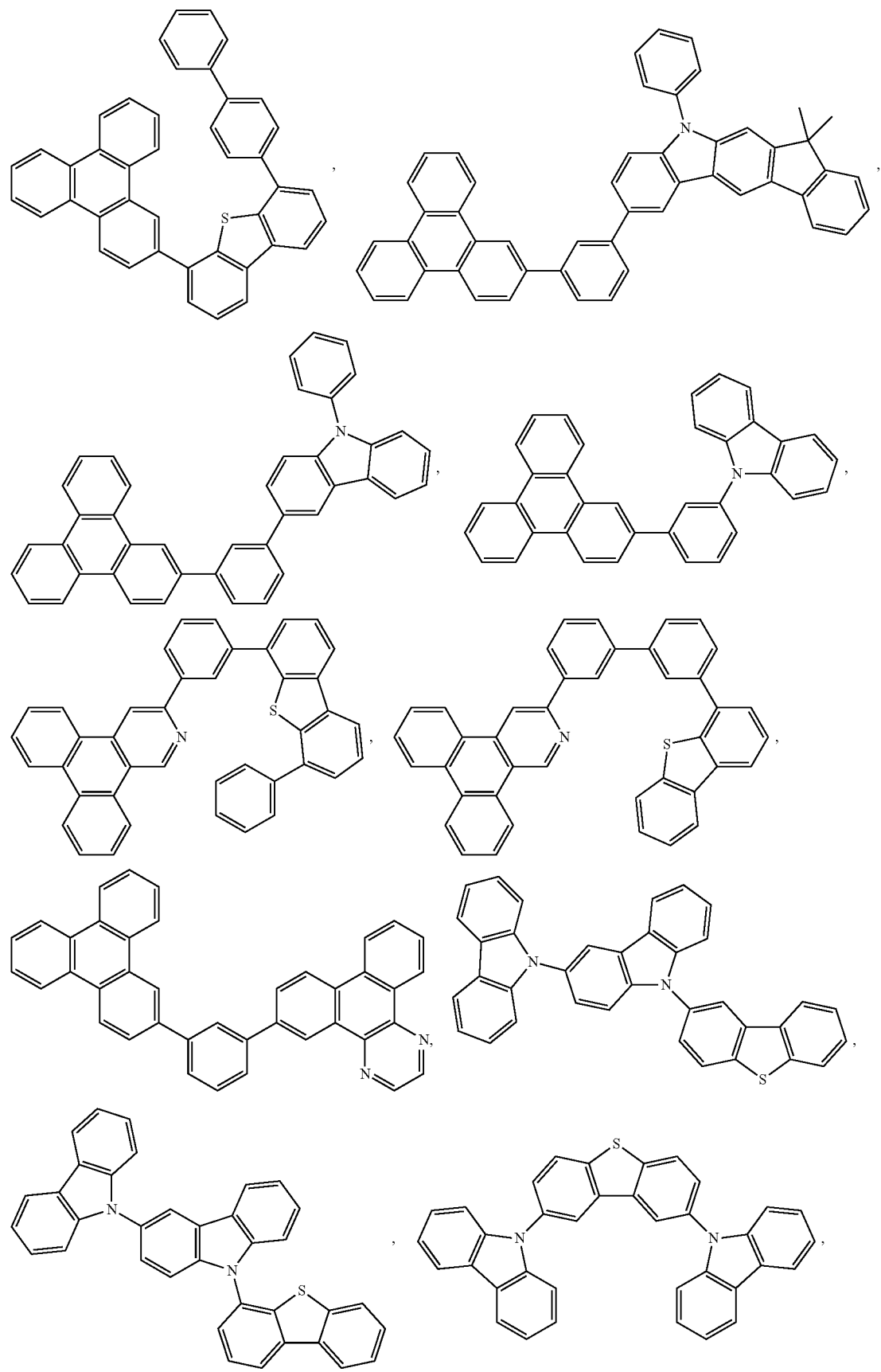

131
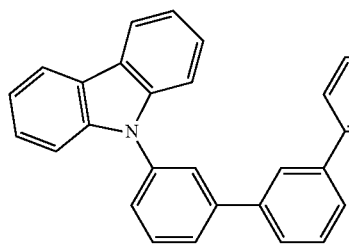
132
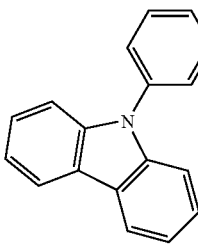
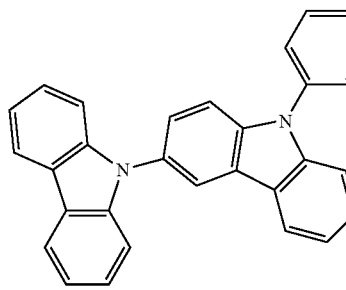
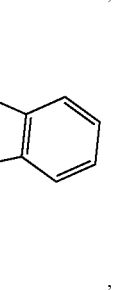
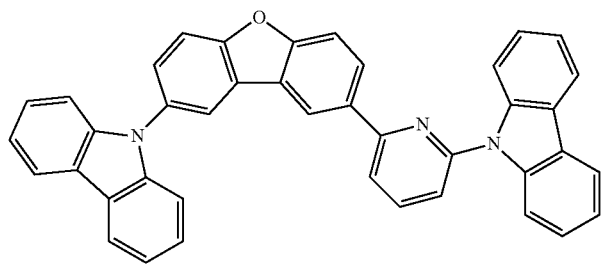
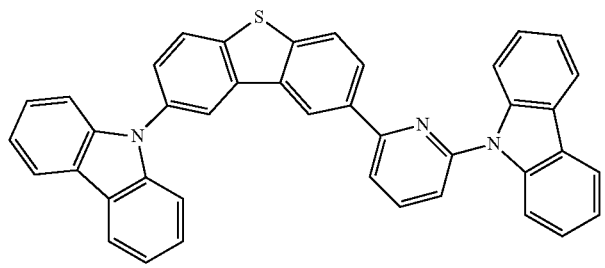
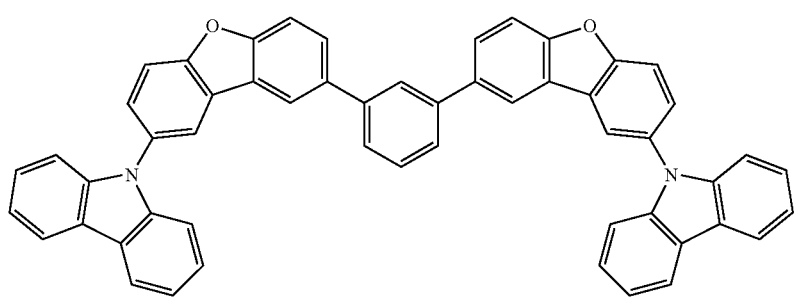

-continued
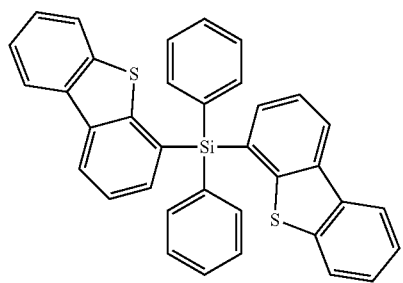
,
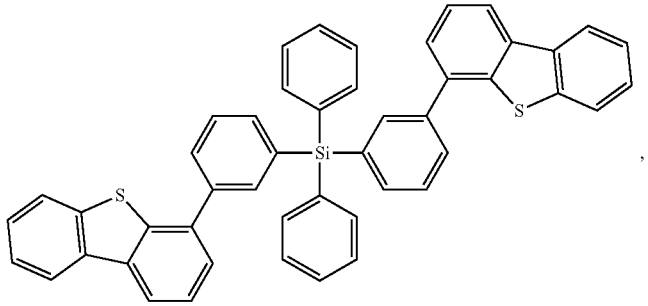
,
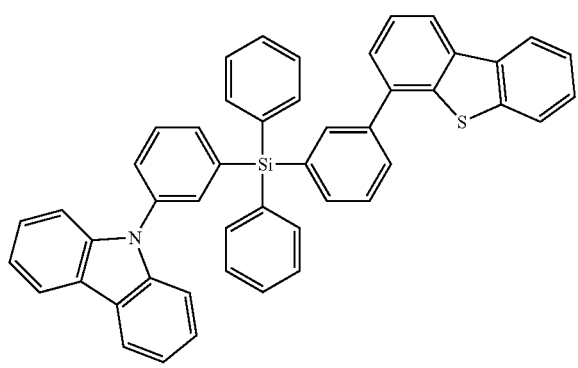
,
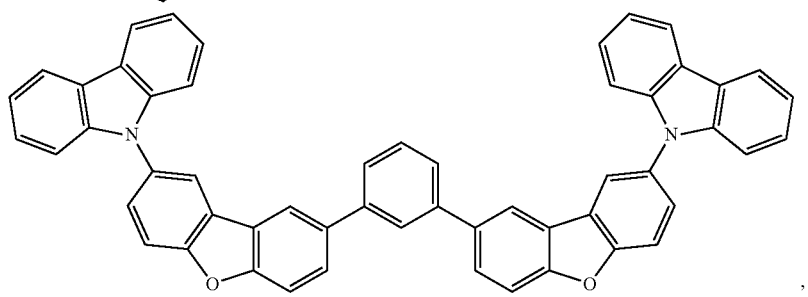
,
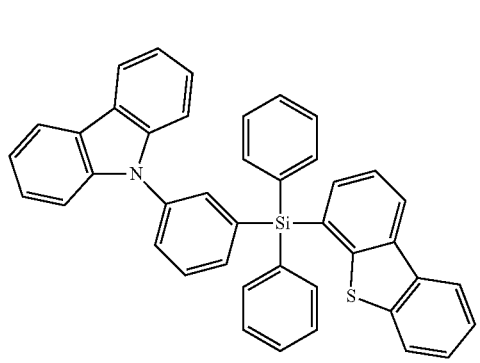
,
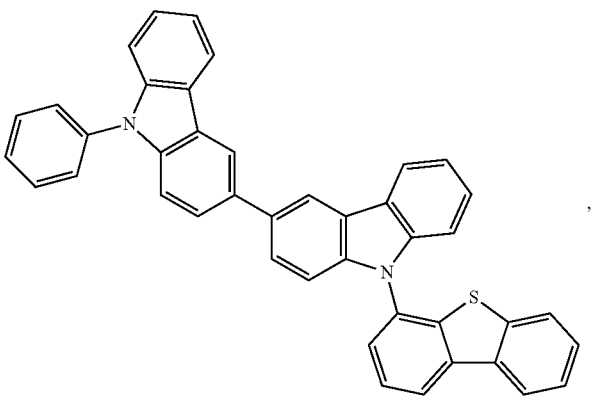
,
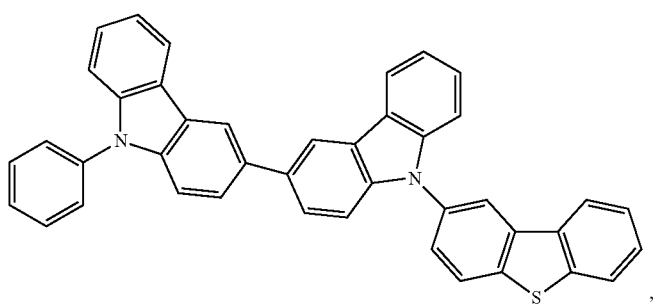
, -continued
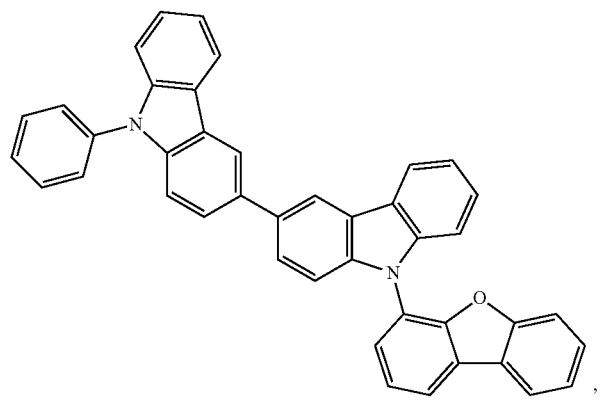
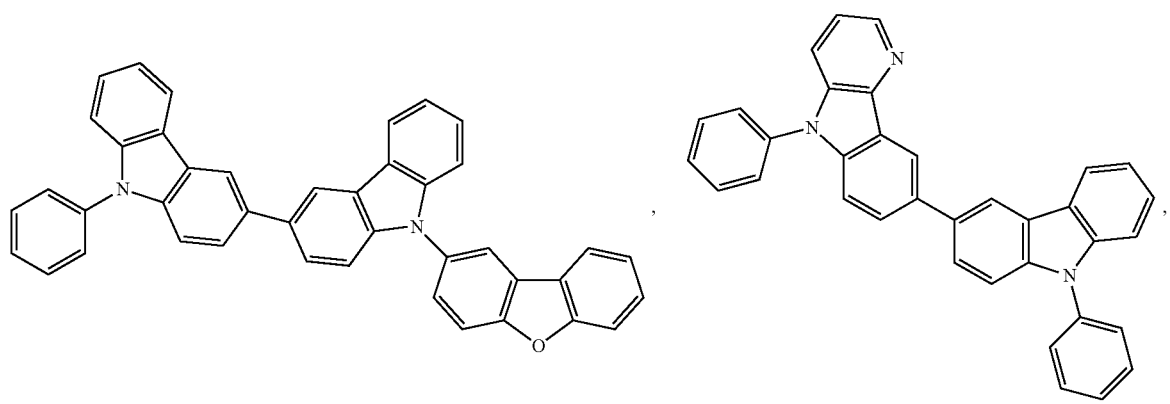
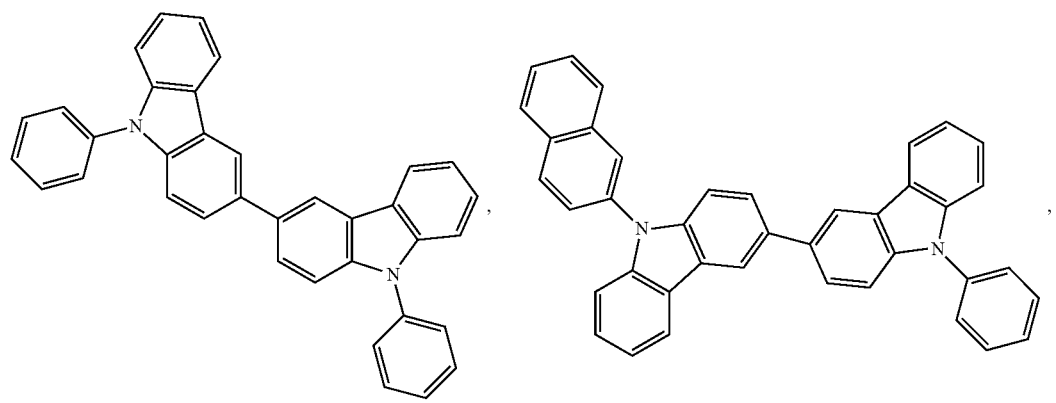
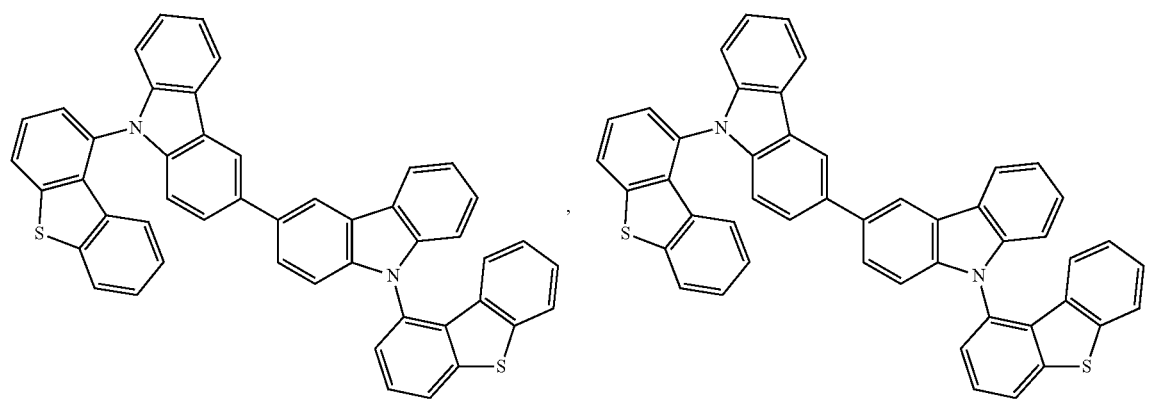

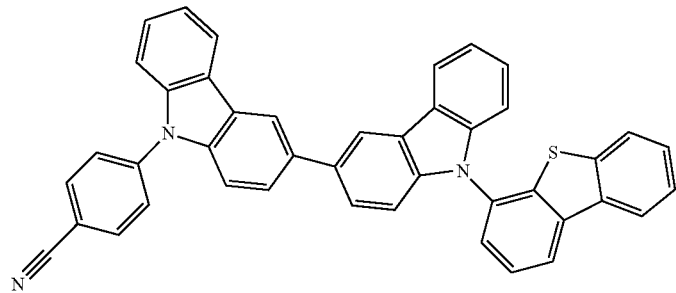
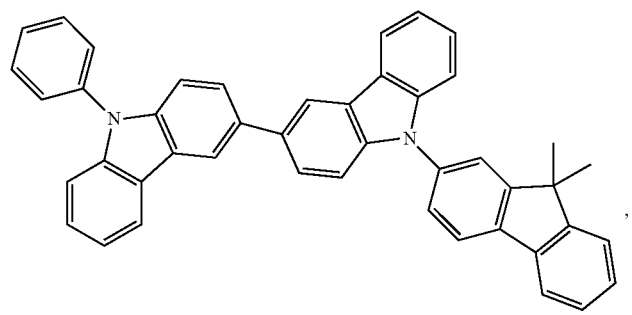
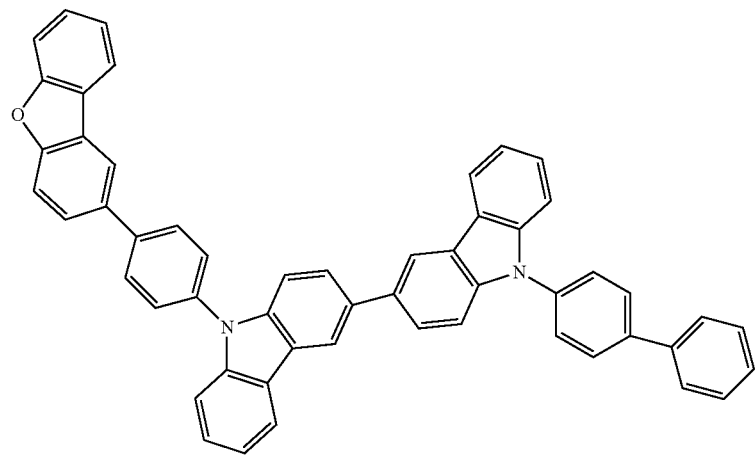
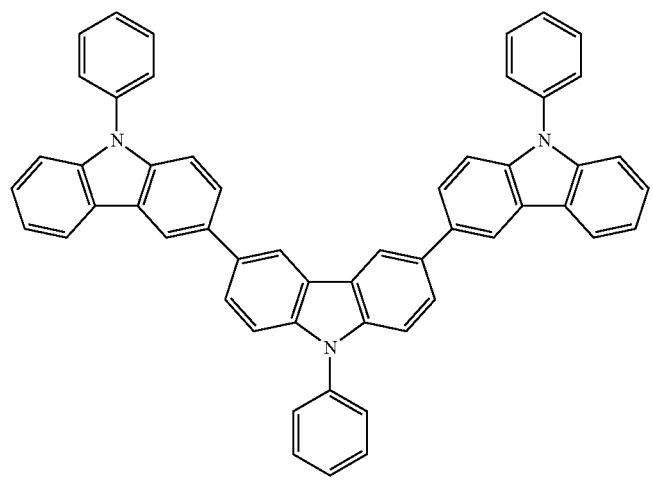

-continued
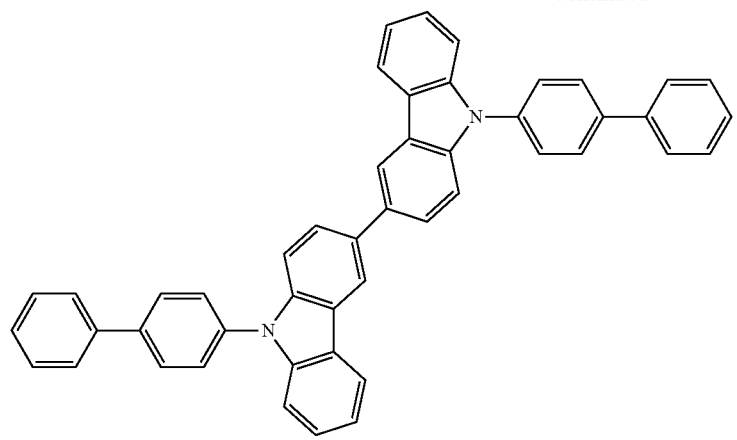
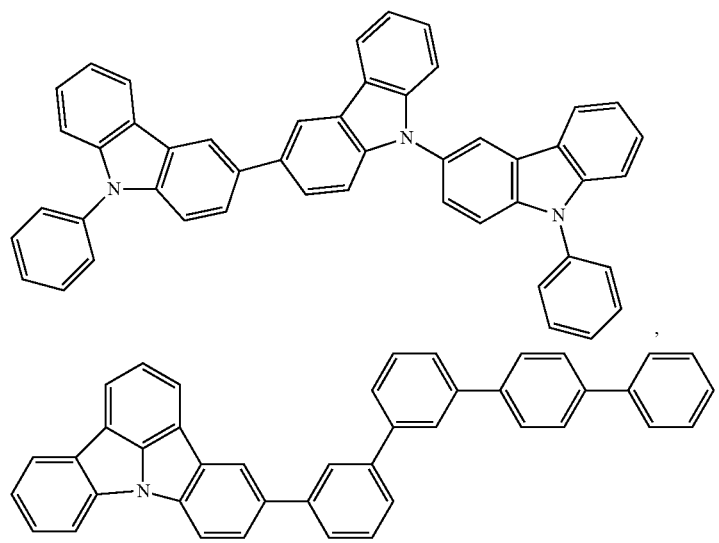
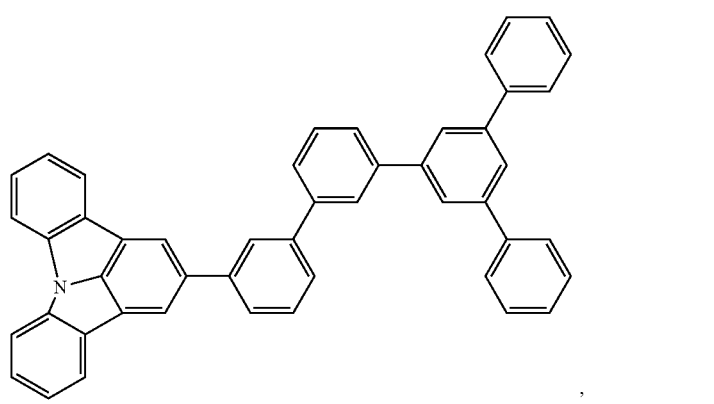
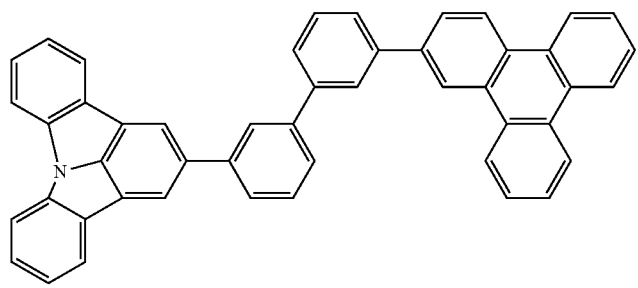

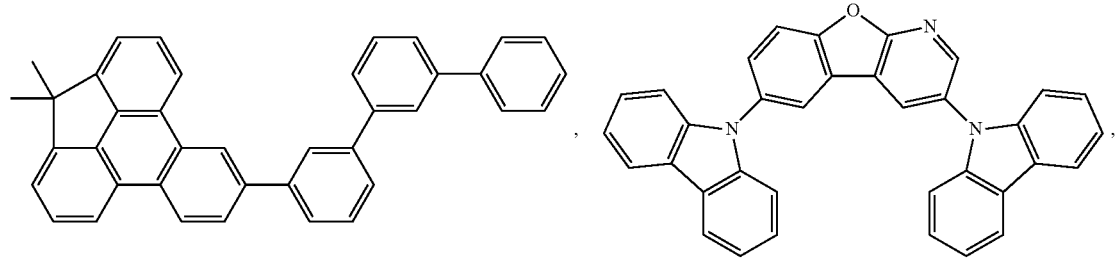
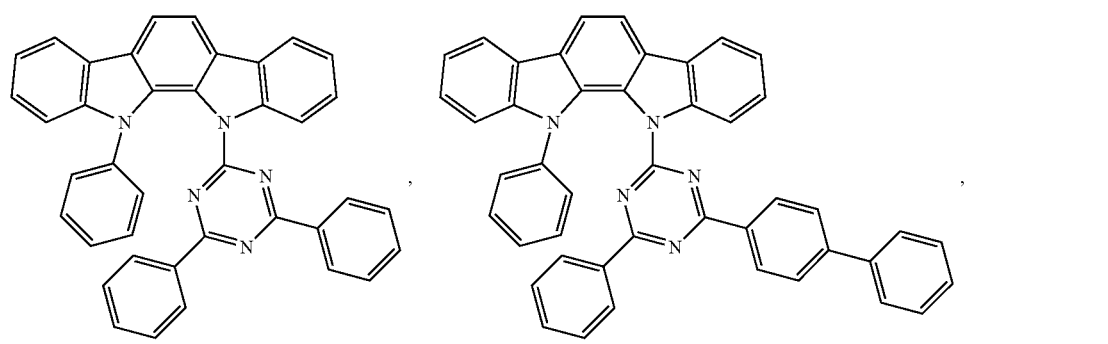
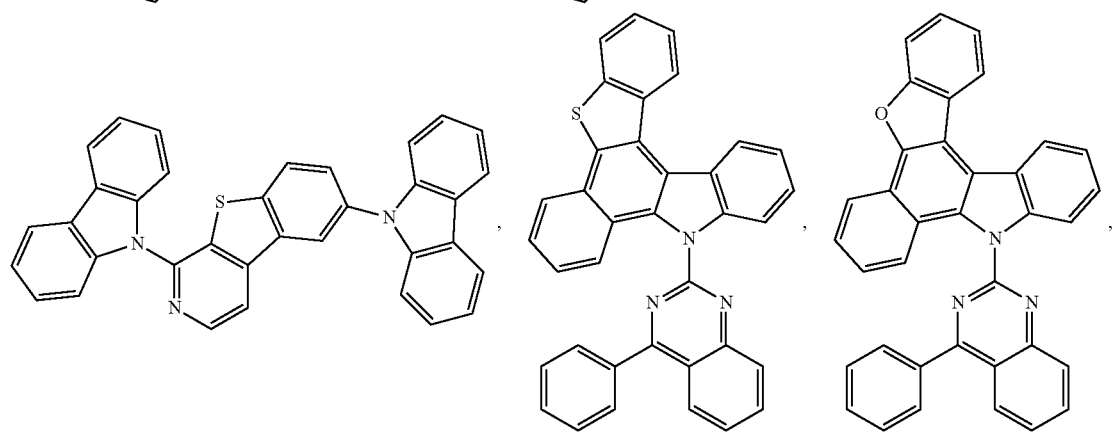
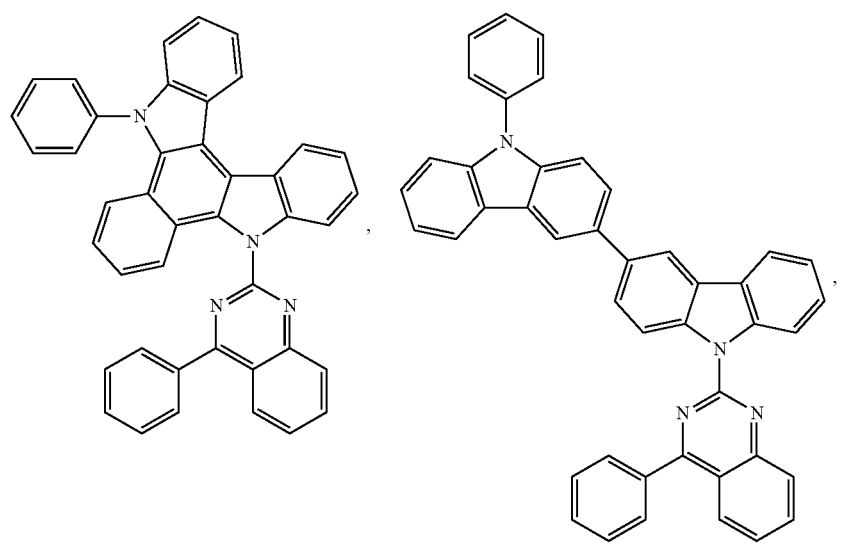

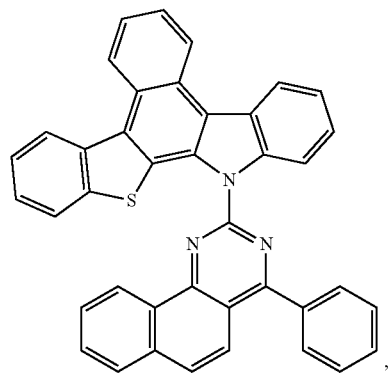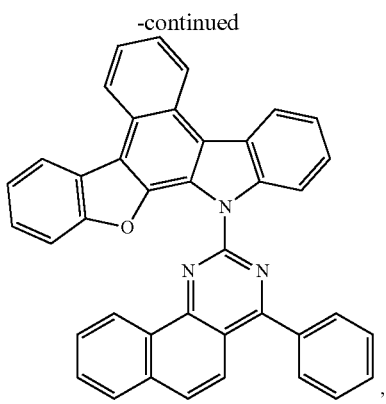
-continued
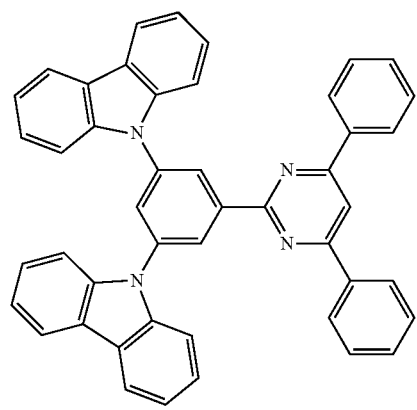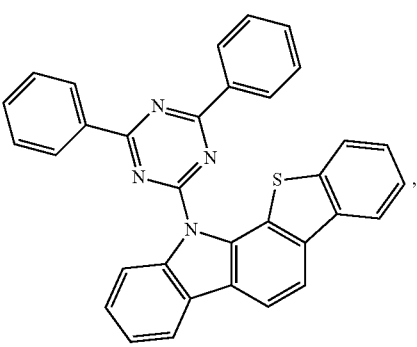
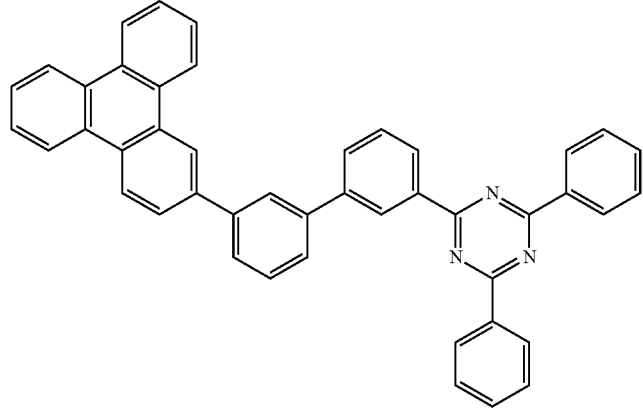
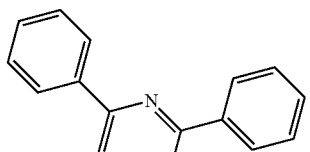
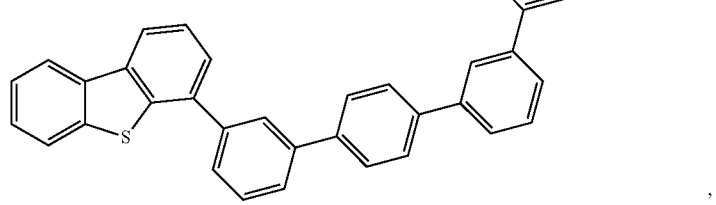

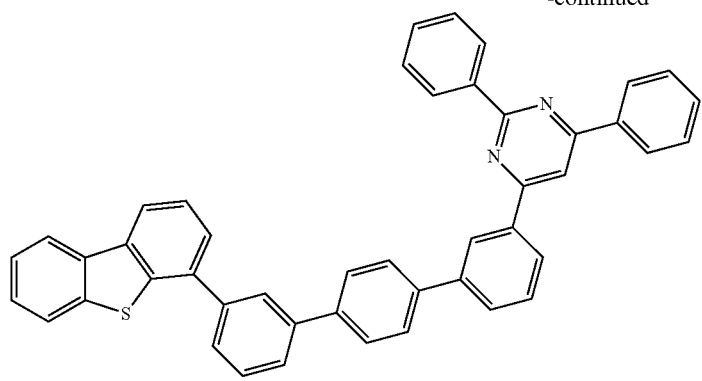
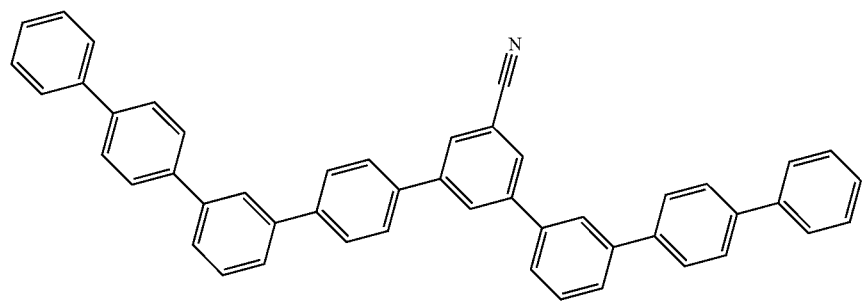
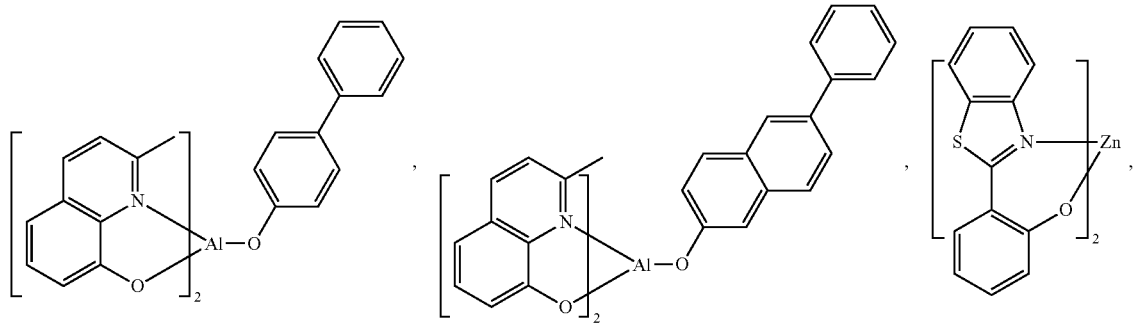
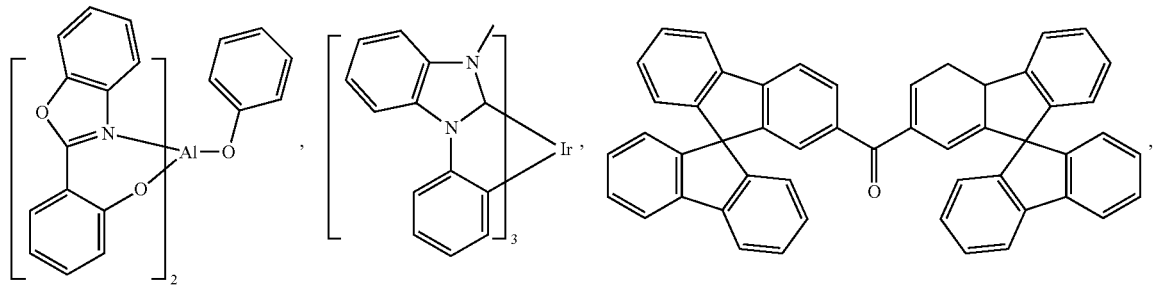
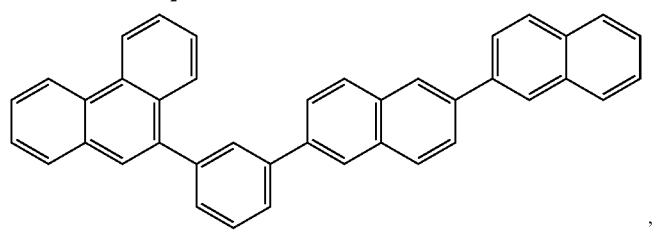

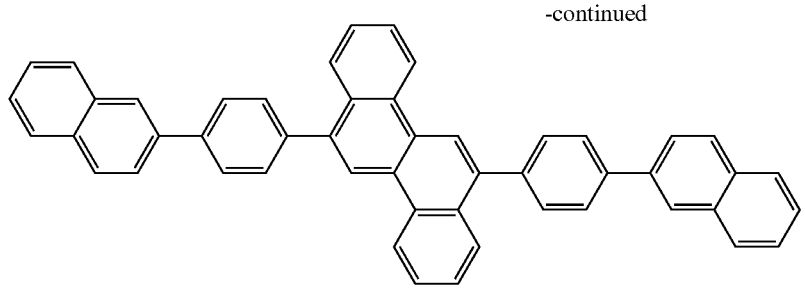

, and

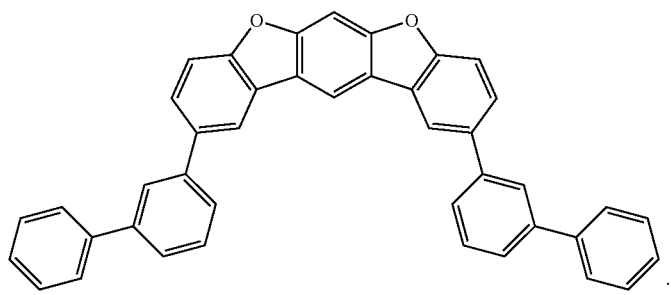

e) Additional Emitters:

One or more additional emitter dopants may be used in conjunction with the compound of the present disclosure. Examples of the additional emitter dopants are not particularly limited, and any compounds may be used as long as the compounds are typically used as emitter materials. Examples of suitable emitter materials include, but are not limited to, compounds which can produce emissions via phosphorescence, fluorescence, thermally activated delayed fluorescence, i.e., TADF (also referred to as E-type delayed fluorescence), triplet-triplet annihilation, or combinations of these processes.

Non-limiting examples of the emitter materials that may be used in an OLED in combination with materials disclosed herein are exemplified below together with references that disclose those materials: CN103694277, CN1696137, EB01238981, EP01239526, EP01961743, EP1239526, EP1244155, EP1642951, EP1647554, EP1841834, EP1841834B, EP2062907, EP2730583, JP2012074444, JP2013110263, JP4478555, KR1020090133652, KR20120032054, KR20130043460, TW201332980, U.S. Ser. No. 06/699,599, U.S. Ser. No. 06/916,554, US20010019782, US20020034656, US20030068526, US20030072964, US20030138657, US20050123788, US20050244673, US2005123791, US2005260449, US20060008670, US20060065890, US20060127696, US20060134459, US20060134462, US20060202194, US20060251923, US20070034863, US20070087321, US20070103060, US20070111026, US20070190359, US20070231600, US2007034863, US2007104979, US2007104980, US2007138437, US2007224450, US2007278936, US20080020237, US20080233410, US20080261076, US20080297033, US200805851, US2008161567, US2008210930, US20090039776, US20090108737, US20090115322, US20090179555, US2009085476, US2009104472, US20090100591, US20100148663, US20100244004, US20100295032, US2010102716, US2010105902, US2010244004, US2010270916, US20110057559, US20110108822, US20110204333, US2011215710, US2011227049, US2011285275, US2012292601, US20130146848, US2013033172, US2013165653, US2013181190, US2013334521, US20140246656, US2014103305, U.S. Pat. Nos. 6,303,238, 6,413,656, 6,653,654, 6,670,645, 6,687,266, 6,835,469, 6,921,915, 7,279,704, 7,332,232, 7,378,162, 7,534,505, 7,675,228, 7,728,137, 7,740,957, 7,759,489, 7,951,947, 8,067,099, 8,592,586, 8,871,361, WO06081973, WO06121811, WO07018067, WO07108362, WO07115970, WO07115981, WO08035571, WO2002015645, WO2003040257, WO2005019373, WO2006056418, WO2008054584, WO2008078800, WO2008096609, WO2008101842, WO2009000673, WO2009050281, WO2009100991, WO2010028151, WO2010054731, WO2010086089, WO2010118029, WO2011044988, WO2011051404, WO2011107491, WO2012020327, WO2012163471, WO2013094620, WO2013107487, WO2013174471, WO2014007565, WO2014008982, WO2014023377, WO2014024131, WO2014031977, WO2014038456, WO2014112450.

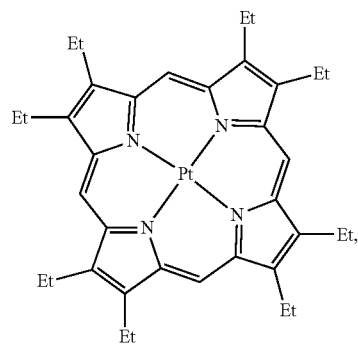

-continued
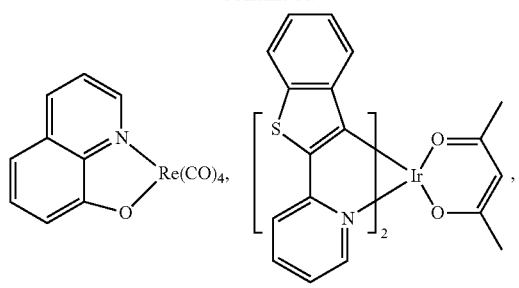
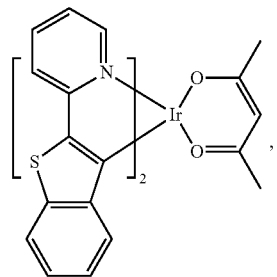
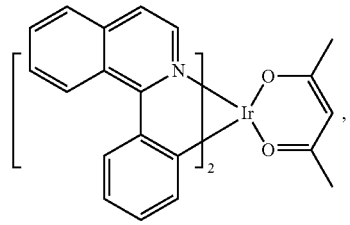
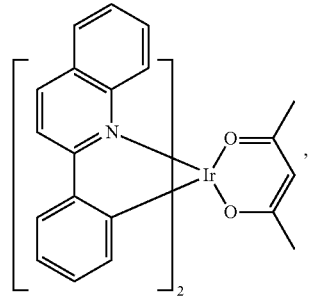
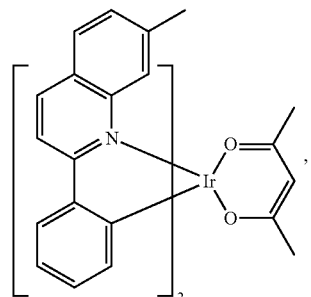
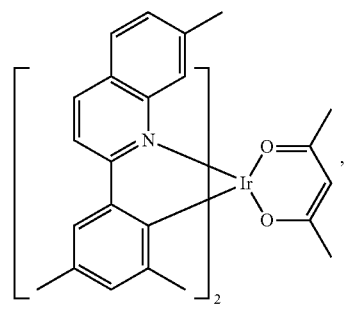
-continued
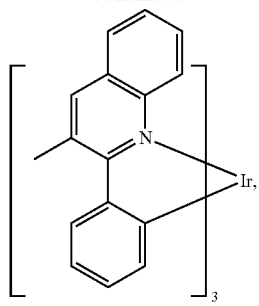
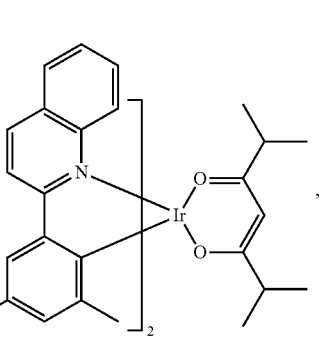
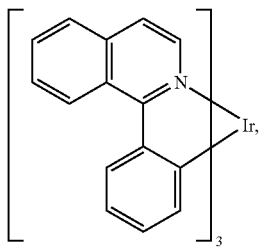
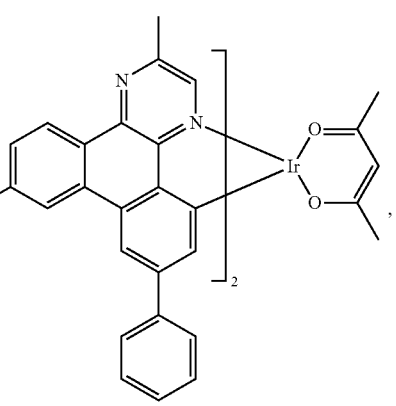
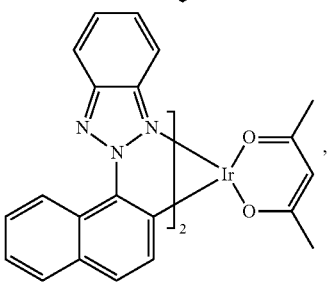

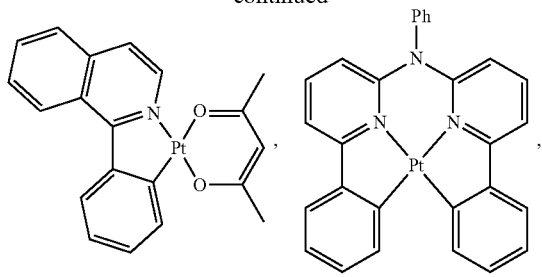
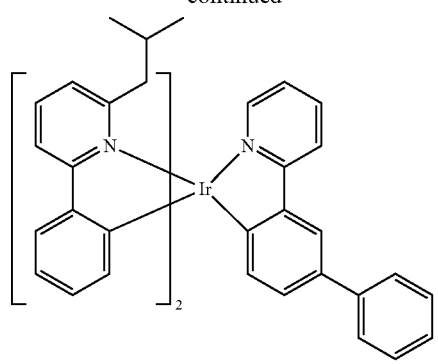
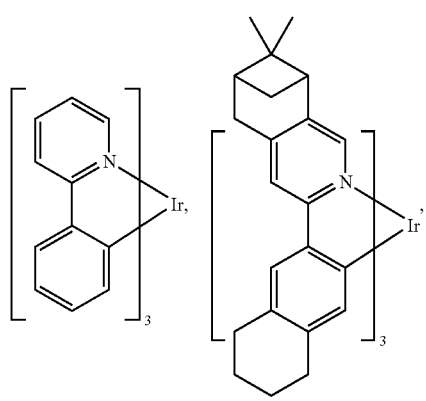
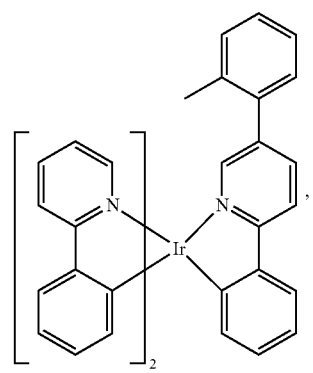
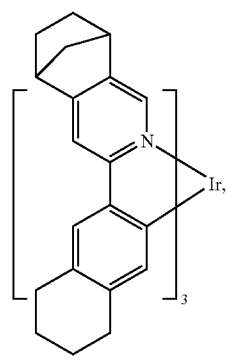
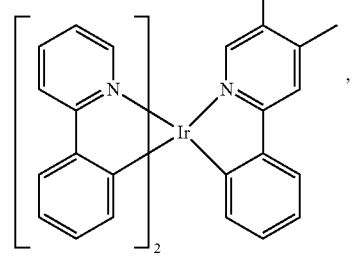
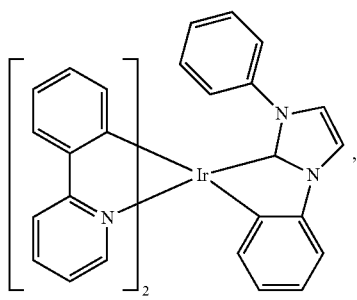
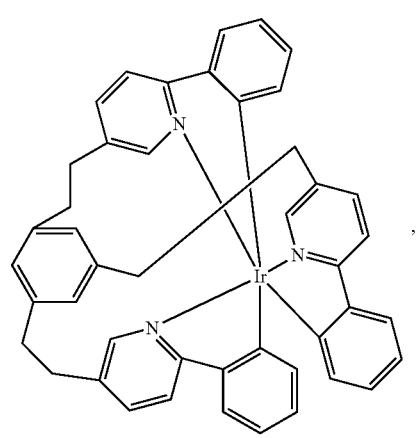
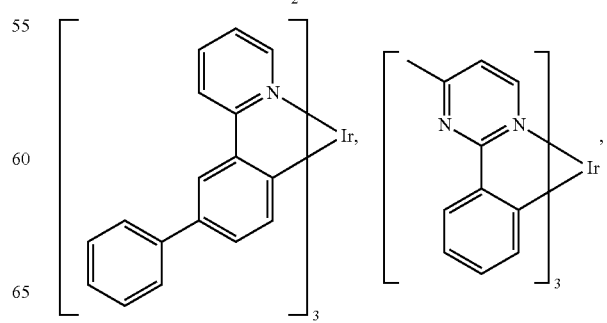

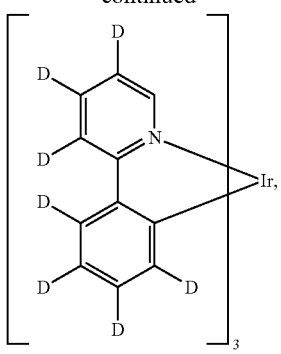
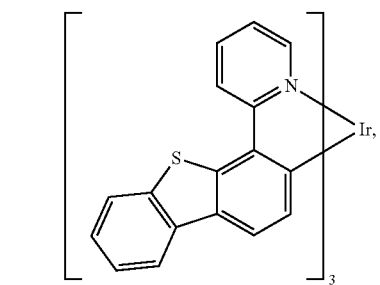
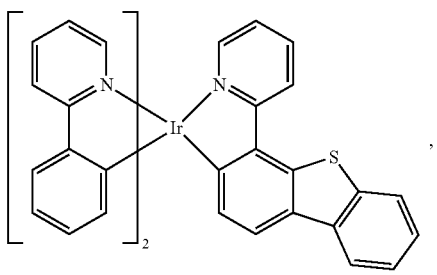
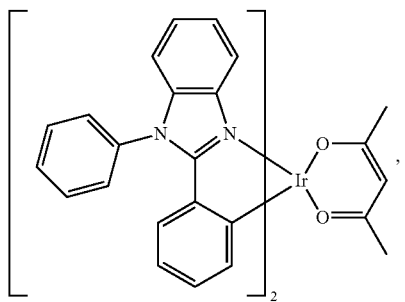
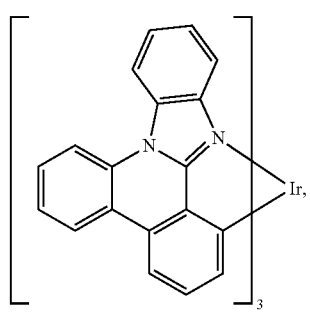
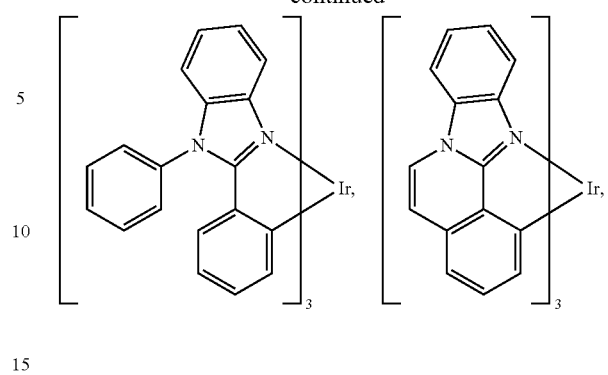
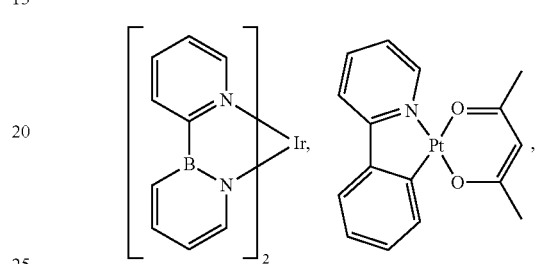
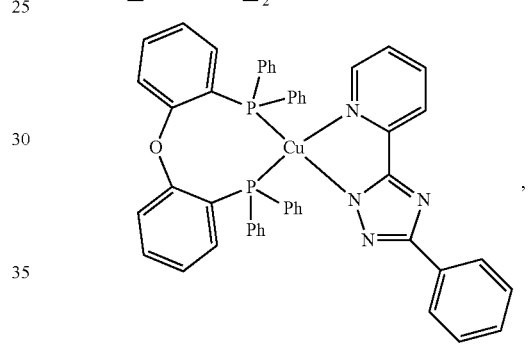
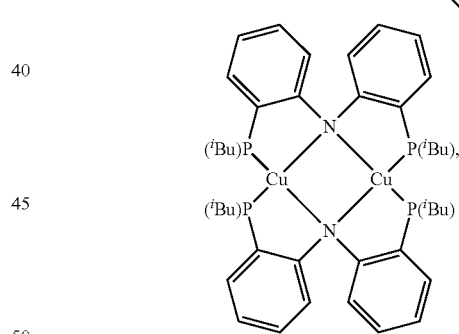
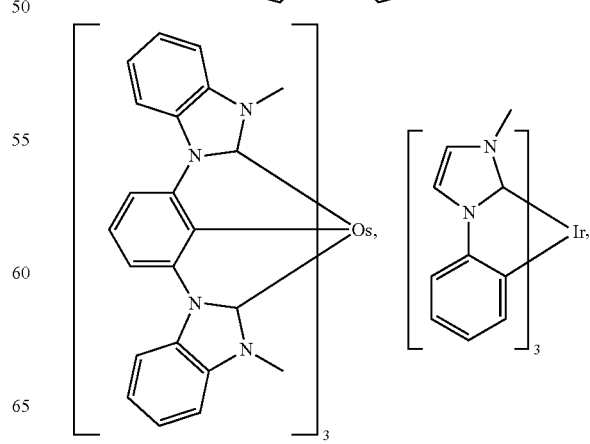

155
-continued
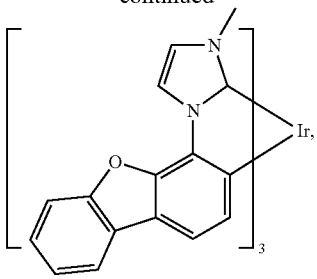
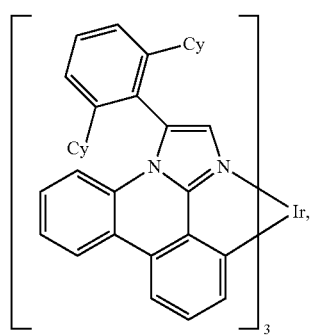
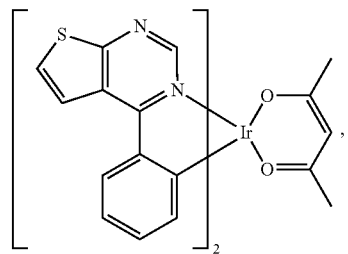
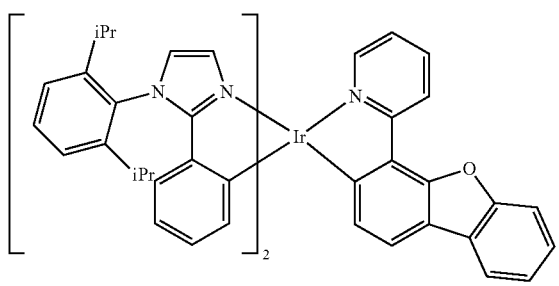
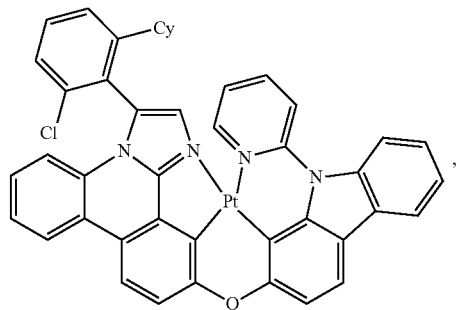
156
-continued
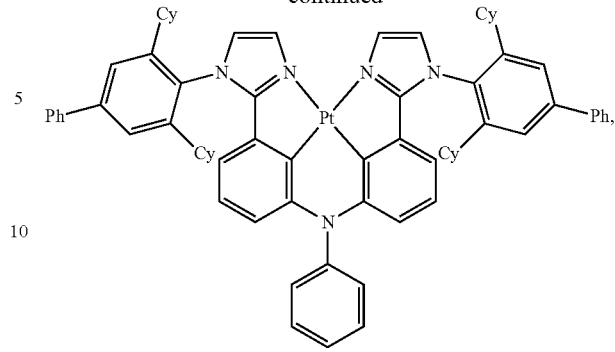
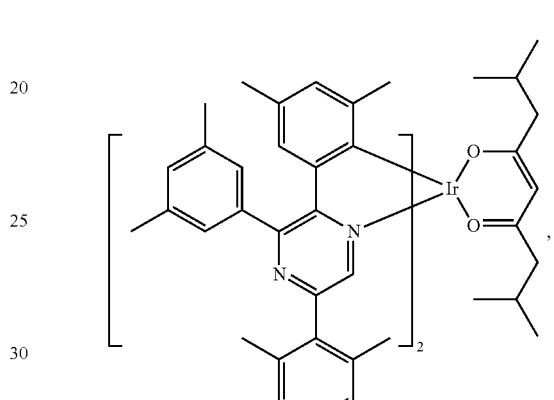
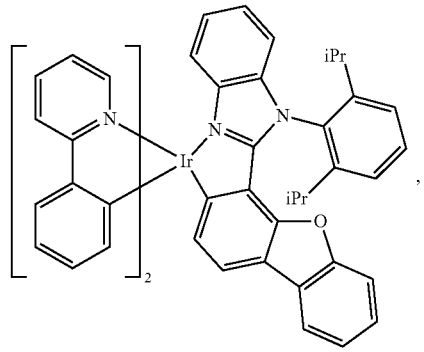
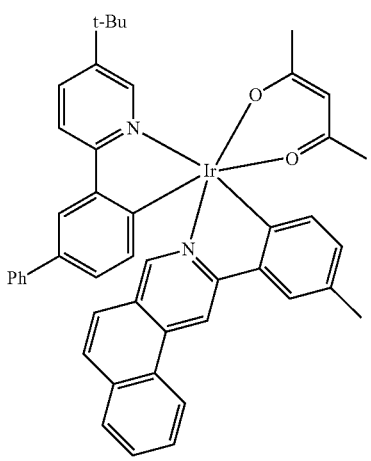

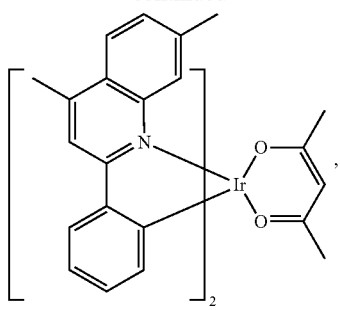
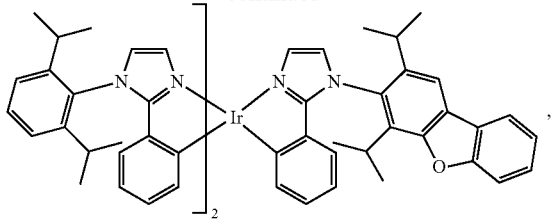
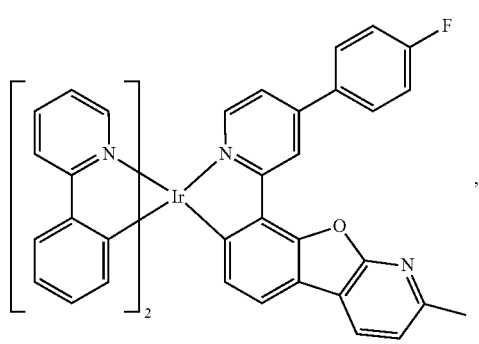
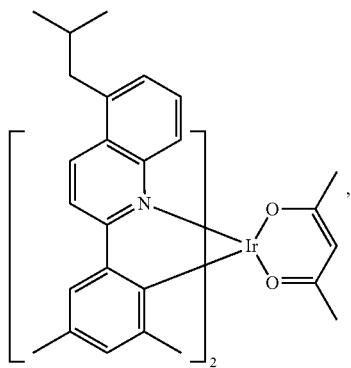
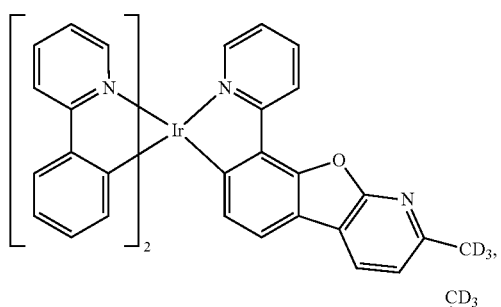
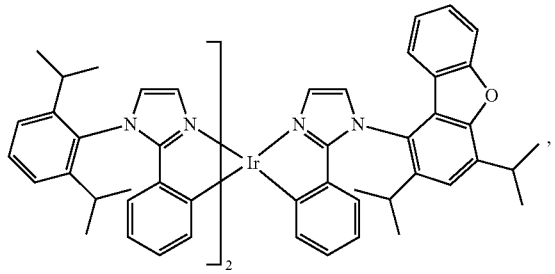
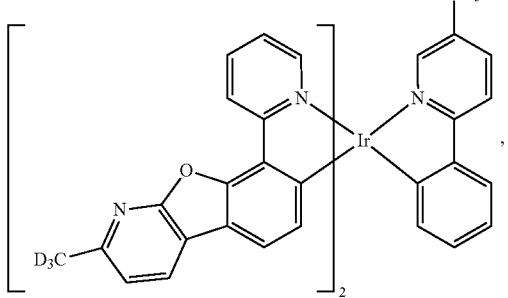
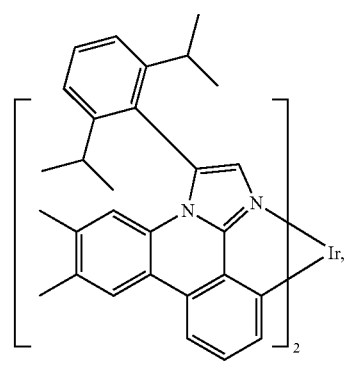
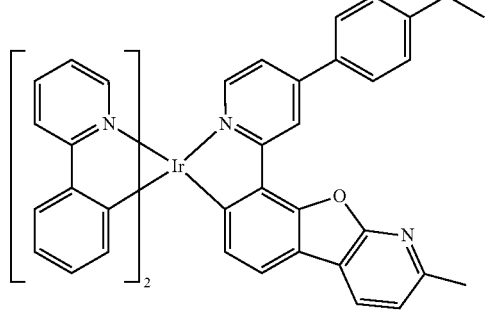
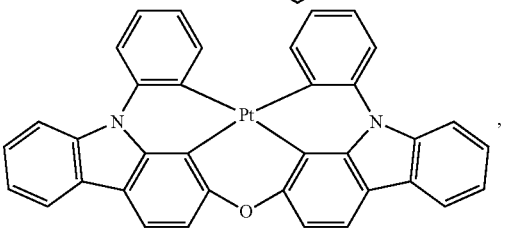

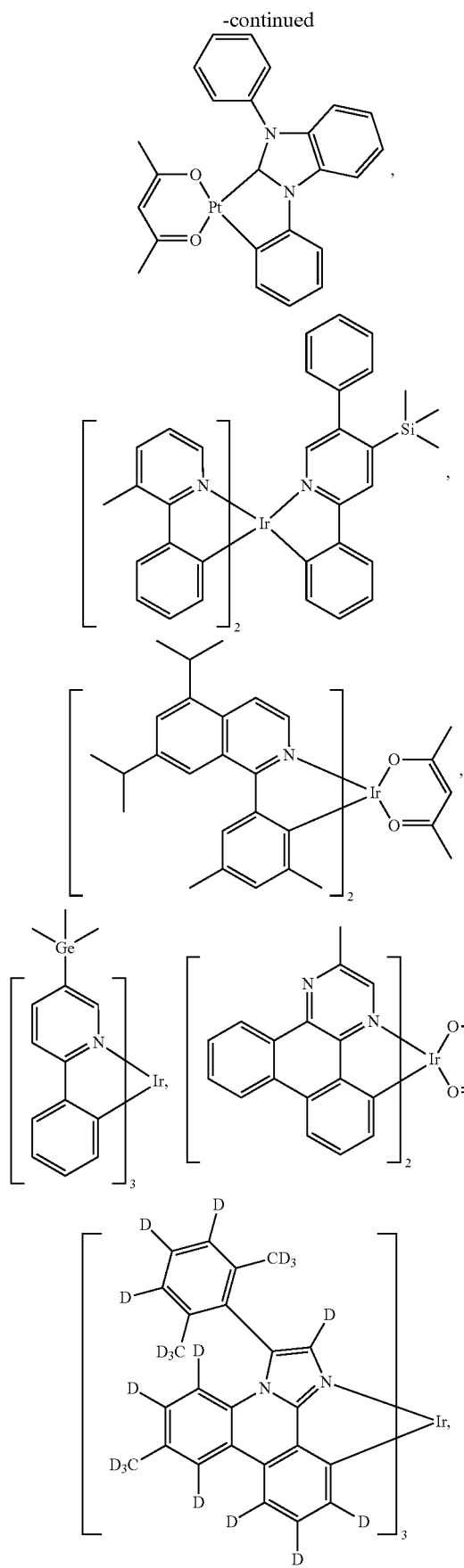
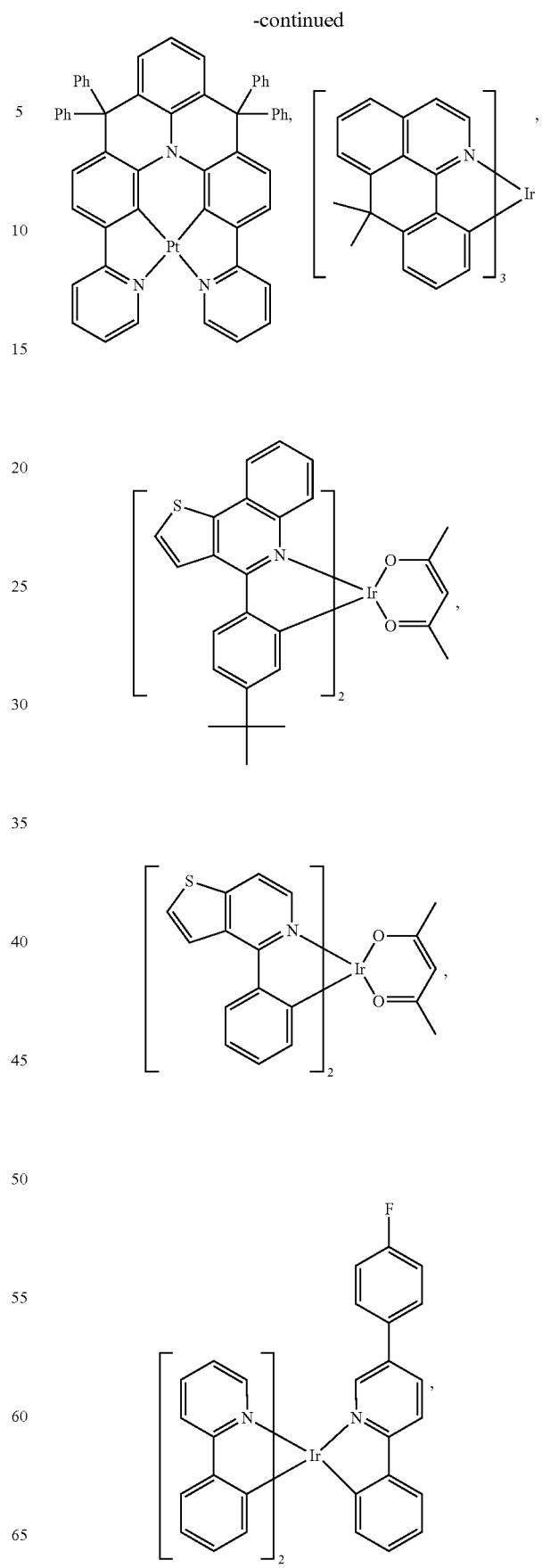

161
-continued
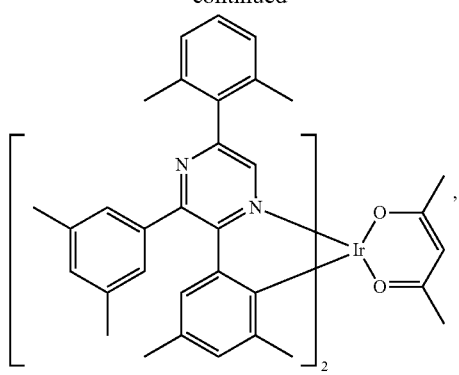
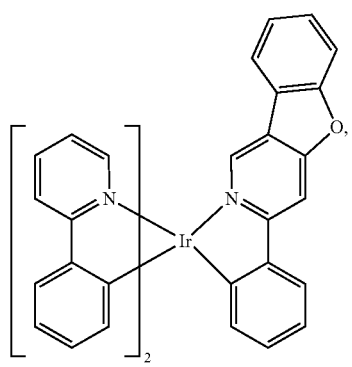
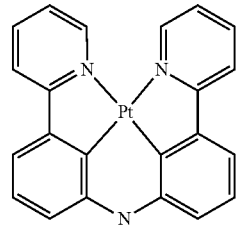
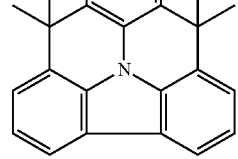
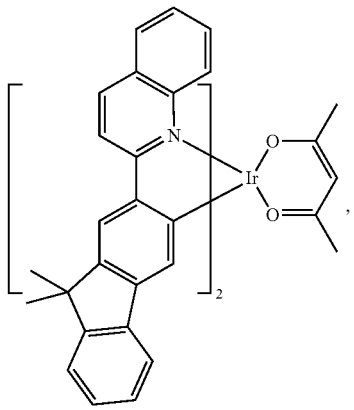
162
-continued
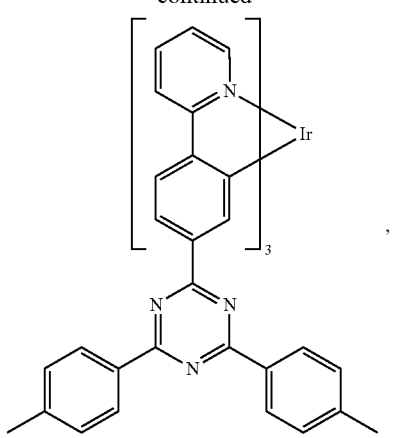
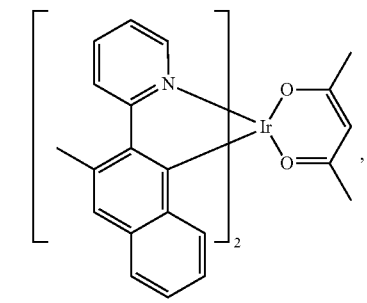
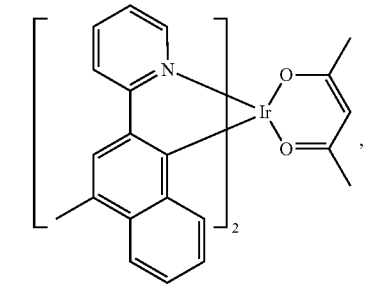
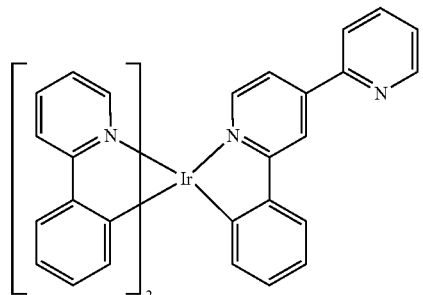
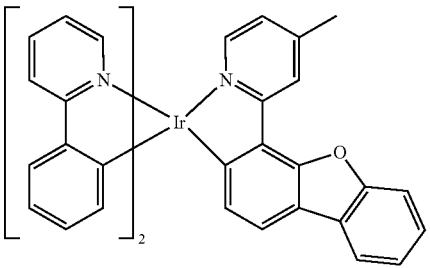

163
-continued
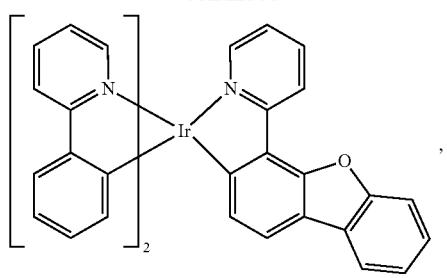
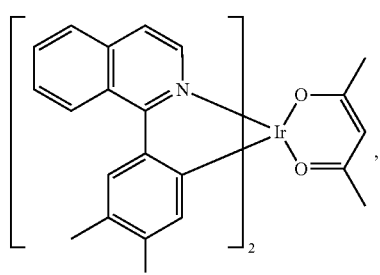
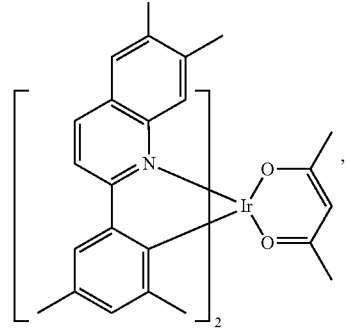
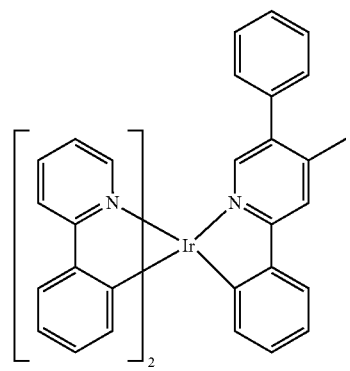
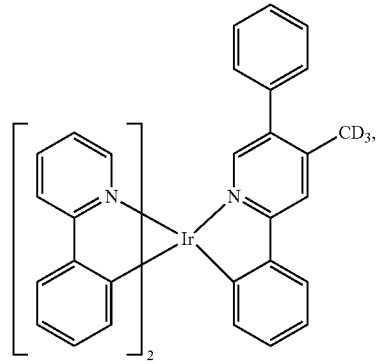
164
-continued
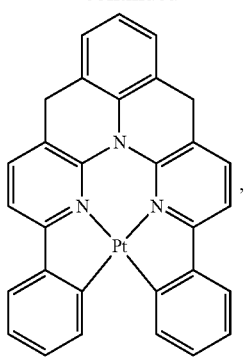
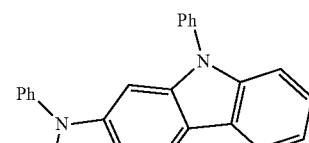
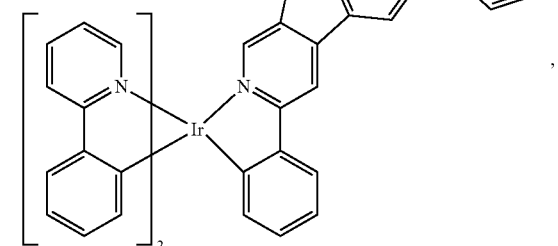
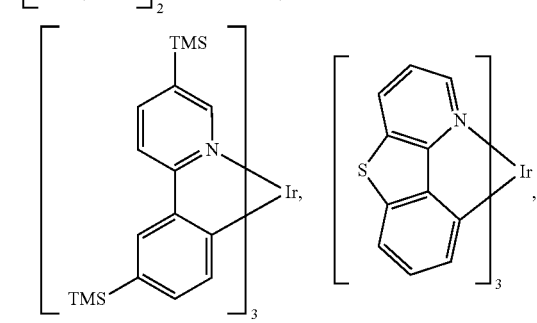
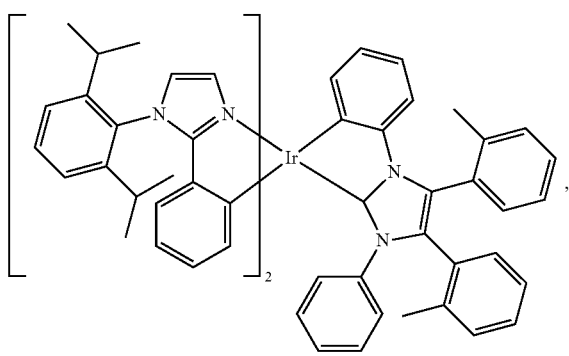
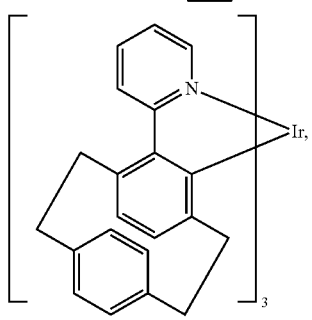

-continued
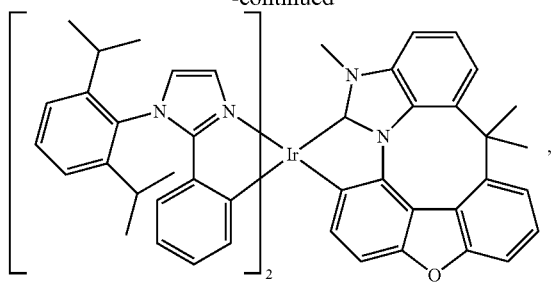
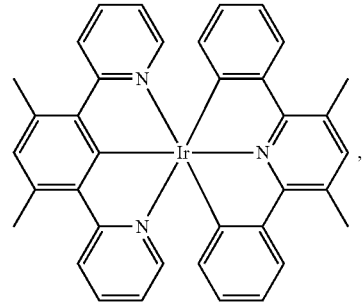
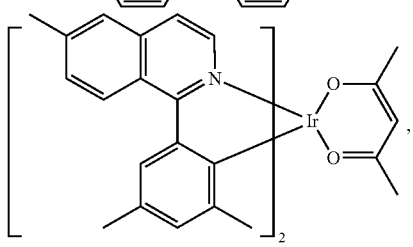
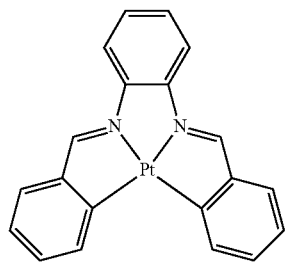
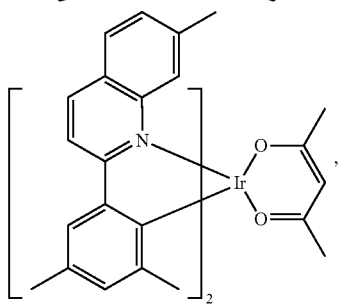
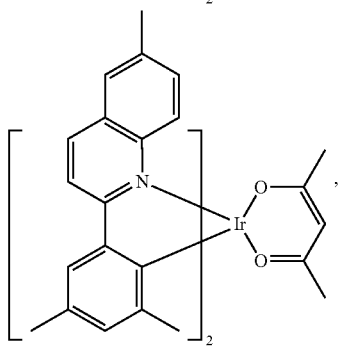
-continued
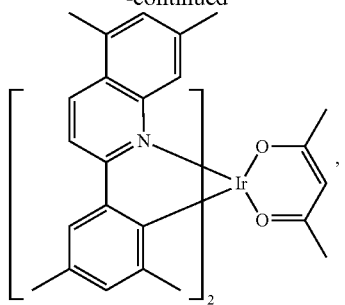
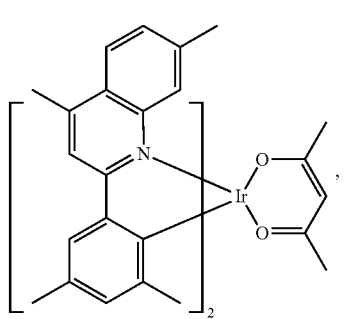
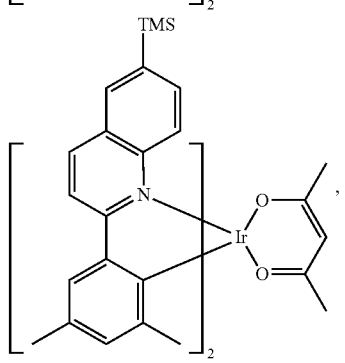
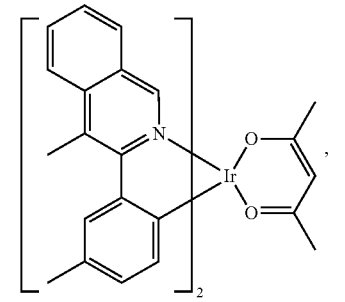
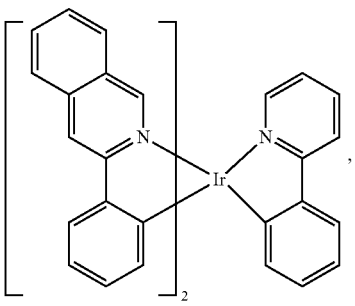

167
-continued
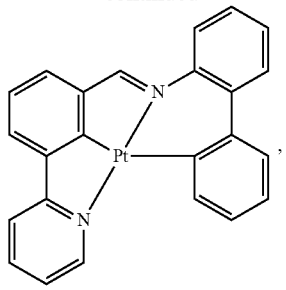
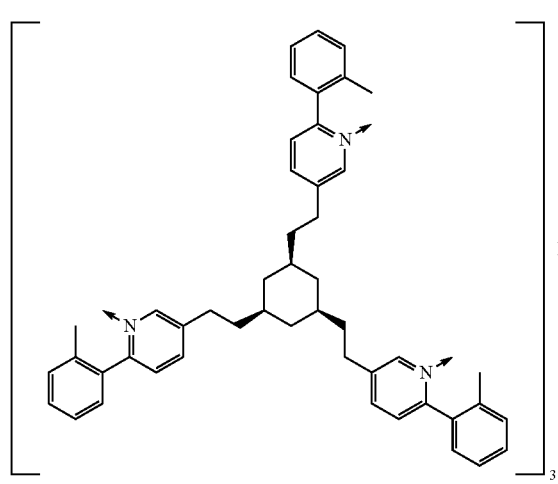
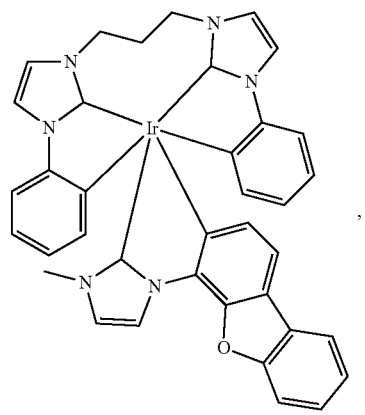
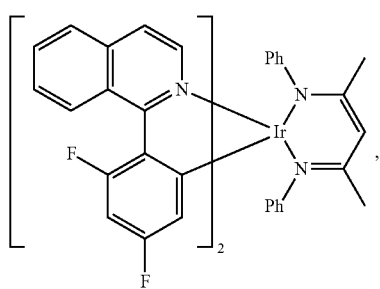
168
-continued
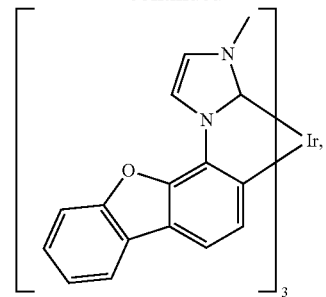
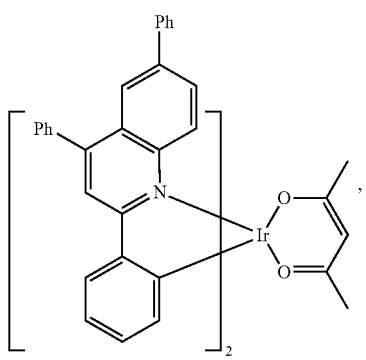
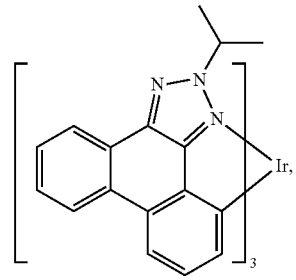
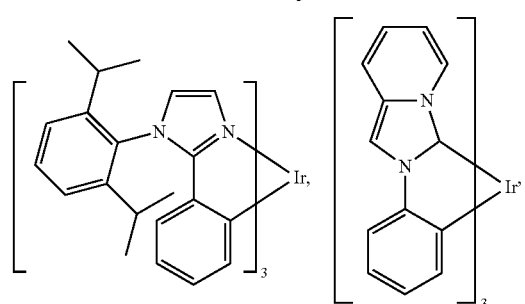
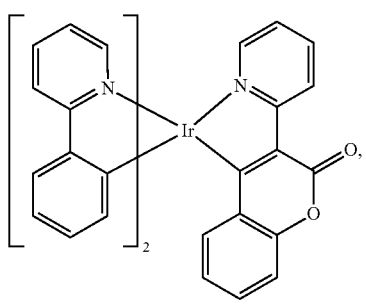

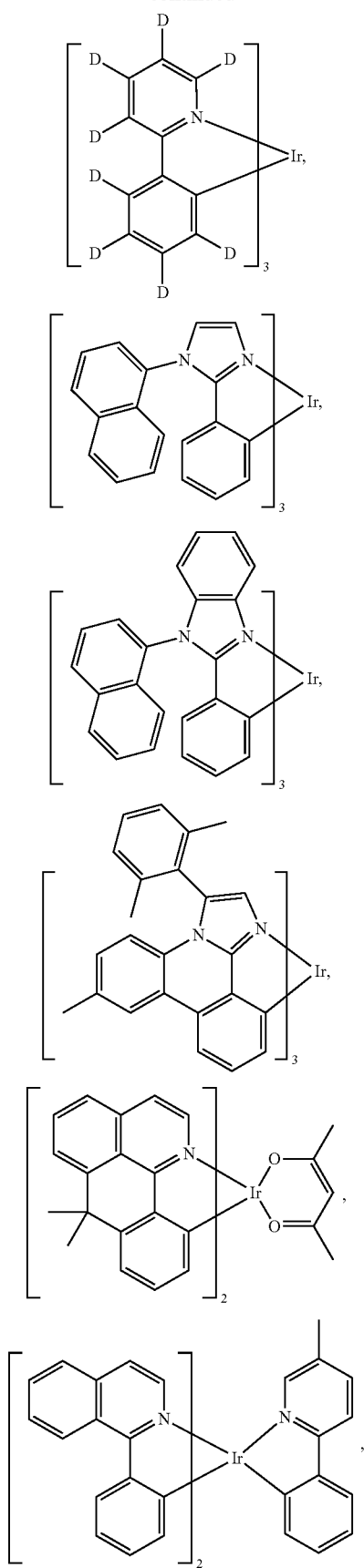

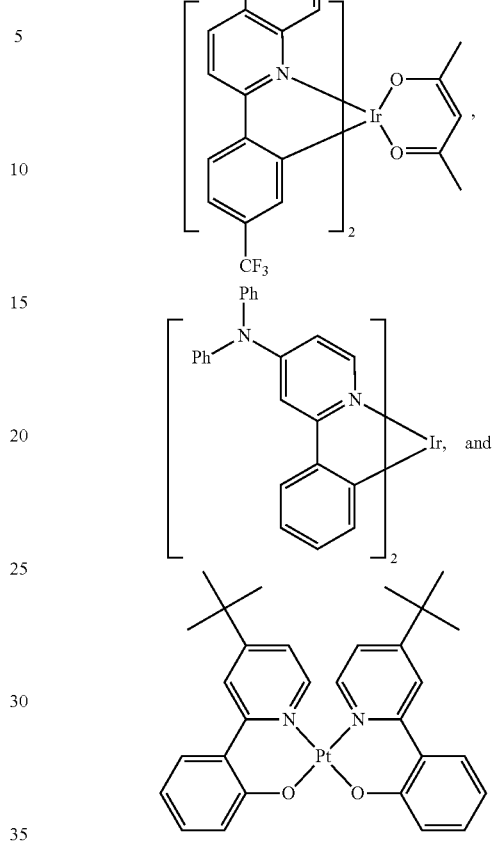

f) HBL:

A hole blocking layer (HBL) may be used to reduce the number of holes and/or excitons that leave the emissive layer. The presence of such a blocking layer in a device may result in substantially higher efficiencies and/or longer lifetime as compared to a similar device lacking a blocking layer. Also, a blocking layer may be used to confine emission to a desired region of an OLED. In some embodiments, the HBL material has a lower HOMO (further from the vacuum level) and/or higher triplet energy than the emitter closest to the HBL interface. In some embodiments, the HBL material has a lower HOMO (further from the vacuum level) and/or higher triplet energy than one or more of the hosts closest to the HBL interface.

In one aspect, compound used in HBL contains the same molecule or the same functional groups used as host described above.

In another aspect, compound used in HBL contains at least one of the following groups in the molecule:

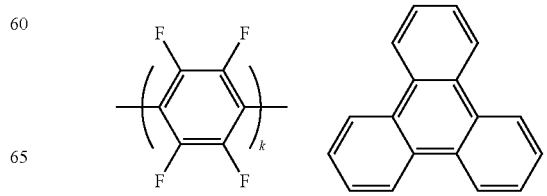

-continued

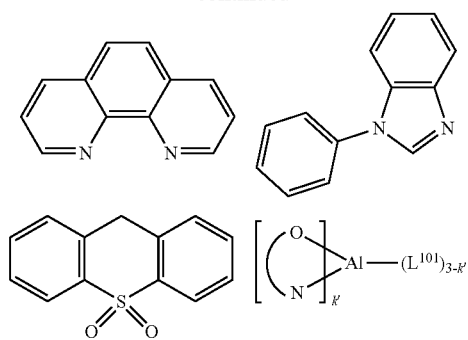

wherein k is an integer from 1 to 20; $L^{101}$ is another ligand, k' is an integer from 1 to 3.

g) ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

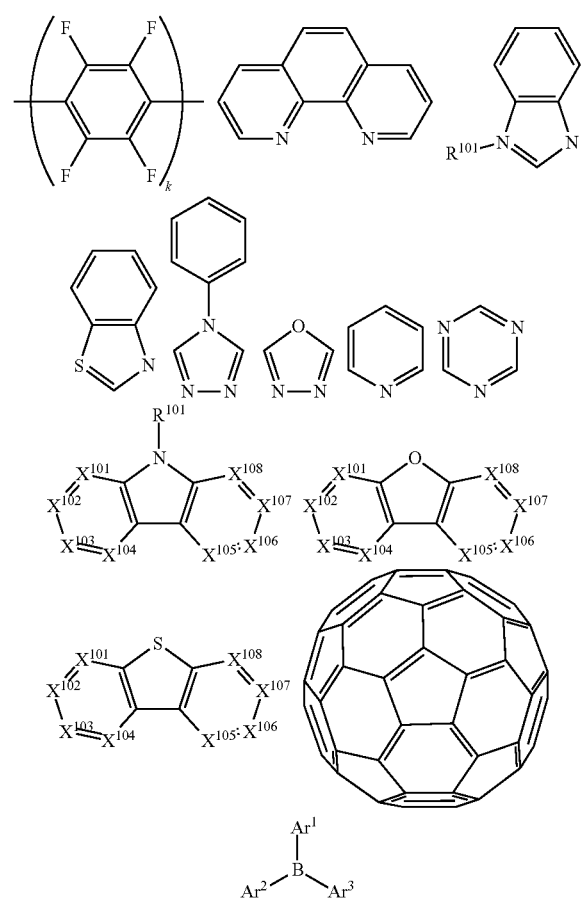

wherein $R^{101}$ is selected from the group consisting of hydrogen, deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL contains, but not limit to the following general formula:

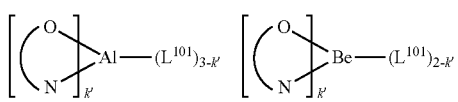

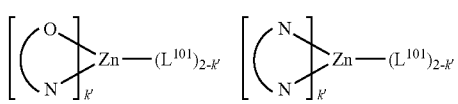

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

Non-limiting examples of the ETL materials that may be used in an OLED in combination with materials disclosed herein are exemplified below together with references that disclose those materials: CN103508940, EP01602648, EP01734038, EP01956007, JP2004-022334, JP2005149918, JP2005-268199, KR0117693, KR20130108183, US20040036077, US20070104977, US2007018155, US20090101870, US20090115316, US20090140637, US20090179554, US2009218940, US2010108990, US2011156017, US2011210320, US2012193612, US2012214993, US2014014925, US2014014927, US20140284580, U.S. Pat. Nos. 6,656,612, 8,415,031, WO2003060956, WO2007111263, WO2009148269, WO2010067894, WO2010072300, WO2011074770, WO2011105373, WO2013079217, WO2013145667, WO2013180376, WO2014104499, WO2014104535,

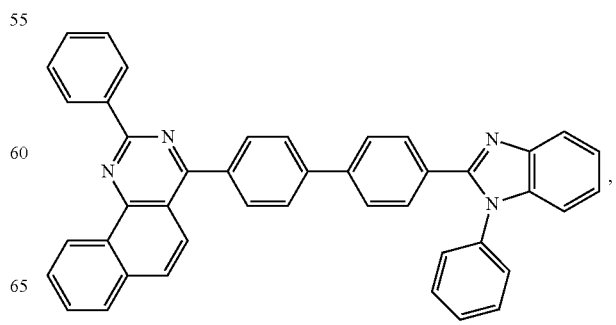

173
-continued
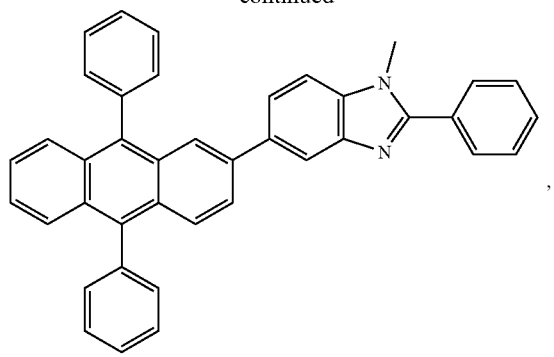
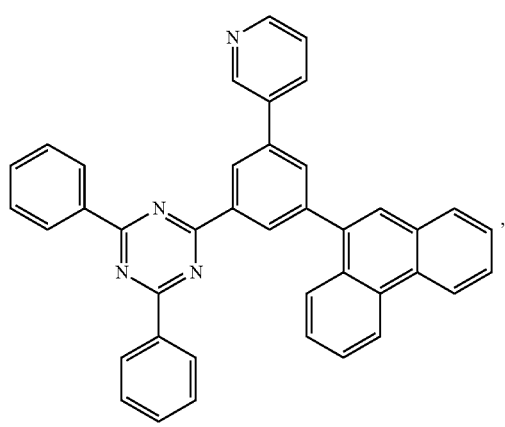
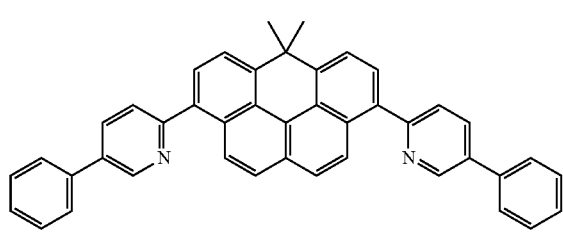
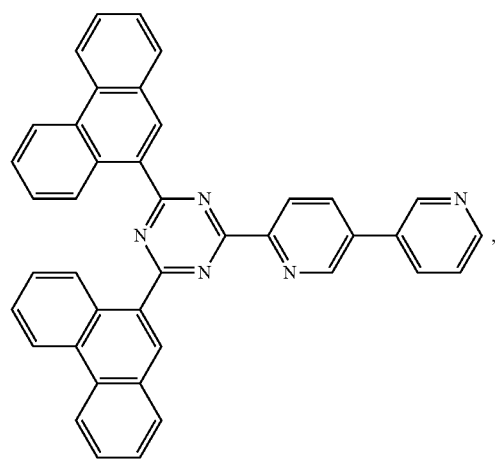
174
-continued
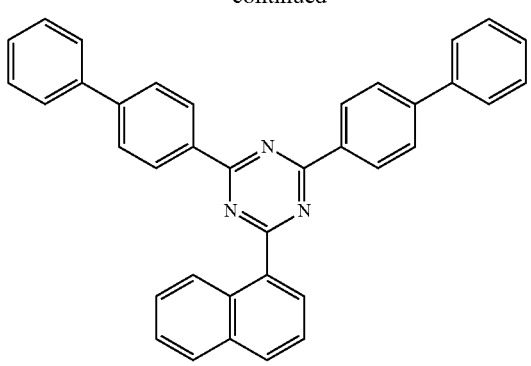
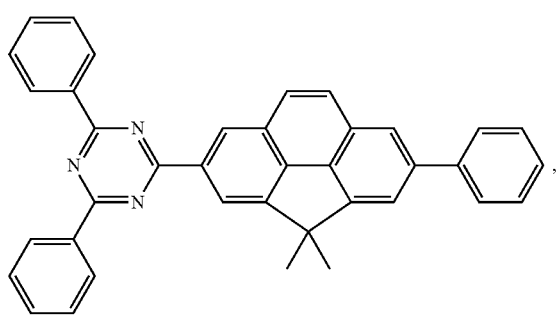
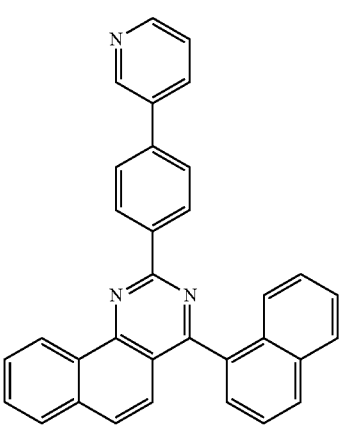

175
-continued
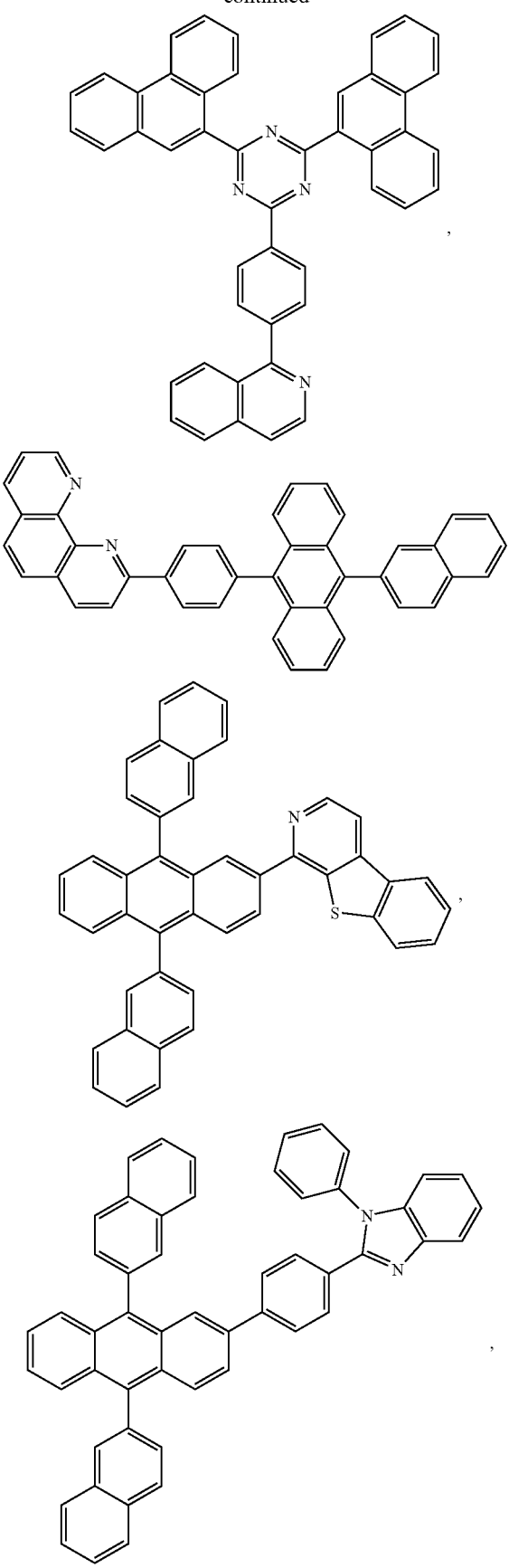
176
-continued
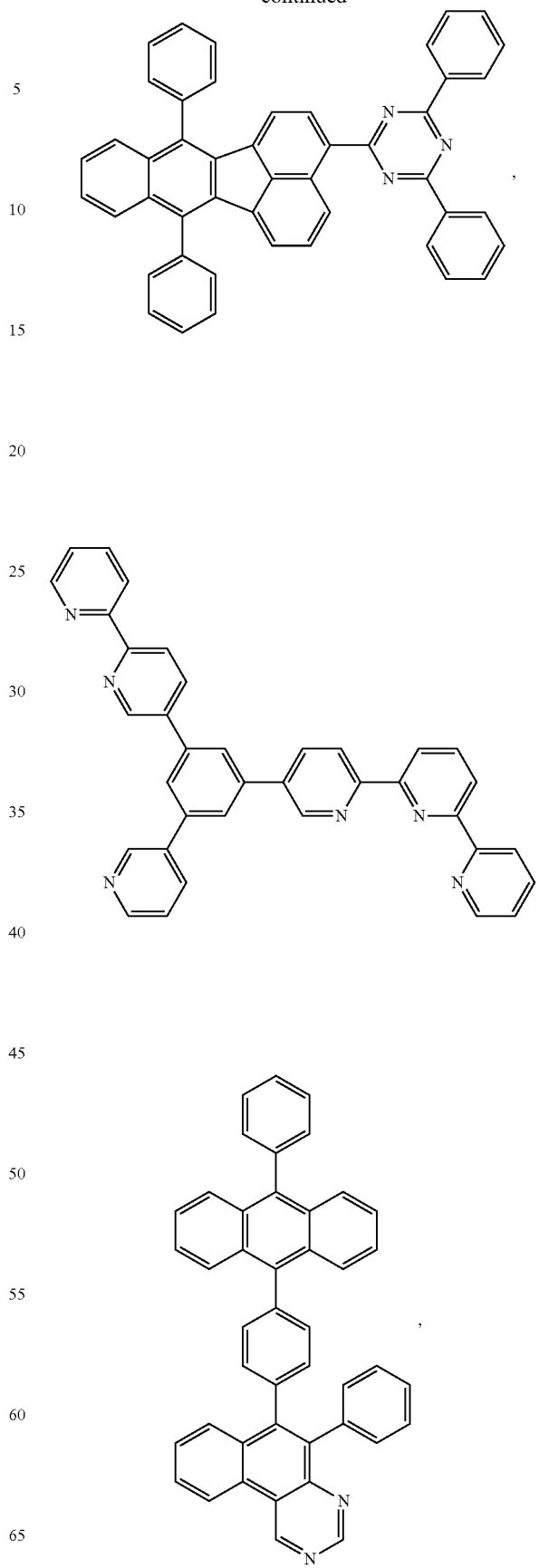

177
-continued
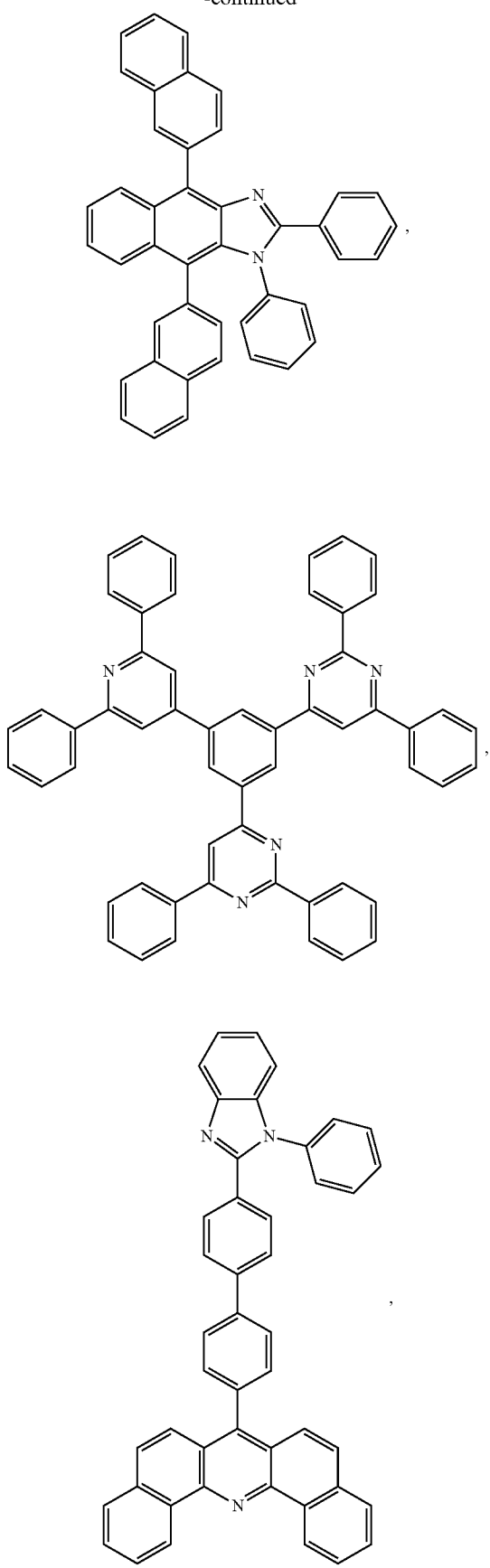
178
-continued
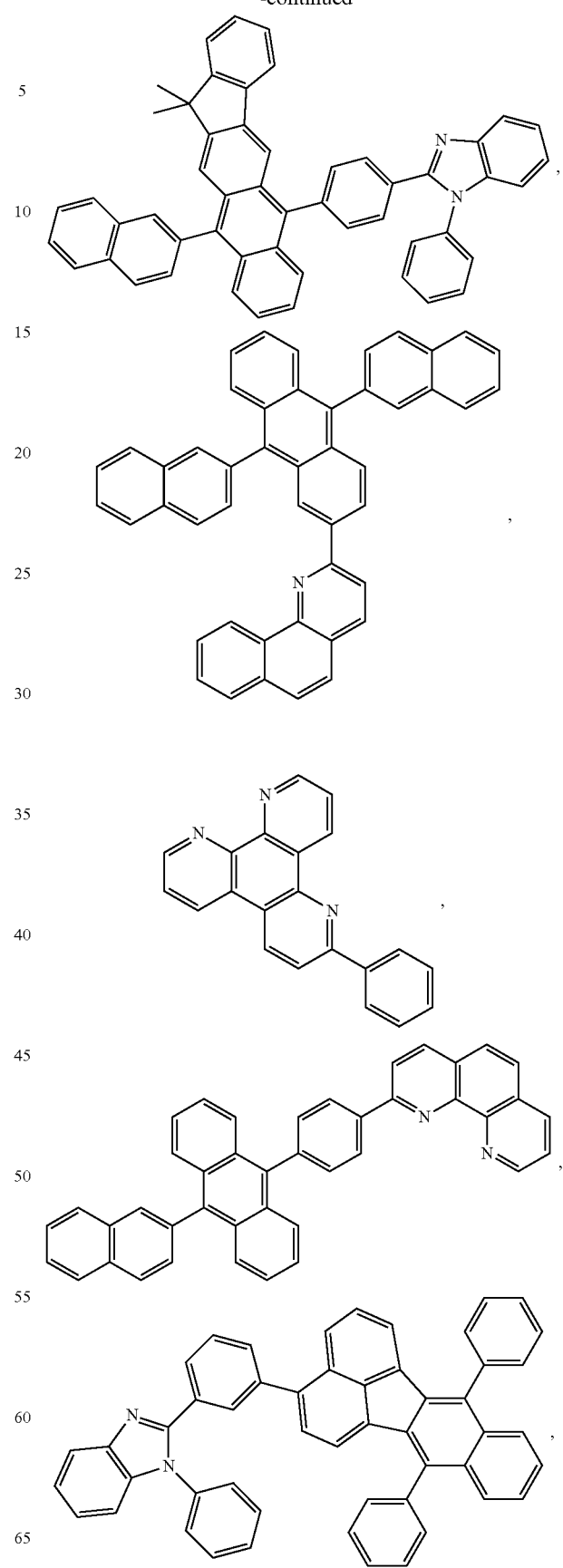

179
-continued
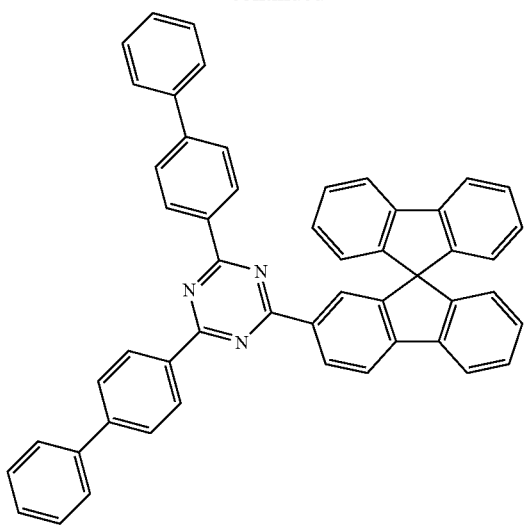
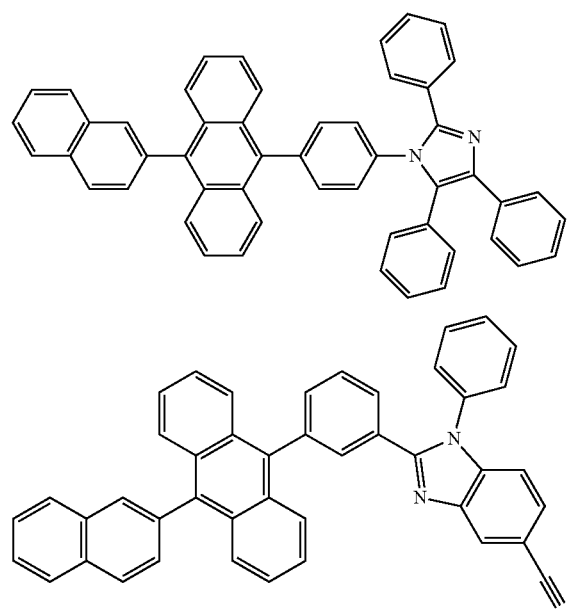
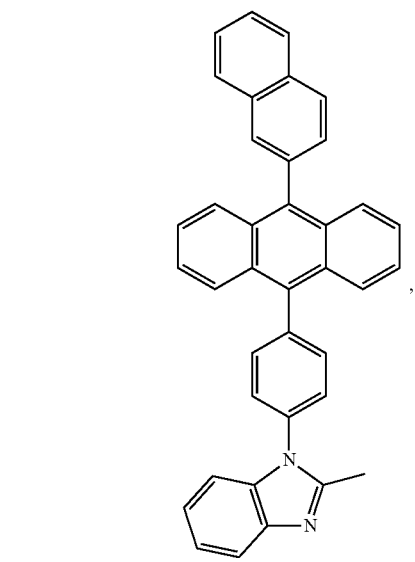
180
-continued
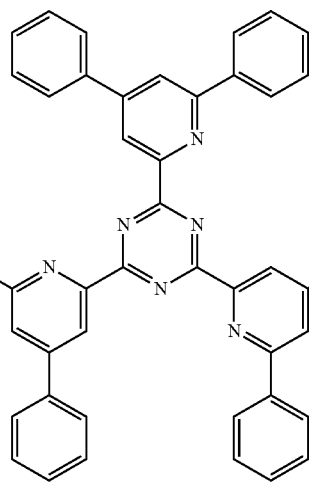
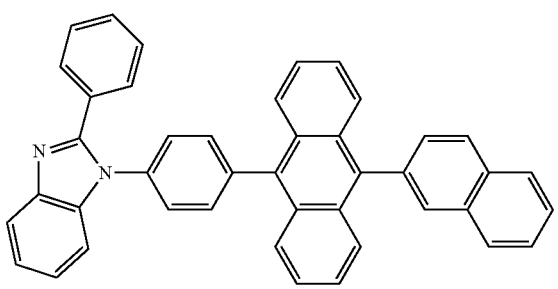
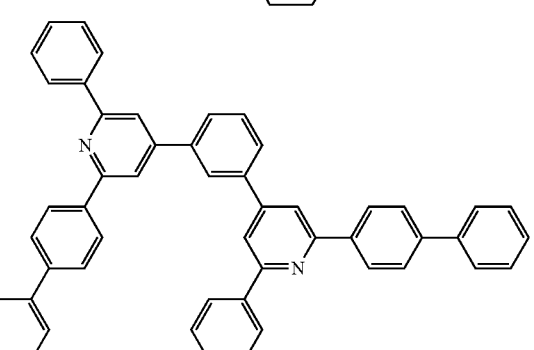
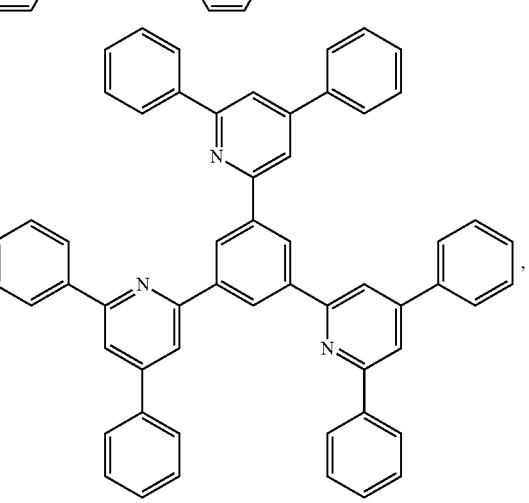

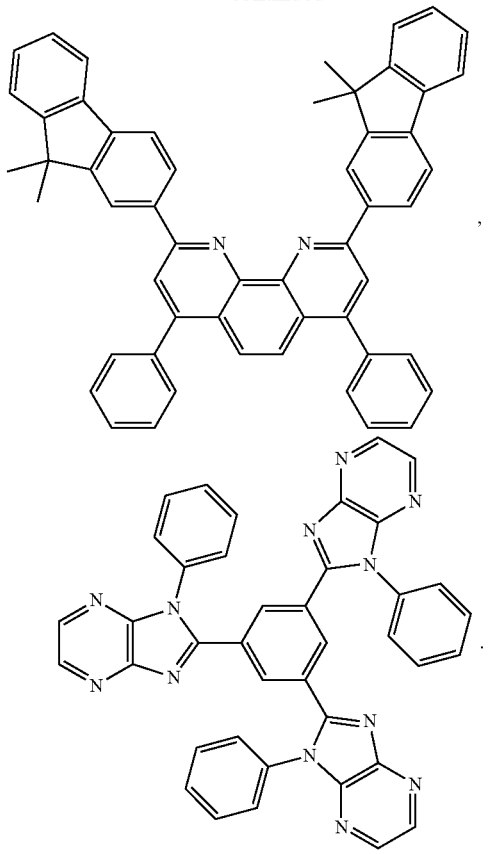

, and

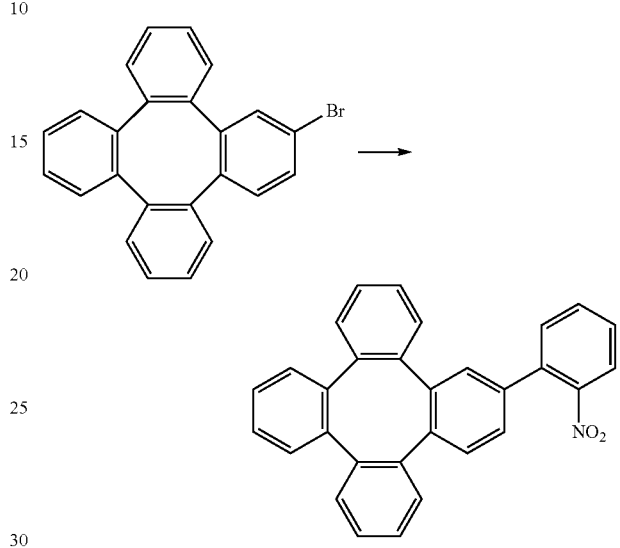

h) Charge Generation Layer (CGL)

In tandem or stacked OLEDs, the CGL plays an essential role in the performance, which is composed of an n-doped layer and a p-doped layer for injection of electrons and holes, respectively. Electrons and holes are supplied from the CGL and electrodes. The consumed electrons and holes in the CGL are refilled by the electrons and holes injected from the cathode and anode, respectively; then, the bipolar currents reach a steady state gradually. Typical CGL materials include n and p conductivity dopants used in the transport layers.

In any above-mentioned compounds used in each layer of the OLED device, the hydrogen atoms can be partially or fully deuterated. The minimum amount of hydrogen of the compound being deuterated is selected from the group consisting of 30%, 40%, 50%, 60%, 70%, 80%, 90%, 95%, 99%, and 100%. Thus, any specifically listed substituent, such as, without limitation, methyl, phenyl, pyridyl, etc. may be undeuterated, partially deuterated, and fully deuterated versions thereof. Similarly, classes of substituents such as, without limitation, alkyl, aryl, cycloalkyl, heteroaryl, etc. also may be undeuterated, partially deuterated, and fully deuterated versions thereof.

It is understood that the various embodiments described herein are by way of example only and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

E. Experimental Section

Synthesis of 2-(2-nitrophenyl)tetraphenylene

A mixture of 4,4,5,5-tetramethyl-2-(2-nitrophenyl)-1,3,2-dioxaborolane (1.365 g, 5.48 mmol), PdCl$_2$(dppf)-DCM adduct (0.149 g, 0.183 mmol), and potassium carbonate (2.52 g, 18.26 mmol) was vacuumed and back-filled with nitrogen. 1,4-Dioxane (20 ml) was added and the reaction was heated at 90° C. for 16 hours. Partitioned between DCM and brine and extracted with DCM. The organic portions was coated on celite and chromatographed on silica (DCM/Hep=2/1) to afford desired product (0.92 g, 59% yield).

Synthesis of 14H-tribenzo[3,4:5,6:7,8]cycloocta[1,2-b]carbazole

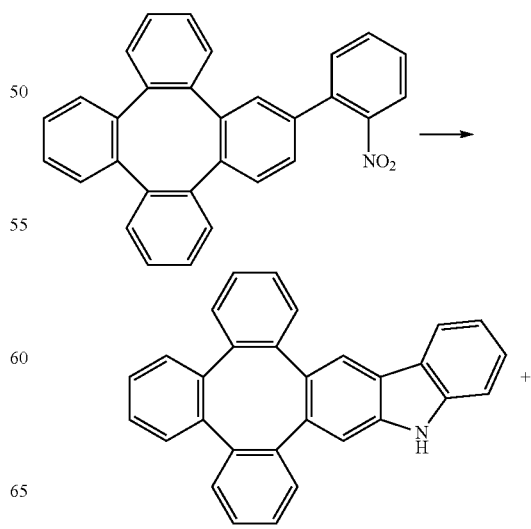

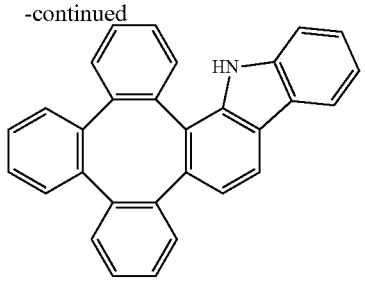

A mixture of 2-(2-nitrophenyl)tetraphenylene (1 g, 2.350 mmol) and 1,3-bis(diphenylphosphaneyl)propane (1.066 g, 2.59 mmol) was added 1,2-dichlorobenzene (10 ml) and the reaction was heated at 190° C. for 16 hours. Removed solvent and the reaction mixture was coated on celite. Chromatographed on silica (DCM/Hep=2/3) to afford the desired product (456 mg, 49% yield). The regioisomer 5H-tribenzo[3,4:5,6:7,8]cycloocta[1,2-a]carbazole was obtained in 33% yield.

Synthesis of 5-(5,9-dioxa-13b-boranaphtho[3,2,1-de]anthracen-7-yl)-5H-tribenzo[3,4:5,6:7,8]cycloocta[1,2-a]carbazole

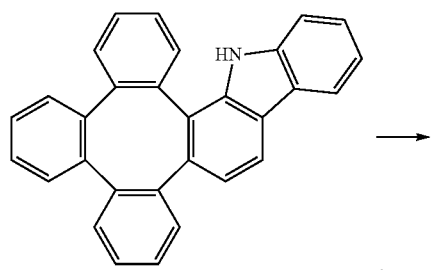

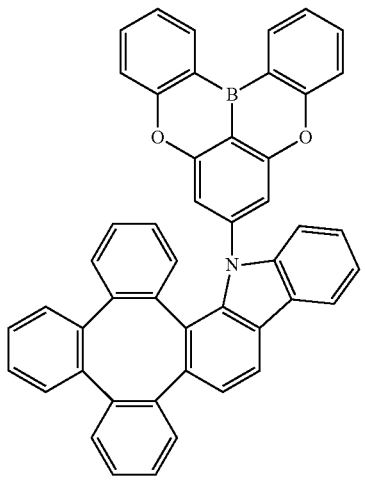

Inventive Compound 1

A mixture of 5H-tribenzo[3,4:5,6:7,8]cycloocta[1,2-a]carbazole (134 mg, 0.341 mmol), 7-chloro-5,9-dioxa-13b-boranaphtho[3,2,1-de]anthracene (104 mg, 0.341 mmol), (allyl)PdCl-dimer (4.98 mg, 0.014 mmol), cBRIDP (19.21 mg, 0.054 mmol), and sodium 2-methylpropan-2-olate (82 mg, 0.851 mmol) was vacuumed and back-filled with nitrogen. Toluene (5 ml) was added to the reaction mixture and refluxed overnight. The reaction mixture was coated on Celite (diatomaceous earth) and chromatographed on silica (DCM/Hep=1/2) to afford desired product.

Synthesis of 5-(4,6-diphenyl-1,3,5-triazin-2-yl)-5H-tribenzo[3,4:5,6:7,8]cycloocta[1,2-a]carbazole

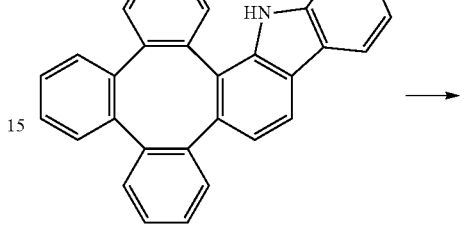

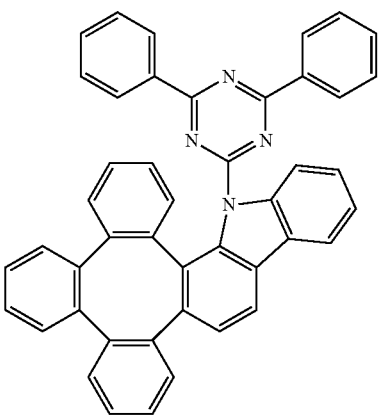

Inventive Compound 2

A mixture of 5H-tribenzo[3,4:5,6:7,8]cycloocta[1,2-a]carbazole (90 mg, 0.229 mmol), 2-chloro-4,6-diphenyl-1,3,5-triazine (61.2 mg, 0.229 mmol), (allyl)PdCl-dimer (3.35 mg, 9.15 μmol), cBRIDP (12.90 mg, 0.037 mmol), and sodium 2-methylpropan-2-olate (55.0 mg, 0.572 mmol) was vacuumed and back-filled with nitrogen. Toluene (3 ml) was added to the reaction mixture and refluxed for 16 hours. The reaction mixture was coated on Celite and chromatographed on silica (DCM/Hep=1/2) to afford desired product (100 mg, 70% yield).

Doped thin films were fabricated using Phosphor 1 as a phosphorescent dopant in a mixed matrix by dropcasting premixed solutions onto quartz substrates. Solutions in toluene of 10% Phosphor 1, 45% Host, and 45% PMMA were prepared where the Host of each sample was Inventive Compound 1, Inventive Compound 2, Comparative Compound 1, or Comparative Compound 2. Doping concentrations are percent by weight. The photoluminescence quantum yield (PLQY) and emission spectra of the thin films were measured using a Hamamatsu Quantaurus-QY Plus UV-NIR absolute PL quantum yield spectrometer with an excitation wavelength of 340 nm. The PLQY values and emission properties of the thin films are shown in Table 1, where the PLQY for Example 1 is reported relative to the PLQY of Comparison 1 device and the PLQY for Example 2 device is reported relative to the PLQY of Comparison 2 device.

TABLE 1

| | Host | PLQY (relative) | λ_max (nm) | FWHM |
|---|---|---|---|---|
| Example 1 | Inventive Compound 1 | 1.9 | 458 | 46 |
| Comparison 1 | Comparative Compound 1 | 1.0 | 460 | 70 |
| Example 2 | Inventive Compound 2 | 4.8 | 457 | 77 |
| Comparison 2 | Comparative Compound 2 | 1.0 | 462 | 128 |

Compounds Used for Doped PLQY Films:

Inventive Compound 1

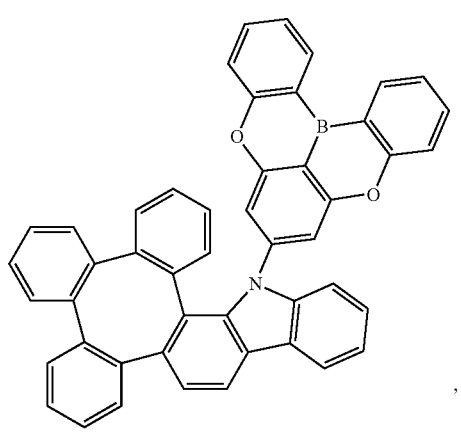

Inventive Compound 2

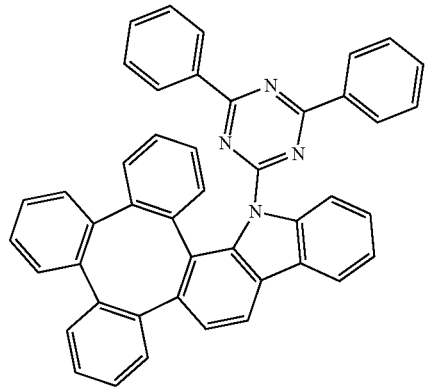

Comparative Compound 1

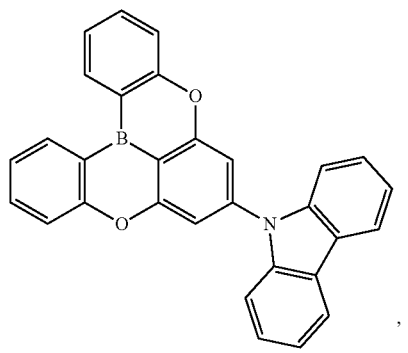

Comparative Compound 2

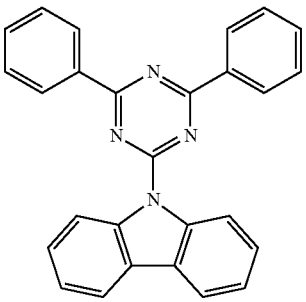

Comparative Compound 3

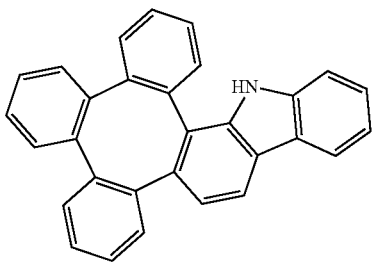

Phosphor 1

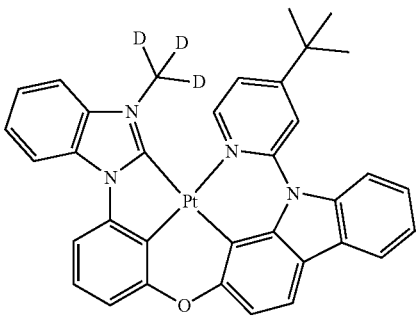

The data in Table 1 shows that both Example 1 and Example 2 devices have higher PLQY and a bluer and narrower spectrum than the films containing their direct analogs Comparison Compound 1 and Comparison Compound 2. The 1.9 times increase in PLQY for Example 1 and 4.8 times increase in PLQY for Example 2 is beyond any value that could be attributed to experimental error and the observed improvement is significant. Based on the fact that the host compounds have similar structures with the only difference being the addition of the fused cyclic ring structures, the significant performance improvement observed in the above data was unexpected. Without being bound by any theories, this improvement may be attributed the increased steric bulk induced by the twisted 8-membered tetraphenylene ring. The larger steric bulk is likely to reduce intermolecular interactions with the phosphorescent dopant to discourage exciplex formation that can reduce PLQY and broaden the emission spectrum as was observed in Comparison Compound 1 and Comparison Compound 2. As a result, both Inventive Compound 1 and Inventive Compound 2 can be useful as electron transporting hosts in phosphorescent OLEDs.

To further illustrate the utility of the inventive compounds as electron transporting host, the energy levels of Inventive Compound 2 were measured along with the parent Comparative Compound 3. Solution cyclic voltammetry and differential pulsed voltammetry were performed using a CH Instruments model 6201B potentiostat using anhydrous dimethylformamide solvent and tetrabutylammonium hexafluorophosphate as the supporting electrolyte. Glassy carbon, and platinum and silver wires were used as the working, counter and reference electrodes, respectively. Electrochemical potentials were referenced to an internal ferrocene-ferroconium redox couple (Fc/Fc+) by measuring the peak potential differences from differential pulsed voltammetry. The corresponding highest occupied molecular orbital (HOMO) and lowest unoccupied molecular orbital (LUMO) energies were determined by referencing the cationic and anionic redox potentials to ferrocene (4.8 eV vs. vacuum) according to literature ((a) Fink, R.; Heischkel, Y.; Thelakkat, M.; Schmidt, H.-W. *Chem. Mater.* 1998, 10, 3620-3625. (b) Pommerehne, J.; Vestweber, H.; Guss, W.; Mahrt, R. F.; Bassler, H.; Porsch, M.; Daub, *J. Adv. Mater.* 1995, 7, 551.

The experimentally measured HOMO and LUMO levels of Inventive Compound 2 were −5.92 eV and −2.78 eV, respectively, compared to HOMO and LUMO levels of −5.53 eV and −1.85 eV, respectively, for Comparison 3 device. The nearly 1V deeper LUMO level for Inventive Compound 2 makes it much more suitable for electron transport than the comparison compound. The ability for the compounds of the present invention to achieve desirable energy levels for charge transport while also inhibiting undesirable intermolecular interaction such as exciplex formation, is a notable improvement. The similarity of the rest of the compounds of the present disclosure, which also contain the desirable bulky fused ring structures, to Inventive Compound 1 and Inventive Compound 2 suggests the other compounds will also have reduced intermolecular interactions and show similar improvement in photophysical properties.

What is claimed is:

1. A compound of Formula I:

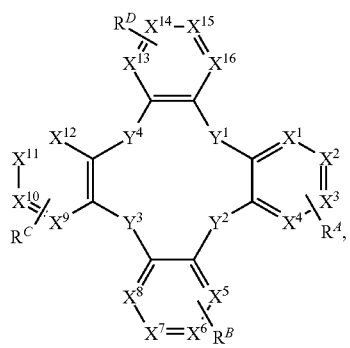

wherein:
$X^1$ to $X^{16}$ are each independently C or N;
$Y^1$ to $Y^4$ are each independently selected from the group consisting of direct bond, NR, PR, O, S, Se, CRR', SiRR', GeRR', BR, and BRR';
at least two adjacent sites from $X^1$ to $X^{16}$ are both carbon and are fused to one of

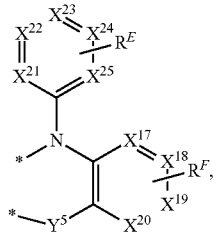 Formula II

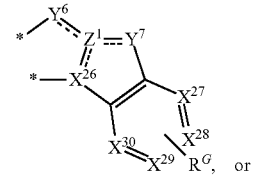 Formula III or

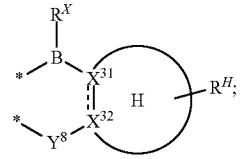 Formula IV wherein:
* indicates the attachment point for each structure;
$Y^5$ and $Y^8$ are each independently selected from the group consisting of direct bond, NR, PR, O, S, Se, CRR', SiRR', GeRR', BR, and BRR';
$Y^6$ and $Y^7$ are each independently selected from the group consisting of N, NR, PR, O, S, Se, CR, CRR', SiRR', GeRR', BR, and BRR';
$Z^1$ is C;
═══ is a single or double bond;
$X^{17}$ to $X^{32}$ are each independently C or N;
if $X^{21}$ to $X^{25}$ are all C, then at least one of $R^E$ comprises a boron atom;
Ring H is a 5 membered or 6 membered carbocyclic or heterocyclic ring;
$R^A$, $R^B$, $R^C$, $R^D$, $R^E$, $R^F$, $R^G$, and $R^H$ each independently represents mono to the maximum allowable substitution, or no substitution;
each R, R', $R^A$, $R^B$, $R^C$, $R^D$, $R^E$, $R^F$, $R^G$, $R^H$, and $R^X$ is independently a hydrogen or a substituent selected from the group consisting of deuterium, halogen, alkyl, cycloalkyl, heteroalkyl, heterocycloalkyl, arylalkyl, alkoxy, aryloxy, amino, silyl, germyl, boryl, selenyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof;
any two adjacent R, R', $R^A$, $R^B$, $R^C$, $R^D$, $R^E$, $R^F$, $R^G$, $R^H$, and $R^X$ may be joined or fused to form a ring; and
at least one of $Y^1$-$Y^4$ is selected from the group consisting of NR, PR, O, S, Se, CRR', SiRR', GeRR', BR, and BRR', or the compound is subject to the following provisos:
if the compound comprises Formula III, then at least one of $Y^6$ and $Y^7$ is N;
in Formula II, if $X^{21}$-$X^{25}$ are each C, then: $Y^5$ is a direct bond; or at least one $R^E$ and $R^F$ is a substituent selected from the group consisting of heterocycloalkyl, germyl, boryl, selenyl, and combinations thereof;

if the compound comprises the structure of Formula IV in which Y' is an atom, then at least one of the following is true:
i) $R^X$ joins with an $R^A$, $R^B$, $R^C$, or $R^D$ of the respective ring to which Formula IV is fused to form a fused ring;
ii) $R^X$ joins with $R^H$ to form a fused ring;
iii) $R^X$ comprises two or more aromatic rings; or
iv) Y' is an atom that has a substituent and said substituent comprises two or more aromatic rings.

2. The compound of claim 1, wherein each R, R', $R^A$, $R^B$, $R^C$, $R^D$, $R^E$, $R^F$, $R^G$, $R^H$, and $R^X$ is independently a hydrogen or a substituent selected from the group consisting of deuterium, fluorine, alkyl, cycloalkyl, heteroalkyl, alkoxy, aryloxy, amino, silyl, boryl, alkenyl, cycloalkenyl, heteroalkenyl, aryl, heteroaryl, nitrile, isonitrile, sulfanyl, and combinations thereof.

3. The compound of claim 1, wherein two or more paired adjacent sites from $X^1$ to $X^{16}$ are fused to Formula II, and/or Formula III, and/or Formula IV.

4. The compound of claim 3, wherein at least one of $X^{21}$ to $X^{25}$ is N.

5. The compound of claim 3, wherein at least one of $R^E$ comprises a carbazole, or silane.

6. The compound of claim 3, wherein $X^{17}$-$X^{20}$ are each independently C, or one of $X^{17}$-$X^{20}$ is N.

7. The compound of claim 3, wherein $X^{26}$ and $Y^7$ are both N, the bond from $Z^1$ to $Y^7$ is a double bond, and the bond from $Z^1$ to $Y^6$ is a single bond; or $X^{26}$ and $Y^6$ are both N and the bond from $Z^1$ to $Y^6$ is a double bond, and the bond from $Z^1$ to $Y^7$ is a single bond.

8. The compound of claim 3, wherein $X^{27}$-$X^{30}$ are each independently C, or one of $X^{27}$-$X^{30}$ is N.

9. The compound of claim 3, wherein ring H comprises a 5-membered or 6-membered aromatic ring.

10. The compound of claim 3, wherein two $R^H$ are joined to form a 5-membered or 6-membered aromatic ring fused to ring H.

11. The compound of claim 3, wherein $R^X$ is joined with one of $R^H$, $R^A$, $R^B$, $R^C$, or $R^D$ to form a ring.

12. The compound of claim 1, wherein $Y^1$ to $Y^4$ are each independently a direct bond; or at least one of $Y^1$ to $Y^4$ is selected from the group consisting of NR, O, S, SiRR, and BR.

13. The compound of claim 1, wherein $X^1$-$X^{16}$ are each independently C, or at least one of $X^1$-$X^{16}$ is N.

14. The compound of claim 1, wherein the compound is selected from the group consisting of:

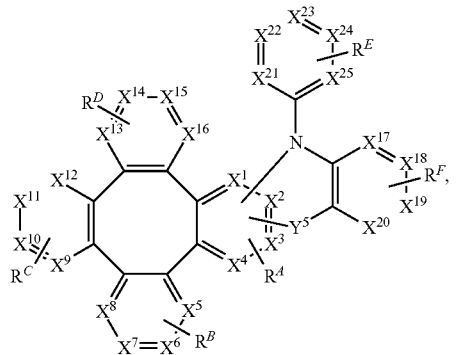

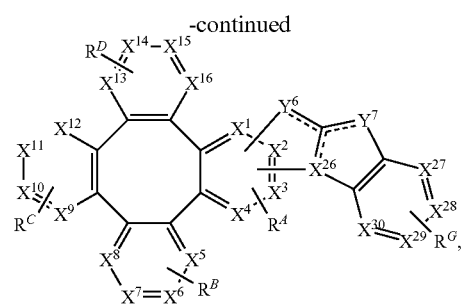

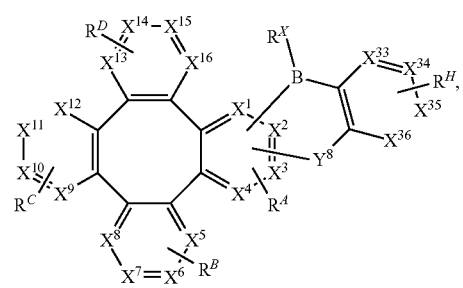

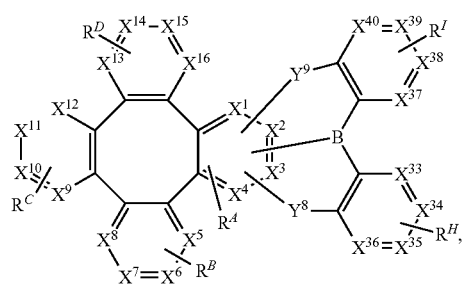

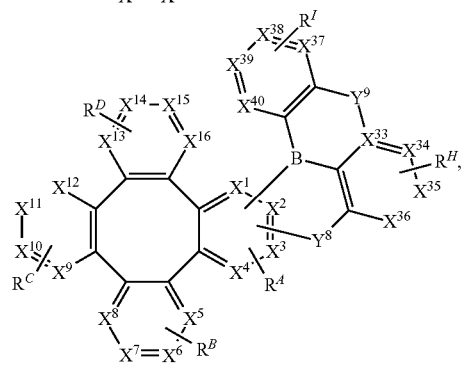

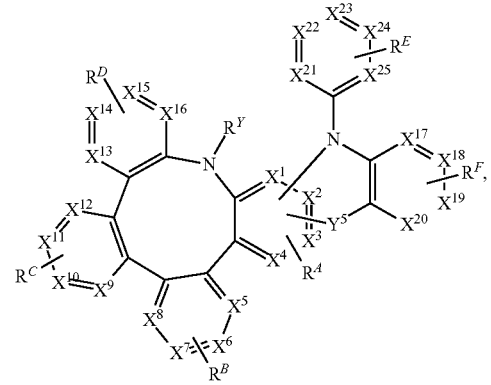

-continued
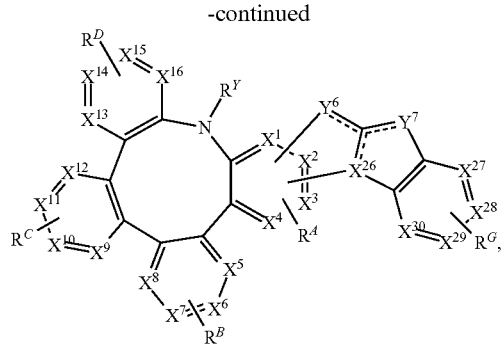
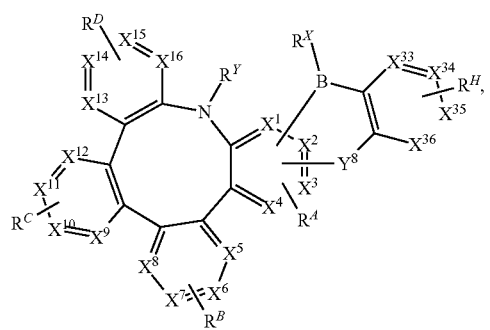
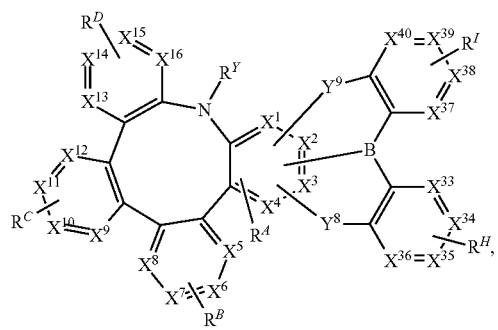
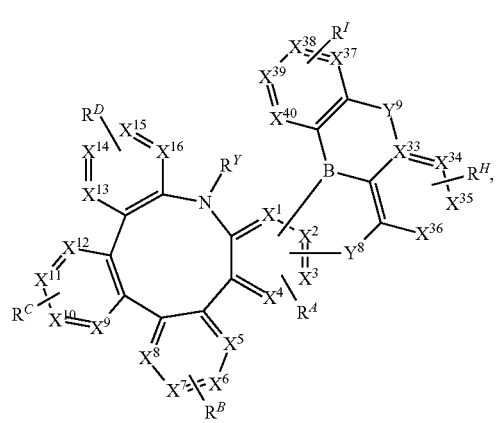
-continued
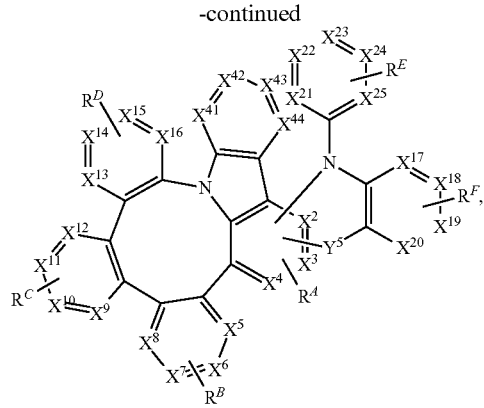
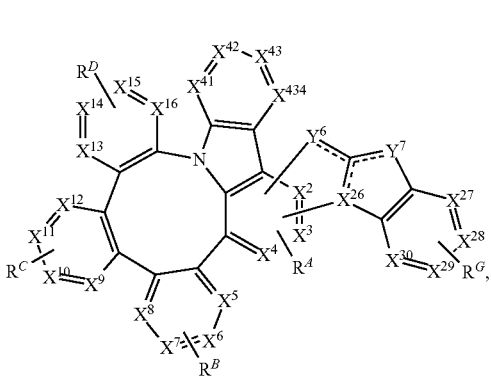
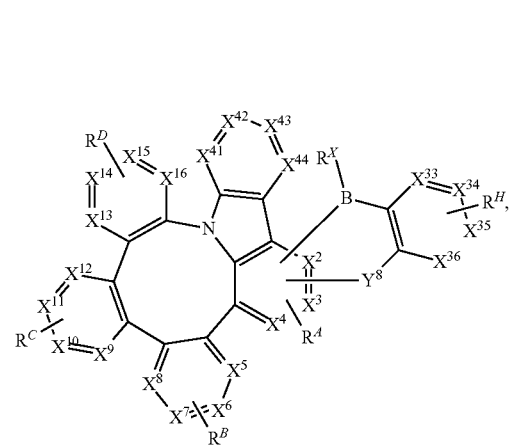
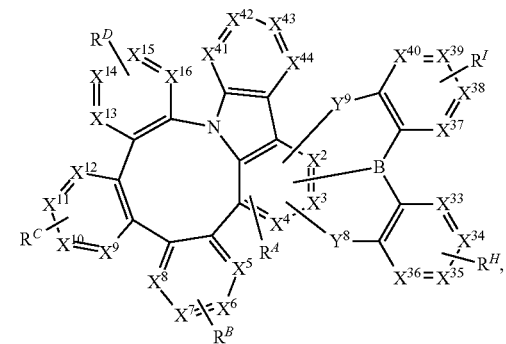

-continued
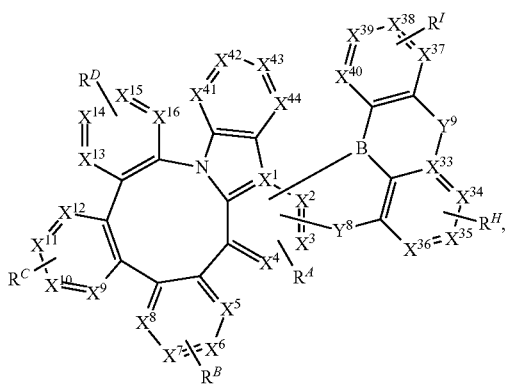
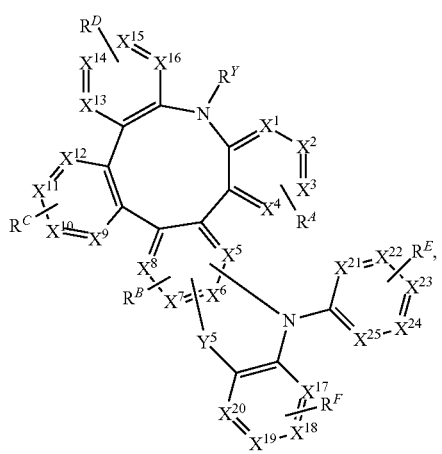
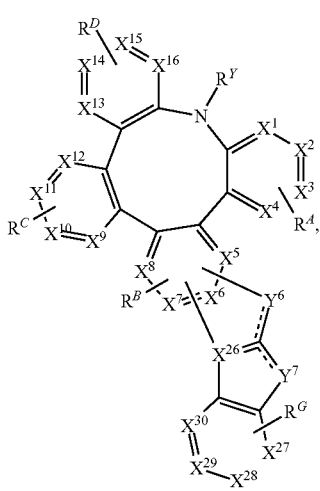
-continued
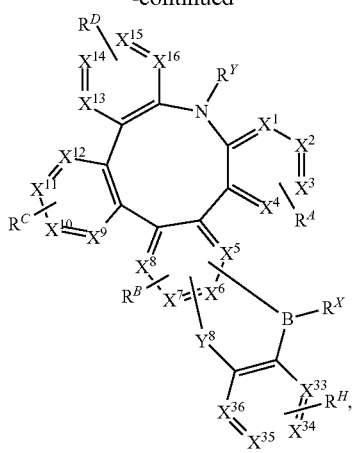
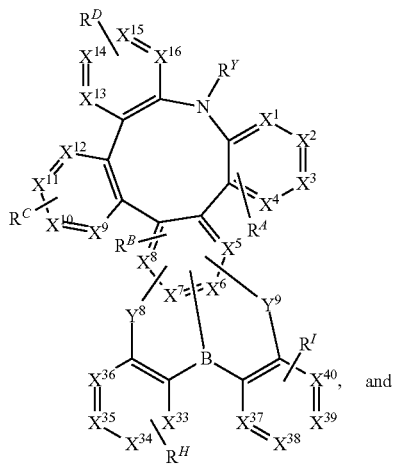
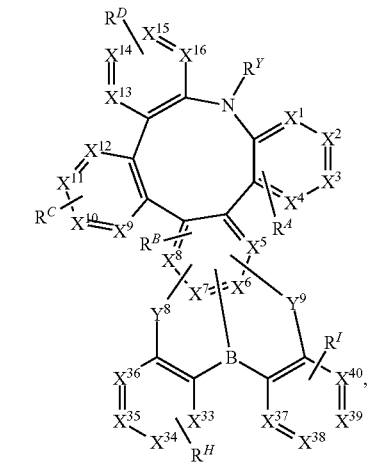
wherein $X^{33}$ to $X^{43}$ are each independently C or N;
$Y^9$ is selected from the group consisting of direct bond, NR, PR, O, S, Se, CRR', SiRR', GeRR', BR, BRR';
$R^I$ has the same definition as $R^A$ to $R^H$; and
$R^Y$ has the same definition as $R^X$.
15. The compound of claim 1, wherein the compound is selected from the group consisting of:

| Compound | Structure of compound |
|---|---|
| Compound-1-(Rm)(Rn)(Ro), wherein Compound-1-(R1)(R1)(R1) to Compound-1-(R23)(R84)(R84) having the structure | |
| Compound-2-(Rm)(Rn)(Ro), wherein Compound-2-(R1)(R1)(R1) to Compound-2-(R23)(R84)(R84) having the structure | |
| Compound-3-(Rm)(Rn)(Ro), wherein Compound-3-(R1)(R1)(R1) to Compound-3-(R23)(R84)(R84) having the structure | |
| Compound-4-(Rn)(Ro)(Rp), wherein Compound-4-(R1)(R1)(R1) to Compound-4-(R84)(R84)(R71) having the structure | |

| Compound | Structure of compound |
|---|---|
| Compound-5-(Rn)(Ro)(Rp), wherein Compound-5-(R1)(R1)(R1) to Compound-5-(R84)(R84)(R71) having the structure | |
| Compound-6-(Rn)(Ro)(Rp), wherein Compound-6-(R1)(R1)(R1) to Compound-6-(R84)(R84)(R71) having the structure | |
| Compound-7-(Rn)(Ro)(Rp), wherein Compound-7-(R1)(R1)(R1) to Compound-7-(R84)(R84)(R71) having the structure | |
| Compound-8-(Rn)(Ro)(Rp), wherein Compound-8-(R1)(R1)(R1) to Compound-8-(R84)(R84)(R71) having the structure | |

-continued

| Compound | Structure of compound |
|---|---|
| Compound-9-(Rn)(Ro)(Rp), wherein Compound-9-(R1)(R1)(R1) to Compound-9-(R84)(R84)(R71) having the structure | |
| Compound-10-(Rn)(Ro)(Rp)(Yq), wherein Compound-10-(R1)(R1)(R1)(Y1) to Compound-10-(R84)(R84)(R71)(Y76) having the structure | |
| Compound-11-(Rn)(Ro)(Rp)(Yq), wherein Compound-11-(R1)(R1)(R1)(Y1) to Compound-11-(R84)(R84)(R71)(Y76) having the structure | |
| Compound-12-(Rn)(Rp)(Yq), wherein Compound-12-(R1)(R1)(Y1) to Compound-12-(R84)(R71)(Y76) having the structure | |

-continued

| Compound | Structure of compound |
|---|---|
| Compound-13-(Rn)(Yq)(Yr), wherein Compound-13-(R1)(Y1)(Y1) to Compound-13-(R84)(Y76)(Y76) having the structure | |
| Compound-14-(Rn)(Yq)(Yr), wherein Compound-14-(R1)(Y1)(Y1) to Compound-14-(R84)(Y76)(Y76) having the structure | |
| Compound-15-(Rn)(Ro)(Yq)(Yr), wherein Compound-15-(R1)(R1)(Y1)(Y1) to Compound-15-(R84)(R84)(Y76)(Y76) having the structure | |
| Compound-16-(Yq)(Yr)(Ys)(Yt), wherein Compound-16-(Y1)(Y1)(Y1)(Y1) to Compound-16-(Y76)(Y76)(Y76)(Y76) having the structure | |

-continued

| Compound | Structure of compound |
|---|---|
| Compound-17-(Yq)(Yr)(Ys)(Yt), wherein Compound-17-(Y1)(Y1)(Y1)(Y1) to Compound-17-(Y76)(Y76)(Y76)(Y76) having the structure | |
| Compound-18-(Rn)(Ro)(Yq)(Yr), wherein Compound-18-(R1)(R1)(Y1)(Y1) to Compound-18-(R84)(R84)(Y76)(Y76) having the structure | |
| Compound-19-(Rn)(Ro), wherein Compound-19-(R1)(R1) to Compound-19-(R84)(R84) having the structure | |
| Compound-20-(Rn)(Ro), wherein Compound-20-(R1)(R1) to Compound-20-(R84)(R84) having the structure | |

| Compound | Structure of compound |
|---|---|
| Compound-21-(Rn)(Ro), wherein Compound-21-(R1)(R1) to Compound-21-(R84)(R84) having the structure | 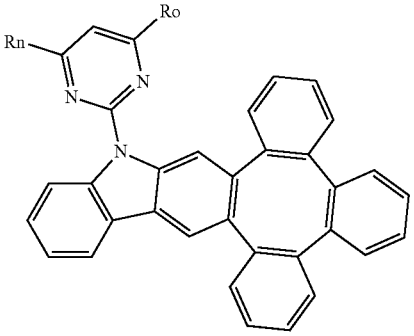 |
| Compound-22-(Rn)(Ro), wherein Compound-22-(R1)(R1) to Compound-22-(R84)(R84) having the structure | 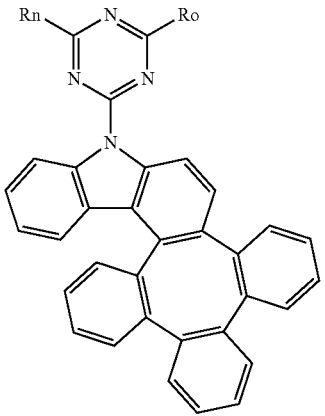 |
| Compound-23-(Rn)(Ro), wherein Compound-23-(R1)(R1) to Compound-23-(R84)(R84) having the structure | 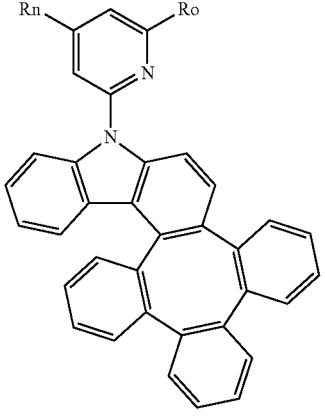 |
| Compound-24-(Rn)(Ro), wherein Compound-24-(R1)(R1) to Compound-24-(R84)(R84) having the structure | 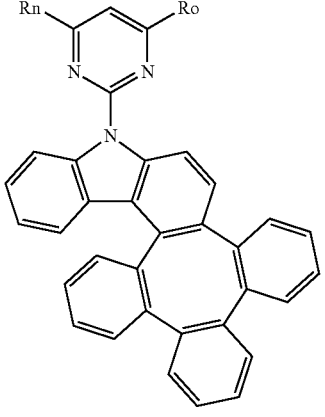 |

-continued

| Compound | Structure of compound |
|---|---|
| Compound-25-(Rn), wherein Compound-25-(R1) to Compound-25-(R84) having the structure | |
| Compound-26-(Rn), wherein Compound-26-(R1) to Compound-26-(R84) having the structure | |
| Compound-27-(Rm)(Rn)(Ro), wherein Compound-27-(R1)(R1)(R1) to Compound-27-(R23)(R84)(R84) having the structure | |
| Compound-28-(Rm)(Rn)(Ro), wherein Compound-28-(R1)(R1)(R1) to Compound-28-(R23)(R84)(R84) having the structure | |

-continued

| Compound | Structure of compound |
|---|---|
| Compound-29-(Rm)(Rn)(Ro), wherein Compound-29-(R1)(R1)(R1) to Compound-29-(R23)(R84)(R84) having the structure | |
| Compound-30-(Rm)(Rn)(Ro), wherein Compound-30-(R1)(R1)(R1) to Compound-30-(R23)(R84)(R84) having the structure | |
| Compound-31-(Rn)(Ro)(Rp), wherein Compound-31-(R1)(R1)(R1) to Compound-31-(R84)(R84)(R71) having the structure | |
| Compound-32-(Rn)(Ro)(Rp), wherein Compound-32-(R1)(R1)(R1) to Compound-32-(R84)(R84)(R71) having the structure | |

-continued

| Compound | Structure of compound |
|---|---|
| Compound-33-(Rn)(Ro)(Rp), wherein Compound-33-(R1)(R1)(R1) to Compound-33-(R84)(R84)(R71) having the structure | |
| Compound-34-(Rn)(Ro)(Rp), wherein Compound-34-(R1)(R1)(R1) to Compound-34-(R84)(R84)(R71) having the structure | |
| Compound-35-(Rn)(Rp)(Yq), wherein Compound-35-(R1)(R1)(Y1) to Compound-35-(R84)(R71)(Y76) having the structure | |

-continued

| Compound | Structure of compound |
|---|---|
| Compound-36-(Rn)(Rp)(Yq), wherein Compound-36-(R1)(R1)(Y1) to Compound-36-(R84)(R71)(Y76) having the structure | |
| Compound-37-(Rp)(Rp)(Yq), wherein Compound-37-(R1)(R1)(Y1) to Compound-37-(R84)(R71)(Y76) having the structure | |
| Compound-38-(Rn)(Rp)(Yq), wherein Compound-38-(R1)(R1)(Y1) to Compound-38-(R84)(R71)(Y76) having the structure | |
| Compound-39-(Rn)(Yq)(Yr), wherein Compound-39-(R1)(Y1)(Y1) to Compound-39-(R84)(Y76)(Y76) having the structure | |

| Compound | Structure of compound |
|---|---|
| Compound-40-(Rn)(Yq)(Yr), wherein Compound-40-(R1)(Y1)(Y1) to Compound-40-(R84)(Y76)(Y76) having the structure | 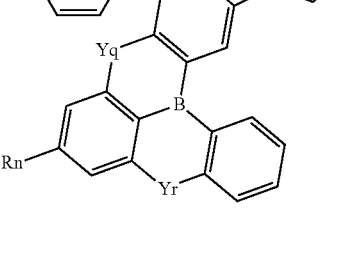 |
| Compound-41-(Rn)(Yq)(Yr), wherein Compound-41-(R1)(Y1)(Y1) to Compound-41-(R84)(Y76)(Y76) having the structure | 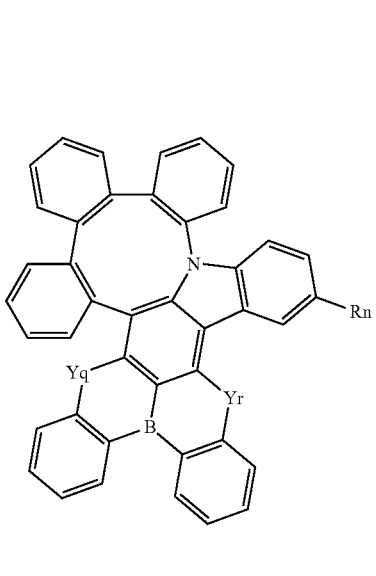 |
| Compound-42-(Rn)(Yq)(Yr), wherein Compound-42-(R1)(Y1)(Y1) to Compound-42-(R84)(Y76)(Y76) having the structure | 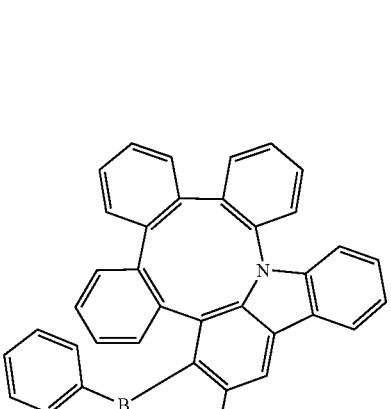 |

| Compound | Structure of compound |
|---|---|
| Compound-43-(Rn)(Yq)(Yr), wherein Compound-43-(R1)(Y1)(Y1) to Compound-43-(R84)(Y76)(Y76) having the structure | | wherein in Compounds 1-9 and 13-43, when present: m is an integer from 1 to 15, n and o are each independently an integer from 1 to 84, p is an integer from 1 to 71, and q, r, s, and t are each independently an integer from 1 to 76;

wherein in Compounds 10-12, when present: n and o are each independently an integer from 1 to 84, and one of the following conditions apply:
  i) p is an integer from 1 to 23 and 26 to 71 and q is an integer from 1 to 76; or
  ii) p is an integer from 1 to 71 and q is an integer from 1 to 23, 26 to 71, and 76, wherein Y1 to Y71 are NR1 to NR71, respectively; Y72 is O, Y73 is S, Y74 is Se, Y75 is $CMe_2$, and Y76 is $SiPh_2$;

wherein R1 to R84 are defined as:

| | Structure |
|---|---|
| R1 | |
| R2 | |
| R3 | |
| R4 | 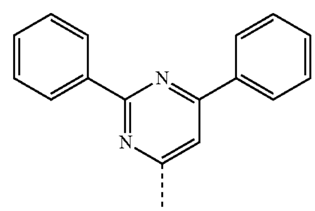 |
| R5 | 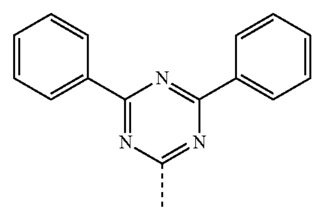 |
| R6 | 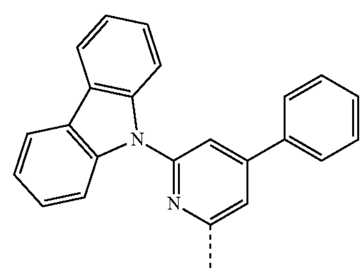 |
| R7 | 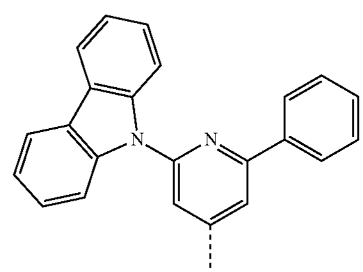 |

| Structure | | Structure |
|---|---|---|
| R8 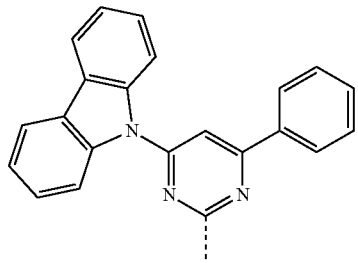 | R13 | 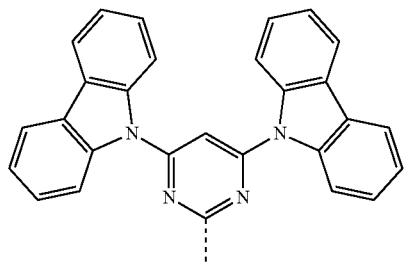 |
| R9 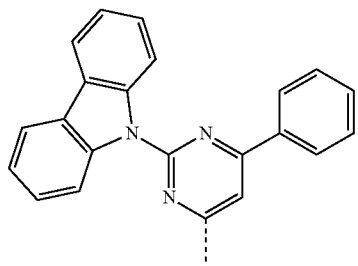 | R14 | 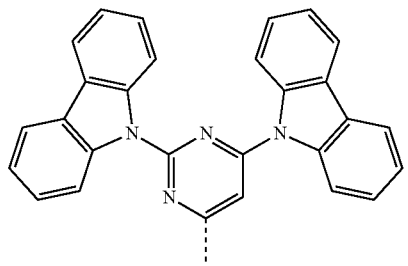 |
| R10 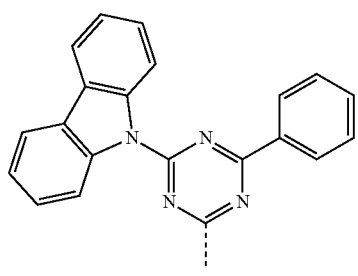 | R15 | 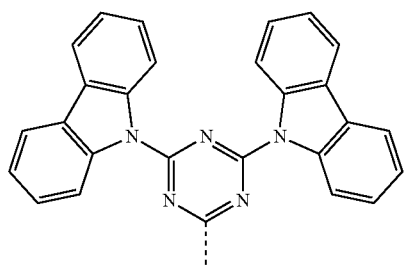 |
| R11 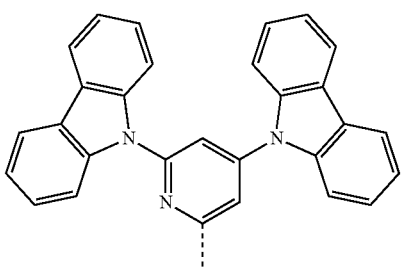 | R16 | 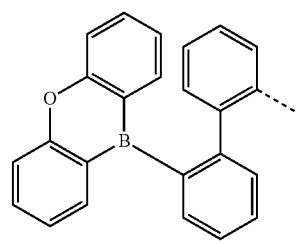 |
| R12 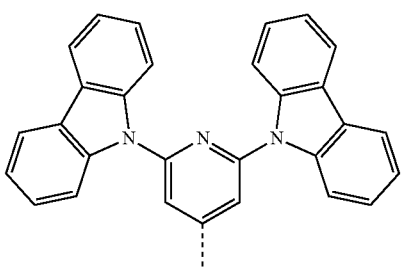 | R17 | 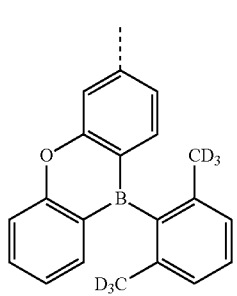 |

| 221 -continued | 222 -continued |
|---|---|
| Structure | Structure |
| R18 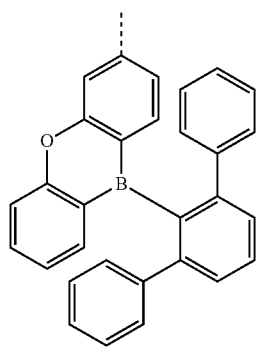 | R24 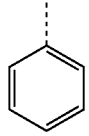 |
| R19 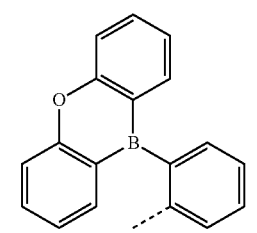 | R25 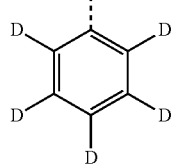 |
| R20 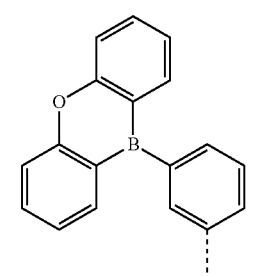 | R26 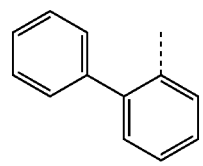 |
| R21 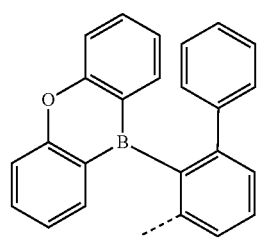 | R27 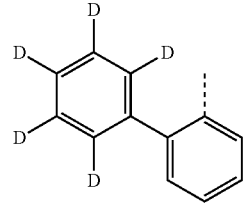 |
| R22 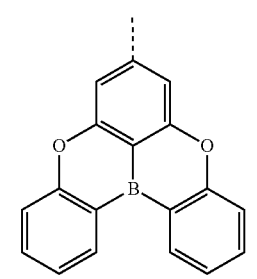 | R28 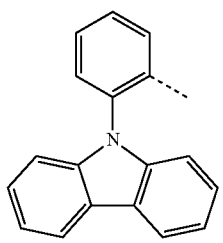 |
| R23 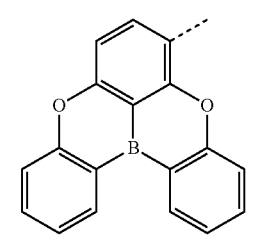 | R29 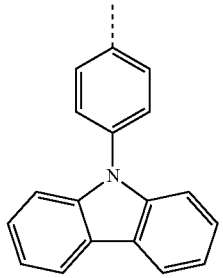 |
|  | R30 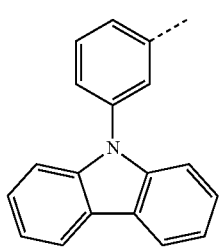 |

223
-continued

| | Structure |
|---|---|
| R31 | (1,3-bis(perdeuterophenyl)phenyl) |
| R32 | (dibenzofuran-3-yl) |
| R33 | (dibenzothiophen-3-yl) |
| R34 | (1,3-diphenylphenyl) |
| R35 | (dibenzofuran-4-yl) |
| R36 | (dibenzothiophen-4-yl) |
| R37 | (benzofuro[3,2-b:4,5-b']dipyridin-yl) |
| R38 | (benzothieno[3,2-d]pyrimidin-4-yl) |
| R39 | (benzothieno dipyridinyl) |
| R40 | (benzofuro[3,2-c]pyridin-yl) |

224
-continued

| | Structure |
|---|---|
| R41 | (benzothieno[3,2-c]pyridin-yl) |
| R42 | (benzofuro[3,2-d]pyrimidin-4-yl) |
| R43 | (9-phenyl-9H-carbazol-3-yl) |
| R44 | (9-phenyl-9H-carbazol-1-yl) |
| R45 | (1,3-di(9H-carbazol-9-yl)phenyl) |
| R46 | (biphenyl-carbazolyl) |

| Structure | Structure |
|---|---|
| R47 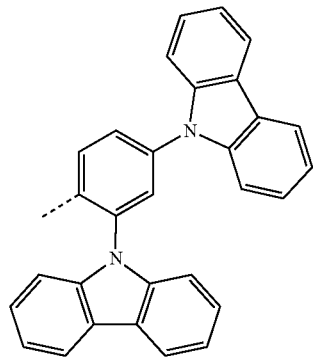 | R51 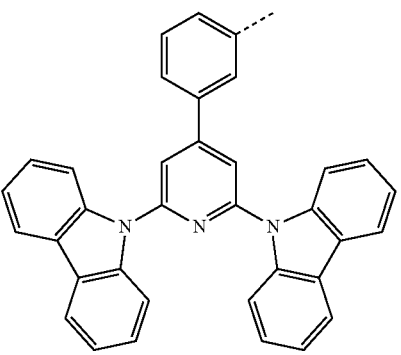 |
| R48 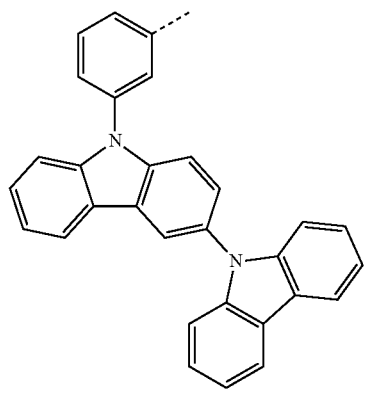 | R52 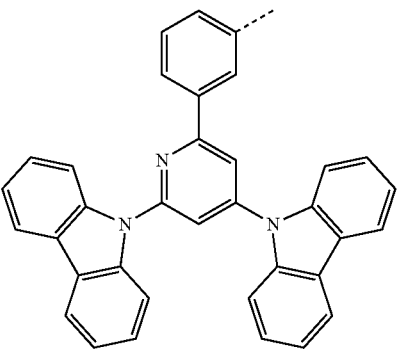 |
| R49 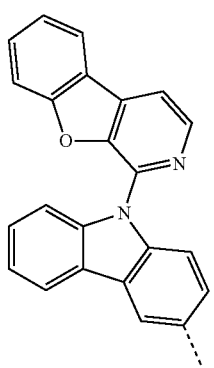 | R53 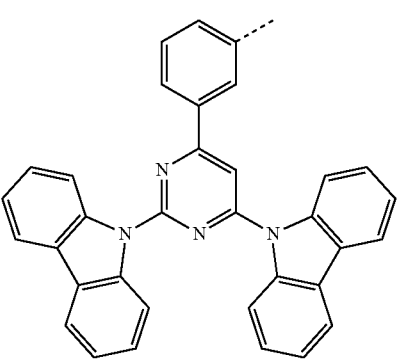 |
| R50 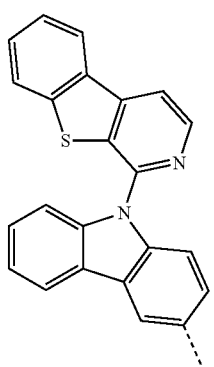 | R54 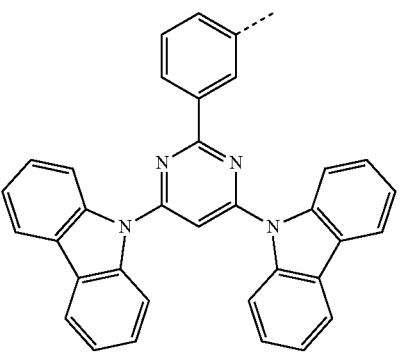 |

227
-continued
| | Structure |
|---|---|
| R55 | 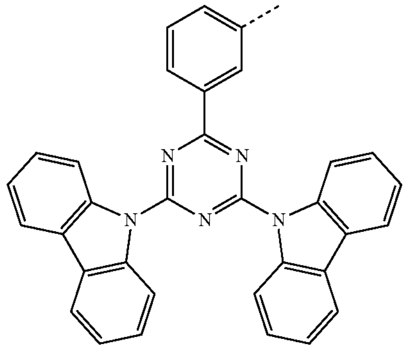 |
| R56 | 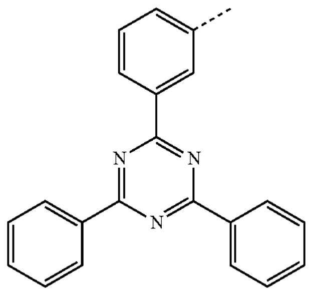 |
| R57 | 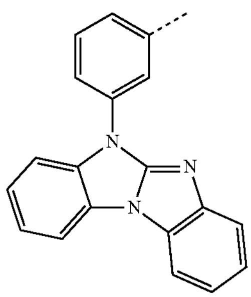 |
| R58 | 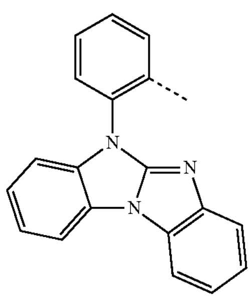 |
| R59 | 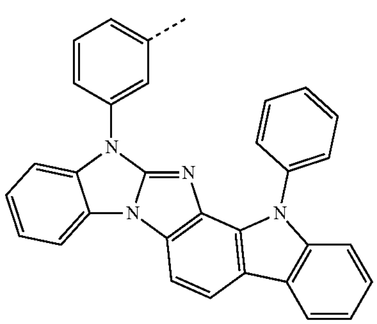 |
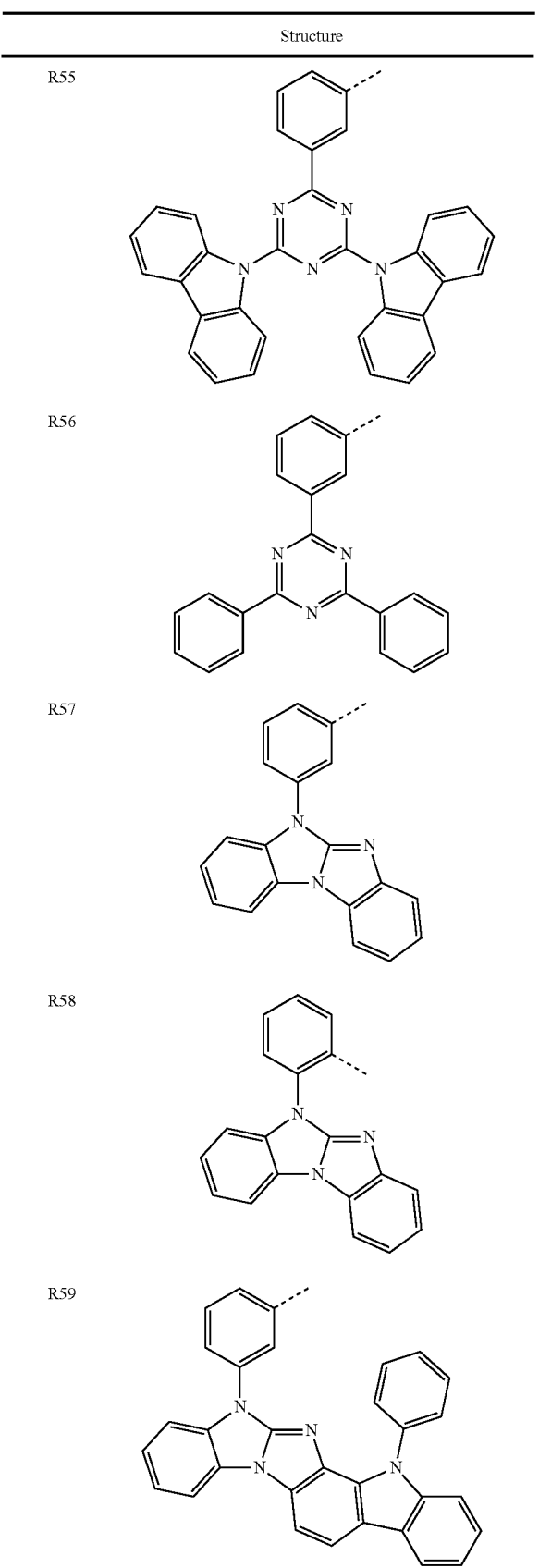
228
-continued
| | Structure |
|---|---|
| R60 | 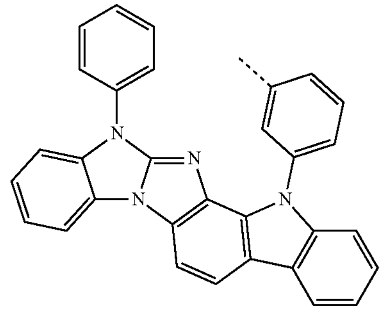 |
| R61 | 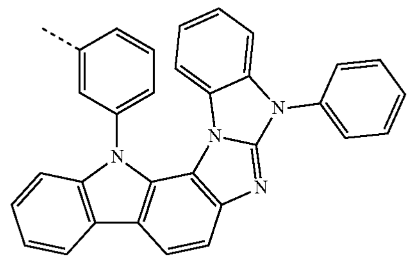 |
| R62 | 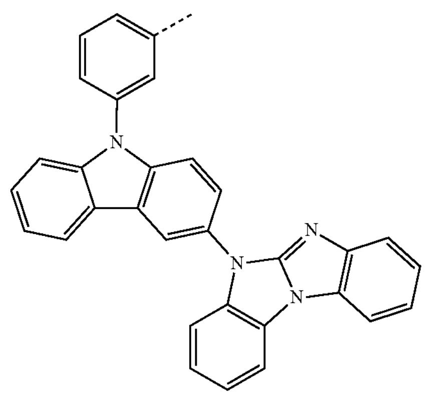 |
| R63 | 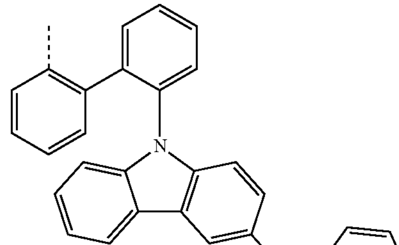 |
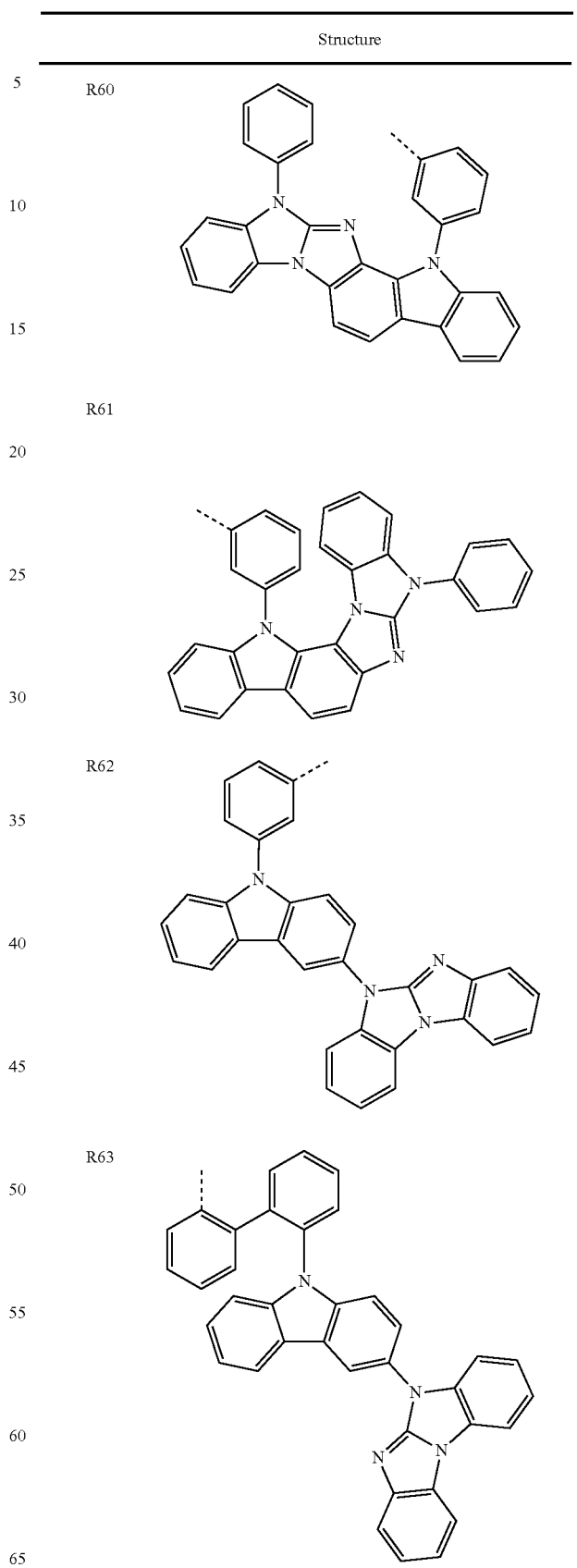

| | Structure |
|---|---|
| R64 | 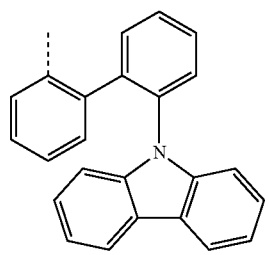 |
| R65 | 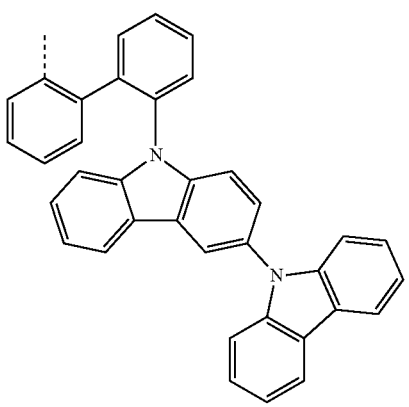 |
| R66 | 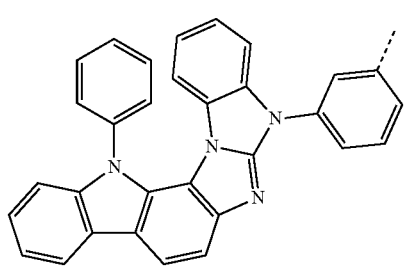 |
| R67 | 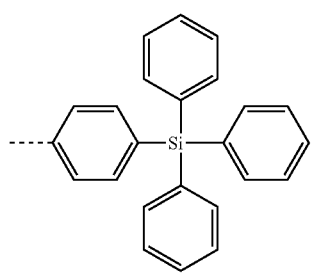 |
| R68 | 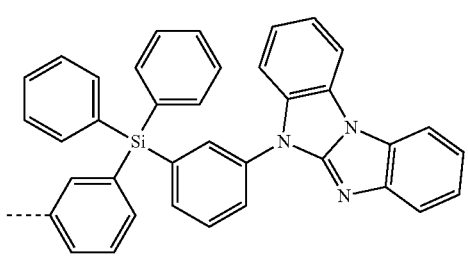 |
| | Structure |
|---|---|
| R69 | 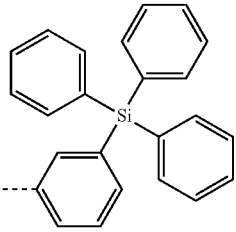 |
| R70 | 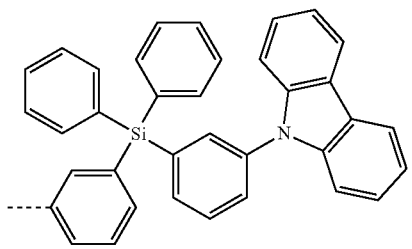 |
| R71 | 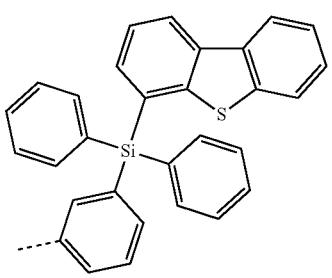 |
| R72 | 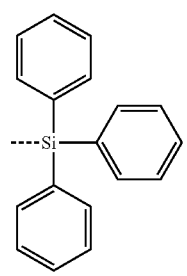 |
| R73 | H |
| R74 | D |
| R75 | N |
| R76 | 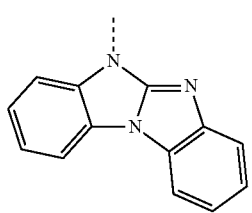 |

231
-continued
| | Structure |
|---|---|
| R77 | 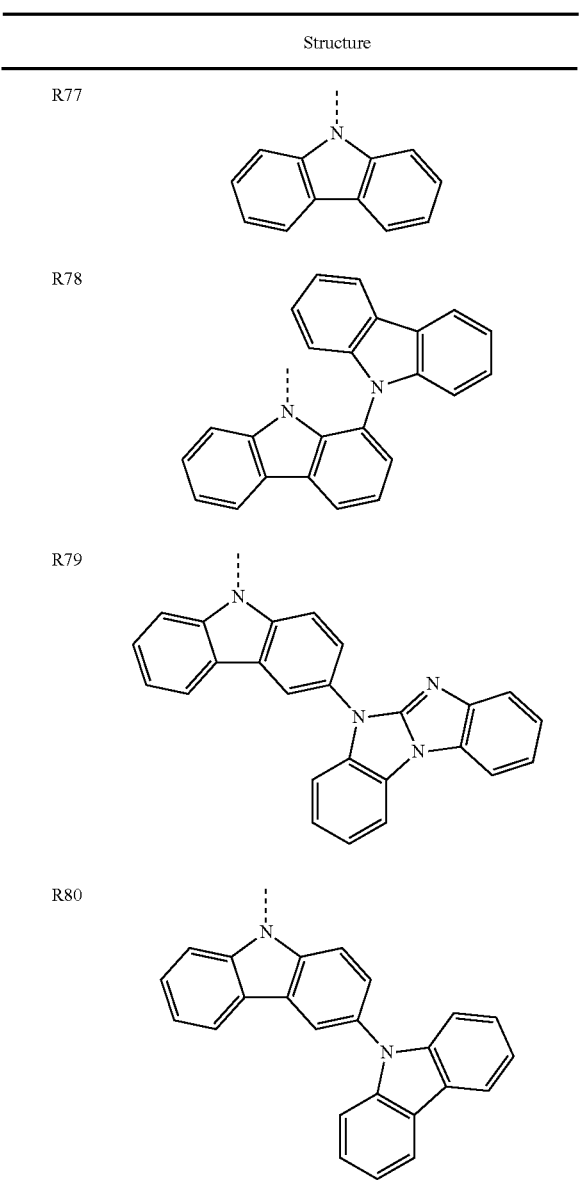 |
| R78 | 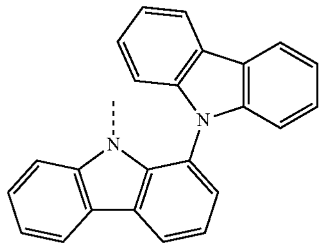 |
| R79 | 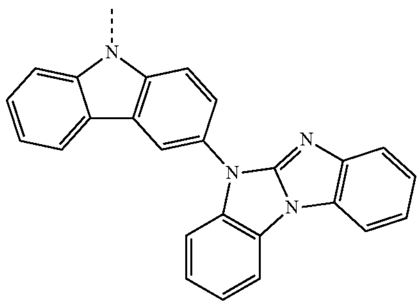 |
| R80 | 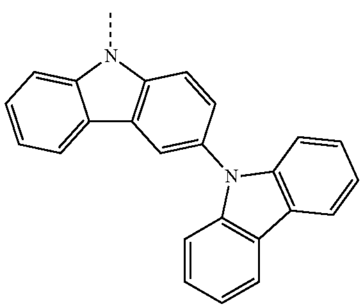 |
232
-continued
| | Structure |
|---|---|
| R81 | 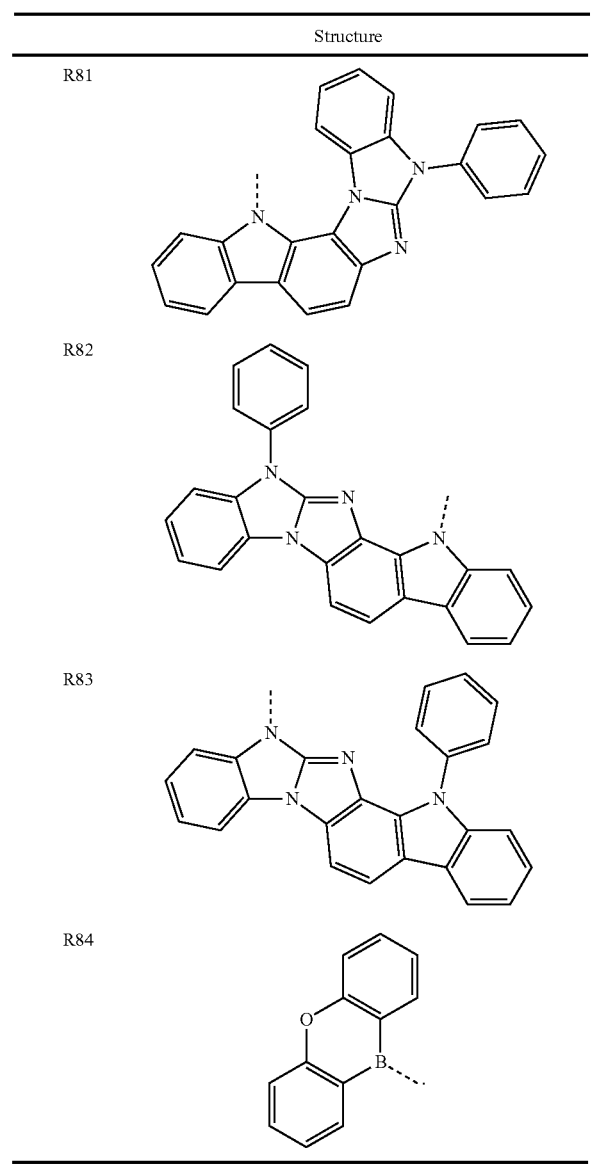 |
| R82 | 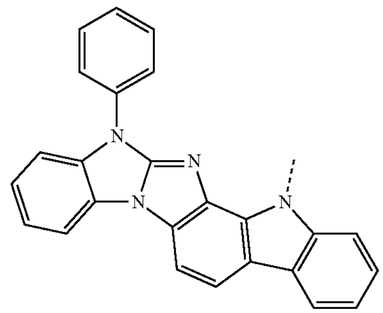 |
| R83 | 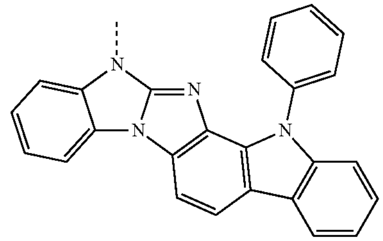 |
| R84 | 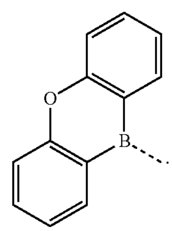 |
16. The compound of claim 1, wherein the compound is selected from the group consisting of:
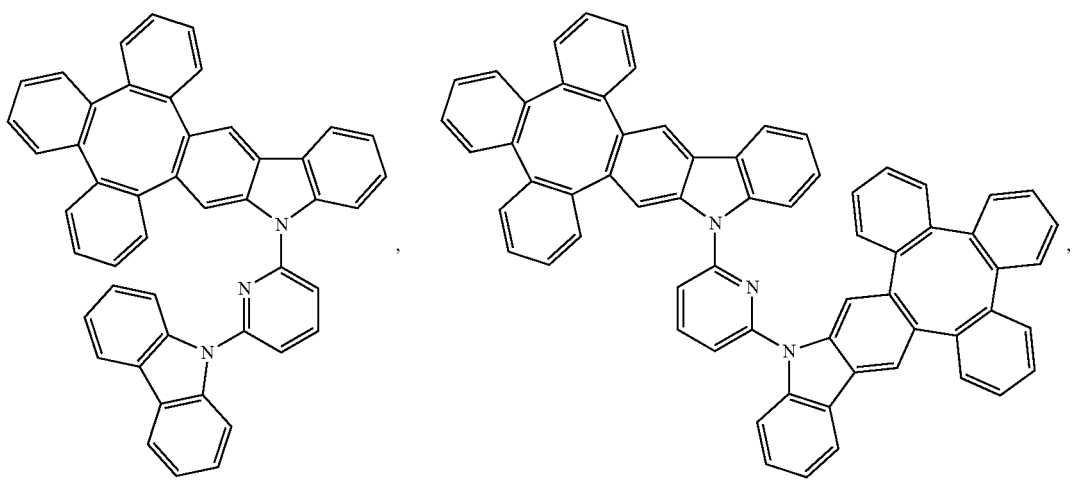

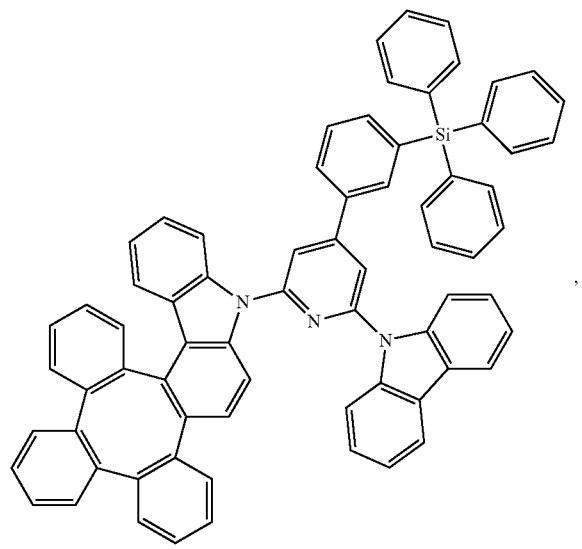
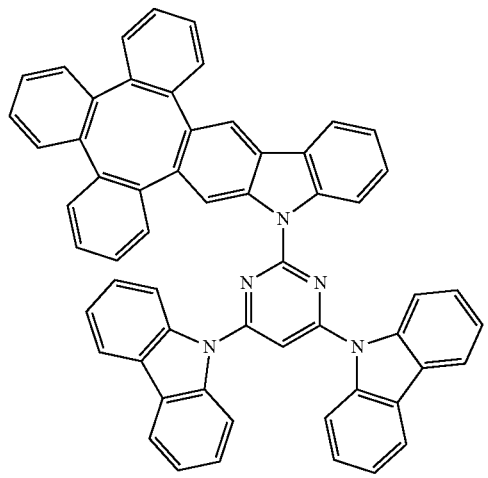
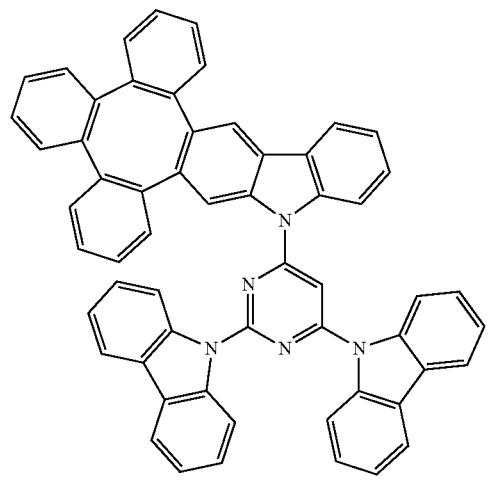
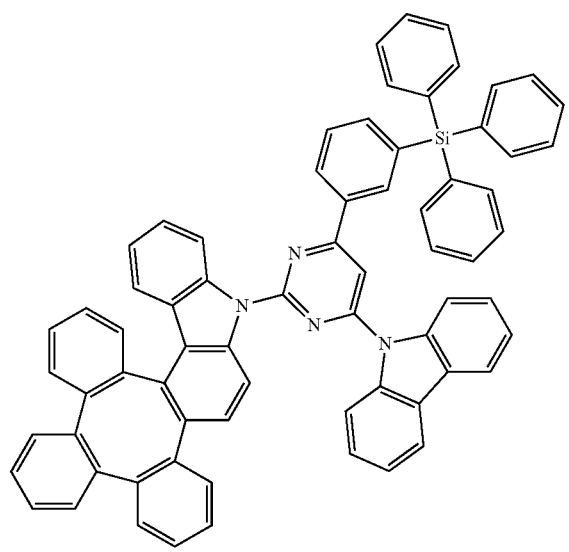
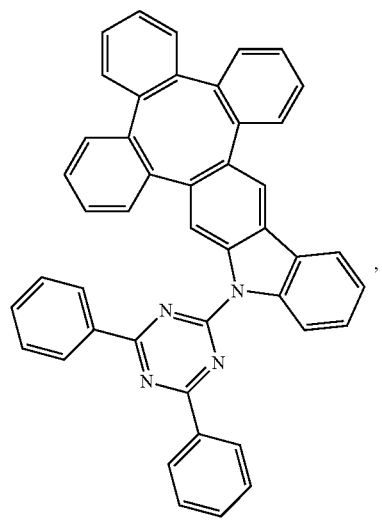
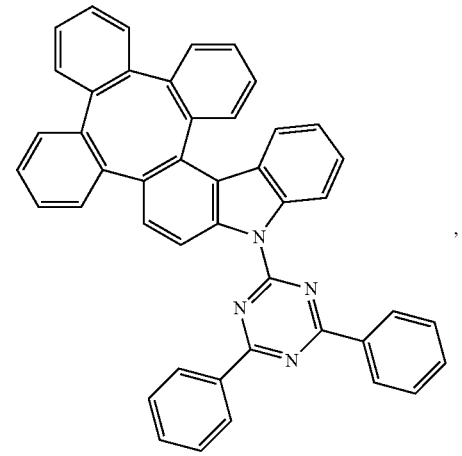

-continued
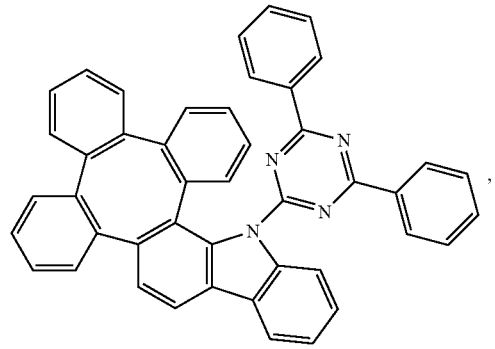
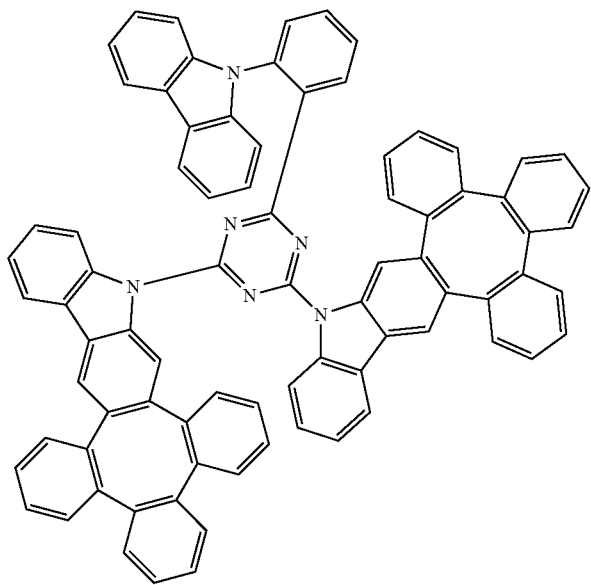
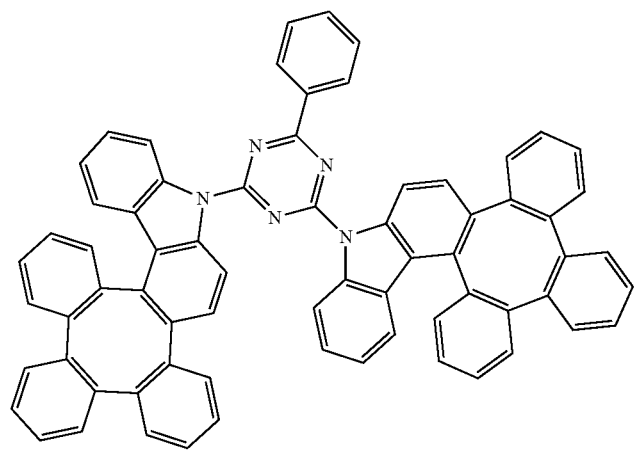
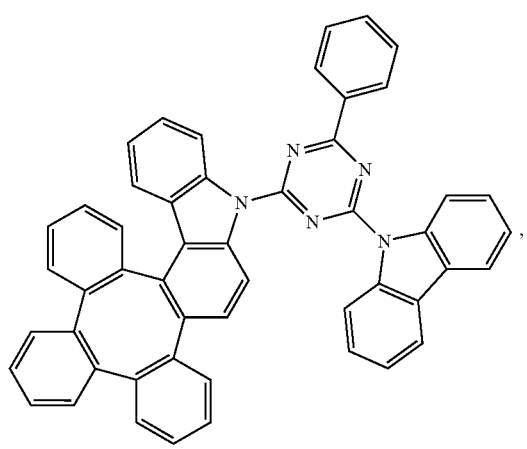
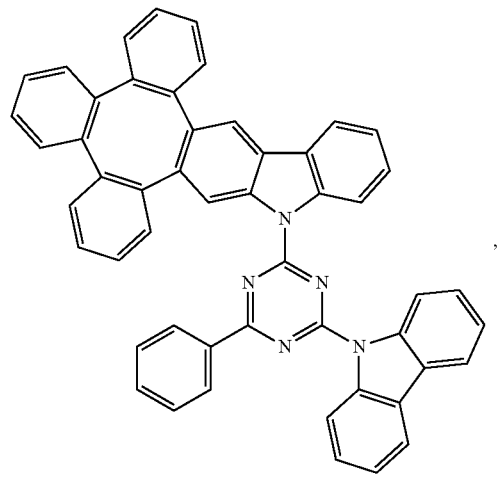
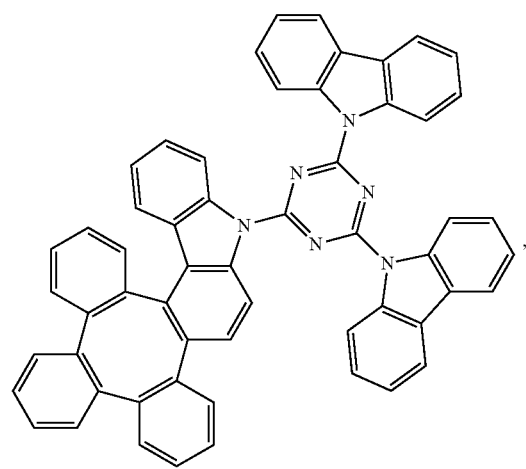

-continued
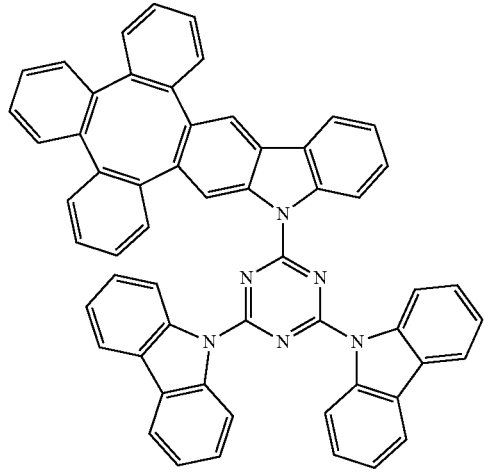
,
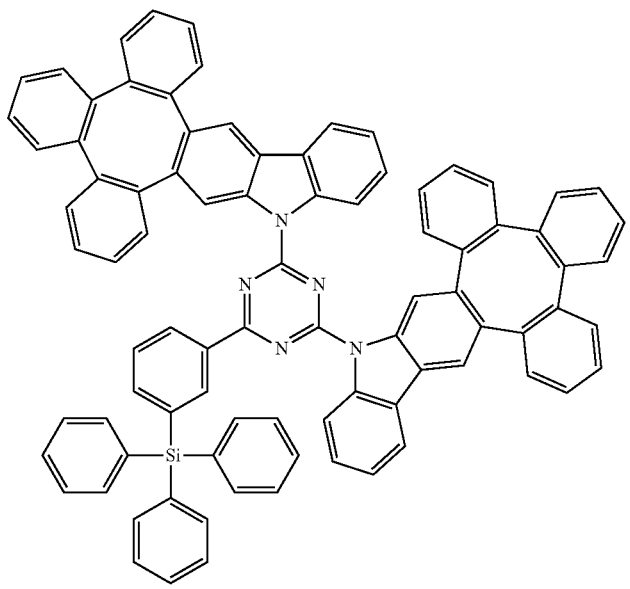
,
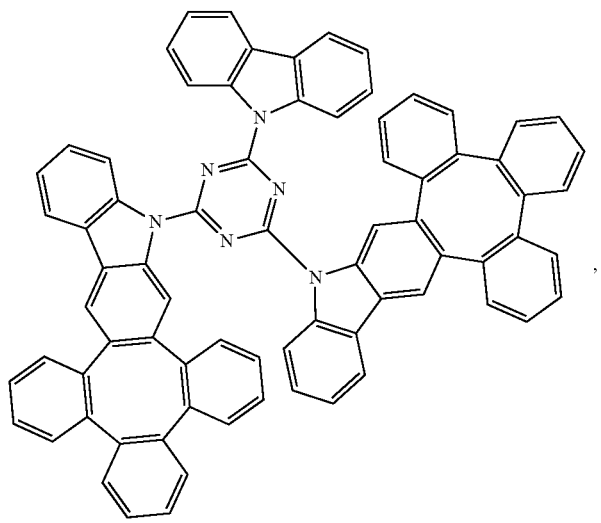
,
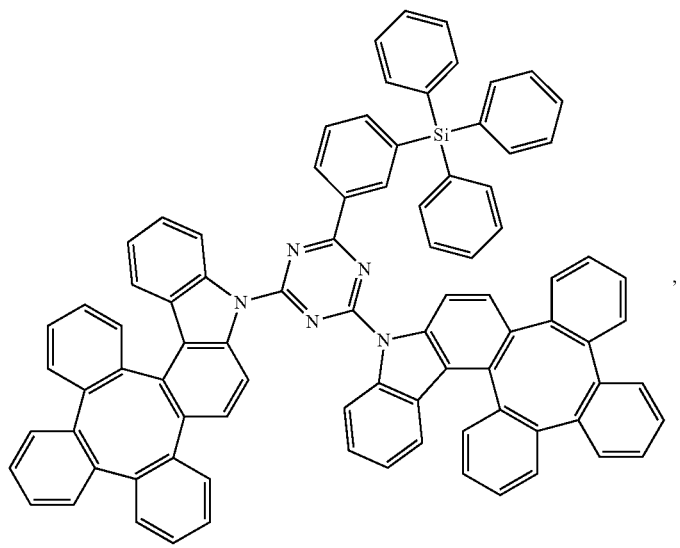
,

-continued
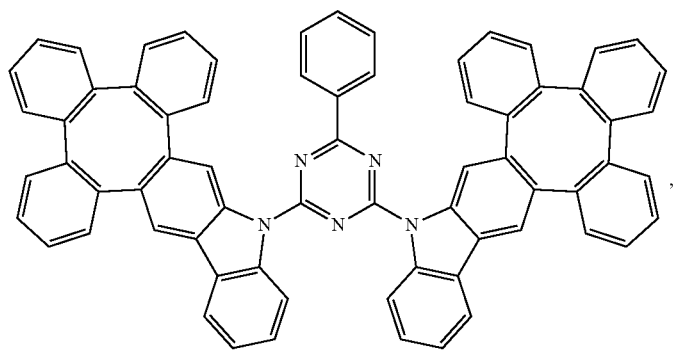
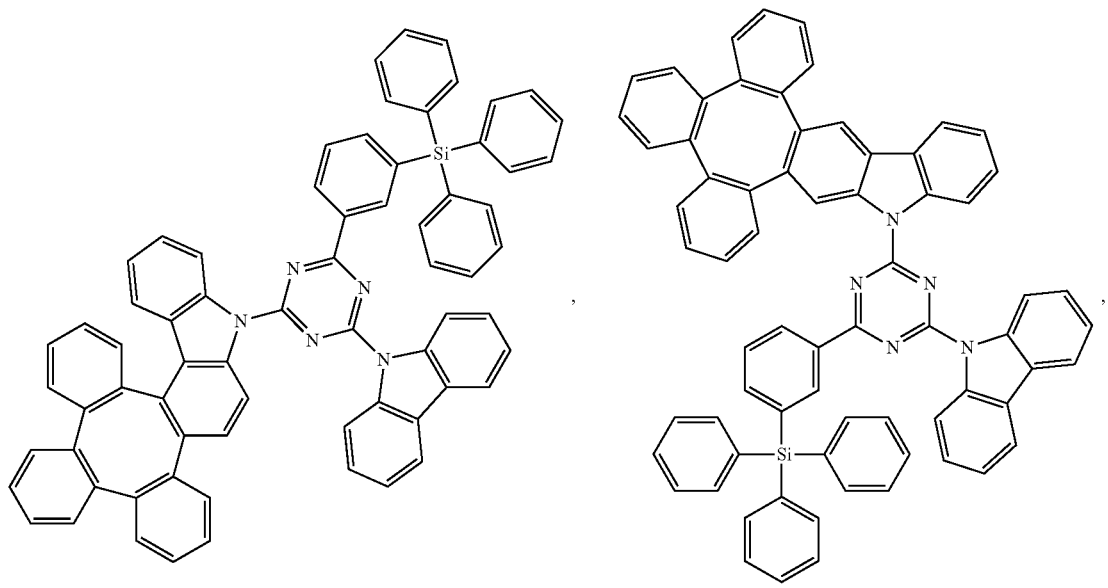
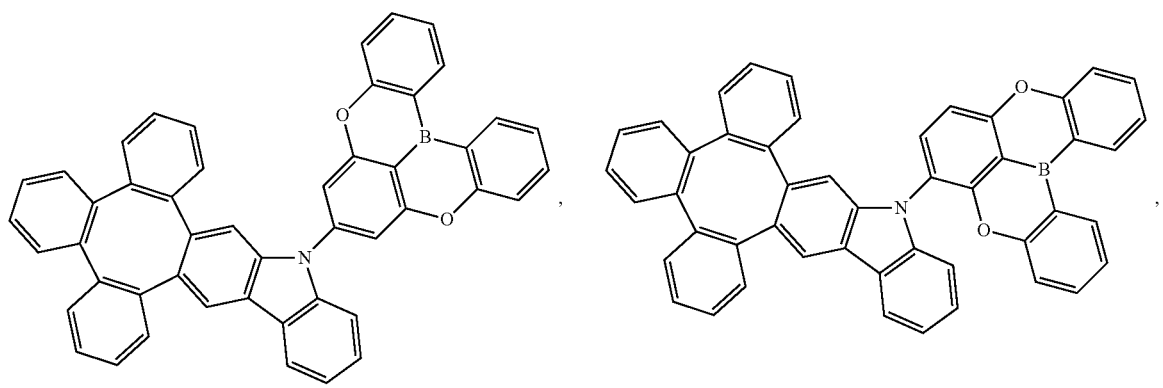
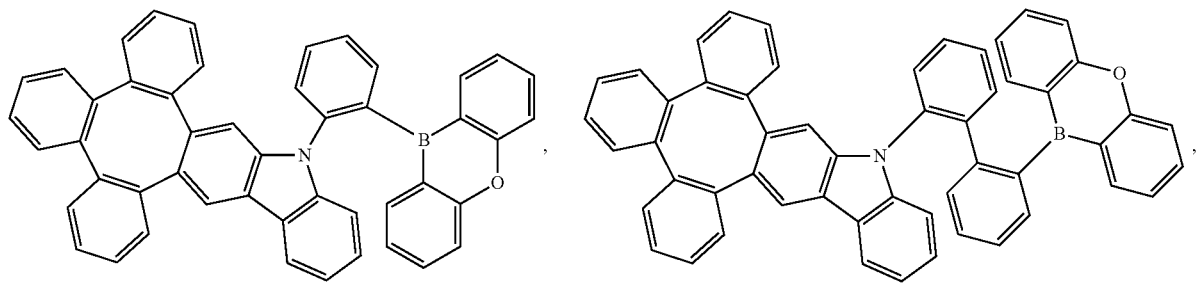

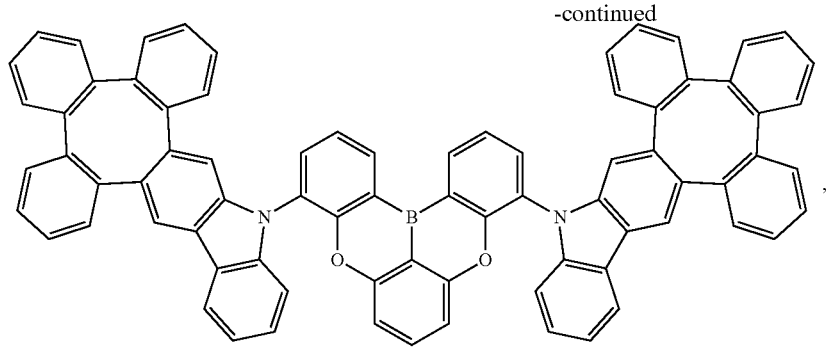
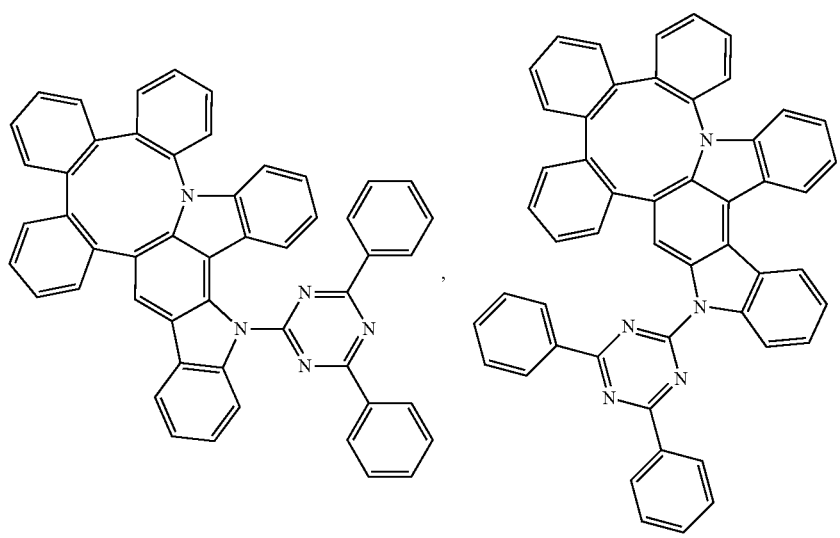
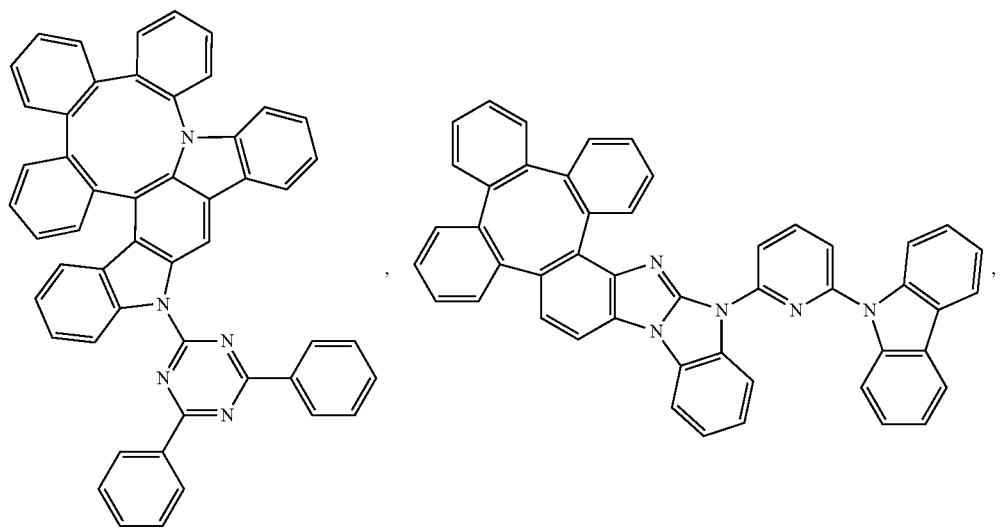

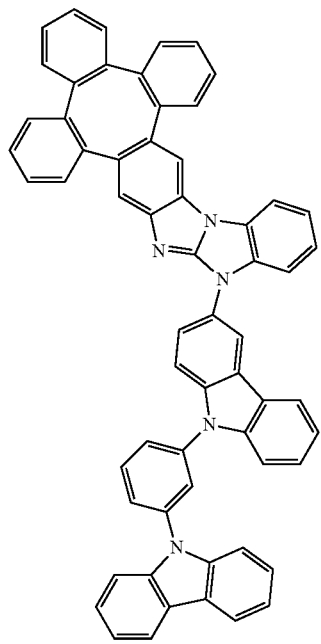
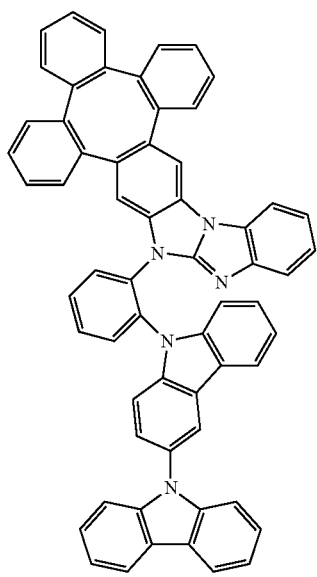
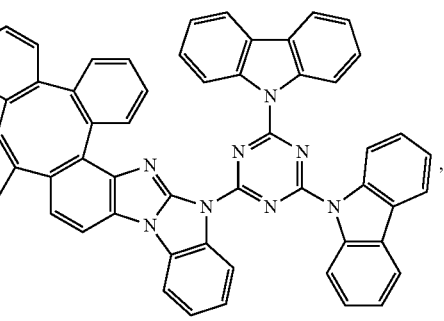
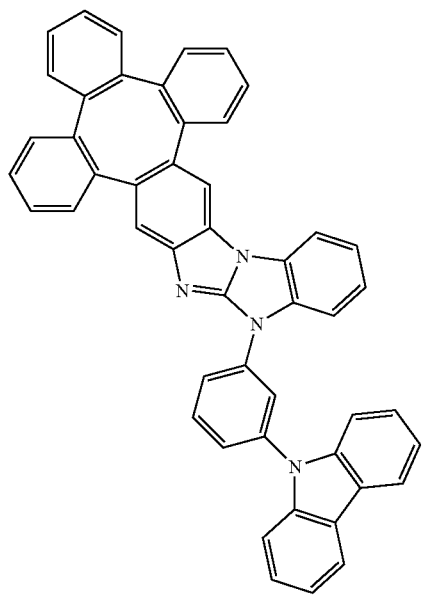
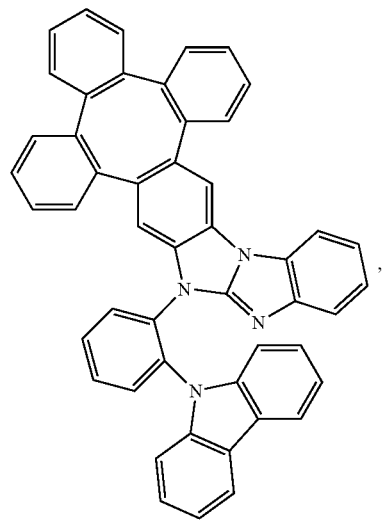

-continued
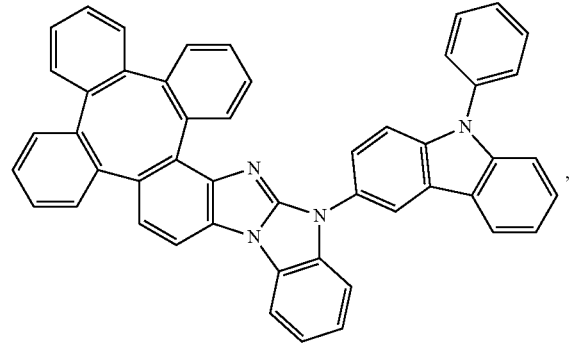
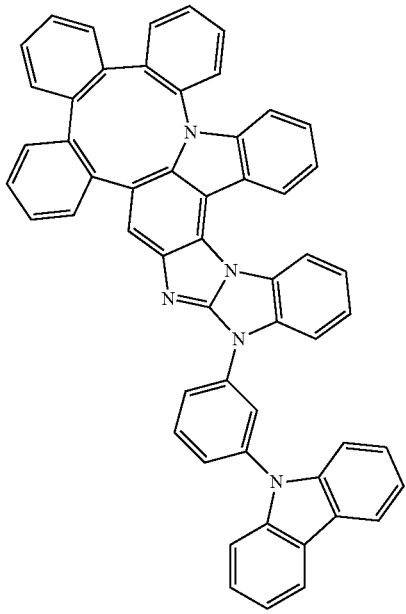
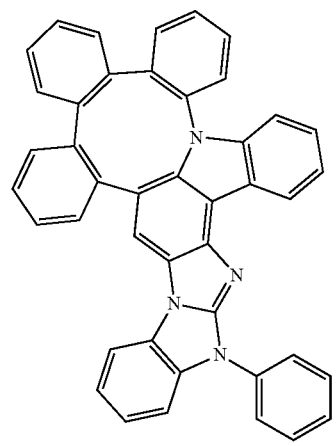
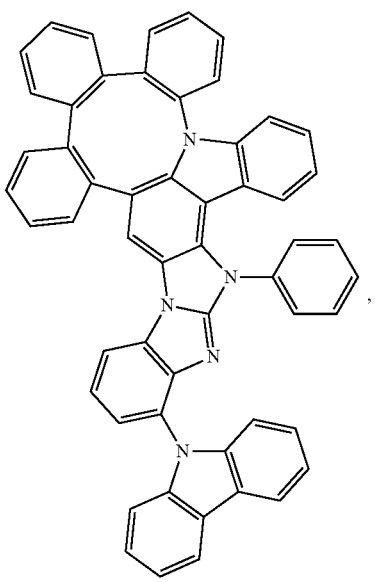
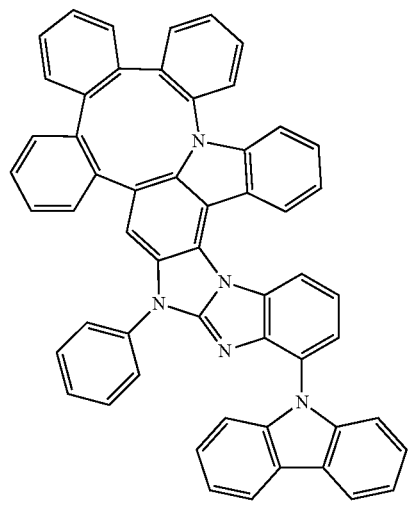
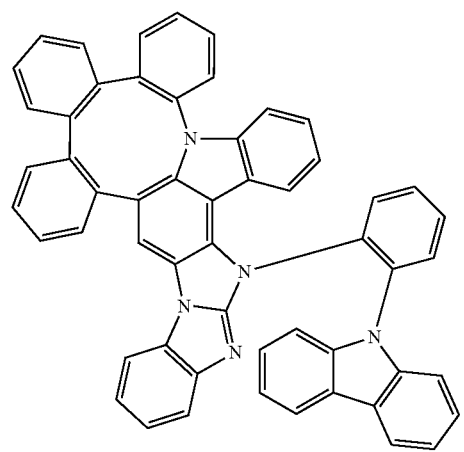
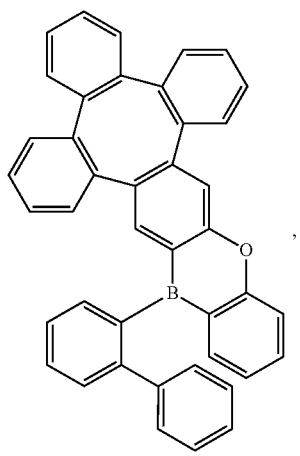
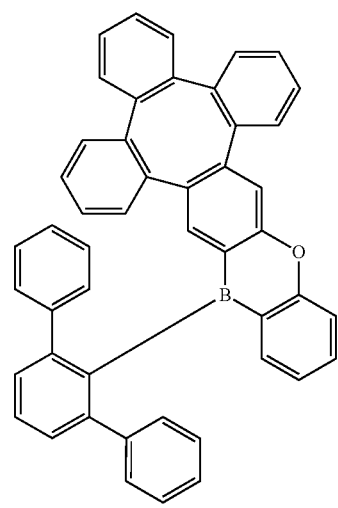

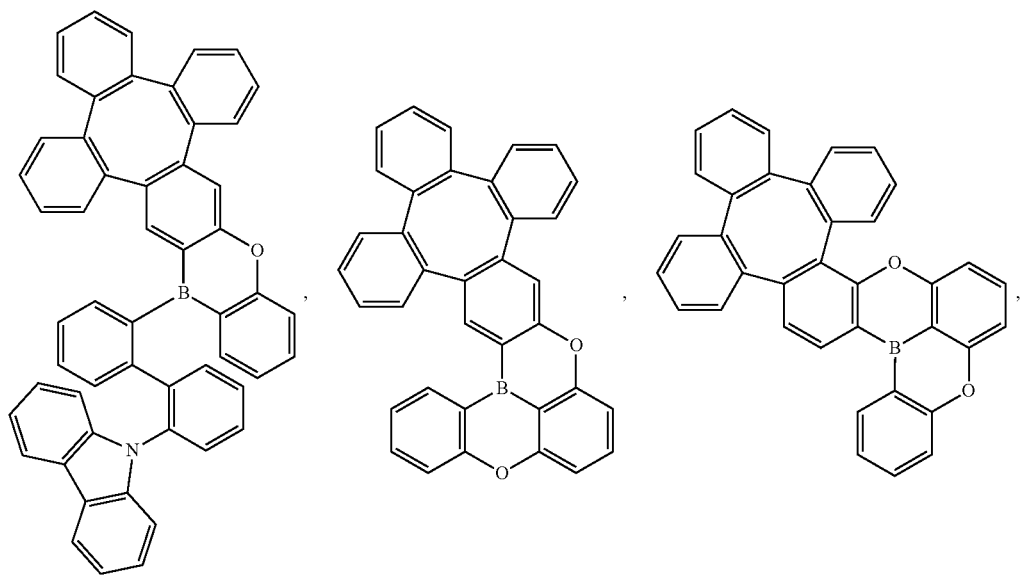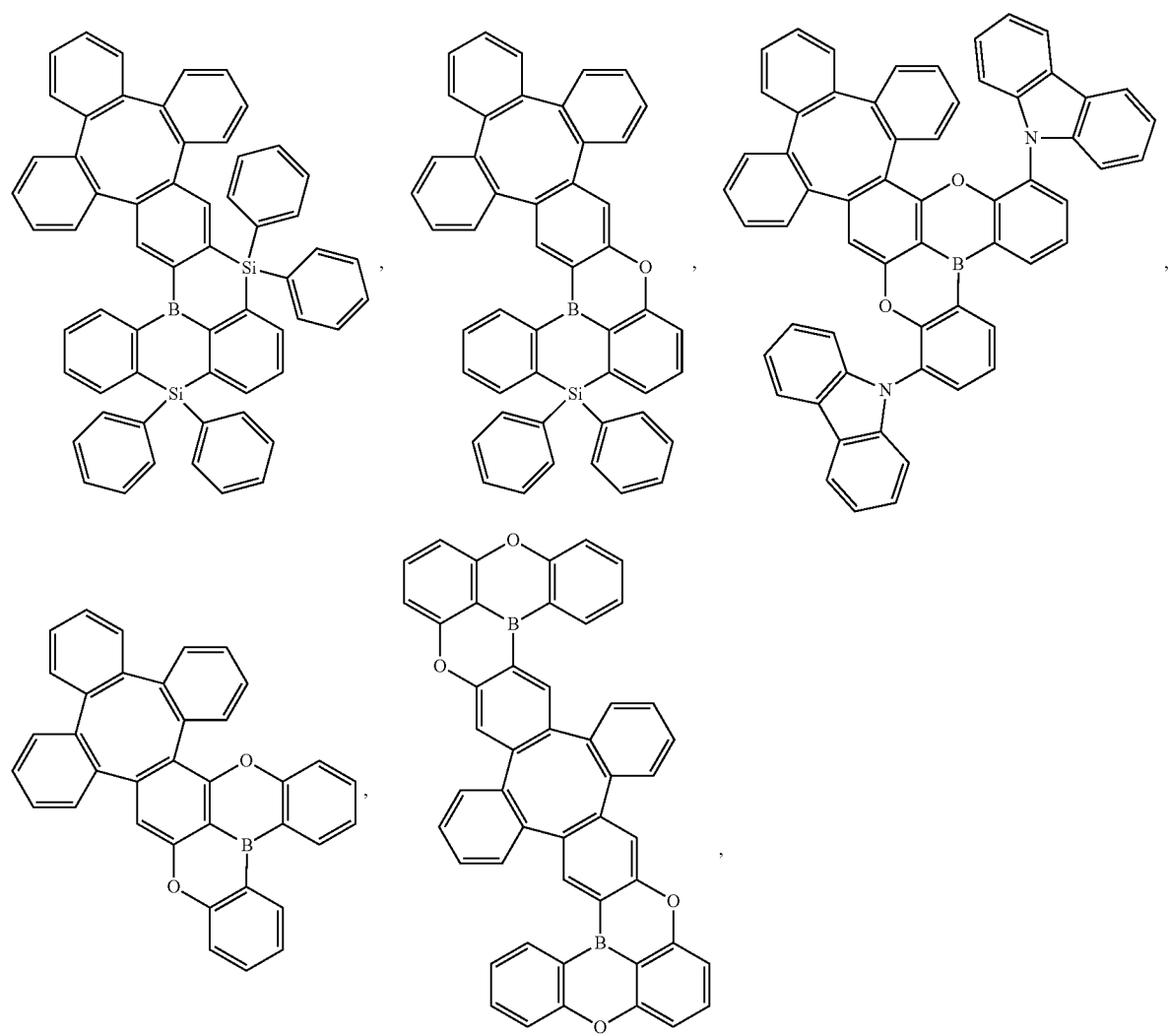

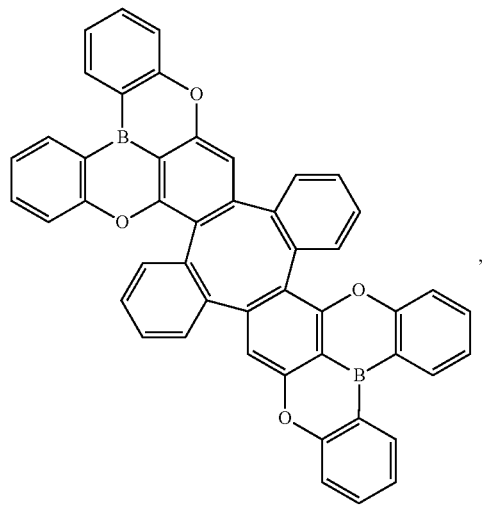,
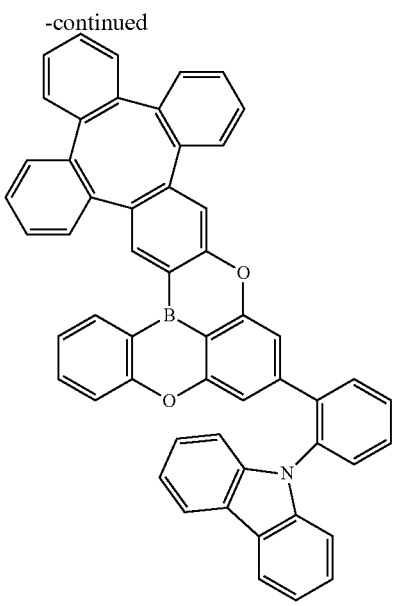,
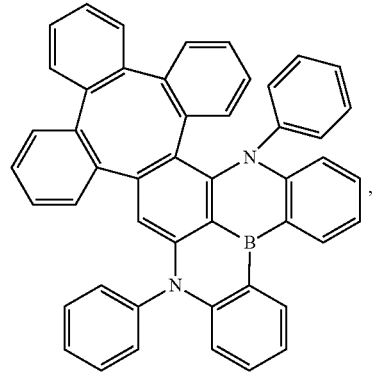,
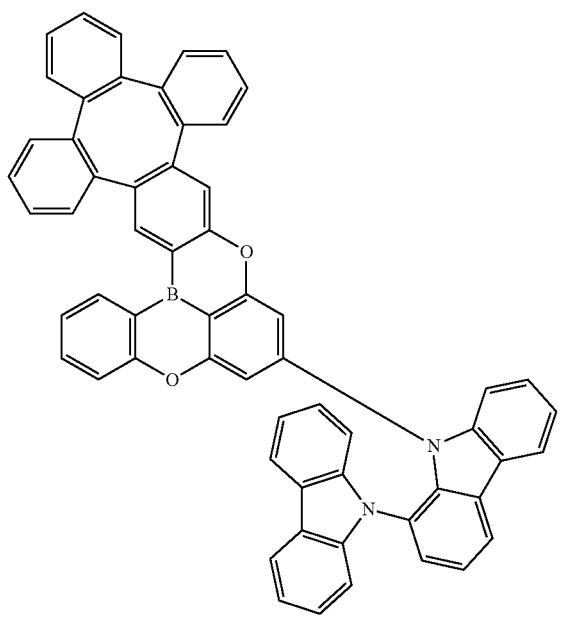,
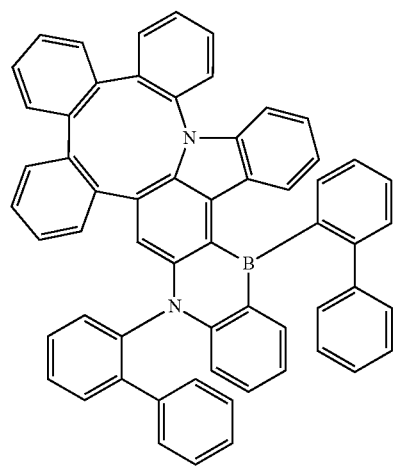,
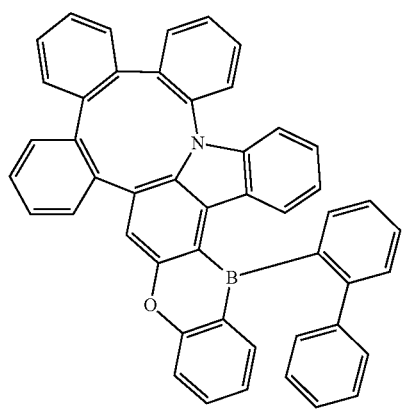,
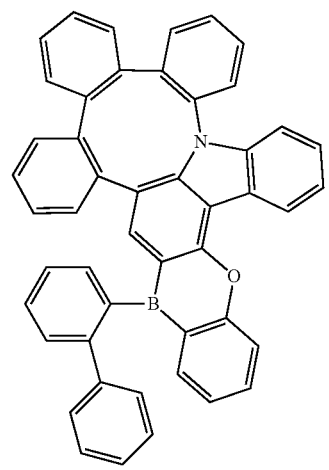,

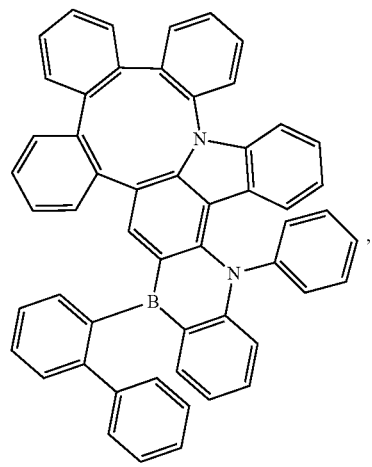 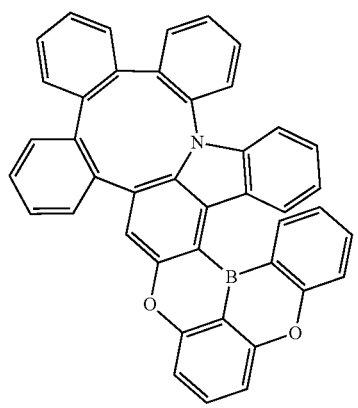 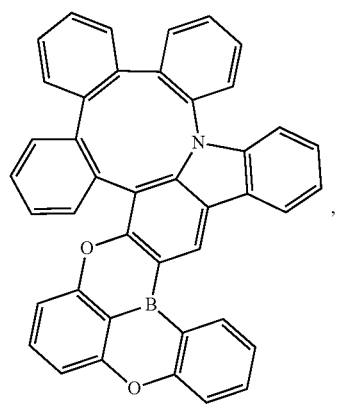

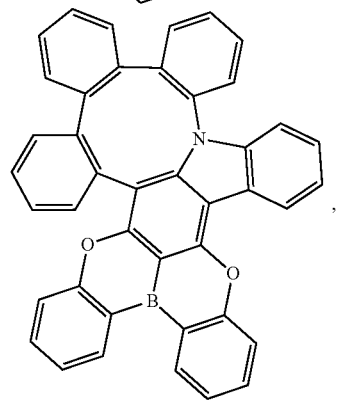, and 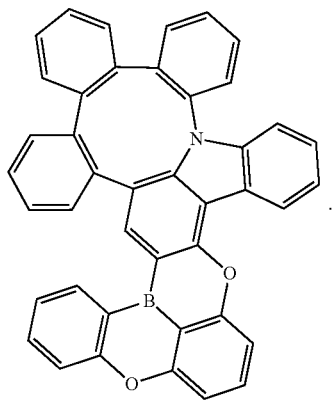.

17. An organic light emitting device (OLED) comprising:
an anode;
a cathode; and
an organic layer disposed between the anode and the cathode,
wherein the organic layer comprises a compound of Formula I:

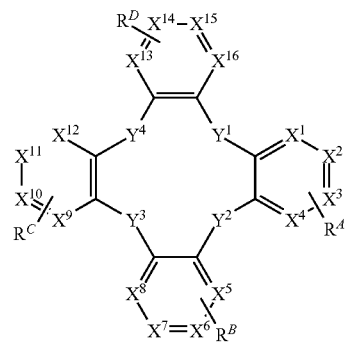

wherein:
X$^1$ to X$^{16}$ are each independently C or N;
Y$^1$ to Y$^4$ are each independently selected from the group consisting of direct bond, NR, PR, O, S, Se, CRR', SiRR', GeRR', BR, and BRR';
at least two adjacent sites from X$^1$ to X$^{16}$ are both carbon and are fused to one of

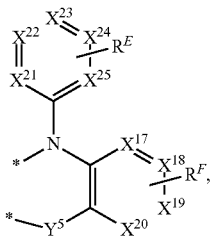 Formula II

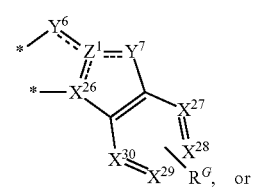, or Formula III

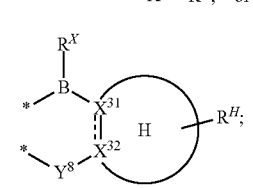 Formula IV wherein:
* shows the attachment point for each structure;
Y$^5$ and Y$^8$ are each independently selected from the group consisting of direct bond, NR, PR, O, S, Se, CRR', SiRR', GeRR', BR, and BRR';

Y⁶ and Y⁷ are each independently selected from the group consisting of N, NR, PR, O, S, Se, CR, CRR', SiRR', GeRR', BR, and BRR';

$Z^1$ is C;

⸺ is a single or double bond;

$X^{17}$ to $X^{32}$ are each independently C or N;

if $X^{21}$ to $X^{25}$ are all C, then at least one of $R^E$ comprises a boron atom;

Ring H is a 5 membered or 6 membered carbocyclic or heterocyclic ring;

$R^A$, $R^B$, $R^C$, $R^D$, $R^E$, $R^F$, $R^G$, and $R^H$ each independently represent mono to the maximum allowable substitution, or no substitution;

each R, R', $R^A$, $R^B$, $R^C$, $R^D$, $R^E$, $R^F$, $R^G$, $R^H$, and $R^X$ is independently a hydrogen or a substituent selected from the group consisting of deuterium, halogen, alkyl, cycloalkyl, heteroalkyl, heterocycloalkyl, arylalkyl, alkoxy, aryloxy, amino, silyl, germyl, boryl, selenyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof;

any two adjacent R, R', $R^A$, $R^B$, $R^C$, $R^D$, $R^E$, $R^F$, $R^G$, $R^H$, and $R^X$ may be joined or fused to form a ring; and at least one of $Y^1$-$Y^4$ is selected from the group consisting of NR, PR, O, S, Se, CRR', SiRR', GeRR', BR, and BRR', or the compound is subject to the following provisos:

if the compound comprises Formula III, then at least one of Y⁶ and Y⁷ is N;

in Formula II, if $X^{21}$-$X^{25}$ are each C, then: Y⁵ is a direct bond; or at least one $R^E$ and $R^F$ is a substituent selected from the group consisting of heterocycloalkyl, germyl, boryl, selenyl, and combinations thereof;

if the compound comprises the structure of Formula IV in which Y⁸ is an atom, then at least one of the following is true:
i) $R^X$ joins with an $R^A$, $R^B$, $R^C$, or $R^D$ of the respective ring to which Formula IV is fused to form a fused ring;
ii) $R^X$ joins with $R^H$ to form a fused ring;
iii) $R^X$ comprises two or more aromatic rings; or
iv) Y⁸ is an atom that has a substituent and said substituent comprises two or more aromatic rings.

18. The OLED of claim 17, wherein the compound is a host, and the organic layer is an emissive layer that comprises a phosphorescent emitter.

19. The OLED of claim 18, wherein the phosphorescent emitter is a transition metal complex having at least one ligand or part of the ligand if the ligand is more than bidentate selected from the group consisting of:

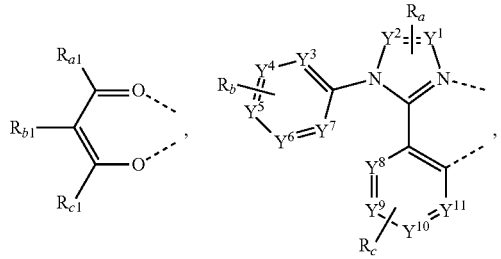

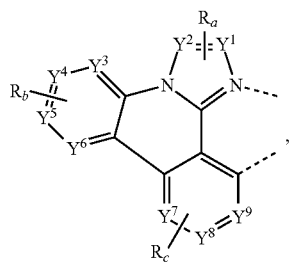

-continued

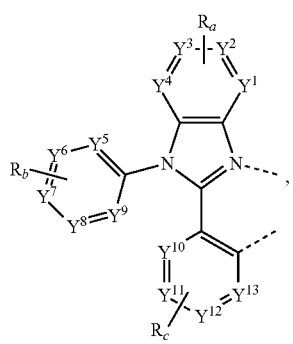

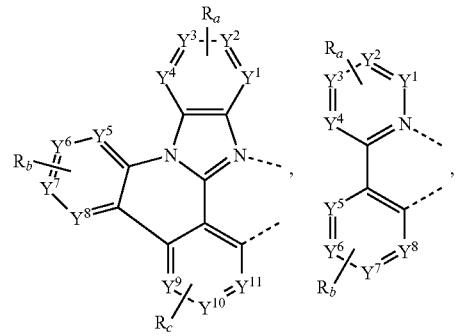

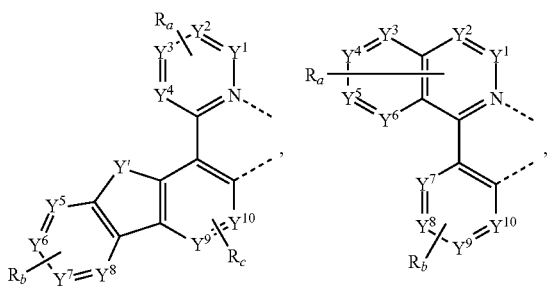

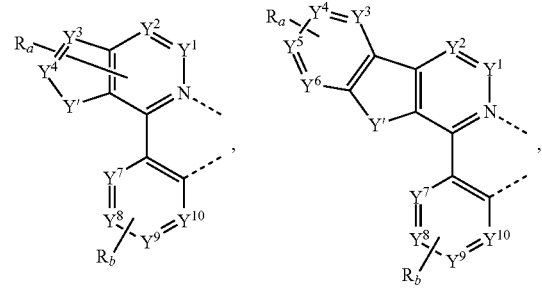

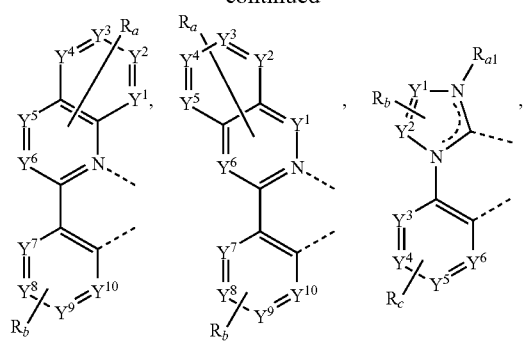
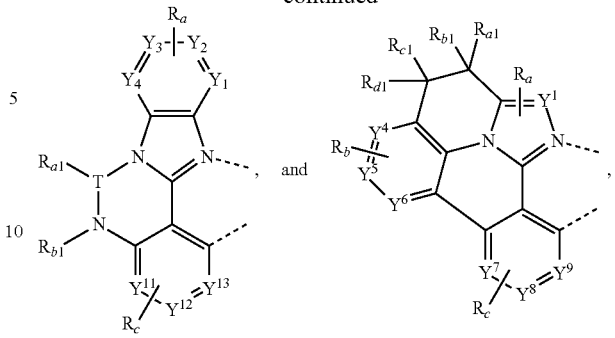

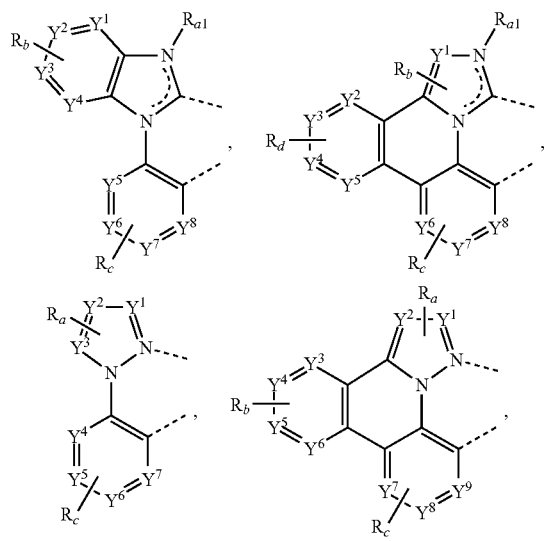

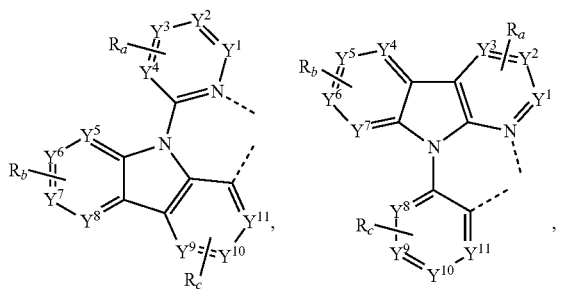

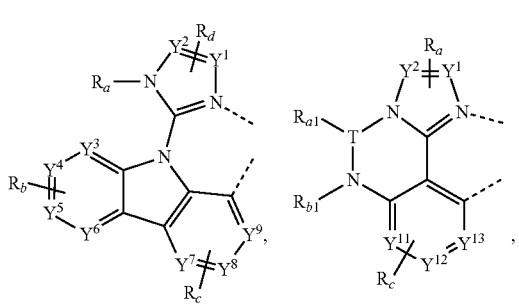
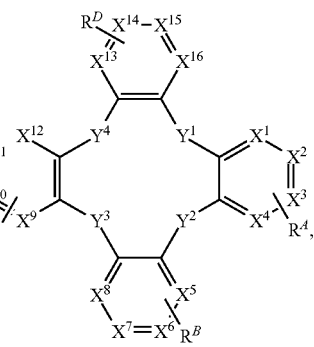

wherein:
T is selected from the group consisting of B, Al, Ga, and In;
each of $Y^1$ to $Y^{13}$ is independently selected from the group consisting of carbon and nitrogen;
Y' is selected from the group consisting of $BR_e$, $NR_e$, $PR_e$, O, S, Se, C=O, S=O, $SO_2$, $CR_eR_f$, $SiR_eR_f$, and $GeR_eR_f$;
$R_e$ and $R_f$ can be fused or joined to form a ring;
each $R_a$, $R_b$, $R_c$, and $R_d$ independently represent zero, mono, or up to a maximum allowed number of substitutions to its associated ring;
each of $R_{a1}$, $R_{b1}$, $R_{c1}$, $R_{d1}$, $R_a$, $R_b$, $R_c$, $R_d$, $R_e$ and $R_f$ is independently a hydrogen or a substituent selected from the group consisting of deuterium, halide, alkyl, cycloalkyl, heteroalkyl, arylalkyl, alkoxy, aryloxy, amino, silyl, boryl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; the general substituents defined herein; and
and any two adjacent $R_{a1}$, $R_{b1}$, $R_{c1}$, $R_{d1}$, $R_a$, $R_b$, $R_c$, $R_d$, $R_e$ and $R_f$ can be fused or joined to form a ring or form a multidentate ligand.

20. A consumer product comprising an organic light-emitting device (OLED) comprising:
an anode;
a cathode; and
an organic layer disposed between the anode and the cathode,
wherein the organic layer comprises a compound of Formula I:

wherein:
$X^1$ to $X^{16}$ are each independently C or N;
$Y^1$ to $Y^4$ are each independently selected from the group consisting of direct bond, NR, PR, O, S, Se, CRR', SiRR', GeRR', BR, and BRR';

at least two adjacent sites from $X^1$ to $X^{16}$ are both carbon and are fused to one of

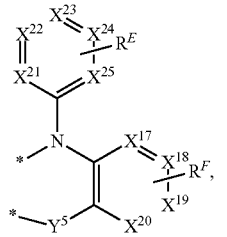

Formula II

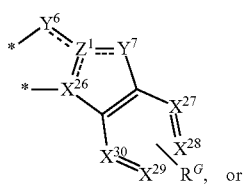

Formula III

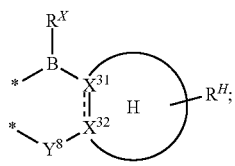

Formula IV wherein:
* shows the attachment point for each structure;
$Y^5$ and $Y^8$ are each independently selected from the group consisting of direct bond, NR, PR, O, S, Se, CRR', SiRR', GeRR', BR, and BRR';
$Y^6$ and $Y^7$ are each independently selected from the group consisting of N, NR, PR, O, S, Se, CR, CRR', SiRR', GeRR', BR, and BRR';
Z' is C;
═══ is a single or double bond;
$X^{17}$ to $X^{32}$ are each independently C or N;
if $X^{21}$ to $X^{25}$ are all C, then at least one of $R^E$ comprises a boron atom;
Ring H is a 5 membered or 6 membered carbocyclic or heterocyclic ring;
$R^A$, $R^B$, $R^C$, $R^D$, $R^E$, $R^F$, $R^G$, and $R^H$ each independently represent mono to the maximum allowable substitution, or no substitution;
each R, R', $R^A$, $R^B$, $R^C$, $R^D$, $R^E$, $R^F$, $R^G$, $R^H$, and $R^X$ is independently a hydrogen or a substituent selected from the group consisting of deuterium, halogen, alkyl, cycloalkyl, heteroalkyl, heterocycloalkyl, arylalkyl, alkoxy, aryloxy, amino, silyl, germyl, boryl, selenyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof;
any two adjacent R, R', $R^A$, $R^B$, $R^C$, $R^D$, $R^E$, $R^F$, $R^G$, $R^H$, and $R^X$ may be joined or fused to form a ring; and
at least one of $Y^1$-$Y^4$ is selected from the group consisting of NR, PR, O, S, Se, CRR', SiRR', GeRR', BR, and BRR', or the compound is subject to the following provisos:
  if the compound comprises Formula III, then at least one of $Y^6$ and $Y^7$ is N;
  in Formula II, if $X^{21}$-$X^{25}$ are each C, then: $Y^5$ is a direct bond; or at least one $R^E$ and $R^F$ is a substituent selected from the group consisting of heterocycloalkyl, germyl, boryl, selenyl, and combinations thereof;
  if the compound comprises the structure of Formula IV in which $Y^8$ is an atom, then at least one of the following is true:
    i) $R^X$ joins with an $R^A$, $R^B$, $R^C$, or $R^D$ of the respective ring to which Formula IV is fused to form a fused ring;
    ii) $R^X$ joins with $R^H$ to form a fused ring;
    iii) $R^X$ comprises two or more aromatic rings; or
    iv) $Y^8$ is an atom that has a substituent and said substituent comprises two or more aromatic rings.

* * * * *